US012486336B2

(12) United States Patent
Keyt et al.

(10) Patent No.: US 12,486,336 B2
(45) **Date of Patent: *Dec. 2, 2025**

(54) BINDING MOLECULES WITH MODIFIED J-CHAIN

(71) Applicant: IGM Biosciences, Inc., Mountain View, CA (US)

(72) Inventors: Bruce A. Keyt, Hillsborough, CA (US); Leonard G. Presta, San Francisco, CA (US); Ramesh Baliga, Redwood City, CA (US)

(73) Assignee: IGM BIOSCIENCES, INC., Mountain View, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 18/054,776

(22) Filed: Nov. 11, 2022

(65) Prior Publication Data

US 2023/0203201 A1 Jun. 29, 2023

Related U.S. Application Data

(63) Continuation of application No. 16/745,059, filed on Jan. 16, 2020, now Pat. No. 11,542,342, which is a continuation of application No. 15/764,859, filed as application No. PCT/US2016/055041 on Sep. 30, 2016, now Pat. No. 10,618,978.

(60) Provisional application No. 62/235,518, filed on Sep. 30, 2015.

(51) Int. Cl.

| | |
|---|---|
| ***C07K 16/46*** | (2006.01) |
| ***A61K 39/00*** | (2006.01) |
| ***A61K 39/395*** | (2006.01) |
| ***A61P 27/00*** | (2006.01) |
| ***A61P 35/02*** | (2006.01) |
| ***C07K 16/28*** | (2006.01) |

(52) U.S. Cl.

CPC ...... *C07K 16/468* (2013.01); *A61K 39/39541* (2013.01); *A61K 39/39558* (2013.01); *C07K 16/28* (2013.01); *C07K 16/2809* (2013.01); *C07K 16/2881* (2013.01); *C07K 16/2887* (2013.01); *A61K 2039/505* (2013.01); *A61P 27/00* (2018.01); *A61P 35/02* (2018.01); *C07K 2317/24* (2013.01); *C07K 2317/31* (2013.01); *C07K 2317/35* (2013.01); *C07K 2317/52* (2013.01); *C07K 2317/569* (2013.01); *C07K 2317/622* (2013.01); *C07K 2317/734* (2013.01); *C07K 2317/90* (2013.01); *C07K 2319/31* (2013.01); *C07K 2319/735* (2013.01); *C07K 2319/91* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly |
| 5,434,340 | A | 7/1995 | Krimpenfort |
| 5,798,229 | A | 8/1998 | Strittmatter |
| 5,831,034 | A | 11/1998 | Katinger |
| 5,911,989 | A | 6/1999 | Katinger |
| 6,165,463 | A | 12/2000 | Platz |
| 6,284,536 | B1 | 9/2001 | Morrison |
| 6,476,198 | B1 | 11/2002 | Kang |
| 6,676,924 | B2 | 1/2004 | Hansen |
| 7,074,403 | B1 | 7/2006 | Goldenberg |
| 7,109,304 | B2 | 9/2006 | Hansen |
| 7,138,496 | B2 | 11/2006 | Hua |
| 7,151,164 | B2 | 12/2006 | Hansen |
| 7,238,785 | B2 | 7/2007 | Govindan |
| 7,251,164 | B2 | 7/2007 | Okhonin |
| 7,282,567 | B2 | 10/2007 | Goldenberg |
| 7,300,655 | B2 | 11/2007 | Hansen |
| 7,311,912 | B1 | 12/2007 | Hein |
| 7,312,318 | B2 | 12/2007 | Hansen |
| 7,387,773 | B2 | 6/2008 | Murray |
| 7,402,312 | B2 | 7/2008 | Rosen |
| 7,541,440 | B2 | 6/2009 | Goldenberg |
| 7,601,351 | B1 | 10/2009 | Rosen |
| 7,612,180 | B2 | 11/2009 | Goldenberg |
| 7,709,615 | B2 | 5/2010 | Irie |
| 7,932,360 | B2 | 4/2011 | Van Berkel |
| 7,951,378 | B2 | 5/2011 | Larrick |
| 8,066,994 | B2 | 11/2011 | Gillies |
| 8,114,965 | B2 | 2/2012 | Maddon |
| 8,153,125 | B2 | 4/2012 | Watkins |
| 8,257,703 | B2 | 9/2012 | Irie |
| 8,333,971 | B2 | 12/2012 | Goldenberg |
| 8,337,844 | B2 | 12/2012 | Carr |

(Continued)

FOREIGN PATENT DOCUMENTS

| | | |
|---|---|---|
| AU | 697387 | 3/1996 |
| AU | 708301 | 5/1996 |

(Continued)

OTHER PUBLICATIONS

U.S. Appl. No. 18/252,759, Specification, Claims, Abstract and Drawings filed May 12, 2023 with U.S. Patent Office.

(Continued)

*Primary Examiner* — Phuong Huynh

(74) *Attorney, Agent, or Firm* — STERNE, KESSLER, GOLDSTEIN & FOX PLLC; Cynthia DeRenzo

(57) ABSTRACT

The present invention concerns binding molecules that comprise an IgM, IgA, IgG/IgM or IgG/IgA antibody with a J-chain modified to include an ADME-modulating moiety, and their uses.

13 Claims, 29 Drawing Sheets

Specification includes a Sequence Listing.

(56) References Cited

U.S. PATENT DOCUMENTS

| | | | | |
|---|---|---|---|---|
| 8,377,435 | B2 | 2/2013 | Bhat | |
| 8,871,216 | B2 | 10/2014 | Chang | |
| 9,173,961 | B2 | 11/2015 | Deckert | |
| 9,409,976 | B2 | 8/2016 | Teng | |
| 9,458,241 | B2 | 10/2016 | Bhat | |
| 9,938,347 | B2 | 4/2018 | Wang | |
| 9,951,134 | B2 * | 4/2018 | Keyt | C07K 16/283 |
| 10,351,631 | B2 | 7/2019 | Keyt | |
| 10,400,038 | B2 * | 9/2019 | Keyt | A61P 35/00 |
| 10,570,191 | B2 | 2/2020 | Keyt | |
| 10,604,559 | B2 | 3/2020 | Carroll | |
| 10,618,978 | B2 * | 4/2020 | Keyt | A61P 25/28 |
| 10,689,449 | B2 | 6/2020 | Wang | |
| 10,787,520 | B2 | 9/2020 | Keyt | |
| 10,822,399 | B2 | 11/2020 | Keyt | |
| 10,899,835 | B2 | 1/2021 | Baliga | |
| 10,954,302 | B2 * | 3/2021 | Keyt | A61P 35/02 |
| 10,975,147 | B2 | 4/2021 | Keyt | |
| 11,192,941 | B2 | 12/2021 | Keyt | |
| 11,401,337 | B2 | 8/2022 | Baliga | |
| 11,535,664 | B2 | 12/2022 | Carroll | |
| 11,542,342 | B2 * | 1/2023 | Keyt | C07K 16/2809 |
| 11,555,075 | B2 | 1/2023 | Keyt | |
| 11,578,131 | B2 | 2/2023 | Wang | |
| 11,639,389 | B2 | 5/2023 | Keyt | |
| 2002/0006630 | A1 | 1/2002 | Sirbasku | |
| 2002/0168367 | A1 | 11/2002 | Larrick | |
| 2003/0224443 | A1 | 12/2003 | Hiatt | |
| 2004/0005318 | A1 | 1/2004 | Davis | |
| 2004/0137001 | A1 | 7/2004 | Schreiber | |
| 2004/0156826 | A1 | 8/2004 | Dangond | |
| 2005/0003431 | A1 | 1/2005 | Wucherpfennig | |
| 2005/0129616 | A1 | 6/2005 | Salcedo | |
| 2005/0202026 | A1 | 9/2005 | Hiatt | |
| 2005/0287153 | A1 | 12/2005 | Dennis | |
| 2006/0063234 | A1 | 3/2006 | Jones | |
| 2006/0153854 | A1 | 7/2006 | Bhat | |
| 2007/0014720 | A1 | 1/2007 | Gazit-Bornstein | |
| 2007/0154469 | A1 | 7/2007 | Irie | |
| 2007/0248601 | A1 | 10/2007 | Cogne | |
| 2007/0249812 | A1 | 10/2007 | Hayasaka | |
| 2008/0044413 | A1 | 2/2008 | Hammond | |
| 2008/0145420 | A1 | 6/2008 | Simon | |
| 2009/0022738 | A1 | 1/2009 | Hofmeister | |
| 2009/0130089 | A9 | 5/2009 | Smith | |
| 2009/0291899 | A1 | 11/2009 | Ferrante | |
| 2010/0093979 | A1 | 4/2010 | Lazar | |
| 2010/0144621 | A1 * | 6/2010 | Kim | A61K 38/2278 514/6.9 |
| 2010/0172899 | A1 | 7/2010 | Irie | |
| 2010/0184959 | A1 | 7/2010 | Guler-Gane | |
| 2010/0279932 | A1 | 11/2010 | Ledbetter | |
| 2010/0279939 | A1 | 11/2010 | Fries | |
| 2011/0110852 | A1 | 5/2011 | Miller | |
| 2011/0129412 | A1 | 6/2011 | Gazit-Bornstein | |
| 2011/0318339 | A1 | 12/2011 | Smider | |
| 2012/0039870 | A9 | 2/2012 | Dolk | |
| 2012/0045432 | A9 | 2/2012 | Yu | |
| 2012/0142593 | A1 * | 6/2012 | Zhao | C07K 14/755 435/69.6 |
| 2012/0258126 | A1 | 10/2012 | Schoeller | |
| 2012/0269830 | A1 | 10/2012 | Horowitz | |
| 2013/0095097 | A1 | 4/2013 | Blankenship | |
| 2013/0164283 | A1 | 6/2013 | Bhat | |
| 2013/0189258 | A1 | 7/2013 | Rother | |
| 2013/0280167 | A1 | 10/2013 | Rodriguez | |
| 2014/0010809 | A1 | 1/2014 | Ledbetter | |
| 2014/0044739 | A1 | 2/2014 | Teng | |
| 2014/0088295 | A1 | 3/2014 | Smith | |
| 2014/0154252 | A1 | 6/2014 | Thompson | |
| 2014/0249044 | A1 | 9/2014 | Braz Gonçalves | |
| 2015/0004167 | A1 | 1/2015 | Wu | |
| 2015/0038682 | A1 | 2/2015 | Tsurushita | |
| 2015/0259420 | A1 | 9/2015 | Triebel | |
| 2016/0222132 | A1 | 8/2016 | Keyt | |
| 2016/0326233 | A1 | 11/2016 | Mondelli | |
| 2016/0368971 | A1 | 12/2016 | Keyt | |
| 2017/0183409 | A1 | 6/2017 | Keyt | |
| 2017/0283510 | A1 | 10/2017 | Keyt | |
| 2017/0320955 | A1 | 11/2017 | Wang | |
| 2018/0009897 | A1 | 1/2018 | Wang | |
| 2018/0118814 | A1 | 5/2018 | Carroll | |
| 2018/0118816 | A1 | 5/2018 | Keyt | |
| 2018/0265596 | A1 | 9/2018 | Keyt | |
| 2019/0002566 | A1 | 1/2019 | Keyt | |
| 2019/0100597 | A1 | 4/2019 | Keyt | |
| 2019/0185570 | A1 | 6/2019 | Keyt | |
| 2019/0330360 | A1 | 10/2019 | Wang | |
| 2019/0330374 | A1 | 10/2019 | Wang | |
| 2019/0338031 | A1 | 11/2019 | Keyt | |
| 2019/0338040 | A1 | 11/2019 | Keyt | |
| 2019/0338041 | A1 | 11/2019 | Baliga | |
| 2020/0190190 | A1 | 6/2020 | Keyt | |
| 2020/0239572 | A1 | 7/2020 | Baliga | |
| 2020/0255546 | A1 | 8/2020 | Keyt | |
| 2020/0377577 | A1 | 12/2020 | Keyt | |
| 2020/0392239 | A1 | 12/2020 | Wang | |
| 2021/0002353 | A1 | 1/2021 | Carroll | |
| 2021/0032357 | A1 | 2/2021 | Keyt | |
| 2021/0047419 | A1 | 2/2021 | Wang | |
| 2021/0087273 | A1 | 3/2021 | Baliga | |
| 2021/0147567 | A1 | 5/2021 | Baliga | |
| 2021/0163600 | A1 | 6/2021 | Keyt | |
| 2021/0380701 | A1 | 12/2021 | Baliga | |
| 2021/0388098 | A1 | 12/2021 | Keyt | |
| 2022/0106398 | A1 | 4/2022 | Baliga | |
| 2022/0106399 | A1 | 4/2022 | Baliga | |
| 2022/0169751 | A1 | 6/2022 | Wang | |
| 2022/0177595 | A1 | 6/2022 | Wang | |
| 2022/0267415 | A1 | 8/2022 | Ku | |
| 2022/0289856 | A1 | 9/2022 | Amoury | |
| 2022/0306760 | A1 | 9/2022 | Keyt | |
| 2022/0340676 | A1 | 10/2022 | Baliga | |
| 2022/0372142 | A1 | 11/2022 | Baliga | |
| 2022/0403009 | A1 | 12/2022 | Hinton | |
| 2023/0058162 | A1 | 2/2023 | Hinton | |
| 2023/0073926 | A1 | 3/2023 | Keyt | |
| 2023/0174660 | A1 | 6/2023 | Wang | |
| 2023/0203119 | A1 | 6/2023 | Baliga | |
| 2023/0203173 | A1 | 6/2023 | Wang | |
| 2023/0212293 | A1 | 7/2023 | Keyt | |
| 2023/0279111 | A1 | 9/2023 | Keyt | |
| 2024/0002514 | A1 | 1/2024 | Keyt | |
| 2024/0002526 | A1 | 1/2024 | Chen | |
| 2024/0076392 | A1 | 3/2024 | Hinton | |
| 2024/0124584 | A1 | 4/2024 | Baliga | |
| 2025/0051473 | A1 | 2/2025 | Li | |

FOREIGN PATENT DOCUMENTS

| | | |
|---|---|---|
| AU | 2004297218 | 6/2005 |
| CA | 2358520 | 7/2000 |
| CA | 2662701 | 10/2008 |
| EP | 642585 | 3/1995 |
| EP | 1169352 | 1/2002 |
| EP | 1301541 | 4/2003 |
| EP | 1617870 | 1/2006 |
| EP | 1833848 | 9/2007 |
| EP | 2219458 | 8/2010 |
| EP | 2254592 | 12/2010 |
| EP | 2264163 | 12/2010 |
| EP | 2300498 | 3/2011 |
| EP | 2465871 | 6/2012 |
| EP | 2649184 | 10/2013 |
| EP | 2655415 | 10/2013 |
| EP | 2771361 | 9/2014 |
| EP | 2962103 | 1/2016 |
| JP | 2004525630 | 8/2004 |
| JP | 2005522998 | 8/2005 |
| WO | 1989001975 | 3/1989 |
| WO | 1998030591 | 7/1998 |
| WO | 1998030592 | 7/1998 |
| WO | 2001012820 | 2/2001 |
| WO | 2001014424 | 3/2001 |

(56) References Cited

FOREIGN PATENT DOCUMENTS

| | | | |
|---|---|---|---|
| WO | 2004110143 | 12/2004 | |
| WO | 2005103081 | 11/2005 | |
| WO | 2006052641 | 5/2006 | |
| WO | 2006130458 | 12/2006 | |
| WO | 2008140477 | 11/2008 | |
| WO | 2009013620 | 1/2009 | |
| WO | 2009130575 | 10/2009 | |
| WO | 2010105256 | 9/2010 | |
| WO | 2013061098 | 5/2013 | |
| WO | 2013087913 | 6/2013 | |
| WO | 2013120012 | 8/2013 | |
| WO | 2013150138 | 10/2013 | |
| WO | 2013158748 | 10/2013 | |
| WO | 2013188870 | 12/2013 | |
| WO | 2014022592 | 2/2014 | |
| WO | 2014124457 | 8/2014 | |
| WO | 2014165093 | 10/2014 | |
| WO | WO-2014165093 A2 * | 10/2014 | ........... C07K 14/765 |
| WO | 2014207064 | 12/2014 | |
| WO | 2015037000 | 3/2015 | |
| WO | 2015053887 | 4/2015 | |
| WO | 2015103072 | 7/2015 | |
| WO | 2015120474 | 8/2015 | |
| WO | 2015151081 | 10/2015 | |
| WO | 2015153912 | 10/2015 | |
| WO | 2016118641 | 7/2016 | |
| WO | 2016141303 | 9/2016 | |
| WO | 2016154593 | 9/2016 | |
| WO | 2016168758 | 10/2016 | |
| WO | 2017059380 | 4/2017 | |
| WO | 2017059387 | 4/2017 | |
| WO | 2017196867 | 11/2017 | |
| WO | 2018017761 | 1/2018 | |
| WO | 2018017763 | 1/2018 | |
| WO | 2018017888 | 1/2018 | |
| WO | 2018017889 | 1/2018 | |
| WO | 2018187702 | 10/2018 | |
| WO | 2019165340 | 8/2019 | |
| WO | 2019169314 | 9/2019 | |
| WO | 2020086745 | 4/2020 | |
| WO | 2020163646 | 8/2020 | |
| WO | 2021030688 | 2/2021 | |
| WO | 2021034646 | 2/2021 | |
| WO | 2021041250 | 3/2021 | |
| WO | 2021055765 | 3/2021 | |
| WO | 2021141902 | 7/2021 | |
| WO | 2021216756 | 10/2021 | |
| WO | 2021231639 | 11/2021 | |
| WO | 2022026475 | 2/2022 | |
| WO | 2022109023 | 5/2022 | |
| WO | 2022177870 | 8/2022 | |
| WO | 2022178047 | 8/2022 | |
| WO | 2023064766 | 4/2023 | |
| WO | 2023064900 | 4/2023 | |
| WO | 2023150677 | 8/2023 | |
| WO | 2023178253 | 9/2023 | |
| WO | 2024073700 | 4/2024 | |
| WO | 2024138072 | 6/2024 | |
| WO | 2024148336 | 7/2024 | |
| WO | 2024148339 | 7/2024 | |
| WO | 2024229151 | 11/2024 | |

OTHER PUBLICATIONS

U.S. Appl. No. 18/261,145, Specification, Claims, Abstract and Drawings filed Jul. 12, 2023 with U.S. Patent Office.

U.S. Appl. No. 18/463,194, Specification, Claims, Abstract and Drawings filed Sep. 7, 2023 with U.S. Patent Office.

Aggarwal, B., et al. (2012), "Historical Perspectives on Tumor Necrosis Factor and Its Superfamily: 25 Years Later, a Golden Journey", Blood, 119(3): 651-665.

Albrecht, H., et al. (2006), "Recombinant Antibodies: From the Laboratory to the Clinic", Cancer Biotherapy & Radiopharmaceuticals, vol. 21: 285-304.

Ammann, J., et al. (2014), "Development and use of IgM/J-Chain Fusion Proteins for Chacterization of Immunoglobulin Superfamily Ligand-Receptor Interactions", Current Protocols in Protein Science, Supplement 75.

Ammann, J., et al., (2012), "Detection of weak receptor-ligand interactions using IgM and J-chain-based fusion proteins", European Journal of Immunology, 42:1354-1356.

Andersen, J., et al., "Extending Serum Half-life of Albumin by Engineering Neonatal Fc Receptor (FcRn) Binding", 2014, Journal of Biological Chemistry, vol. 289, No. 19, pp. 13492-13502.

Arnold, J., et al., (2005), "Human serum IgM glycosylation: identification of glycoforms that can bind to mannan-binding lectin", The Journal of Biological Chemistry, vol. 280(32): 29080-29087.

Azuma, Y., et al., "Recombinant Human Hexamer-Dominant IgM Monoclonal Antibody to Ganglioside GM3 for Treatment of Melanoma", 2007, Clin Cancer Res, vol. 13 (No. 9), pp. 2745-2750 with correction on article.

Bacac, M., et al., (2018), "CD20-TCB with Obinutuzumab Pretreatment as Next-Generation Treatment of Hematologic Malignancies", Clinical Cancer Research, 24(19): 4785-4797, includes supplementary methods, Binding to CD20- and CD3-expressing cells, 24 additional pages.

Bakema et al, "Immunoglobulin A, A next generation of therapeutic antibodies?", mAbs, Aug. 2011, vol. 3, No. 4, 352-361.

Baliga, R., et al, (2019), "IGM-2323: High Avidity IgM-based CD20×CD3 Bispecific Antibody for Enhanced T-Cell Dependent Killing with Minimal Cytokine Release", Abstract 1574 at American Society of Hematology Annual Meeting, Dec. 7-10, 2019, Orlando, FL.

Baliga, R., et al., (2016) "High Avidity Anti-CD20 IgM Antibody for enhanced Complement-Dependent Cell Killing of Low CD20 Expressing Tumor Cells", Poster Presented at the PEGS Boston Meeting Apr. 25-29, 2016.

Beers, S., et al., (2010), "Antigenic modulation limits the efficacy of anti-CD20 antibodies: implications for antibody selection", Blood, 115(25): 5191-5201.

Binz, et al., "Engineering novel binding proteins from nonimmunoglobulin domains," Nature Biotechnology 2005, vol. 23, No. 10, pp. 1257-1268.

Bornstein, G., et al., (2010), "Development of a new fully human anti-CD20 monoclonal antibody for the treatment of B-cell malignancies", Invest New Drugs, 28:561-574.

Bortoletto, N., et al., (2002), "Optimizing anti-CD3 affinity for effective T cell targeting against tumor cells", Eur. J. Immunol, 32: 3102-3107.

Bowles, J., et al., (2006), "Anti-CD20 monoclonal antibody with enhanced affinity for CD16 activates NK cells at lower concentrations and more effectively than rituximab", Blood, 108(8): 2648-2654.

Braathen, R., et al. (2002), "The Carboxyl-terminal Domains of IgA and IgM Direct Isotype-specific Polymerization and Interaction with the Polymeric Immunoglobulin Receptor", The Journal of Biological Chemistry, 277(45): 42755-42762.

Brodska et al., "Correlation of PD-L1 Surface Expression on Leukemia Cells with the Ratio of PD-L1 mRNA Variants and with Electrophoretic Mobility", Cancer Immunology Research, Aug. 2016, pp. 815-819, vol. 4, No. 10.

Brüggemann, M., et al., (1987), "Comparison of the effector functions of human immunoglobulins using a matched set of chimeric antibodies", J. Exp. Med, 166: 1351-1361.

Cao, Y., et al., (2011), "Targeting cell surface B2-microglobulin by pentameric IgM antibodies", Br J Haematol, 154: 111-121.

Casset, F., et al., (2003), "A peptide mimetic of an anti-CD4 monoclonal antibody by rational design", Biochemical and biophysical Research Communications, 307: 198-205.

Castro, C., et al., (2014), "Putting J chain back on the map: how might its expression define plasma cell development?", The Journal of Immunology, 193: 3248-3255.

Cazet et al., "Tumour-associated carbohydrate antigens in breast cancer," Breast Cancer Research 2010, vol. 12, No. 3, p. 204.

Chen, Y., et al., (1999), Selection and Analysis of an Optimized Anti-VEGF Antibody: Crystal Structure of an Affinity-matured Fab in Complex with Antigen, 293: 865-881.

(56) References Cited

OTHER PUBLICATIONS

Chintalacharuvu, K.R., et al., "Hybrid IgA2/igG1 Antibodies with Tailor-Made Effector Functions", Clinical Immunology, Oct. 2001, pp. 21-31, vol. 101, No. 1, pp. 21-31.
Chu, S., et al., (2014), "Immunotherapy with Long-Lived Anti-CD20×Anti-CD3 Bispecific Antibodies Stimulates Potent T Cell-mediated Killing of Human B Cell lines and Circulating and Lymphoid B Cells in Monkeys: A Potential Therapy for B Cell Lymphomas and Leukemias", Xencor, Inc., Monrovia, California 91016 USA, Poster.
Ciric B., et al. (2009), "Effect of Valency on Binding Properties of the Antihuman IgM Monoclonal Antibody 202", Hybridoma, vol. 14. No. 6, pp. 537-544.
Clackson et al., " Making antibody fragments using phage display libraries" Nature 1991, vol. 352, pp. 624-628.
Colman, P.M. (1994) "Effects of amino acid sequence changes on antibody-antigen interactions", Biomolecular Research Institute, 55th Forum in Immunology, pp. 33-35.
Cregger, M., et al., (2006), "Immunohistochemistry and Quantitative Analysis of Protein Expression", Arch Pathol Lab Med., 130: 1026-1030.
Czajkowsky D., et al., (2009), "The human IgM pentamer is a mushroom-shaped molecule with a flexural bias," PNAS, 106(35): 14960-14965.
Czuczman, M., et al., (2008), "Acquirement of rituximab resistance in lymphoma cell lines is associated with both global CD20 gene and protein down-regulation regulated at the pretranscriptional and posttranscriptional levels", Clin Cancer Res, 14(5): 1561-1570.
Davis et al., "On the structure of polymeric IgM," Eur. J. Immunol. 1988, vol. 18, No. 7, pp. 1001-1008.
Davis, A., et al., (1989), "IgM—Molecular requirements for its assembly and function", Immunology Today, 10(4): 118-128.
Davis, T., et al., (1999), "Single-agent monoclonal antibody efficacy in bulky non-Hodgkin's lymphoma: results of a phase II trial of rituximab", J. Clin Oncol. 17: 1851-1857.
Davis, T., et al., (2000), "Rituximab anti-CD20 monoclonal antibody therapy in non-Hodgkin's lymphoma: safety and efficacy of re-treatment", Journal of Clinical Oncology, 18(17): 3135-3143.
De Pascalis, R., et al., (2002), "Grafting of "Abbreviated" Complementarity-Determining Regions Containing specificity-Determining Residues Essential for Ligand Contact to Engineer a Less Immunogenic Humanized Monoclonal Antibody", The Journal of Immunology, 169: 3076-3084.
Dennis, M., et al. (2002), "Albumin Binding as a General Strategy for Improving the Pharmacokinetics of Proteins", J. Biol. Chem. 277(38): 35035-35043.
Dennis, M., et al., (2012), "Transferrin Antibodies into the Brain", Neuropsychopharmacology Reviews, 37: 302-303.
Dorai et al., "The complete nucleotide sequence of a human immunoglobulin genomic Cu gene," GenBank Accession Number X14940.1, Nucleic Acids Research 1989, vol. 17, No. 15, p. 6412.
Ducry, L., et al., "Antibody-drug conjugates: linking cytotoxic payloads to monoclonal antibodies", 2010, Bioconjug. Chem. 21, 5-13.
Duramad, O., et al., (2014), "IGM-55.5, a novel monoclonal human recombinant IgM antibody with potent activity against B cell leukemia and lymphoma", IGM Biosciences, Inc.—Research and Development, SRI International—Cancer Pharmacology, Stanford—Department of Obstetrics and Gynecology, Abstract No. 645, AACR Annual Meeting, Apr. 5-9, 2014, San Diego CA.
Edwards, B., et al., (2003), "The Remarkable Flexibility of the Human Antibody Repertoire; Isolation of Over One Thousand Different Antibodies to a Single Protein, BLyS", J. Mol. Biol, 334: 103-118.
Ellman, "Biosynthetic method for introducing unnatural amino acids site-specifically into proteins," Meth. Enzym. 1991, vol. 202, pp. 301-336.
Fournier et al., "Bispecific antibodies and trispecific immunocytokines for targeting the immune system against cancer: preparing for the future," BioDrugs. 2013, vol. 27, No. 1, pp. 35-53.
Frutiger, S., et al., 1992, "Disulfide Bond Assignment in Human J Chain and its Covalent Pairing with Immunoglobulin M", Biochemistry, vol. 31, pp. 12643-12647.
Fukushima, N., et al., (2002), "Chacterization of Recombinant Monoclonal IgA Anti-PDC-E2 Autoantibodies Derived From patients with PBC", Hepatology: 35: 1383-1392.
Gaetano, N., et al., (2003), "Complement Activation Determines the Therapeutic Activity of Rituximab in Vivo", The Journal of Immunology, 171: 1581-1587.
Garcia-Pardo et al., " J chain is covalently bound to both monomer subunits in human secretory IgA," J. Biol. Chem. 1981, vol. 256, pp. 11734-11738.
Ghielmini, M., (2004), "Prolonged treatment with rituximab in patients with follicular lymphoma significantly increases event-free survival and response duration compared with the standard weekly x 4 schedule", Blood, 103(12): 4416-4423.
Gibson Josefine, "Anti-PD-L1 for metastatic triple-negative breast cancer.", The Lancet. Oncology Jun. 2015, (Jun. 2015), vol. 16, No. 6, ISSN 1474-5488, p. e264, XP002765988.
Gilmour, J.E.M., et al. (2008), "Effect of the presence or absence of J Chain on expresion of recombinant anti-kell immunoglobulin", Transfusion Medicine, 18: 167-174.
Golay, J., et al. (2012), "Mechanism of action of therapeutic monoclonal antibodies: Promises and pitfalls of in vitro and in vivo assays", Archives of Biochemistry and Biophysics, 526: 146-153.
Goswami et al., "Developments and challenges for mAb-Based therapeutics," Antibodies 2013, vol. 2, No. 3, pp. 452-500.
Hagenbeek, A., et al., (2009), "Evaluation of Ofatumumab, a Novel Human CD20 Monoclonal Antibody, as Single Agent Therapy in Rituximab-Refractory Follicular Lymphoma", Blood, 114(22): 935, 6 pages.
Haidar, JH., et al., (2003), "Loss of CD20 expression in relapsed lymphomas after rituximab therapy", Eur J. Haematol, 70: 330-332.
Harao M., et al. , (2014), "Abstract LB-263: Enhancing of CD8+ tumor-infiltrating lymphocyte expansion from triple-negative breast cancer patients using of 41BB costimulation", American Associaton for Cancer Research, URL: http://cancerres.aacrjournals.org/content/74/19_Supplement/LB-263, XP002765987.
Hay, M., et al., (2014), "Clinical development success rates for investigational drugs", Nature Biology, 32(1): 40-51.
Hensel, F., et al., (2013), "Early development of PAT-SM6 for the treatment of melanoma", Melanoma Research, 23(4): 264-275.
Hirayasu, K. and Arase, H., "Immunoglobulin mu heavy chain, partial [*Homo sapiens*]," GenBank Accession No. AFM37312, Jun. 18, 2012 (2 pages).
Hopp, J., et al., (2010), "The effects of affinity and valency of an albumin-binding domain (ABD) on the half-life of a single-chain diabody-ABD fusion protein", vol. 23(11): 827-834.
Houghton, J., et al., (2015), "Site-specifically labeled CA19.9-targeted immunoconjugates for the PET, NIRF, and multimodal PET/NIRF imaging of pancreatic cancer", PNAS, vol. 112, No. 52: 15850-15855.
Hsu, D., et al., (1999), "A humanized anti-CD3 antibody, HuM291, with low mitogenic activity, mediates complete and reversible T-cell depletion in chimpanzees", Transplantation, 68(4): 545-554.
Jeon, H., et al., (2014), "Structure and Cancer Immunotherapy of the B7 Family Member B7x", Cell Rep., vol. 9(3): 1089-1098.
Johansen, F., et al., (2000), "Role of J Chain in Secretory Immunoglobulin Formation", Scand. J. Immunol., 52: 240-248.
Johansen, F., et al., (2001), "The J Chain Is Essential for Polymeric Ig Receptor-Mediated Epithelial Transport of IgA", The Journal of Immunology, 167: 5185-5192.
Johnson, R., et al. (2012) "Biological Activity of Anti-CD20 Multivalent HPMA Copolymer-Fab' Conjugates", Biomacromolecules, vol. 13, pp. 727-735.
Jones et al., "Replacing the complementarity-determining regions in a human antibody with those from a mouse," Nature 1986, vol. 321, pp. 522-525.
Jones, A., et al., (2007), "Blood-Brain Barrier Transport of Therapeutics via Receptor-Mediation", Pharm Res., 24(9): 1759-1771.
Joos, B., et al., 2006, "Long-Term Multiple-Dose Pharmacokinetics of Human Monoclonal Antibodies (MAbs) against Human Immu-

(56) References Cited

OTHER PUBLICATIONS nodeficiency Virus Type 1 Envelope gp120 (MAb 2G12) and gp41 (MAbs 4E10 and 2F5)", Antimicrob Agents Chemother 50, 1773-1779.
Jubala, C.M., et al. (2005), "CD20 Expression in Normal Canine B Cells and in Canine non-Hodgkin Lymphoma" Vet Pathol 42: 468-476.
Klein, J., et al., (2014,) "Design and characterization of structured protein linkers with differing flexibilities" Protein Eng Des Sel 27, 325-330.
Klimovich, V. B., (2011), "IgM and Its Receptors: Structural and Functional Aspects", Biochemistry, 76(5): 534-549.
Kohler et al., "Continuous cultures of fused cells secreting antibody of predefined specificity," Nature 1975, vol. 256, No. 495-7.
Kragten, E., et al., (1995), "Site-specific analysis of the N-Glycans on Murine Polymeric Immunoglobulin A. Using Liquid Chromatography/Electrospray Mass Spectrometry", vol. 30, 1679-1686.
Krugmann, S., et al. (1997), "Structural Requirements for Assembly of Dimeric IgA Probed by Site-Directed Mutagenesis of J Chain and a Cysteine Residue of the α-chain CH2 Domain", The Journal of Immunology, 159: 244-249.
Ksiezak-Reding, H., et al., 1988, "Alz 50, a monoclonal antibody to Alzheimer's disease antigen, cross-reacts with tau proteins from bovine and normal human brain", J. Biol. Chem. 263, 7943-7947.
Lamminmäki, U., et al., (2001), "Crystal Structure of a Recombinant Anti-estradiol Fab Fragment in Complex with 17β Estradiol", The Journal of Biological Chemistry, vol. 276(39): 36687-36694.
Lederman, S., et al. (1991), "A Single Amino Acid Substitution in a Common African Allele of the CD4 Molecule Ablates Binding of the Monoclonal Antibody, OKT4", Molecular Immunology, 28(11): 1171-1181.
Lewis, A.K., et al., 2014, "Open and Closed Conformations of the Isolated Transmembrane Domain of Death Receptor 5 Support a New Model of Activation" Biophys J 106, L21-L24.
Liedtke, M., et al., (2012), "Phase I trial of a novel human monoclonal antibody mAb216 in patients with relapsed or refractory B-cell acute lymphoblastic leukemia" Haematologica 97(1), 30-37.
Lines, J., et al., (2014), "VISTA Is an Immune Checkpoint Molecule for Human T Cells", Cancer Research 74(7): 1924-1932.
Liu, X., et al., (2005), "Preliminary study on recombination of J-HNP-1 and its antibacterial effect in vitro" Shijie Huaren Xiaohua Zazhi, 13(22), 2640-2644, English Abstract Only Available.
Liu, X., et al., (2005), "Recombinant of J chain-HNP-1 cDNA and the construction of expression vector", Di-San Junyi Daxue Xuebao, 27(8), 697-699. English Abstract Only Available.
Liu, Xianhua, et al., 2006, "Expression Detection of the gene of α-defensin-1 with J chain in the transfected COS-7 cells", Chin Crit Care Med, vol. 18, No. 2, pp. 71 to 73 with Full English translation.
Lloyd, C., et al., (2009), "Modelling the human immune response: performance of a 10" human antibody repertoire against a broad panel of therapeutically relevant antigens", Protein Engineering, Design & Selection, 22(3), 159-168.
MacCallum R., et al. (1996), "Antibody-antigen Interactions: Contact Analysis and binding Site Topography", J. Mol. Bio. 262: 732-745.
Maekawa, N., et al., (2014), "Expression of PD-L1 on Canine Tumor Cells and Enhancement of IFN-γ Production from Tumor-Infiltrating Cells by PD-L1 Blockade", PLOS One, vol. 9(6), e98415.
Maloney, D., et al., (1997), "IDEC-C2B8 (Rituximab) anti-CD20 monoclonal antibody therapy in patients with relapsed low-grade non-Hodgkin's lymphoma", Blood, 90(6): 2188-2195.
Mandikian, D., et al., (2018), "Relative Target Affinities of T Cell-Dependent Bispecific Antibodies Determine Biodistribution in a Solid Tumor Mouse Model", Mol Cancer Ther., 17(4): 776-785, doi: 10.1158/1535-7163.MCT-17-0657.
Marcus, R., et al., (2017), "Obinutuzumab for the First-Line Treatment of Follicular Lymphoma", N Engl. J. Med. 377(14): 1331-44.
Mariuzza, R. A., (1987), "The Structural Basis of Antigen-Antibody Recognition", vol. 16: 139-159.
Marks et al., "By-passing immunization. Human antibodies from V-gene libraries displayed on phage," J. Mol. Biol. 1991, vol. 222, pp. 582-597.
Mestecky, J., et al., (1973), "J-chain of polymeric IgA myeloma proteins", Protides of the Biological Fluids, vol. 20: 279-283 , Abstract Only Available.
Meyer et al., "Improved In Vivo Anti-Tumor Effects of IgA-Her2 Antibodies Through Half-Life Extension and Serum Exposure Enhancement by FcRn Targeting", mAbs, Jan. 2016, pp. 87-98, vol. 8, Issue 1.
Mølhøj, M., et al., (2007), "CD19-/CD3-bispecific antibody of the BiTE class is far superior to tandem diabody with respect to redirected tumor cell lysis", Molecular Immunology 44: 1935-1943.
Mongini, P., et al., (1995), "Human B Cell Activation, Effect of T Cell Cytokines on the Physicochemical Binding Requirements for Achieving Cell cycle Progression via the Membrane IgM Signaling Pathway", The Journal of Immunology, 155: 3385-3400.
Mordenti, J., et al. (1999), "Intraocular Pharmacokinetics and Safety of a Humanized Monoclonal Antibody in Rabbits after Intravitreal Administration of a Solution or a PLGA Microsphere Formulation", Toxicological Sciences, 52: 101-106.
Mordenti, J., et al., (1999), "Comparisons of the Intraocular Tissue Distribution, Pharmacokinetics, and Safety of 125I-Labeled Full-Length and Fab Antibodies in Rhesus Monkeys Following Intravitreal Administration", Investigative Pathology, vol. 27, No. 5, pp. 536-544.
Morrison et al., " Chimeric human antibody molecules: mouse antigen-binding domains with human constant region domains," PNAS 1984, vol. 81, pp. 6851-6855.
Mosmann, T.R., et al. (1978), "Modification and Fate of J. Chain in myeloma cells in the presence and absence of polymeric immunoglobulin secretion", Eur. J. Immunol. 8: 84-101.
Müller, M. et al., (2012), "Improving the pharmacokinetic properties of biologics by fusion to an anti-HSA shark VNAR domain" MAbs 4, 673-685.
NCBI Reference Sequence (2018): NP_653247.1, 17.04.2013, Immunoglobulin J chain precursor [*Homo sapiens*].
Niles, M., et al., (1995), "Polymer IgM assembly and secretion in lymphoid and nonlymphoid cell lines: evidence that J chain is required for pentamer IgM synthesis", Proc. Natl. Acad. Sci. USA, 92: 2884-2888.
Niwa, H., Yamamura, K., Miyazaki, J., 1991. Efficient selection for high-expression transfectants with a novel eukaryotic vector. Gene 108, 193-199.
Nocentini, G., et al., (1997), "A new member of the tumor necrosis factor/nerve growth factor receptor family inhibits T cell receptor-induced apoptosis", Proc. Natl. Acad. Sci. U.S.A. 94, 6216-6221.
Non-final Office Action issued in U.S. Appl. No. 15/764,859 on Aug. 6, 2019.
Noren et al., "A general method for site-specific incorporation of unnatural amino acids into proteins," Science 1989, vol. 244, p. 182-188.
Ofei et al., "Effects of an engineered human anti-TNF-a antibody (CDP571) on insulin sensitivity and glycemic control inpatients with NIDDM," Diabetes 1996, vol. 45, pp. 881-885.
Office Action issued Sep. 27, 2019 in U.S. Appl. No. 15/764,870.
Padlan, E., et al.., (1989), "Structure of an antibody-antigen complex: crystal structure of the HyHel-10 Fab-lysozyme complex;", Proc. Natl. Acad. Sci. USA, vol. 86: 5938-5942.
Palanichamy Arumugam et al, "Rituximab efficiently depletes increased CD20-expressing T cells in multiple sclerosis patients.", Journal of Immunology (Baltimore, MD. : 1950) Jul. 15, 2014, (Jul. 15, 2014), vol. 193, No. 2, pp. 580-586.
Pardoll, D.M., (2012), "The blockade of immune checkpoints in cancer immunotherapy" Nat. Rev. Cancer 12(4): 252-264.
Pascal, V., et al. (2012) "Anti-CD20 IgA can protect mice against lymphoma development: evaluation of the direct impact of IgA and cytotoxic effector recruitment on CD20 Target cells", Haematologica, the Hematology Journal, vol. 97(11), pp. 1686-1694.

(56) References Cited

OTHER PUBLICATIONS

Paterson, J., et al., (2006), "The differential expression of LCK and BAFF-receptor and their role in apoptosis in human lymphomas", Haematologica 91: 772-780.
Paulik et al., "Drug-antibody conjugates with anti-HIV activity," Biochem. Pharmacol. 1999, vol. 58, pp. 1781-1790.
Ponders and Richards, "Tertiary templates for proteins. Use of packing criteria in the enumeration of allowed sequences for different structural classes," J. Mol. Biol. 1987, vol. 193, pp. 775-791.
Postow, M., et al., (2015), "Immune Checkpoint Blockade in Cancer Therapy", J. Clin. Oncol. 33(17): 1974-1982.
Presta, "Antibody engineering," Curr. Op. Struct. Biol. 1992, vol. 2, pp. 593-596.
Rabbitts et al. "Human immunoglobulin heavy chain genes: evolutionary comparisons of C mu, C delta and C gamma genes and associated switch sequences," GenBank Accession Number CAB37838, Nucleic Acids Research 1981 vol. 9, No. 18, pp. 4509-4524.
Raju et al., "Potential therapeutic roles for antibody mixtures," Exp. Op. Biol. Ther. 2013, vol. 13, No. 10, pp. 1347-1352.
Randall, T., et al., (1992), "Direct Evidence That J Chain Regulates the Polymeric Structure of IgM in Antibody-secreting B Cells", The Journal of Biological Chemistry, vol. 267(25), 18002-18007.
Rasche, L., et al., (2015), "GRP78-directed immunotherapy in relapsed or refractory multiple myeloma—results from a phase 1 trial with the monoclonal immunoglobulin M antibody PAT-SM6", Haematologica, 100(3): 377-384.
Redwan, E., et al. (2006), "Recombinant human J-chain: fix the protein aggregations and yield maximize" Human Antibodies 15, 95-102.
Request for Supplement Examination as filed on Jun. 18, 2021 with USPTO re U.S. Pat. No. 9,951,134, issued Apr. 24, 2018.
Rezvani, A., et al., (2011), "Rituximab Resistance", Best Pract Res Clin Haematol, 24(2): 203-216.
Riechmann et al., "Reshaping human antibodies for therapy," Nature 1988, vol. 332, pp. 323-329.
Roopenian, D., et al., (2007), "FcRn: the neonatal Fc receptor comes of age", Nature Reviews, vol. 7, 715-725.
Rossi, E., et al. (2008) "Novel Designs of Multivalent Anti-CD20 Humanized Antibodies as Improved Lymphoma Therapeutics", Cancer Res, vol. 68(20), pp. 8384-8392.
Rudikoff, S., et al., (1982), "Single amino acid substitution altering antigen-binding specificity", Proc. Natl. Acad. Sci. USA, 79: 1979-1983.
Saber, H., et al., (2017), "An FDA oncology analysis of CD3 bispecific constructs and first-in-human dose selection", Regulatory Toxicology and Pharmacology, 90: 144-152.
Seifert, O., et al., (2012), "The IgM CH2 domain as covalently linked homodimerization module for the generation of fusion proteins with dual specificty", Protein engineering, Design & Selection, vol. 25: 603-612.
Singer, M., et al., "Genes and Genomes", Moscow, "Mir", 1998, vol. 1: 63-64, no translation available, reference is believed to be a standard textbook reference on antibody structure.
Smith, E., et al., (2015), "A novel, native-format bispecific antibody triggering T-cell killing of B-cells is robustly active in mouse tumor models and cynomolgus monkeys", Scientific Reports, 5: 17943, 12 pages.
Smith, R. et al., (1995), "Addition of a mu-tailpiece to IgG results in polymeric antibodies with enhanced effector functions including complement-mediated cytolysis by IgG4" The Journal of Immunology 154, 2226-2236.
Sørensen, V., et al., (2000), "Structural requirements for incorporation of J chain into human IgM and IgA", International Immunology, vol. 12(1): 19-27.
Stancovski, I., et al. (1991), "Mechanistic aspects of the opposing effects of monoclonal antibodies to the ERBB2 receptor on tumor growth", Cell Biology, Proc. Natl. Acad. Sci. USA, vol. 88, 8691-8695.
Strohl, W., et al., (2015), "Fusion Proteins for Half-Life Extension of Biologics as a Strategy to Make Biobetters", BioDrugs, 29: 215-239.
Sun, L., et al., (2015), "Anti-CD20/CD3 T cell-dependent bispecific antibody for the treatment of B cell malignancies", Immunotherapy, vol. 7(287), 287ra70, 11 pages.
Supplemental Examination Certificate Issued on Aug. 16, 2021 with USPTO re U.S. Pat. No. 9,951,134.
Symersky, J., et al., (2000), "Expression of the recombinant human immunoglobulin J Chain in *Escherichia coli*", Molecular Immunology, 37: 133-140.
Tabrizi, M., et al. (2010), "Biodistribution Mechanisms of Therapeutic Monoclonal Antibodies in Health and Disease", The AAPS Journal, vol. 12, No. 1, pp. 33-43.
Tavolaro, S., et al. (2013), "IgD cross-linking induces gene expression profiling changes and enhances apoptosis in chronic lymphocytic leukemia cells", Leukemia Research, 37: 455-462.
Tchoudakova, A., et al., 2009, "High level expression of functional human IgMs in human PER.C6 cells", MAbs 1, 163-171.
Teachey, D., et al., (2013), "Cytokine release syndrome after blinatumomab treatment related to abnormal macrophage activation and ameliorated with cytokine directed therapy", Blood Journal, DOI 10.1182/blood-2013-02-485623.
Tussiwand, R., et al., (2012), "BAFF-R expression correlates with positive selection of immature B cells", European Journal of Immunology, 42: 206-216.
U.S. Appl. No. 18/052,388, Specification, Claims, Abstract and Drawings filed Nov. 3, 2022 with U.S. Patent Office.
Vajdos, F., et al., (2002), "Comprehensive Functional Maps of the Antigen-binding Site of an Anti-ErbB2 Antibody Obtained with Shotgun Scanning Mutagenesis", J. Mol. Biol. 320: 415-428.
Valley, C., et al., (2012), "Tumor Necrosis Factor-Related Apoptosis-Inducing Ligand (TRAIL) Induces Death Receptor 5 Networks That Are Highly Organized", Journal of Biological Chemistry, 287 (25): 21265-21278.
Van Imhoff, G., et al., (2017), "Ofatumumab Versus Rituximab Salvage Chemoimmunotherapy in Relapsed or Refractory Diffuse Large B-Cell Lymphoma: The ORCHARRD Study", Journal of Clinical Oncology, 35(5): 544-551.
Vasquez, K., et al., (2011), "Quantitative Whole Body biodistribution of fluorescent-labeled Agents by Non-Invasive Tomographic Imaging", PLOS one, vol. 6, Issue 6, e20594.
Vcelar et al., "Reassessment of autoreactivity of the broadly neutralizing HIV antibodies 4E10 and 2F5 and retrospective analysis of clinical safety data," AIDS 2007, vol. 21, No. 16, pp. 2161-2170.
Vitolo, U., et al., (2017), "Obinutuzumab or Rituximab Plus Cyclophosphamide, Doxorubicin, Vincristine, and Prednisone in Previously Untreated Diffuse Large B-Cell Lymphoma", Journal of Clinical Oncology, 35(31): 3529-3537.
Wajant, H. (2015), "Principles of antibody-mediated TNF receptor activation", Cell Death and Differentiation, 22: 1727-1741.
Wang, W., et al. (2008), "Monoclonal Antibody Pharmacokinetis and Pharmacodynamics", State of the Art, vol. 84, No. 5, pp. 548-558.
Wang, Y., et al., (2007), "The design, construction and function of a new chimeric anti-CD20 antibody", Journal of Biotechnology, 129: 726-731.
Weiskopf, K., et al. (2013) "Engineered SIRPa Variants as Immunotherapeutic Adjuvants to Anticancer Antibodies", Science Express, vol. 341, pp. 89-91 with supplemental materials, 36 pages.
Wing, M., (2008), "Monoclonal Antibody First Dose Cytokine Release Syndromes—Mechanisms and Prediction", Journal of Immunotoxicology, 5: 11-18.
Wood, C.R., et al., (1990), "High level synthesis of immunoglobulins in Chinese hamster ovary cells". J. Immunol. 145, 3011-3016.
Woof, JM., et al., (2011), ,"Structure and Function Relationships in IgA", Mucosal Immunology, vol. 4(6): pp. 590-597.
Wu, H., et al., (1999), "Humanization of a Murine Monoclonal Antibody by simultaneous Optimization of Framework and CDR Residues", J. Mol. Biol. 294: 151-162.

(56) References Cited

OTHER PUBLICATIONS

Wu, J., et al., (2015), "Blinatumomab: a bispecific T cell engager (BiTE) antibody against CD19/CD3 for refractory acute lymphoid leukemia", Journal of Hematology & Oncology, 8:104, DOI 10.1186/s13045-015-0195-4, 7 pages.
Yoo et al., "Structural requirements for polymeric immunoglobulin assembly and association with J chain," J. Biol. Chem. 1999, vol. 274, No. 47, pp. 33771-33777.
Yu, L., et al. (2008), "Interaction between bevacizumab and Murine VEGF-A: A Reassessment", Investigative Opthalmology & Visual-Science, 49(2), 522-527.
Yu, X., et al., 2009, "The surface protein TIGIT suppresses T cell activation by promoting the generation of mature immunoregulatory dendritic cells, " Nat. Immunol. 10, 48-57.
Yu, Y., et al. (2014), "Therapeutic bispecific antibodies cross the blood-brain barier in nonhuman primates", Antibody Therapeutics, vol. 6, Issue 261, 261ra154, 11 pages.
Zuchero, Y., et al., (2015), "Discovery of Novel Blood-Brain Barrier Targets to Enhance Brain Uptake of Therapeutic Antibodies", Neuron 89: 70-82.
U.S. Appl. No. 17/386,397, Specification, Claims, Abstract and Drawings filed Jul. 27, 2021 with U. S. Patent Office.
U.S. Appl. No. 17/635,078, Specification, Claims, Abstract and Drawings filed Feb. 14, 2022 with U.S. Patent Office.
U.S. Appl. No. 17/758,207, Specification, Claims, Abstract and Drawings filed Jun. 29, 2022 with U.S. Patent Office.
U.S. Appl. No. 17/761,428, Specification, Claims, Abstract and Drawings filed Mar. 17, 2022 with U.S. Patent Office.
U.S. Appl. No. 17/812,614, Specification, Claims, Abstract and Drawings filed Jul. 14, 2022 with U.S. Patent Office.
U.S. Appl. No. 17/996,760, Specification, Claims, Abstract and Drawings filed Oct. 20, 2022 with U.S. Patent Office.
U.S. Appl. No. 17/998,307, Specification, Claims, Abstract and Drawings filed Nov. 9, 2022 with U.S. Patent Office.
U.S. Appl. No. 18/055,340, Specification, Claims, Abstract and Drawings filed Nov. 14, 2022 with U.S. Patent Office.
U.S. Appl. No. 18/719,191 Specification, Claims, Abstract and Drawings filed Jun. 12, 2024 with U.S. Patent Office.
U.S. Patent Application No. 19/106, 184 Specification, Claims, Abstract and Drawings as filed Feb. 24, 2025 with U.S. Patent Office.
U.S. Patent Application No. 19/106, 186 Specification, Claims, Abstract and Drawings as filed Feb. 24, 2025 with U.S. Patent Office.

* cited by examiner

Five (A,B) unit, A = B in natural IgM

FIG. 3

Mature Human J Chain

- QEDERIVLVDNKCKCARITSRIIRSSEDPNEDIVERNI RIIVPLNNRENISDPTSPLRTRFVYHLSDLCKKCDPT EVELDNQIVTATQSNICDEDSATETCYTYDRNKCYT AVVPLVYGGETKMVETALTPDACYPD (SEQ ID NO: 1)
- Number of amino acids: 137
- Molecular weight: 15594.4
- Theoretical pI: 4.59

Orientation of J-chain Constructs

Orientation of J-chain Constructs

Asymmetric IgM Pentamer with modified J-chain

Anti-CD20 $_{IgM}$ x Anti-CD3$_J$ bi-specific IgM can be expressed and assembled into pentamer with various scFv at either N- or C- terminus of J-chain

Anti-CD20 IgM x Anti-CD3J bi-specific IgM with Anti-CD3 scFv at N- or C- terminus of J-chain: Bi-specific IgMs are functional in CDC

| EC50 (nM) | | | |
|---|---|---|---|
| Rituxan | CD20 IgM J15V | CD20 IgM V15J | CD20 IgM wtJ |
| 3.29 | 0.04 | 0.05 | 0.05 |

Anti-CD20 $_{IgM}$ x Anti-CD3$_J$ Bi-specific IgM
Induces T-cell activation in presence of target cells

IGM-55.5 has reduced in-vivo half life in mice in the absence of half-life extension

Panel A

Panel B

MEAN (± SD) PLASMA PHARMACOKINETIC PARAMETERS FOR IGM 55.5 IN MICE (N=3)

| Route | IV | IP |
|---|---|---|
| CL (mL/hr kg) | 7.1 | |
| Vss (mL /kg) | 56 | |
| Cmax (µg/mL) | 563 | 106 |
| T1/2α (hr) | 0.49 | |
| T1/2β (hr) | 5.83 | |
| AUMC (µg.hr.hr/mL) | 22,400 | 1540 |
| MRT (hr) | 7.94 | |

Multimer specific ELISA for CD20 IgMs

FIG. 11
Panel A
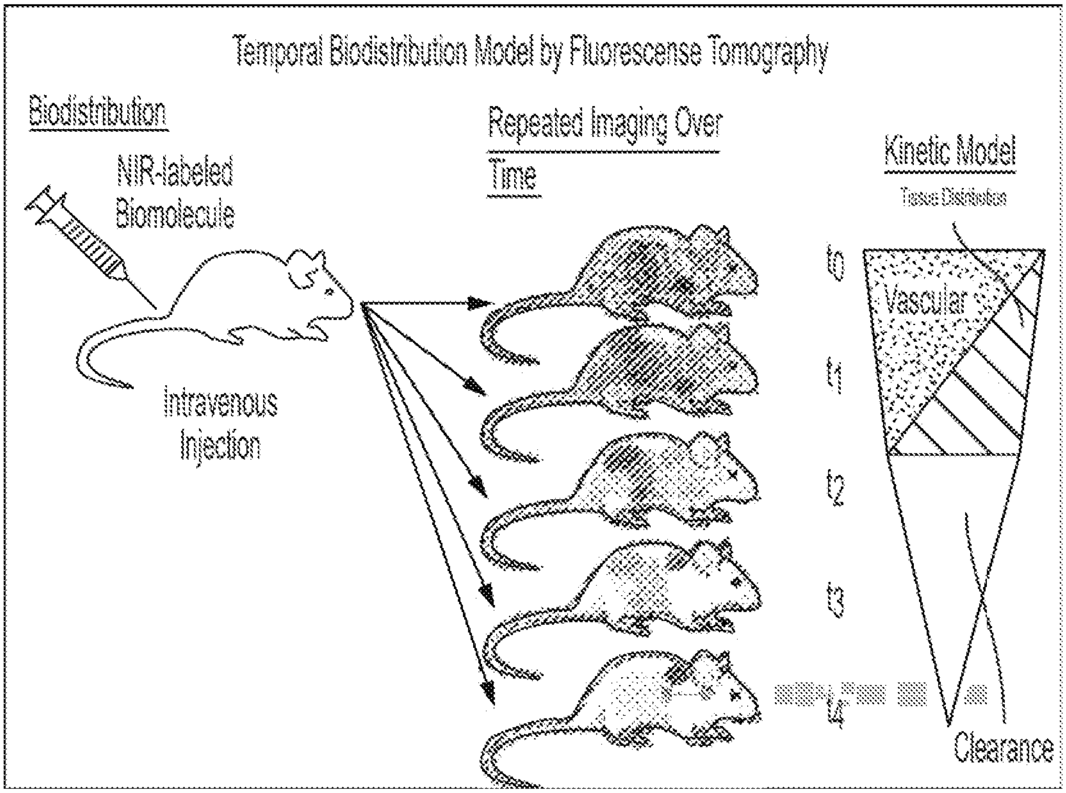
Panel B
A. Antibody Injected
B. Control Mouse
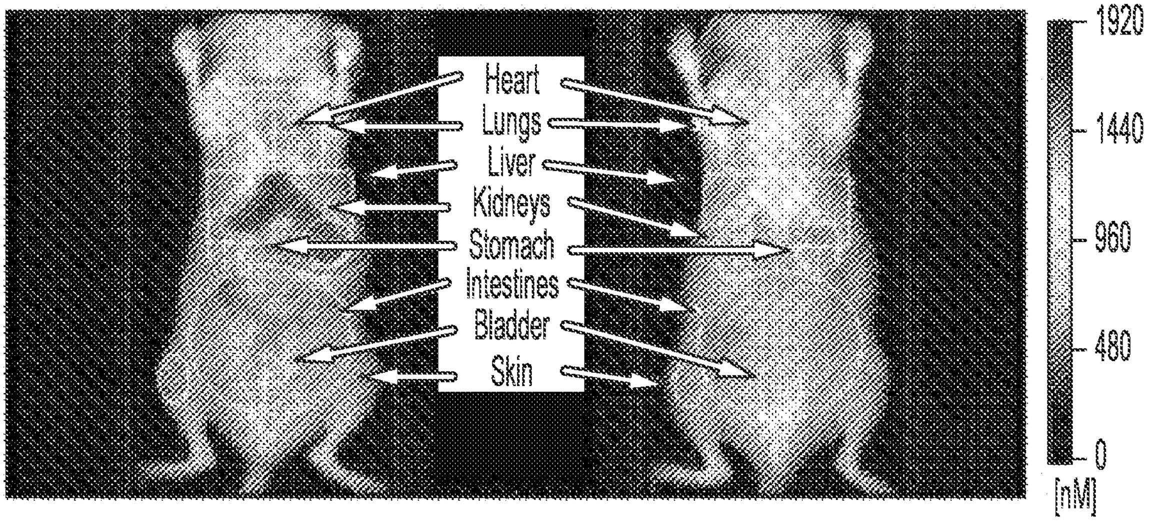

A.

Site Specific labeling of IgM glycans using chemo-enzymatic approaches

FIG. 13

Combinatorial approach to compartmentalization uses of J-chain binding molecules:

Antibody Target

Super agonist targets:
CD137 (4-1BB), OX40, CD40, GITR, CD27, HVEM

Low expression level targets:
EGFR, HER2, HER3, EpCAM, CEACAM, Gp100, MAGE1

Low affinity targets:
NY-ESO-1, Sialyl Lewis X antigen, Tn antigen

Hematologic cancer targets:
CD19, CD20, CD22, CD33, CD38, CD52, CD70

Other binding targets:
VEGF, TNF alpha, amyloid beta, BACE

J-chain binding moiety target

Targets for regulating half-life
Human serum albumin (HSA)
HSA binding peptides
Neonatal Fc Receptor (FcRn)
Fc domain

Targets for regulating bio-distribution
Transferrin, Transferrin receptor (TfR)
Insulin, Insulin Receptor
IGF-1, IGF-1 receptor
Leptin, Leptin receptor
basigin
Glut1
CD98hc

Target for retention in intra-ocular or intra-articular compartments
Hyaluronic Acid
TSG-6

Tn R = H or Me

Alternating units of 1,4-linked N-acetylglucosamine and glucuronic acid

Panel A:

Panel B:

| Antibody | $t_{1/2}$ α (hrs) | $t_{1/2}$ β (hrs) | $AUC_{0-\infty}$ (μg/ml*hr) |
|---|---|---|---|
| Rituximab | 2.4 | 158.7 | 12180 |
| Polyclonal IgM | 0.99 | 14.3 | 1412 |
| 55.5 (CHO IgM) | 0.2 | 4.7 | 549 |

Panel A:

Panel B:

| Antibody | $t_{1/2}$ α (hrs) | $t_{1/2}$ β (hrs) | $AUC_{0-\infty}$ (μg/ml*hr) |
|---|---|---|---|
| αCD20 IgM | 0.38 | 9.8 | 477 |
| αCD20 IgM + wtJ | 0.24 | 7.3 | 169 |
| αCD20 IgM + V15J | 0.23 | 4.0 | 82 |

Panel A:

Panel B:

| Antibody | $t_{1/2}$ α (hrs) | $t_{1/2}$ β (hrs) | $AUC_{0-\infty}$ (μg/ml*hr) |
|---|---|---|---|
| Rituximab | 2.4 | 158.7 | 12180 |
| αCD20 IgM+V15J | 0.23 | 4.0 | 82 |
| αCD20 IgM+A15J | 3.2 | 32.4 | 1341 |

FIG. 22

| Antibody | $t_{1/2}$ α (hrs) | $t_{1/2}$ β (hrs) | $AUC_{0-\infty}$ (µg/ml*hr) |
|---|---|---|---|
| Rituximab | 2.4 | 158.7 | 12180 |
| 1.5.3 IgM+V15J | 0.23 | 4.0 | 82 |
| 1.5.3 IgM+J15A | 3.2 | 32.4 | 1341 |
| 1.5.3 IgM+A15J | 0.85 | 10.3 | 1196 |
| 1.5.3 IgM+J15H | 2.3 | 14.5 | 1380 |
| 1.5.3 IgM+H15J | 0.71 | 17.7 | 1259 |

1. Marker
2. 1.5.3 IgM
3. 1.5.3 IgM + wt J
4. 1.5.3 + V15J15ABD
5. 1.5.3 + V15J
6. 1.5.3 + V15J15HSA

FIG. 27

| | $t_{1/2\ Alpha}$ | $t_{1/2\ Beta}$ | $AUC_{0\text{-}inf}$ |
|---|---|---|---|
| 153 IgM HSAJ | 0.78 | 17.8 | 1260 |
| 153 IgM JHSA | 2.33 | 14.5 | 1380 |
| 153 IgM VJABD | 3.22 | 26.0 | 2212 |
| 153 IgM VJHSA | 4.22 | 25.6 | 2167 |

BINDING MOLECULES WITH MODIFIED J-CHAIN

CROSS REFERENCE TO RELATED APPLICATIONS

This application is a continuation of U.S. patent application Ser. No. 16/745,059, filed Jan. 16, 2020, now U.S. Pat. No. 11,542,342, which is a continuation of U.S. patent application Ser. No. 15/764,859, filed Mar. 29, 2018, now U.S. Pat. No. 10,618,978, which is a US National Stage Entry of PCT Application No. PCT/US2016/055041, filed Sep. 30, 2016, which claims priority benefit of the filing date of U.S. Provisional Patent Application Ser. No. 62/235,518, filed on Sep. 30, 2015, the disclosures of which applications are incorporated herein by reference in their entireties.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Nov. 10, 2022, is named 017US3-Sequence-Listing and is 167,391 bytes in size.

FIELD OF THE INVENTION

The present invention concerns binding molecules that comprise an IgM, IgA, IgG/IgM or IgG/IgA antibody comprising a modified J-chain.

BACKGROUND OF THE INVENTION

J-chain is an acidic 15-kDa polypeptide, which is associated with pentameric IgM and dimeric IgA via disulfide bonds involving the penultimate cysteine residue in the 18-amino acid secretory tail-piece (tp) at the C-terminus of the IgM μ or IgA α heavy chain. The three disulfide bridges are formed between Cys 12 and 100, Cys 71 and 91, and Cys 108 and 133, respectively. See, e.g., Frutiger et al. 1992, *Biochemistry* 31, 12643-12647. Structural requirements for incorporation of the J-chain into human IgM and IgA and for polymeric immunoglobulin assembly and association with the J-chain are reported by Sorensen et al. 2000, *Int. Immunol.* 12(1): 19-27 and Yoo et al. 1999, *J. Biol. Chem.* 274(47):33771-33777, respectively. Recombinant production of soluble J-chain in *E coli* is reported by Redwan et al. 2006, *Human Antibodies* 15:95-102.

Methods for making hybrid IgA/IgG and IgM/IgG antibodies are known in the art. Thus, recombinant production of hybrid IgA2/IgG1 antibodies is reported in Chintalacharuvu et al. 2001, *Clin Immunol* 101(1):21-31. It has been reported that addition of αtp or μtp at the end of IgG γ heavy chain facilitates polymerization and enhances effector function such as complement activation (Smith et al., *J Immunol* 1995, 154:2226-2236). The IgA/IgG hybrid antibodies possess properties of both IgA and IgG. Methods for recombinant production of IgM antibodies are also known in the art. E.g., Tchoudakova A, et al., High level expression of functional human IgMs in human PER.C6 cells. *mAbs.* 2009; 1(2):163-171.

Despite the advances made in the design of antibodies, there remains a need for modified antibodies with improved properties, such as improved affinity, specificity and/or avidity, as well as the ability to bind to multiple binding targets.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g., antibody-drug conjugates). Another approach to improving antibody function takes advantage of the bivalent binding of the immunoglobulin G (IgG) structure which allows one IgG molecule to bind two antigens. Indeed, in certain applications, there exists good potential for asymmetric antibodies to exert useful functions by simultaneously binding two different target antigens. To address this need, a variety of constructs have been produced to yield a single molecule that can bind two different antigens, allowing for functions never before seen in nature. An example of this bi-specific approach is "blinatumomab" (MT103 or AMG103) which binds the CD3 and CD19 receptors, on T- and B-cells, respectively. This tethering of a cytotoxic T-cell to a cancerous B-cell, allows for effective treatment of B-cell leukemia.

The blockade of immune checkpoints has emerged as a promising area for the advancement of cancer treatment. Immune checkpoints refer to inhibitory signaling pathways that are encoded into the immune system, and which play a vital role in maintaining self-tolerance, as well as modulating the duration and amplitude of immune responses. See, e.g., Pardoll, Drew M. "The blockade of immune checkpoints in cancer immunotherapy." *Nature Reviews Cancer* 12.4 (2012): 252-264; Postow, Michael A. et al., "Immune Checkpoint Blockade in Cancer Therapy," *J Clin Oncol.* 2015 Jun. 10; 33(17):1974-82. doi: 10.1200/JCO.2014.59.4358.

Despite positive proof of concept results in preclinical models, investigators have reported that monoclonal IgG blocking antibodies directed against T-cell inhibitory signaling pathway components (for example, ipilimumab (Bristol-Myers Squibb) and tremelimumab (MedImmune/AstraZenica), both directed against CTLA4) have only achieved minimal efficacy results in a clinical setting. E.g., Postow et al., pp. 1-2. In addition, treatments involving monoclonal IgG antibodies have resulted in immune-related adverse events, such as dermatologic, GI, hepatic, endocrine and other inflammatory events. E.g., Id. at p. 4. As such, the use of monoclonal IgG antibodies in immune checkpoint blockade may be limited by the therapeutic index of such molecules, in that the dose of a monoclonal IgG antibody required to elicit the desired therapeutic effect also causes immune-related adverse events.

Accordingly, there is a need for binding molecules with increased avidity that will provide increased potency so that lower dosage levels can be used, thereby preventing the occurrence of immune-related adverse events, while still achieving effective blockade of T-cell inhibitory signaling pathways.

The pharmacokinetics and pharmacodynamics of monoclonal antibodies are complex, and depend on both the structure of the monoclonal antibody, as well as the physiological system that it targets. Moreover, different antibody classes are typically processed within a subject via different cellular and physiological systems. For example, secretion into the bile is an important pathway of elimination for IgA antibodies, whereas this route is not a significant contributor to the elimination of IgG antibodies. Rather, the majority of IgG elimination occurs via intracellular catabolism, following fluid-phase or receptor-mediated endocytosis. E.g., Wang et al., *Nature* 84:5 (2008). Furthermore, full-length IgG antibodies have been shown to be primarily distributed within the blood stream, while smaller IgG antibody fragments appear to distribute within the extra-vascular space to a greater extent. E.g., Tabrizi et al., *AAPS J* 2010 March; 12(1): 33-43. The blood brain barrier generally prevents immunoglobulin molecules from entering the central nervous system via the circulation. E.g., Yu et al., *Science Translational Medicine* 16:261 (2014). Furthermore, immunoglobulins that are directly injected into an extra-vascular space, such as the eyeball, typically only remain in the space on the order of hours. See, e.g., Mordenti, J. et al., *Toxicological Sciences* 52, 101-106 (1999); Mordenti, J. et al., *Toxicological Sciences* 27(5), 536-544 (1999). As such, control and manipulation of factors that influence the absorption, distribution, metabolism and/or excretion (ADME) characteristics of monoclonal antibodies is an important consideration when designing a therapeutic antibody composition.

Accordingly, there is a need for binding molecules whose ADME characteristics can be controlled and modulated to achieve a desired therapeutic effect.

SUMMARY OF THE INVENTION

The present invention is based, at least in part, on the recognition that the J-chain of an IgM or IgA antibody can be modified by introducing one or more ADME-modulating moieties into a native J-chain sequence, and the modified J-chain can be introduced into IgM, IgA, IgG/IgM or IgG/IgA antibodies without compromising the functionality of the recipient antibody or the ADME-modulating moiety. This allows the IgM, IgA, IgG/IgM or IgG/IgA antibody to achieve improved properties, such as an increased concentration and/or an increased half-life in a subject.

The invention is further based on the recognition that due to their multivalent nature, IgM, IgA, IgG/IgM or IgG/IgA antibodies can provide increased avidity between the antibody and a target antigen, thereby facilitating binding of antigens with low level expression and/or low binding affinity. Furthermore, the optional multi-specific nature of the IgM, IgA, IgG/IgM or IgG/IgA portion of the subject binding molecules allows binding between specific numbers and/or specific types of binding targets, thereby facilitating binding between specific combinations of antigen targets. The modified J-chain portion of the subject binding molecules comprises an ADME-modulating moiety, which facilitates an increased concentration and/or an increased half-life in a target tissue.

Aspects of the invention include binding molecules comprising an IgM, IgA, IgG/IgM or IgG/IgA antibody with a modified J-chain, or an antigen binding fragment thereof, wherein the modified J-chain comprises an ADME-modulating moiety. In some embodiments, the ADME-modulating moiety is selected from the group consisting of: antibodies, antigen-binding fragments of antibodies, antibody-like molecules, antigen-binding fragments of antibody-like molecules, proteins, ligands and receptors. In some embodiments, the ADME-modulating moiety is an antigen-binding fragment of an antibody, and is selected from the group consisting of: $F(ab')_2$, $F(ab)_2$, Fab', Fab, Fv, scFv, VHH, scFab and dAb.

In some embodiments, the ADME-modulating moiety reduces clearance of the binding molecule from a subject's circulation. In some embodiments, the ADME-modulating moiety comprises an albumin protein, or a fragment of an albumin protein. In some embodiments, the ADME-modulating moiety comprises an albumin-binding peptide. In some embodiments, the ADME-modulating moiety comprises an albumin-binding antibody fragment. In some embodiments, the albumin-binding antibody fragment is selected from the group consisting of Fab, scFv, VHH, scFab and dAb. In some embodiments, the ADME-modulating moiety comprises an FcRn-binding peptide. In some embodiments, the ADME-modulating moiety comprises an FcRn-binding antibody fragment. In some embodiments, the FcRn-binding antibody fragment is selected from the group consisting of: Fab, scFv, VHH, scFab and dAb. In some embodiments, the ADME-modulating moiety comprises an Fc domain.

In some embodiments, the ADME-modulating moiety increases a concentration of the binding molecule in a central nervous system tissue of a subject. In some embodiments, the ADME-modulating moiety binds to a member of a receptor mediated transcytosis (RMT) pathway. In some embodiments, the ADME-modulating moiety comprises a ligand that is a member of an RMT pathway. In some embodiments, the ADME-modulating moiety comprises a transferrin protein. In some embodiments, the ADME-modulating moiety comprises a transferrin receptor-binding antibody fragment. In some embodiments, the transferrin receptor-binding antibody fragment is selected from the group consisting of Fab, scFv, VHH, scFab and dAb. In some embodiments, the ADME-modulating moiety comprises a transferrin-binding antibody fragment. In some embodiments, the transferrin-binding antibody fragment is selected from the group consisting of: Fab, scFv, VHH, scFab and dAb. In some embodiments, the IgM, IgA, IgG/IgM or IgG/IgA antibody binds to beta-secretase 1 (BACE). In some embodiments, the ADME-modulating moiety comprises an insulin receptor-binding antibody fragment. In some embodiments, the insulin receptor-binding antibody fragment is selected from the group consisting of Fab, scFv, VHH, scFab and dAb. In some embodiments, the ADME-modulating moiety comprises an IGF-1 receptor-binding antibody fragment. In some embodiments, the IGF-1 receptor-binding antibody fragment is selected from the group consisting of: Fab, scFv, VHH, scFab and dAb. In some embodiments, the ADME-modulating moiety comprises a leptin protein. In some embodiments, the ADME-modulating moiety comprises a leptin receptor-binding antibody fragment. In some embodiments, the leptin receptor-binding antibody fragment is selected from the group consisting of: Fab, scFv, VHH, scFab and dAb.

In some embodiments, the ADME-modulating moiety increases retention of the binding molecule in an extra-vascular space of a subject. In some embodiments, the extra-vascular space is an intra-articular space. In some embodiments, the extra-vascular space is an intra-vitreal space. In some embodiments, the ADME-modulating moiety comprises a hyaluronic acid binding protein (HABP). In some embodiments, the ADME-modulating moiety comprises a hyaluronic acid-binding antibody fragment. In some embodiments, the hyaluronic acid-binding antibody fragment is selected from the group consisting of: Fab, scFv, VHH, scFab and dAb. In some embodiments, the ADME-modulating moiety comprises a TSG-6 protein. In some embodiments, the ADME-modulating moiety comprises a TSG-6-binding antibody moiety. In some embodiments, the TSG-6-binding antibody moiety is selected from the group consisting of Fab, scFv, VHH, scFab and dAb.

In some embodiments, the modified J-chain comprises a modified human J-chain sequence, or a functional fragment thereof. In some embodiments, the modified human J-chain sequence comprises the native human J-chain sequence of SEQ ID NO: 1. In some embodiments, the ADME-modulating moiety is introduced into the native human J-chain sequence of SEQ ID NO: 1 by direct or indirect fusion. In some embodiments, the ADME-modulating moiety is introduced by indirect fusion through a peptide linker. In some embodiments, the indirect fusion is through a peptide linker at or around a C- and/or an N-terminus of the half-life extending moiety. In some embodiments, the ADME-modulating moiety is introduced into the native human J-chain sequence of SEQ ID NO: 1 at or around the C-terminus. In some embodiments, the ADME-modulating moiety is introduced into the native human J-chain sequence of SEQ ID NO: 1 within about 10 residues from the C-terminus. In some embodiments, the ADME-modulating moiety is introduced into the native human J-chain sequence of SEQ ID NO: 1 at or around the N-terminus. In some embodiments, the ADME-modulating moiety is introduced into the native human J-chain sequence of SEQ ID NO: 1 within about 10 amino acid residues from the N-terminus. In some embodiments, the ADME-modulating moiety is introduced into the native human J-chain sequence in between cysteine residues 92 and 101 of SEQ ID NO: 1. In some embodiments, the ADME-modulating moiety is introduced into the native human J-chain sequence of SEQ ID NO: 1 at or near a glycosylation site. In some embodiments, the peptide linker is about 10 to 20 amino acids long. In some embodiments, the peptide linker is about 15 to 20 amino acids long. In some embodiments, the peptide linker is 15 amino acids long. In some embodiments, the ADME-modulating moiety is introduced into the native human J-chain sequence of SEQ ID NO: 1 by chemical or chemo-enzymatic derivatization. In some embodiments, the ADME-modulating moiety is introduced into the native human J-chain sequence of SEQ ID NO: 1 by a chemical linker. In some embodiments, the chemical linker is a cleavable or non-cleavable linker. In some embodiments, the cleavable linker is a chemically labile linker or an enzyme-labile linker. In some embodiments, the linker is selected from the group consisting of N-succinimidyl-3-(2-pyridyldithio) propionate (SPDP), succinimidyl-4-(N-maleimidomethyl) cyclohexane-1-carboxylate (SMCC), N-succinimidyl-4-(2-pyridylthio) pentanoate (SPP), iminothiolane (IT), bifunctional derivatives of imidoesters, active esters, aldehydes, bis-azido compounds, bis-diazonium derivatives, diisocyanates, and bis-active fluorine compounds. In some embodiments, the modified J-chain is modified by insertion of an enzyme recognition site, and by post-translationally attaching an ADME-modulating moiety at the enzyme recognition site through a peptide or non-peptide linker.

In some embodiments, the modified J-chain is in an ADME-linker-J orientation, with the ADME-modulating moiety at an N-terminus of the modified J-chain. In some embodiments, the modified J-chain is in a J-linker-ADME orientation, with the ADME-modulating moiety at a C-terminus of the modified J-chain. In some embodiments, the modified J-chain further comprises a second binding moiety. In some embodiments, the ADME-modulating moiety is located at an N-terminus of the modified J-chain, and the second binding moiety is located at a C-terminus of the modified J-chain. In some embodiments, the ADME-modulating moiety is located at a C-terminus of the modified J-chain, and the second binding moiety is located at an N-terminus of the modified J-chain. In some embodiments, the binding molecule comprises an IgM antibody comprising a heavy chain amino acid sequence of SEQ ID NO: 82, a light chain amino acid sequence of SEQ ID NO: 84, and a J-chain amino acid sequence of SEQ ID NO: 102. In some embodiments, the second binding moiety is a second ADME-modulating moiety.

In some embodiments, the IgM, IgA, IgG/IgM or IgG/IgA antibody is a bispecific antibody. In some embodiments, the IgM, IgA, IgG/IgM or IgG/IgA antibody is a multispecific antibody.

Aspects of the invention include pharmaceutical compositions for the treatment of cancer, wherein the pharmaceutical composition comprises an effective amount of a binding molecule and a pharmaceutically acceptable carrier. In some embodiments, aspects of the invention include use of a binding molecule in the preparation of a medicament for treating cancer. In some embodiments, the cancer is a hematologic cancer, an epithelial cancer or a central nervous system cancer. In some embodiments, the hematologic cancer is a leukemia, lymphoma, myeloma, or myelodysplastic syndrome. In some embodiments, the leukemia is an acute myeloid leukemia, acute lymphoblastic leukemia, chronic myelogenous leukemia, or chronic lymphocytic leukemia. In some embodiments, the lymphoma is Hodgkin's lymphoma or non-Hodgkin's lymphoma. In some embodiments, the epithelial cancer is a melanoma, non-small-cell lung, nasopharyngeal, colorectal, liver, urinary bladder, ovarian, gastric, esophageal, pancreatic, renal, thyroid or breast cancer. In some embodiments, the breast cancer is hormone receptor negative or triple negative breast cancer. In some embodiments, the central nervous system cancer is a glioma, astrocytoma, meningioma, neuroma and oligodendroglioma. In some embodiments, the medicament further comprises an effective amount of a second therapeutic agent.

Aspects of the invention include pharmaceutical compositions for the treatment of rheumatoid arthritis, wherein the pharmaceutical composition comprises an effective amount of a binding molecule and a pharmaceutically acceptable carrier. In some embodiments, aspects of the invention include use of a binding molecule in the preparation of a medicament for treating rheumatoid arthritis.

Aspects of the invention include pharmaceutical compositions for the treatment of age-related macular degeneration, wherein the pharmaceutical composition comprises an effective amount of a binding molecule and a pharmaceutically acceptable carrier. In some embodiments, aspects of the invention include use of a binding molecule in the preparation of a medicament for treating age-related macular degeneration.

Aspects of the invention include pharmaceutical compositions for the treatment of Alzheimer's disease, wherein the pharmaceutical composition comprises an effective amount of a binding molecule and a pharmaceutically acceptable carrier. In some embodiments, aspects of the invention include use of a binding molecule in the preparation of a medicament for treating Alzheimer's disease.

BRIEF DESCRIPTION OF THE DRAWINGS

FIG. 3 shows the amino acid sequence of mature human J-chain (SEQ ID NO: 1).

FIG. 11, Panel A shows an illustration of a temporal biodistribution model. Panel B shows data for the biodistribution of IGM-55.5 in vivo using conjugated far infra-red dye Vivo Tag 680 (Perkin Elmer).

FIG. 13 lists IgM, IgA, IgG/IgM or IgG/IgA antibody targets and ADME-modulating moieties that can be placed on the J-chain. Any of the antibody targets listed in the left column can be combined with any of the ADME-modulating moieties on a J-chain listed in the right column.

FIG. 22 is a table showing alpha and beta half-life in hours and AUC for 6 different antibodies.

FIG. 27 is a table showing alpha and beta half-life in hours and AUC parameters for 4 different antibodies with various configurations of their J-chains.

DETAILED DESCRIPTION OF THE INVENTION

I. Definitions

Figure 1:
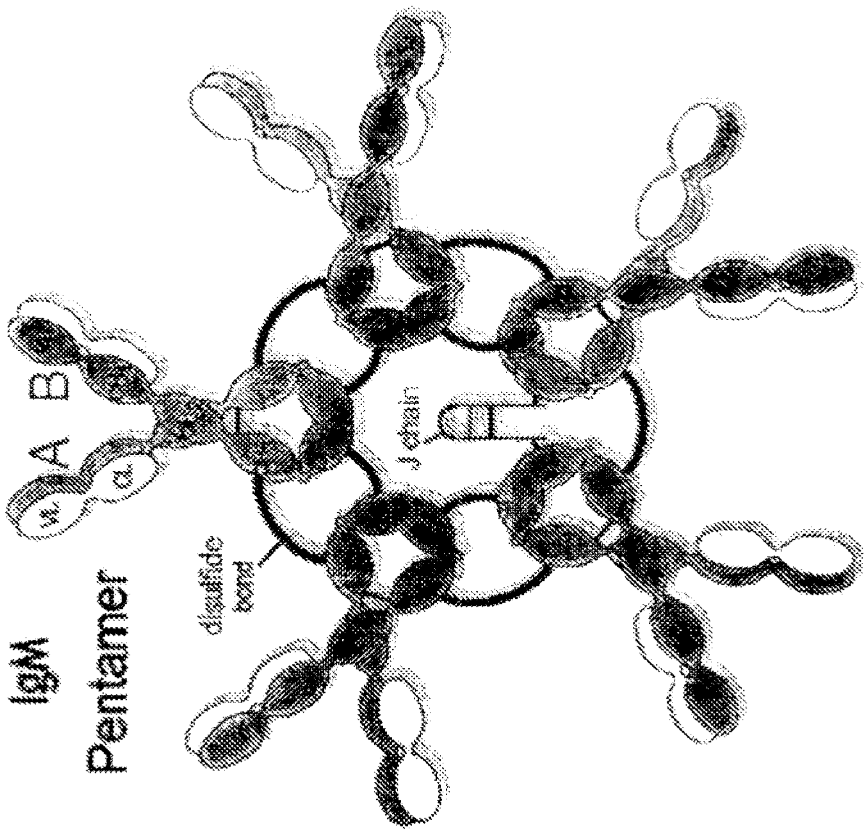
FIG. 1 illustrates the structure of an IgM pentamer, comprising a J-chain, wherein chains A and B are identical in native IgM.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, NY 1994), provides one skilled in the art with a general guide to many of the terms used in the present application.

All publications mentioned herein are expressly incorporated herein by reference to disclose and describe the methods and/or materials in connection with which the publications are cited.

The term "ADME" as used herein is an abbreviation for absorption, distribution, metabolism, and excretion, and is used in the broadest sense to describe the disposition of a pharmaceutical compound within an organism.

The term "ADME-modulating moiety" is used herein in the broadest sense to encompass any chemical entity capable of modulating one or more of the absorption, distribution, metabolism and excretion characteristics of a molecule to which it is attached. Examples of ADME-modulating moieties include, without limitation, antibodies, antigen-binding fragments of antibodies, antibody-drug conjugates, antibody-like molecules, antigen-binding fragments of antibody-like molecules, ligands, receptors, proteins, and polypeptides (including peptides). Preferred binding moieties are antigen-binding fragments of antibodies, preferably with a biological function. An example of a biological function is the ability of an ADME-modulating moiety to bind to a target that extends the half-life of a subject binding molecule.

The term "antibody" includes monoclonal antibodies (including full length antibodies which have an immunoglobulin Fc region), single-chain molecules, as well as antibody fragments (e.g., Fab, $F(ab')_2$, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains. Unless noted otherwise, the term "antibody" is used herein in the broadest sense and specifically includes all isotypes, sub-classes and forms of antibodies, including IgG, IgM, IgA, IgD, and IgE antibodies and their fragments, preferably antigen-binding fragments. Preferred antibodies herein include IgM and IgA antibodies and their antigen-binding fragments, which may be modified to include sequences from other isotypes, such as IgG to produce chimeric antibodies.

In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

IgM is a glycoprotein which forms polymers where multiple immunoglobulins are covalently linked together with disulfide bonds. IgM mostly exists as a pentamer but also as a hexamer and therefore contains 10 or 12 antigen binding sites. The pentameric form typically contains an additional polypeptide, called the J-chain, but can also be made in the absence of J-chain. The pentameric IgM molecule has a molecular weight of approximately 970 kDa. Due to its polymeric nature, IgM possesses high avidity and is particularly effective in complement activation. Unlike in IgG, the heavy chain in IgM monomers is composed of one variable and four constant domains. The IgM constant domains are designated herein as CM1 or Cμ1, CM2 or Cμ2, CM3 or Cμ3, and CM4 or Cμ4, wherein the "CM" and Cμ" designations are used interchangeably. The structure of an IgM pentamer is illustrated in FIG. 1.

The term "IgM" is used herein in the broadest sense and specifically includes mono-, and multi-specific (including bispecific) IgM molecules, such as, for example, the multi-specific IgM binding molecules disclosed in PCT Application No. PCT/US2014/054079, the entire disclosure of which is expressly incorporated by reference herein.

The term "IgM binding unit" or "IgM antibody binding unit" is used in the broadest sense and specifically covers an IgM antibody heavy chain constant region polypeptide, comprising at least a CM4 constant domain, fused to a variable domain sequence ($V_H$) binding to a target (e.g., antigen), with or without an associated antibody light chain variable domain ($V_L$) sequence.

The term "bispecific IgM binding unit" or "bispecific IgM antibody binding unit" is used in the broadest sense and specifically covers a pair of IgM antibody heavy chain constant region polypeptides, comprising at least a CM4 constant domain, fused to a variable domain sequence ($V_H$), each variable domain sequence binding to a different target, with or without associated antibody light chain variable domain ($V_L$) sequences. In one embodiment, the bispecific IgM antibody comprises two $V_HV_L$ antigen binding regions, each capable of binding to a different epitope on one antigen or epitopes on two different antigens. The bispecific IgM antibody binding units can be full length from a single species, or be chimerized or humanized. The bispecific IgM antibodies of the present invention have a penta- or hexameric ring structure comprising five or six bispecific IgM binding units.

The term "multi-specific IgM" is used herein in the broadest sense to refer to IgM antibodies with two or more binding specificities. Thus, the term "multi-specific" includes "bispecific", e.g., bispecific antibodies or bispecific binding units, including IgM pentamers comprising at least two monospecific subunits, each binding to a different antigen (AA, BB), or five or six bispecific subunits, each binding to two different antigens (AB, AB). Thus, the bispecific and multi-specific IgM pentamers may include five identical bispecific binding units, monospecific IgM binding units, at least two of them have different binding specificities, or any combination thereof.

A "full length IgM antibody heavy chain" is a polypeptide consisting in N-terminal to C-terminal direction of an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4). The bispecific full length IgM antibodies as defined herein comprise five or six monomers (binding units), each with two antigen binding sites, which specifically bind to two different binding targets (epitopes). The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

Figure 2:
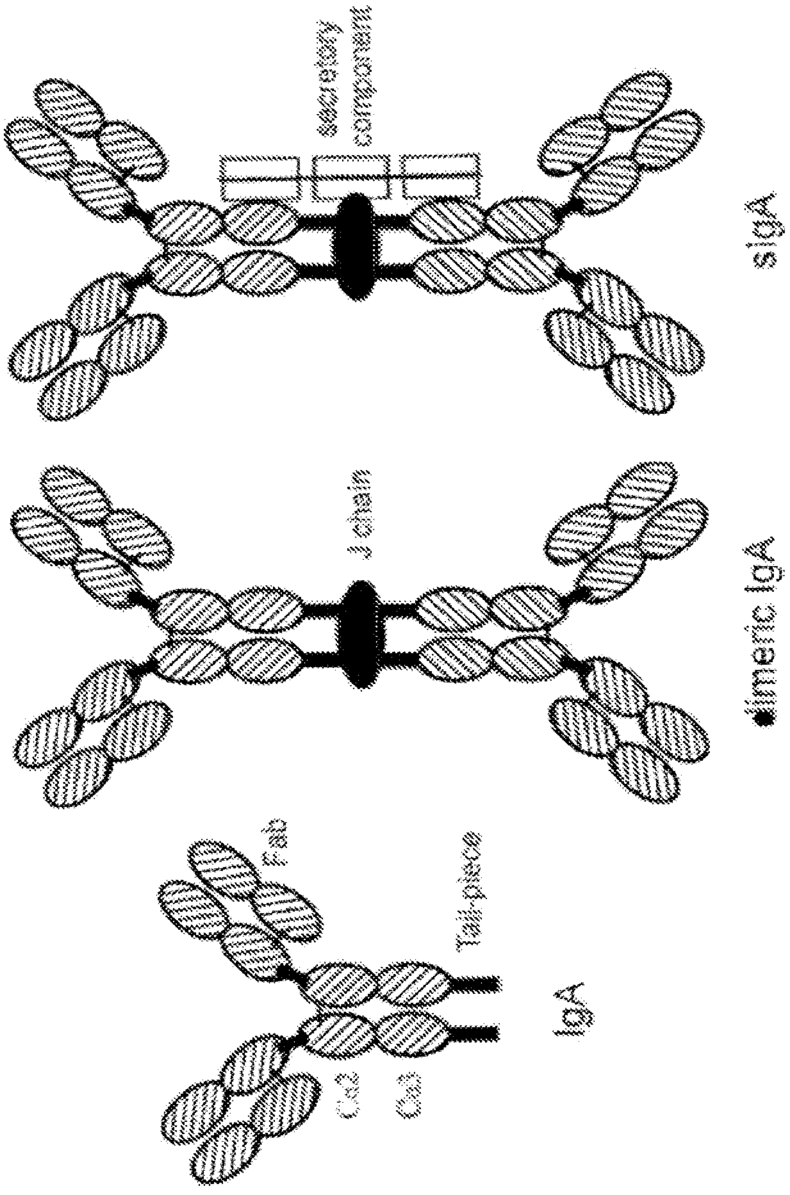
FIG. 2 shows the schematic structures of IgA, dimeric IgA with J-chain, and dimeric J-chain integrated IgA with secretory IgA (sIgA).

Native IgA is a tetrameric protein comprising two identical light chains (κ or λ) and two identical heavy chains (α). In the human, there are two IgA isotypes, IgA1 and IgA2. IgA, similarly to IgG, contains three constant domains (CA1-CA3 or Cα1-Cα3), with a hinge region between the Cal and Cα2 domains, wherein the "CA" and "Cα" designations are used interchangeably. All IgA isotypes have an 18 amino acid "tailpiece", which is located C-terminal to the Cα3 domain, which enables polymeric Ig formation (see, e.g., Garcia-Pardo et al., 1981, *J. Biol. Chem.* 256, 11734-11738 and Davis et al., 1988, *Eur. J. Immunol.* 18, 1001-1008). Serum IgA is a monomer but can also polymerize. In its secretory form IgA comprises from 2-5 of the basic 4-chain units, linked by a J-chain, which may include a tail-piece, and may be associated by a secretory component. The structures of tail-piece, dimeric IgA and secretory IgA, associated with a secretory component (sIgA) are illustrated in FIG. 2. IgA antibodies can be further divided into IgA1 and IgA2 sub-classes. The term "IgA" antibody is used herein to specifically include all sub-classes, i.e., IgA1 and IgA2 antibodies, including dimeric and multimeric forms, with and without a secretory component, as well as fragments, preferably antigen-binding fragments, of such antibodies. For the purposes of the present invention, the IgA antibody preferably is a dimer, where two tail-pieces are connected by a J-chain (see, FIG. 2).

The term "IgA" is used herein in the broadest sense and specifically includes mono-, and multi-specific IgA molecules, such as, for example, the multi-specific IgA binding molecules disclosed in PCT Application No. PCT/US2015/015268, the entire disclosure of which is expressly incorporated by reference herein.

The term "multi-specific IgA" is used herein in the broadest sense to refer to IgA antibodies with two or more binding specificities. Thus, the term "multi-specific" includes "bispecific", e.g., bispecific antibodies or bispecific binding units, including IgA dimers comprising two monospecific subunits, each binding to a different antigen (AA, BB), or two bispecific subunits, each binding to two different antigens (AB, AB).

In one embodiment, the dimeric multi-specific IgA molecules consist of two monospecific binding units, each binding unit having binding specificity to a different binding target (AA, BB). In another embodiment, in the dimeric IgA molecules at least one of the two binding units has two different binding specificities (i.e., is a bispecific, e.g., AA, A,B or AA, BC). In another embodiment, each of the two binding units has two specificities, which may be the same (AB, AB) or different (AC, CD or AB, AC, for example).

The term "bispecific IgA antibody binding unit" is used in the broadest sense and specifically covers a pair of IgA antibody heavy chain constant region polypeptides, comprising at least a CA3 constant domain, fused to a variable domain sequence ($V_H$), each variable domain sequence binding to a different target, with or without associated antibody light chain variable domain ($V_L$) sequences. In one embodiment, the bispecific IgA antibody comprises two $V_HV_L$ antigen binding regions, each capable of binding to a different epitope on one antigen or epitopes on two different antigens. The bispecific IgA antibody binding units can be full length from a single species, or be chimerized or humanized.

A "full length IgA antibody heavy chain" is a polypeptide consisting in N-terminal to C-terminal direction of an antibody heavy chain variable domain (VH), an antibody constant heavy chain constant domain 1 (CA1 or Cα1), an antibody constant heavy chain constant domain 2 (CA2 or Cα2), and an antibody heavy chain constant domain 3 (CA3 or Cα3). The bi- or multi-specific full length IgA antibodies according to the invention comprise two monomers (binding units), each of which may be mono- or bispecific, with or without a secretory component. Thus, the multi-specific IgA antibodies of the present invention may include monospecific and bispecific binding units, provided that the resultant IgA antibody has at least two binding specificities. The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

For further details of the structure and properties of the different classes of antibodies, see e.g., Basic and Clinical Immunology, 8th Edition, Daniel P. Stites, Abba I. Terr and Tristram G. Parslow (eds), Appleton & Lange, Norwalk, Conn., 1994, page 71 and Chapter 6.

The term "interface", as used herein, is used to refer to a region, which comprises those "contact" amino acid residues (or other non-amino acid groups such as, for example, carbohydrate groups,) in a first IgM heavy chain constant region which interact with one or more "contact" amino acid residues (or other non-amino acid groups) in a second IgM heavy chain constant region.

The term "asymmetric interface" is used to refer to an interface (as hereinabove defined) formed between two antibody chains, such as a first and a second IgM heavy chain constant region and/or between an IgM heavy chain constant region and its matching light chain, wherein the contact residues in the first and the second chains are different by design, comprising complementary contact residues. The asymmetric interface can be created by knobs/holes interactions and/or salt bridges coupling (charge swaps) and/or other techniques known in the art, such as for example, by the CrossMab approach for coupling a p heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g., by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, omithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e., genetically engineered or mutated) to encode a protuberance or cavity. The original or starting nucleic acid may be a naturally occurring nucleic acid or may comprise a nucleic acid which has been subjected to prior alteration (e.g., a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g., by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g., a humanized monoclonal antibody).

Preferably the import amino acid residue for forming the protuberance has a relatively small number of "rotamers" (e.g., about 3-6). A "rotamer" is an energetically favorable conformation of an amino acid side chain. The number of rotamers for the various amino acid residues are reviewed in Ponders and Richards, J. Mol. Biol. 193: 775-791 (1987).

Unless stated otherwise, the term "antibody" specifically includes native human and non-human IgG1, IgG2, IgG3, IgG4, IgE, IgA, IgD and IgM antibodies, including naturally occurring variants. Thus, for example, the human IgM sequence is available under GenBank Accession Number X14940.1, while variants have been reported as GenBank CAB37838.1, CAC20458.1, AFM37312.1, X57331.1, and J00260.1.

The term "native" with reference to a polypeptide (e.g., an antibody or a J-chain) is used herein to refer to a polypeptide having a sequence that occurs in nature, regardless of its mode of preparation. Thus, the terms "native" and "native sequence" are used herein interchangeably, and expressly encompass recombinant polypeptides with a sequence that is found in nature.

The term "native sequence J-chain" or "native J-chain" as used herein refers to J-chain of native sequence IgM or IgA antibodies of any animal species, including mature human J-chain, the amino acid sequence of which is shown in FIG. 3 (SEQ ID NO: 1).

The term "modified J-chain" is used herein to refer to variants of native sequence J-chain polypeptides comprising an extraneous ADME-modulating moiety introduced into the native sequence. The introduction can be achieved by any means, including direct or indirect fusion of an extraneous ADME-modulating moiety or by attachment through a chemical linker. The term "modified human J-chain" specifically encompasses, without limitation, a native sequence human J-chain of the amino acid sequence of SEQ ID NO: 1 modified by the introduction of an ADME-modulating moiety. The term specifically encompasses, without limitation, a native sequence human J-chain of the amino acid sequence of SEQ ID NO: 1 modified by the introduction of an extraneous ADME-modulating moiety which does not interfere with efficient polymerization (dimerization) of IgM or IgA and binding of such polymers (dimers) to a target The term "polypeptide" is used herein in the broadest sense and includes peptide sequences. The term "peptide" generally describes linear molecular chains of amino acids containing up to about 60, preferably up to about 30 amino acids covalently linked by peptide bonds.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fe), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

An "isolated" antibody herein is one which has been identified and separated and/or recovered from a component of its natural environment in a recombinant host cell. Contaminant components of its natural environment are materials which would interfere with diagnostic or therapeutic uses for the antibody, and may include enzymes, hormones, and other proteinaceous or nonproteinaceous solutes, as well as undesired byproducts of the production. In a preferred embodiment, an isolated antibody herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of a amino acid sequencer, or (3) to homogeneity by SDS-PAGE under reducing or non-reducing conditions using Coomassie blue or, preferably, silver stain. Ordinarily, an isolated antibody will be prepared by at least one purification step.

The term "specific binding" or "specifically binds to" or is "specific for" refers to the binding of two members of a binding pair, such as the binding of an antibody to a target antigen, e.g., an epitope on a particular polypeptide, peptide, or other target (e.g., a glycoprotein target), and means binding that is measurably different from a non-specific interaction (e.g., a non-specific interaction may be binding to bovine serum albumin or casein). Specific binding can be measured, for example, by determining binding of a half-life extending moiety, or an antibody, or an antibody modified by introduction of a half-life extending moiety, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-

2000 or a BIAcore™-3000 (BIAcore, Inc., Piscataway, N.J.) at 25° C. with immobilized antigen CM5 chips at about 10 response units (RU).

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin.

The term "valent" as used herein denotes the presence of a specified number of binding sites in an antibody. As such, the terms "bivalent", "tetravalent", and "hexavalent" denote the presence of two binding sites, four binding sites, and six binding sites, respectively. Thus, if in a bispecific IgA antibody according to the present invention each binding unit is bivalent, the bispecific IgA antibody will have 4 valencies.

The term "epitope" includes any molecular determinant capable of specific binding to an antibody. In certain embodiments, epitope determinants include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. A "binding region" is a region on a binding target bound by a binding molecule.

"Polyepitopic specificity" refers to the ability to specifically bind to two or more different epitopes on the same or different target(s). "Monospecific" refers to the ability to bind only one epitope. According to one embodiment the bispecific IgM antibody binds to each epitope with an affinity of at least $10^{-7}$ M, or $10^{-8}$ M or better.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an antibody or trigger a cellular immune response. An immunogen refers to an antigen, which can elicit an immune response in an organism, particularly an animal, more particularly a mammal including a human. The term antigen includes regions known as antigenic determinants or epitopes, as defined above.

As used herein, the term "immunogenic" refers to substances that elicit the production of antibodies, and/or activate T-cells and/or other reactive immune cells directed against an antigen of the immunogen.

An "antigen-binding site" or "antigen-binding region" of an antibody of the present invention typically contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs may be sufficient for binding to some binding targets. Thus, in some instances, the CDRs of a VH or a VL domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "extraneous" with reference to an "ADME-modulating moiety" is used herein to refer to an ADME-modulating moiety not present in a reference native polypeptide sequence at the same location. Thus, an extraneous polypeptide sequence (including peptide sequences), might be comprised within the corresponding native sequence but at a different location. In a preferred embodiment, the "extraneous" sequence is not present in the corresponding native sequence in any location. The term "antagonist" as used herein refers to a molecule that causes a decrease in a function or activity as compared to the same function or activity in the absence of the molecule. An "antagonist" of a signaling pathway is therefore a molecule whose presence causes a decrease in a function or activity of the signaling pathway. The term "antagonize" as used herein refers to causing a decrease in a function or activity.

The term "agonist" as used herein refers to a molecule that causes an increase in a function or activity as compared to the same function or activity in the absence of the molecule. An "agonist" of a signaling pathway is therefore a molecule whose presence causes an increase in a function or activity of the signaling pathway. The term "agonize" as used herein refers to causing an increase in a function or activity.

The term "T-cell inhibitory signaling pathway" as used herein refers to a T-cell signaling pathway that leads to a qualitative or quantitative decrease in, blocking or, or halting of a T-cell immune response.

The term "T-cell stimulatory signaling pathway" as used herein refers to a T-cell signaling pathway that leads to a qualitative or quantitative increase in or maintenance of a T-cell immune response.

The term "low level expression target" as used herein refers to a target whose expression level on a target cell ranges from 0 to 1+, as determined by immunohistochemistry (IHC) tissue analysis, preferably performed on frozen, formalin-fixed, paraffin-embedded tissue sections. Guidelines for determining expression level via IHC are provided, for example, by the College of American Pathologists (CAP), and are exemplified by the ASCO-CAP HER2 Test Guideline Recommendations, available at http://www.cap.org/apps/docs/committees/immunohistochemistry/summary_of_recommendations.pdf.

The term "low affinity target" as used herein refers to a target whose binding interaction with an antibody has a dissociation constant $K_d$ that is greater than or equal to a value ranging from about 10 to 100 nM, such as about 25 to about 75 nM, as measured by ELISA.

The term "half-life" is used herein in the broadest sense to refer to the period of time required for the concentration or amount of a binding molecule to be reduced by one-half in the body of a subject.

The term "albumin-binding polypeptide" as used herein refers to a polypeptide that specifically binds to an albumin protein.

The term "Fc domain" as used herein broadly refers to a C-terminal region of an immunoglobulin heavy chain, including native sequence Fc domains and variant Fc domains.

The terms "extra-vascular" and "extra-vascular space" as used herein broadly refer to a portion of a subject that is situated outside of the subject's blood vessels (e.g., arteries and veins).

The term "intra-articular space" as used herein refers to any portion of a subject that is situated inside of a joint that is located, e.g., between two bones (e.g., the inside of a knee joint).

The term "intra-vitreal space" as used herein refers to any portion of a subject that is situated inside of an eyeball.

DETAILED DESCRIPTION

Design and Production of Binding Molecules with Modified J-Chain

IgM is the first immunoglobulin produced by B cells in response to stimulation by antigen, and is present at around 1.5 mg/ml in serum with a half-life of 5 days. IgM is a pentameric or hexameric molecule. Just as IgG, IgM monomers consist of two light and two heavy chains. However, while IgG contains three heavy chain constant domains ($C_H1$, $C_H2$ and $C_H3$), the heavy (μ) chain of IgM additionally contains a fourth constant domain ($C_H4$), similarly to the ε heavy chains in IgE. This extra constant domain is located in place of the IgG and IgA proline-rich hinge region that is responsible for the rotational flexibility of the antigen-binding Fab domains relative to the Fc domain of IgG and IgA antibodies.

Five IgM monomers form a complex with an additional small polypeptide chain (the J-chain) to form a native IgM molecule. The J-chain is considered to facilitate polymerization of μ chains before IgM is secreted from antibody-producing cells. While crystallization of IgM has proved to be notoriously challenging, Czajkowsky and Shao (PNAS 106(35):14960-14965, 2009) recently published a homology-based structural model of IgM, based on the structure of the IgE Fc domain and the known disulfide pairings. The authors report that the human IgM pentamer is a mushroom-shaped molecule with a flexural bias. The IgM heavy (μ) chain contains five N-linked glycosylation sites: Asn-171, Asn-332, Asn-395, Asn-402 and Asn-563.

Immunoglobulin A (IgA), as the major class of antibody present in the mucosal secretions of most mammals, represents a key first line of defense against invasion by inhaled and ingested pathogens. IgA is also found at significant concentrations in the serum of many species, where it functions as a second line of defense mediating elimination of pathogens that have breached the mucosal surface. Receptors specific for the Fc region of IgA, FcαR, are key mediators of IgA effector function. Human IgA may have two different IgA heavy constant region (Cα) genes which give rise to the two subclasses, IgA1 and IgA2. The main difference between IgA1 and IgA2 resides in the hinge region that lies between the two Fab arms and the Fc region. IgA1 has an extended hinge region due to the insertion of a duplicated stretch of amino acids, which is absent in IgA2. IgA has the capacity to form dimers, in which two monomer units, each comprising two heavy chains and light chains, are postulated to be arranged in an end-to-end configuration stabilized by disulfide bridges and incorporation of a J-chain. Dimeric IgA, produced locally at mucosal sites, is transported across the epithelial cell boundary and out into the secretions by interaction with the polymeric immunoglobulin receptor (pIgR). During this process, the pIgR is cleaved and the major fragment, termed secretory component (SC), becomes covalently attached to the IgA dimer.

Both IgA and IgM possess an 18-amino acid extension in the C terminus called the "tail-piece" (tp). The IgM (μtp) and IgA (αtp) tail-pieces differ at seven amino acid positions. The IgM and IgA tail-piece is highly conserved among various animal species. The conserved penultimate cysteine residue in the IgA and IgM tail-pieces has been demonstrated to be involved in polymerization. Both tail-pieces contain an N-linked carbohydrate addition site, the presence of which is required for dimer formation in IgA and J-chain incorporation and pentamer formation in IgM. However, the structure and composition of the N-linked carbohydrates in the tail-pieces differ, suggesting differences in the accessibility of the glycans to processing by glycosyltransferases.

The nucleotide and/or protein sequences of J-chains of human, and various vertebrate animal species, such as cow, mouse, avian, amphibian, and rabbit, have been reported. The human J-chain contains eight cysteine residues, two (Cys13 and Cys69) are involved in disulfide bridges with the α or μ-chains (in IgA and IgM, respectively), and six are involved in intrachain disulfide bridges (Cys13: Cys101, Cys72: Cys92, Cys109: Cys134). The three-dimensional crystal structure of the J-chain has not been reported.

Figure 5:
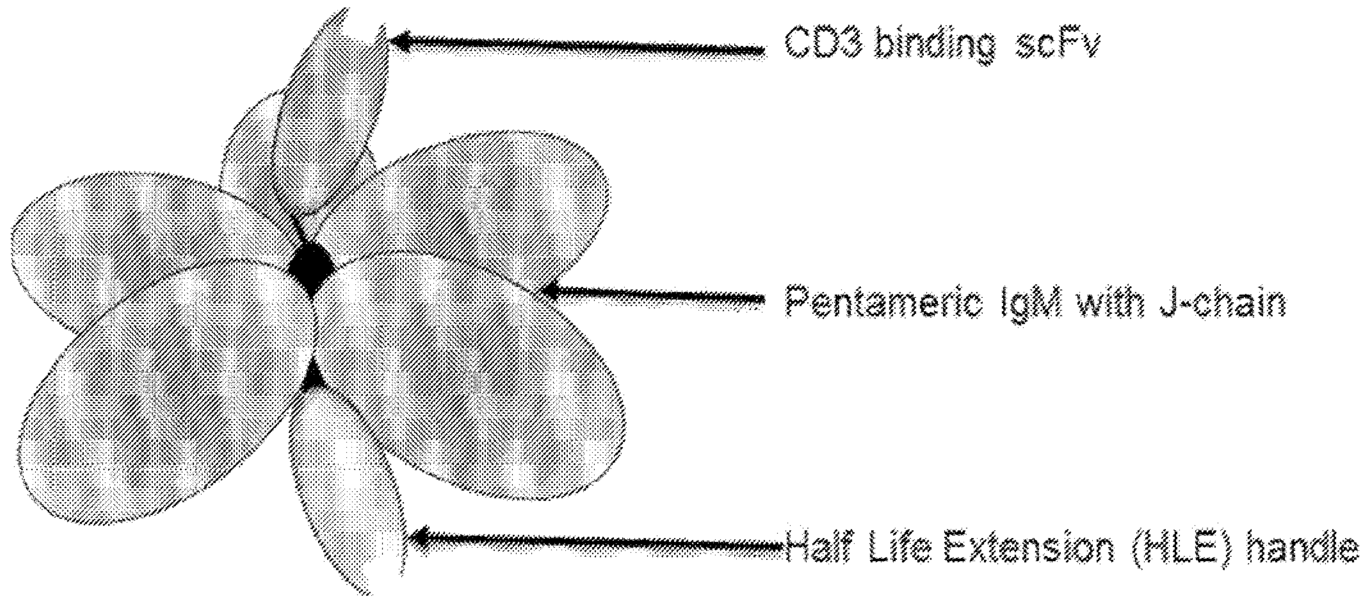
FIG. 5 is a schematic illustration of an asymmetric IgM pentamer with binding specificity for a target antigen, comprising an ADME-modulating moiety fused to the J-chain at one end, and a CD3 binding moiety at the opposite end of the J-chain.

The binding molecules of the present invention include a J-chain that comprises an ADME-modulating moiety that modulates one or more ADME characteristics of the binding molecule, without interfering with the ability of the IgM, IgA, IgG/IgM or IgG/IgA antibody to bind to its binding target(s). A binding molecule can, for example, be an IgM antibody, an IgA antibody, or an IgG/IgM or IgG/IgA hybrid antibody, which may contain an IgM or IgA tail-piece at the IgG heavy chain and thus combine the properties of IgG and IgA or IgA, including the ability to incorporate and form polymers with a modified J-chain whose ADME-modulating moiety modulates an ADME characteristic of the binding molecule. For further details on IgG/IgM and IgG/IgA hybrid antibodies see, e.g., Koteswara et al., *Clinical Immunology* 2001, 101(1):21-31. An illustration of an example binding molecule in accordance with aspects of the invention is depicted in FIG. 5. The depicted binding molecule comprises an IgM pentamer with binding specificity for a target antigen, and comprises an ADME-modulating moiety attached to the J-chain.

An ADME-modulating moiety in accordance with embodiments of the invention can include, without limitation, antibodies, antigen-binding fragments of antibodies, antibody-like molecules, antigen-binding fragments of antibody-like molecules, proteins, ligands and receptors. It is emphasized that any type of ADME-modulating moiety can be introduced into a J-chain, following the teaching of the present disclosure, by appropriately selecting the location and type of addition (e.g., direct or indirect fusion, chemical tethering, etc.).

In some embodiments, a binding molecule comprises an amino acid sequence listed in Table 10. In some embodiments, a binding molecule comprises an amino acid sequence that is substantially similar to an amino acid sequence listed in Table 10, for example, has at least about 80% amino acid sequence identity, alternatively, has about 81%, 82%, 83%, 84%, 85%, 86%, 87%, 88%, 89%, 90%, 91%, 92%, 93%, 94%, 95%, 96%, 97%, 98%, 99%. 99.5%, or about 99.9% amino acid sequence identity to an amino acid sequence that is listed in Table 10.

In a preferred embodiment, an ADME-modulating moiety comprises an antibody or an antigen-binding fragment of an antibody (also referred to as an "antibody fragment"), including monospecific, bispecific, and multi-specific antibodies and antibody fragments, that modulates an ADME characteristic of the binding molecule. The term "antibody fragment" is used in the broadest sense and includes, without limitation, Fab, Fab', $F(ab')_2$, scFab, scFv, and $(scFv)_2$ fragments, complementarity determining region (CDR) fragments, linear antibodies, single-chain antibody molecules, minibodies, and multi-specific antibodies formed from antibody fragments. In a preferred embodiment, the antibody fragment is an scFv.

In another preferred embodiment, an ADME-modulating moiety comprises an antibody-like molecule, such as, for example, a human domain antibody (dAb), Dual-Affinity Re-Targeting (DART) molecule, a diabody, a di-diabody, dual-variable domain antibody, a Stacked Variable Domain antibody, a Small Modular ImmunoPharmaceutical (SMIP), a Surrobody, a strand-exchange engineered domain (SEED)-body, VHH (e.g., a camelid-like antibody molecule), or TandAb that functions by modulating an ADME characteristic of the binding molecule.

An ADME-modulating moiety can be introduced into a native J-chain sequence at any location that allows the ADME-modulating moiety to modulate an ADME characteristic of the binding molecule without interfering with the binding of the recipient IgM, IgA, IgG/IgM or IgG/IgA molecule to its binding target or binding targets. Preferred locations include at or near the C-terminus, at or near the N-terminus or at an internal location that, based on the three-dimensional structure of the J-chain, is accessible. In preferred embodiments, an ADME-modulating moiety is introduced into a native sequence J-chain within about 10 residues from the C-terminus or within about 10 amino acid residues from the N-terminus, where the native sequence J-chain preferably is human J-chain of SEQ ID NO: 1. In another embodiment, an ADME-modulating moiety is introduced into the native sequence human J-chain of SEQ ID NO: 1 in between cysteine residues 92 and 101 of SEQ ID NO: 1, or at an equivalent location of another native sequence J-chain. In a further embodiment, an ADME-modulating moiety is introduced into a native sequence J-chain, such as a J-chain of SEQ ID NO: 1, at or near a glycosylation site. Most preferably, an ADME-modulating moiety is introduced into the native sequence human J-chain of SEQ ID NO: 1 within about 10 amino acid residues from the C-terminus.

Introduction can be accomplished by direct or indirect fusion, i.e., by the combination of an ADME-modulating moiety amino acid sequences in one polypeptide chain by in-frame combination of their coding nucleotide sequences, with or without a peptide linker. The peptide linker (indirect fusion), if used, may, for example, be about 1 to 50, or about 1 to 40, or about 1 to 30, or about 1 to 20, or about 1 to 10, or about 10 to 20 amino acid residues, and may be present at one or both ends of an ADME-modulating moiety to be introduced into a J-chain sequence. In a preferred embodiment, the peptide linker is about 10 to 20, or 10 to 15 amino acids long. In another preferred embodiment, the peptide linker is 15 amino acids long.

An ADME-modulating moiety can also be appended to a native J-chain sequence by chemical linkage using heterobifunctional protein crosslinkers containing two different functional groups, which have their own reactivity and selectivity. These crosslinkers can be used in a one step process or can be used to create activated proteins, which can often be preserved and reacted with the second biomolecule in a separate step. Thus, for example, a heterobifunctional crosslinking reagent can be used to form conjugates between a J-chain and an ADME-modulating moiety. The reactive groups include, without limitation, imine reactive groups (such as NHS or sulfo-NHS), maleimide groups, and the like. Such crosslinkers, which can be cleavable or non-cleavable, have been used, for example, in the formation of hapten carrier proteins and in preparing enzyme-antibody conjugates. Chemically, the cleavable crosslinkers specifically include, without limitation, disulfide-based, hydrazone, and peptide linkers. A well-known and much studied enzyme-labile linker is a valine-citrulline linker, but other peptide linkers are also known and suitable. Typical representatives of non-cleavable linkers include thioethers, such as SMCC (N-succinimidyl-4-(N-maleimidomethyl)-cyclohexane-1-carboxylate). For further details see, e.g., Ducry L and Stump B, *Bioconjugate Chem.* 2010, 21:5-13, the entire disclosure of which is expressly incorporated by reference herein. For listing of further suitable linkers see, e.g., Klein et al., *Protein Engineering, Design & Selection;* 2014, 27(10): 325-330, the entire disclosure of which is expressly incorporated by reference herein.

In some embodiments, a modified J-chain comprises one extraneous ADME-modulating moiety. In some embodiments, a modified J-chain comprises more than one ADME-modulating moiety. For example, in some embodiments, one ADME-modulating moiety is introduced into a modified J-chain at either the N-terminus or the C-terminus. In some embodiments, a first ADME-modulating moiety is introduced into a modified J-chain at the N-terminus, and a second ADME-moiety is introduced into the same modified J-chain at the C-terminus. In some embodiments, an ADME-modulating moiety is introduced into a modified J-chain, and a binding moiety is introduced into the same modified J-chain. For examples, in some embodiments, an ADME-modulating moiety is introduced into a modified J-chain at the N-terminus, and a binding moiety (e.g., a CD3-binding antibody fragment, e.g., a CD3-binding scFv antibody fragment) is introduced into the same modified J-chain at the C-terminus. In some embodiments, an ADME-modulating moiety is introduced into a modified J-chain at the C-terminus, and a binding moiety (e.g., a CD3-binding antibody fragment, e.g., a CD3-binding scFv antibody fragment) is introduced into the same modified J-chain at the N-terminus. A binding molecule that comprises a binding moiety at both the N-terminus and the C-terminus of the J-chain is referred to herein as a binding molecule that comprises a "bidentate" J-chain.

The modified J-chain may be produced by well-known techniques of recombinant DNA technology, e.g., by expressing a nucleic acid encoding the modified J-chain in a suitable prokaryotic or eukaryotic host organism, such as CHO cells or *E. coli*. Thus, the modified J-chain may, for example, be expressed in *E. coli*, as described by Symersky et al., *Mol Immunol* 2000, 37:133-140.

In one embodiment, the J-chain can be initially modified by insertion of an enzyme recognition site, and post-translationally modified by a peptide or non-peptide linker, which can tether any extraneous ADME-modulating moiety to the J-chain.

The modified J-chain can also be co-expressed with the heavy and light chains of the recipient IgM, IgA, IgG/IgM or IgG/IgA antibody. Although due to its complex structure, the large scale production of recombinant IgM has been difficult, several recombinant production systems for IgM using non-lymphoid cells have been reported, including co-expression of the IgM heavy (H) and light (L) chains in C6 glioma cells, CHO cells, and HeLa cells (see, e.g., WO89/01975 and Wood et al., *J Immunol.* 145, 3011-3016 (1990) for expression in CHO cells). Expression of an IgM monoclonal antibody in *E. coli*, with or without a J-chain is described, e.g., in Azuma et al., *Clin Cancer Res* 2007, 13(9):2745-2750. Production of IgM in an immortalized human retina cell line expressing E1A and E1B proteins of an adenovirus is described in U.S. Application Publication No. 20060063234.

The recipient IgM, IgA, IgG/IgM or IgG/IgA antibody may be monospecific, bispecific or multi-specific. Bispecific and multi-specific IgM and IgA binding molecules, including antibodies, are described, for example, in PCT Application No. PCT/US2014/054079 and PCT/US2015/015268, the entire disclosures of which are expressly incorporated by reference herein.

A subject binding molecule can bind to any binding target via the IgM, IgA, IgG/IgM or IgG/IgA antibody, while an ADME-modulating moiety located on the J-chain modulates one or more ADME characteristics of the binding molecule. As such, the subject binding molecules can be used to provide high avidity binding to a target that is targeted by the IgM, IgA, IgG/IgM or IgG/IgA antibody, while the ADME-modulating moiety on the J-chain modulates one or more ADME characteristics of the binding molecule. Different types of ADME-modulating moieties are described herein, as are different classes of targets that can be targeted by an antibody portion of a subject binding molecule.

ADME-Modulating Moieties that Reduce Clearance

Aspects of the invention include binding molecules having an ADME-modulating moiety that reduces clearance of a binding molecule from the circulation of a subject, thereby increasing the half-life of the binding molecule in the subject. Albumin binding is known in the art as a general strategy for improving the pharmacokinetics of a protein. For example, non-covalent association with albumin has been shown to extend the half-life of short lived proteins. E.g., Dennis, Mark S. et al., *J. Biol. Chem.,* 2002, 277: 35035-35043, the disclosure of which is incorporated by reference herein in its entirety. As such, the use of albumin (human serum albumin), albumin-like proteins, albumin binding peptides, albumin binding antibody moieties (e.g., albumin binding scFv antibody fragments) as ADME-modulating moieties in a subject binding molecule provides an effective strategy for manipulating the pharmacokinetics of a binding molecule. In addition, the neonatal Fc receptor (FcRn) is known to provide a recycling pathway that provides immunoglobulin molecules with a longer circulating half-life. E.g., Roopenian D. C. et al., *Nature Reviews Immunology* 7, 715-725 (2007). As such, the use of FcRn-binding proteins, Fc domains that bind to FcRn, or antibody moieties that bind to FcRn, also provide an effective strategy for manipulating the pharmacokinetics of a binding molecule. Without being held to theory, in some embodiments, ADME-modulating moieties that bind to FcRn provide an extended half-life by accessing an FcRn-mediated recycling pathway, rather than merely providing extended half-life due to an increase in the molecular weight of the binding compound.

In some embodiments, an ADME-modulating moiety comprises an albumin protein. Albumin proteins are soluble, non-glycosylated proteins that are commonly found in blood plasma. Albumin proteins are known to interact with the FcRn-mediated recycling pathway, and as a result, have an extraordinarily long circulatory half-life.

In certain embodiments, an ADME-modulating moiety binds to an albumin protein, thereby connecting itself to an albumin protein and taking advantage of the FcRn-mediated recycling pathway. As such, in certain embodiments, an ADME-modulating moiety comprises an albumin binding peptide. Non-limiting examples of albumin-binding peptides are described in US Patent Publication No. US20050287153, the disclosure of which is incorporated by reference herein in its entirety. In some embodiments, an ADME-modulating moiety comprises an albumin-binding antibody moiety. Non-limiting examples of antibody moieties that bind to albumin include anti-albumin scFv, anti-albumin VHH, anti-albumin scFab, and anti-albumin dAb.

In some embodiments, an ADME-modulating moiety comprises an FcRn-binding peptide. In certain embodiments, an ADME-modulating moiety comprises an FcRn-binding antibody moiety. In some embodiments, an ADME-modulating moiety comprises an Fc domain of an immunoglobulin molecule that is bound by an FcRn receptor. Non-limiting examples of ADME-modulating moieties that reduce the clearance of a binding molecule are provided below in Table 1. Non-limiting examples of proteins that can be used to generate an antibody moiety that can be used as an ADME-modulating moiety in the subject binding molecules are provided in Table 1.

TABLE 1

| Sequence information for ADME-modulating moieties | |
|---|---|
| ADME-modulating moiety | Amino acid sequence information |
| albumin | GenBank Accession No.: NP_000468.1 |
| albumin binding peptide | DLCLRDWGCLW (SEQ ID NO: 2) |
| albumin binding peptide | DICLPRWGCLW (SEQ ID NO: 3) |
| albumin binding peptide | MEDICLPRWGCLWGD (SEQ ID NO: 4) |
| albumin binding peptide | QRLMEDICLPRWGCLWEDDE (SEQ ID NO: 5) |
| albumin binding peptide | QGLIGDICLPRWGCLWGRSV (SEQ ID NO: 6) |
| albumin binding peptide | QGLIGDICLPRWGCLWGRSVK (SEQ ID NO: 7) |
| albumin binding peptide | EDICLPRWGCLWEDD (SEQ ID NO: 8) |
| albumin binding peptide | RLMEDICLPRWGCLWEDD (SEQ ID NO: 9) |
| albumin binding peptide | MEDICLPRWGCLWEDD (SEQ ID NO: 10) |
| albumin binding peptide | MEDICLPRWGCLWED (SEQ ID NO: 11) |
| albumin binding peptide | RLMEDICLARWGCLWEDD (SEQ ID NO: 12) |
| albumin binding peptide | EVRSFCTRWPAEKSCKPLRG (SEQ ID NO: 13) |
| albumin binding peptide | RAPESFVCYWETICFERSEQ (SEQ ID NO: 14) |
| albumin binding peptide | EMCYFPGICWM (SEQ ID NO: 15) |
| FcRn | GenBank Accession No.: P55899.1 |
| Fc domain of IgG1 | GenBank Accession No.: AAB24269.1 |
| Fc domain of IgG2 | GenBank Accession No.: AAR26706.1 |
| Fc domain of IgG3 | GenBank Accession No.: ACO54886.1 |
| Fc domain of IgG4 | GenBank Accession No.: AAG00912.1 |

ADME-Modulating Moieties that Enhance Penetration of the Blood Brain Barrier

Aspects of the invention include binding molecules having an ADME-modulating moiety that enhances the ability of a binding molecule to penetrate the blood brain barrier of a subject, thereby increasing the concentration of the binding molecule in the brain extracellular fluid and central nervous system. The blood brain barrier is formed by brain endothelial cells, which are connected by tight Junctions. The blood brain barrier permits selective transport of certain molecules into the brain extracellular fluid and the central nervous system, while denying passage to others.

Aspects of the invention include binding molecules having a moiety that binds to one or more targets in a receptor-mediated transcytosis (RMT) pathway, thereby facilitating transportation of a binding molecule across the blood brain barrier. Specific non-limiting examples of binding targets that are associated with an RMT pathway include: transferrin, transferrin receptor, insulin, insulin receptor, IGF-1, IGF-1 receptor, leptin, leptin receptor, basigin, Glut1 and CD98hc. RMT pathways are known in the art to facilitate passage of their respective ligands through the blood brain barrier and into the brain extracellular fluid and central nervous system of a mammalian subject. E.g., Dennis et al., *Neuropsychopharmacology Reviews* (2012) 37, 302-303, the disclosure of which is incorporated by reference herein in its entirety; Joy Yu Zuchero et al., Neuron 89, 70-82 (2016), the disclosure of which is incorporated by reference herein in its entirety. As such, the use of RMT binding moieties (e.g., antibody moieties that bind to an RMT pathway target (e.g., an RMT-associated cell surface receptor and/or its associated ligand)) as ADME-modulating moieties in a subject binding molecule provides an effective strategy for enhancing penetration of the blood brain barrier and increasing the concentration of the binding molecule in the brain extracellular fluid and the central nervous system. Non-limiting examples of antibody moieties that can bind to an RMT pathway target include scFv, VHH, scFab, and dAb moieties.

In some embodiments, an ADME-modulating moiety comprises an antibody moiety that binds to a receptor in an RMT pathway. In some embodiments, an ADME-modulating moiety comprises an antibody moiety that binds to a ligand in an RMT pathway. In some embodiments, an ADME-modulating moiety comprises a ligand, or a portion of a ligand that is capable of binding to a receptor, in an RMT pathway (e.g., comprises a transferrin protein, or comprises at least a portion of a transferrin protein that is capable of binding to a transferrin receptor).

In some embodiments, an ADME-modulating moiety comprises a transferrin receptor-binding antibody moiety (e.g., a transferrin receptor-binding scFv). In some embodiments, an ADME-modulating moiety comprises a transferrin-binding antibody moiety (e.g., a transferrin-binding scFv). In certain embodiments, an ADME-modulating moiety comprises an insulin receptor-binding antibody moiety (e.g., an insulin receptor-binding scFv). In certain embodiments, an ADME-modulating moiety comprises an insulin-binding antibody moiety (e.g., an insulin-binding scFv). In certain embodiments, an ADME-modulating moiety comprises an IGF-1 receptor-binding antibody moiety (e.g., an IGF-1 receptor-binding scFv). In certain embodiments, an ADME-modulating moiety comprises an IGF-1-binding antibody moiety (e.g., an IGF-1-binding scFv). In certain embodiments, an ADME-modulating moiety comprises a leptin receptor-binding antibody moiety (e.g., a leptin receptor-binding scFv). In certain embodiments, an ADME-modulating moiety comprises a leptin-binding antibody moiety (e.g., a leptin-binding scFv). In some embodiments, an ADME-modulating moiety comprises a basigin-binding antibody moiety (e.g., a basigin-binding scFv). In some embodiments, an ADME-modulating moiety comprises a Glut1-binding antibody moiety (e.g., a Glut1-binding scFv). In some embodiments, an ADME-modulating moiety comprises a CD98hc-binding antibody moiety (e.g., a CD98hc-binding scFv).

In some embodiments, an ADME-modulating moiety comprises a transferrin protein. In some embodiments, an ADME-modulating moiety comprises an IGF-1 protein. In some embodiments, an ADME-modulating moiety comprises a leptin protein. In some embodiments, an ADME-modulating moiety comprises a basigin protein. In some embodiments, an ADME-modulating moiety comprises a Glut1 protein. In some embodiments, an ADME-modulating moiety comprises a CD98hc protein. Non-limiting examples of proteins that can be used to generate an antibody moiety that can be used as an ADME-modulating moiety that enhances penetration of the blood brain barrier are provided in Table 2.

TABLE 2

Sequence information for ADME-modulating moieties

| ADME-modulating moiety | GenBank Accession No. |
|---|---|
| Transferrin receptor | AAA61153.1 |
| Insulin receptor | P06213.4 |
| IGF-1 receptor | P08069.1 |
| Leptin receptor | P48357.2 |
| Transferrin | AAB22049.1 |
| Leptin | AAH69452.1 |
| Insulin | AAA59172.1 |
| IGF-1 | CAA01954.1 |
| basigin | BAA08109.1 |
| Glut1 | P11166.2 |
| CD98hc (4F2 cell-surface antigen heavy chain) | P08195.3 |

ADME-Modulating Moieties that Increase Half-Life in Extra-Vascular Spaces

Aspects of the invention include binding molecules having an ADME-modulating moiety that increases a half-life of a binding molecule in an extra-vascular space of a subject. Therapeutic proteins that are delivered directly to extra-vascular spaces such as intra-articular spaces, or intra-vitreal spaces, typically have a characteristically short half-life in the extra-vascular space. E.g., Mordenti, J. et al., *Toxicological Sciences* 52, 101-106 (1999); Mordenti, J. et al., *Toxicological Sciences* 27(5), 536-544 (1999).

Figure 15:
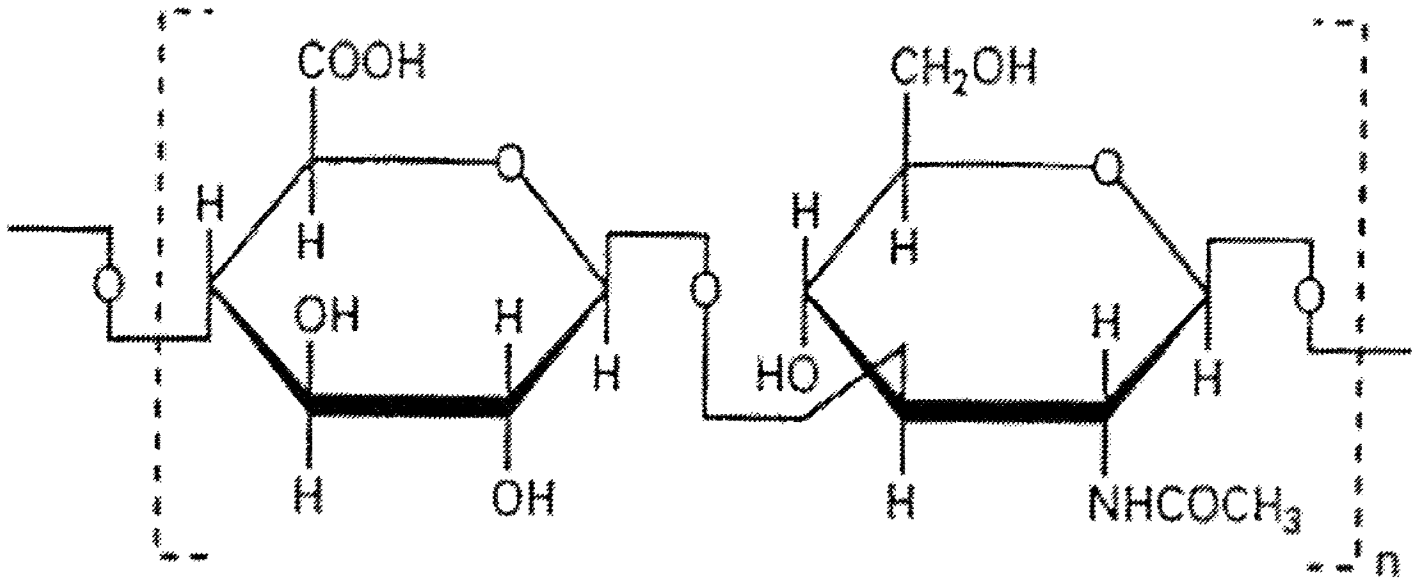
FIG. 15 is an illustration of the structure of hyaluronic acid.

Hyaluronic acid is an anionic, non-sulfated glycosaminoglycan that is a major component of the extracellular matrix in certain extra-vascular spaces, such as intra-articular spaces and intra-vitreal spaces. As such, the use of compounds that bind to hyaluronic acid as ADME-modulating moieties provides an effective strategy for retaining a therapeutic molecule in such an extracellular space. The structure of hyaluronic acid is provided in FIG. 15.

Tumor necrosis factor-inducible gene 6 protein (TSG-6) is a 30 kDa secreted protein that contains a hyaluronan-binding domain. The hyaluronan-binding domain interacts with extracellular matrix in extra-vascular spaces and is involved with cell migration. As such, the use of TSG-6 as an ADME-modulating moiety provides an effective strategy for retaining a therapeutic molecule in an extracellular space.

In some embodiments, an ADME-modulating moiety comprises a hyaluronic acid binding protein (HABP). In some embodiments, an ADME-modulating moiety comprises a TSG-6 protein. In certain embodiments, an ADME-modulating moiety comprises a hyaluronic acid-binding antibody moiety. In certain embodiments, an ADME-modulating moiety comprises a TSG-6-binding antibody moiety. Non-limiting examples of antibody moieties include scFv, VHH, scFab, and dAb moieties. Non-limiting examples of ADME-modulating moieties that retain a binding molecule in an extracellular space are provided below in Table 3.

TABLE 3

Sequence information for ADME-modulating moieties

| ADME-modulating moiety | Amino acid sequence information |
|---|---|
| Hyaluronic acid binding protein (HABP) | GenBank Accession No.: 2207280A |
| TSG-6 | GenBank Accession No.: CAD13434.1 |

Antagonist Targets

Aspects of the invention include binding molecules having an IgM, IgA, IgG/IgM or IgG/IgA antibody that antagonizes a T-cell inhibitory signaling pathway. T-cell inhibitory signaling pathways are known in the art, and include, without limitation, those described in Pardoll et al. Non-limiting examples of T-cell inhibitory signaling pathways and components thereof are described in further detail below.

One example of a T-cell inhibitory signaling pathway is the signaling pathway involving programmed cell death-1 (PD-1) and its ligand, programmed cell death ligand-1 (PD-L1). PD-1 is an inhibitory cell surface receptor protein of the immunoglobulin superfamily, and is involved in the regulation of T-cell function in immunity and self-tolerance. PD-L1 interacts with PD-1 on the surface of T-cells, and inhibits proliferation of T-cells by blocking cell cycle progression and cytokine production. Id.

Another example of a T-cell inhibitory signaling pathway is the signaling pathway involving T-cell immunoglobulin and mucin domain 3 (TIM3). TIM3 is a cell surface glycoprotein that is expressed on the surface of T-cells, and functions as an inhibitory molecule that is involved in the termination of Th1 cells. Id.

Another example of a T-cell inhibitory signaling pathway is the signaling pathway involving lymphocyte-activation gene 3 (LAG3). LAG3 belongs to the immunoglobulin superfamily, and functions as an inhibitor of cellular proliferation, activation and homeostasis of T-cells. Id.

As reviewed above, the subject binding molecules comprise a J-chain that comprises an ADME-modulating moiety. In some embodiments, an IgM, IgA, IgG/IgM or IgG/IgA antibody binds to a target that is involved in a T-cell inhibitory signaling pathway and antagonizes the inhibitory signaling pathway, thereby blocking or diminishing inhibitory signals that are received by a T-cell via the pathway, while the ADME-modulating moiety on the J-chain modulates an ADME characteristic of the binding molecule. Due to their higher avidity, the subject IgM, IgA, IgG/IgM or IgG/IgA antibodies act more effectively as antagonists when directed against T-cell inhibitory signaling pathway targets, as compared to IgG antibodies, which only have two binding sites. As a result, the T-cell's immune response is not blocked, halted or diminished, or, at least, the inhibition of the T-cell's immune response is reduced or diminished. The antibody of a subject binding molecule can be used to antagonize any T-cell inhibitory signaling pathway, including but not limited to the inhibitory signaling pathways that involve the proteins listed in Table 4, below. The GenBank Accession Numbers corresponding to the human protein sequences of these T-cell inhibitory signaling pathway targets are provided in Table 4, below.

TABLE 4

Sequence information for T-cell stimulatory signaling pathway targets

| T-cell stimulatory signaling pathway member: | GenBank Accession No. |
|---|---|
| PD-1 | AAC51773.1 |
| PD-L1 | Q9NZQ7.1 |
| TIM3 | AAL65158.1 |
| LAG3 | AAH52589.1 |

Agonist Targets

Aspects of the invention include binding molecules having an IgM, IgA, IgG/IgM or IgG/IgA antibody that agonizes a T-cell stimulatory signaling pathway. T-cell stimulatory signaling pathways are known in the art, and include, without limitation, those described in Pardoll et al. Non-limiting examples of T-cell stimulatory signaling pathways and components thereof are described in further detail below.

CD137 is a member of the tumor necrosis factor receptor (TNF-R) superfamily, and is expressed on the surface of T-cells. Its function is to stimulate T-cell proliferation and cytokine secretion. E.g., Pardoll at 254. OX40 is another member of the tumor necrosis factor receptor superfamily that is expressed on T-cells, and it functions by delivering a stimulatory signal to T-cells that helps to maintain the immune response over time. Id.

Another T-cell stimulatory signaling pathway involves CD40. CD40 is a member of the tumor necrosis factor receptor superfamily, and is expressed on antigen presenting cells. Engagement of CD40 with its ligand CD40L results in various T-cell stimulatory signals. Id.

Another T-cell stimulatory signaling pathway involves glucocorticoid-induced TNFR-related protein (GITR). GITR is a member of the tumor necrosis factor receptor superfamily, and is expressed on T-cells. It functions by increasing T-cell proliferation, activation and cytokine production. E.g., Nocentini, G. et al., Proc Natl Acad Sci USA. 1997 Jun. 10; 94(12):6216-21.

CD27 is another protein that is involved in a T-cell stimulatory signaling pathway. Another member of the tumor necrosis factor receptor superfamily, CD27 is expressed on the surface of T-cells and functions by delivering a stimulatory signal to T-cells when it interacts with CD70. E.g., Pardoll at 254.

Another T-cell stimulatory signaling pathway involves herpesvirus entry mediator (HVEM). HVEM is a member of the tumor necrosis factor receptor superfamily, and is expressed on the surface of antigen presenting cells. When HVEM interacts with certain ligands, such as CD258, it delivers a stimulatory signal to T-cells. Id.

As reviewed above, the subject binding molecules comprise ADME-modulating moiety on the J-chain that modulates an ADME characteristic of the binding molecule. In some embodiments, an IgM, IgA, IgG/IgM or IgG/IgA antibody binds to a target that is involved in a T-cell stimulatory signaling pathway and agonizes the stimulatory signaling pathway, thereby maintaining or increasing stimulatory signals that are received by a T-cell via the pathway, while the ADME-modulating moiety on the J-chain modulates an ADME characteristic of the binding molecule. Due to their higher avidity, the subject IgM, IgA, IgG/IgM or IgG/IgA antibodies act more effectively as agonists when directed against T-cell stimulatory signaling pathway targets, as compared to IgG antibodies, which only have two binding sites. As a result, a T-cell's immune response is maintained or increased. An antibody of a subject binding molecule can be used to agonize any T-cell stimulatory signaling pathway, including but not limited to the stimulatory signaling pathways that involve the proteins listed in Table 5, below. The GenBank Accession Numbers corresponding to the human protein sequences of these T-cell stimulatory signaling pathway targets are provided in Table 5, below.

TABLE 5

| Sequence information for T-cell stimulatory signaling pathway targets | |
|---|---|
| T-cell stimulatory signaling pathway member: | GenBank Accession No. |
| CD137 (4-1BB) | NP_001552.2 |
| OX40 | CAE11757.1 |
| CD40 | P25942.1 |
| GITR | Q9Y5U5.1 |
| CD27 | P26842.2 |
| HVEM | AAQ89238.1 |

Other non-limiting examples of T-cell stimulatory signaling pathways include those mediated by: TNFR1 (DR1) (GenBank Accession No. P19438.1); TNFR2 (GenBank Accession No. P20333.3); Fas (CD95, Apo1, DR2) (GenBank Accession No. AAH12479.1); CD30 (GenBank Accession No. AAA51947.1); TRAILR1 (DR4, Apo2) (GenBank Accession No. 000220.3); DR5 (TRAILR2) (GenBank Accession No. 014763.2); TRAILR3 (DcR1) (GenBank Accession No. 014798.3); TRAILR4 (DcR2) (GenBank Accession No. Q9UBN6.1); OPG (OCIF) (GenBank Accession No. 000300.3); TWEAKR (FN14) (GenBank Accession No. Q9NP84.1); DcR3 (GenBank Accession No. 095407.1); DR3 (GenBank Accession No. AAQ88676.1); EDAR (GenBank Accession No. Q9UNE0.1); and XEDAR (GenBank Accession No. AAQ89952.1). See, e.g., Aggarwal et al., Blood, 119:651-665, 2012, the disclosure of which is herein incorporated by reference in its entirety. In some embodiments, an IgM, IgA, IgG/IgM or IgG/IgA antibody binds to any one of these targets and agonizes a T-cell stimulatory signaling pathway, thereby maintaining or increasing stimulatory signals that are received by a T-cell via the pathway, while the ADME-modulating moiety on the J-chain modulates an ADME characteristic of the binding molecule.

Low Level Expression Targets

Aspects of the invention include binding molecules having an IgM, IgA, IgG/IgM or IgG/IgA antibody that binds to a low level expression target. Due to their higher avidity, the subject binding molecules are more potent than IgG antibodies. As such, the subject binding molecules can be employed in settings where a particular binding target is expressed at a low level, and where higher avidity is beneficial in facilitating binding between an antibody and a target. An antibody of a subject binding molecule can be used to target any low level expression target. Specific examples of low level expression targets that may be targeted by an IgM, IgA, IgG/IgM or IgG/IgA antibody of the subject binding molecules include, without limitation, EGFR, HER2, HER3, EpCAM, CEACAM, Gp100, MAGE1 and PD-L1. The GenBank Accession Numbers corresponding to the human protein sequences of these targets are provided in Table 6, below.

TABLE 6

| Sequence information for low level expression targets | |
|---|---|
| Target Name | GenBank Accession No. |
| EGFR | AAI18666.1 |
| HER2 | P04626.1 |
| HER3 | P21860.1 |
| EpCAM | P16422.2 |
| CEACAM | P06731.3 |
| Gp100 | AAC60634.1 |

TABLE 6-continued

| Sequence information for low level expression targets | |
|---|---|
| Target Name | GenBank Accession No. |
| MAGE1 | NP_004979.3 |
| PD-L1 | Q9NZQ7.1 |

Low Affinity Targets

Figure 14:
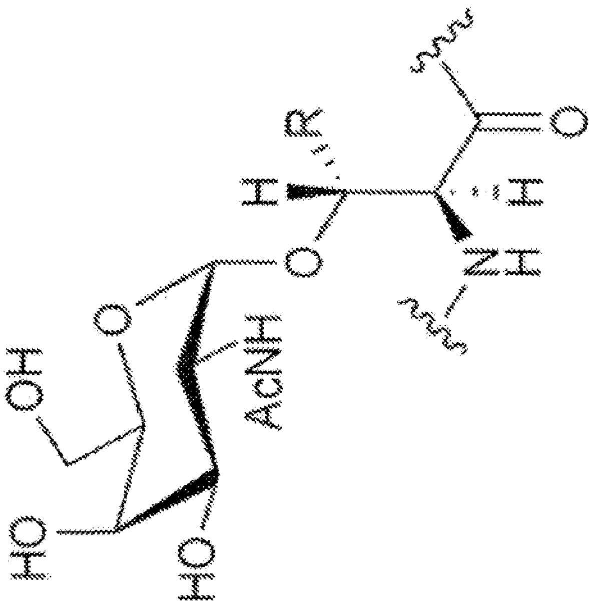
FIG. 14 is an illustration of the structure of Tn antigen.

Aspects of the invention include binding molecules having an IgM, IgA, IgG/IgM or IgG/IgA antibody that binds to a low affinity target. Due to their higher avidity, the subject binding molecules are more potent than IgG antibodies. As such, the subject binding molecules can be employed in settings where a particular binding target has a low binding affinity, and where higher avidity is beneficial in facilitating binding between an antibody and a target. An antibody of a subject binding molecule can be used to target any low affinity target. Specific examples of low affinity targets that may be targeted by an IgM, IgA, IgG/IgM or IgG/IgA antibody of the subject binding molecules include, without limitation, NY-ESO-1, Sialyl Lewis X antigen, and Tn antigen. The GenBank Accession Numbers corresponding to the human protein sequences of NY-ESO-1 and Sialyl Lewis X antigen are provided in Table 7, below. The structure of Tn antigen is provided in FIG. 14.

TABLE 7

| Sequence information for low affinity targets | |
|---|---|
| Target Name | GenBank Accession No. |
| NY-ESO-1 | CAA05908.1 |
| Sialyl Lewis X antigen | NP_001241688.1 |

Hematologic Cancer Targets

Aspects of the invention include binding molecules having an IgM, IgA, IgG/IgM or IgG/IgA antibody that binds to a hematologic cancer target. Due to their higher avidity, the subject binding molecules are more potent than IgG antibodies. As such, the subject binding molecules can be employed in settings where a particular binding target is expressed at a low level, as is the case in certain hematologic cancers. The higher avidity of the subject binding molecules facilitates binding between an antibody and a target. An antibody of a subject binding molecule can be used to target any binding target, such as a low level expression target on a hematologic cancer cell. Specific examples of hematologic cancer targets that can be targeted by an IgM, IgA, IgG/IgM or IgG/IgA antibody of the subject binding molecules include, without limitation, CD19, CD20, CD22, CD33, CD38, CD52 and CD70. The GenBank Accession Numbers corresponding to the human protein sequences of these targets are provided in Table 8, below.

TABLE 8

| Sequence information for hematologic cancer targets | |
|---|---|
| Target Name | GenBank Accession No. |
| CD19 | AAA69966.1 |
| CD20 | NP_690605.1 |
| CD22 | P20273.2 |
| CD33 | P20138.2 |
| CD38 | BAA18966.1 |
| CD52 | AJC19276.1 |
| CD70 | NP_001243.1 |

Other Binding Targets

Aspects of the invention include binding molecules having an IgM, IgA, IgG/IgM or IgG/IgA antibody that binds to a target that is associated with a particular disease or disorder. Due to their higher avidity, the subject binding molecules are more potent than IgG antibodies. As such, the subject binding molecules can be employed in settings where high avidity binding to a particular binding target is desirable. An antibody of a subject binding molecule can be used to target any binding target. Specific examples of binding targets that can be targeted by an IgM, IgA, IgG/IgM or IgG/IgA antibody of the subject binding molecules include, without limitation, VEGF, TNF-alpha, amyloid beta, and Beta-secretase 1 (BACE) proteins. The GenBank Accession Numbers corresponding to the human protein sequences of these targets are provided in Table 9, below.

TABLE 9

Sequence information for other binding targets

| Target Name | GenBank Accession No. |
|---|---|
| VEGF | AAP86646.1 |
| TNF alpha | CAA26669.1 |
| Amyloid beta A4 | P05067.3 |
| BACE (Beta-secretase 1) | P56817.2 |

Applications of Binding Molecules with ADME-Modulating Moieties

Binding molecules comprising a modified J-chain that comprises an ADME-modulating moiety have widespread therapeutic and diagnostic applications, including but not limited to the treatment of various diseases by modulating one or more ADME characteristics of a binding molecule.

In some embodiments, the subject binding molecules comprising a modified J-chain may broadly be used for the treatment of any of a variety of cancers. It is anticipated that any type of tumor and any type of tumor-associated antigen may be targeted by the subject binding molecules. Examples of cancer types include, without limitation, acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer. However, the skilled artisan will realize that tumor-associated antigens are known in the art for virtually any type of cancer.

In some embodiments, the J-chain of a subject binding molecule includes an ADME-modulating moiety that reduces clearance of the binding molecule from the circulation of a subject, while the antibody antagonizes a T-cell inhibitory signaling pathway. Without being held to theory, the purpose of such a binding molecule is to increase the half-life of the binding molecule via the J-chain ADME-modulating moiety, while simultaneously blocking or decreasing T-cell inhibitory signaling via the antibody. Due to their increased avidity, the subject IgM, IgA, IgG/IgM and IgG/IgA antibodies act as effective antagonists when directed to certain binding targets, such as members of a T-cell inhibitory signaling pathway, as described above. Such binding molecules find utility, for example, in the treatment of diseases wherein blocking or decreasing the inhibition of a T-cell immune response is desirable, such as, e.g., certain cancers and immune disorders. Such cancers include, but are not limited to, epithelial cancers as well as hematologic cancers.

Epithelial cancers that are suitable for treatment with the subject binding molecules having an antagonist antibody and an ADME-modulating moiety on the J-chain include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. Hematologic cancers that are suitable for treatment with the subject binding molecules having an antagonist antibody and an ADME-modulating moiety on the J-chain include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, the J-chain of a subject binding molecule includes an ADME-modulating moiety that enhances penetration of the blood brain barrier by the binding molecule, while the antibody antagonizes a T-cell inhibitory signaling pathway. Without being held to theory, the purpose of such a binding molecule is to increase the concentration of the binding molecule in the brain extracellular fluid and the central nervous system via the J-chain ADME-modulating moiety, while simultaneously blocking or decreasing T-cell inhibitory signaling via the antibody. Due to their increased avidity, the subject IgM, IgA, IgG/IgM and IgG/IgA antibodies act as effective antagonists when directed to certain binding targets, such as members of a T-cell inhibitory signaling pathway, as described above. Such binding molecules find utility, for example, in the treatment of diseases wherein blocking or decreasing the inhibition of a T-cell immune response is desirable, such as, e.g., certain cancers and immune disorders of the brain and central nervous system. Such cancers include, but are not limited to, glioma, astrocytoma, meningioma, neuroma and oligodendroglioma.

In some embodiments, the J-chain of the subject binding molecules includes an ADME-modulating moiety that reduces clearance of the binding molecule from the circulation of a subject, while the antibody agonizes a T-cell stimulatory signaling pathway. Without being held to theory, the purpose of such a binding molecule is to increase the half-life of the binding molecule via the ADME-modulating moiety on the J-chain, while simultaneously maintaining or increasing T-cell stimulatory signaling via the antibody. Due to their increased avidity, the subject IgM, IgA, IgG/IgM and IgG/IgA antibodies act as super agonists when directed to certain binding targets, such as members of a T-cell stimulatory signaling pathway, as described above. Such binding molecules find utility, for example, in the treatment of diseases wherein maintenance or activation of a T-cell immune response is desirable, such as, e.g., certain cancers and immune disorders. Such cancers include, but are not limited to, epithelial cancers as well as hematologic cancers.

Epithelial cancers that are suitable for treatment with the subject binding molecules having an agonist antibody and an ADME-modulating moiety include on the J-chain include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. Hematologic cancers that are suitable for treatment with the subject binding molecules having an agonist antibody and an ADME-modulating moiety include on the J-chain include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, the J-chain of a subject binding molecule includes an ADME-modulating moiety that enhances penetration of the blood brain barrier by the binding molecule, while the antibody agonizes a T-cell stimulatory signaling pathway. Without being held to theory, the purpose of such a binding molecule is to increase the concentration of the binding molecule in the brain extracellular fluid and the central nervous system via the ADME-modulating moiety on the J-chain, while simultaneously maintaining or increasing T-cell stimulatory signaling via the antibody. Due to their increased avidity, the subject IgM, IgA, IgG/IgM and IgG/IgA antibodies act as super agonists when directed to certain binding targets, such as members of a T-cell stimulatory signaling pathway, as described above. Such binding molecules find utility, for example, in the treatment of diseases wherein maintenance or activation of a T-cell immune response is desirable, such as, e.g., certain cancers and immune disorders of the brain and central nervous system. Such cancers include, but are not limited to, glioma, astrocytoma, meningioma and oligodendroglioma.

In some embodiments, the J-chain of a subject binding molecule includes an ADME-modulating moiety that increases the half-life of the binding molecule, while the antibody binds to a low level expression target. Without being held to theory, the purpose of such a binding molecule is to increase the half-life of the binding molecule via the ADME-modulating moiety on the J-chain, while simultaneously binding to a low level expression target using the higher avidity of the subject IgM, IgA, IgG/IgM and IgG/IgA antibodies. Such binding molecules find utility in the treatment of diseases wherein high avidity binding to a low level expression target is beneficial, such as, for example, in certain cancers and immune disorders. For example, certain epithelial cancers are known to express tumor antigens that have a low level of expression, as described above. Such epithelial cancers include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. In some embodiments, the subject binding molecules find use in the treatment of any of these conditions.

In some embodiments, the J-chain of the subject binding molecules includes an ADME-modulating moiety that increases the half-life of the binding molecule, while the antibody binds to a low affinity target. Without being held to theory, the purpose of such a binding molecule is to increase the half-life of the binding molecule via the ADME-modulating moiety on the J-chain, while simultaneously binding to a low affinity target using the higher avidity of the subject IgM, IgA, IgG/IgM and IgG/IgA antibodies. As reviewed above, due to their increased avidity, the subject IgM, IgA, IgG/IgM and IgG/IgA antibodies, comprising a modified J-chain comprising an ADME-modulating moiety are especially advantageous in situations where IgG antibodies bind to their target with low affinity. Thus, in some embodiments, the IgM, IgA, IgG/IgM and IgG/IgA antibodies herein may comprise the binding domain of a therapeutic IgG antibody. Such binding molecules find utility in the treatment of diseases wherein high avidity binding to a low affinity target is beneficial, such as, for example, in certain cancers and immune disorders. For example, certain epithelial cancers are known to express tumor antigens that have a low binding affinity, as described above. Such epithelial cancers include, without limitation, melanoma, non-small-cell lung, nasopharyngeal, colorectal, liver, urinary bladder, ovarian, gastric, esophageal, pancreatic, renal, thyroid or breast cancer, hormone receptor negative breast cancer, or triple negative breast cancer. In some embodiments, the subject binding molecules find use in the treatment of any of these conditions.

In some embodiments, the J-chain of a subject binding molecule includes an ADME-modulating moiety that increases the half-life of the binding molecule, while the antibody binds to a target on a hematologic cancer cell. Without being held to theory, the purpose of such a binding molecule is to increase the half-life of the binding molecule via the ADME-modulating moiety on the J-chain, while simultaneously binding to a hematologic cancer target using the higher avidity of the subject IgM, IgA, IgG/IgM and IgG/IgA antibodies. Such binding molecules find utility in the treatment of hematologic cancers wherein high avidity binding to a tumor antigen is beneficial. For example, certain hematologic cancers are known to express tumor antigens at a low level, as described above. Such hematologic cancers include, without limitation, leukemia, lymphoma, myeloma, myelodysplastic syndrome, acute myeloid leukemia, acute lymphoblastic leukemia, chronic myelogenous leukemia, chronic lymphocytic leukemia, Hodgkin's lymphoma and non-Hodgkin's lymphoma. In some embodiments, the subject binding molecules find use in the treatment of any of these conditions.

In some embodiments, the J-chain of a subject binding molecule includes an ADME-modulating moiety that increases the retention of the binding molecule in an extra-vascular space, while the antibody binds to a binding target in the extra-vascular space. Without being held to theory, the purpose of such a binding molecule is to increase the residence time of the binding molecule in the extra-vascular space via the ADME-modulating moiety on the J-chain, while simultaneously binding to a binding target using the higher avidity of the subject IgM, IgA, IgG/IgM and IgG/IgA antibodies. Such binding molecules find utility in the treatment of diseases or disorders wherein high avidity binding to a binding target in an extra-vascular space is beneficial. For example, tumor necrosis factor alpha (TNF alpha) is a binding target in the treatment of rheumatoid arthritis, which is an autoimmune disease that affects the joints of a subject. The subject binding molecules find use in the treatment of rheumatoid arthritis by providing high avidity binding to TNF alpha via the IgM, IgA, IgG/IgM or IgG/IgA antibody, while also providing extended retention time within an intra-articular space via the ADME-modulating moiety on the modified J-chain.

In another non-limiting example, vascular endothelial growth factor (VEGF) is a binding target in the treatment of age-related macular degeneration (AMD), which is a disease that affects the retina of a subject. The subject binding molecules find use in the treatment of AMD by providing high avidity binding to VEGF via the IgM, IgA, IgG/IgM or IgG/IgA antibody, while also providing extended retention time in an intra-vitreal space via the ADME-modulating moiety on the modified J-chain.

In some embodiments, the J-chain of a subject binding molecule includes an ADME-modulating moiety that enhances penetration of the blood brain barrier by the binding molecule, while the antibody binds to a binding target in the brain extracellular fluid or a central nervous system tissue. Without being held to theory, the purpose of such a binding molecule is to increase the concentration of the binding molecule in the brain extracellular fluid and central nervous system tissue via the ADME-modulating moiety on the J-chain, while simultaneously binding to a binding target using the higher avidity of the subject IgM, IgA, IgG/IgM and IgG/IgA antibodies. Such binding molecules find utility in the treatment of diseases or disorders wherein high avidity binding to a binding target in the brain extracellular fluid or central nervous system tissue is beneficial. For example, amyloid beta is a binding target in the treatment of Alzheimer's disease, which is a disease that affects the central nervous system of a subject. Beta secretase 1 (BACE) is also a binding target in the treatment of Alzheimer's disease. The subject binding molecules find use in the treatment of Alzheimer's disease by providing high avidity binding to, e.g., amyloid beta or BACE via the IgM, IgA, IgG/IgM or IgG/IgA antibody, while also providing increased concentration of the binding molecule within the brain extracellular fluid or central nervous system tissue via the ADME-modulating moiety on the modified J-chain.

Examples of IgM, IgA, IgG/IgM, or IgG/IgA antibodies including a modified J-chain that modulates an ADME characteristic of a binding molecule can include the binding regions of known IgG antibodies to tumor-associated antigens, such as, for example, blinatumomab (also known as MT103) (anti-CD19), CD19hA19 (anti-CD19, U.S. Pat. No. 7,109,304), hPAM4 (anti-mucin, U.S. Pat. No. 7,282,567), hA20 (anti-CD20, U.S. Pat. No. 7,251,164), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the disclosures of which are expressly incorporated by reference herein.

Other antibodies that can provide binding regions for use in combination with a modified J-chain that increases the half-life of a subject binding molecule include, for example, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), atalizumab (anti-.alpha.4 integrin), omalizumab (anti-IgE); anti-TNF-.alpha. antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), BENLYSTA® (Human Genome Sciences); antibodies for therapy of Alzheimer's disease such as Alz 50 (Ksiezak-Reding et al., 1987, J Biol Chem 263:7943-47), gantenerumab, solanezumab and infliximab; anti-fibrin antibodies like 59D8, T2G1s, MH1; anti-CD38 antibodies such as MOR03087 (MorphoSys AG), MOR202 (Celgene), HuMax-CD38 (Genmab) or daratumumab (Johnson & Johnson); trastuzumab (anti-HER2); tremelimumab (anti-CTLA4); urelumab (anti-CD137 (4-1BB)); vorsetuzumab (anti-CD70); duligotumab (anti-HER3); dacetuzumab (anti-CD40); varlilumab (anti-CD27); atezolizumab (anti-PD-L1); anti-MAGE1 antibodies such as MA454 (Thermo Scientific, Rockford, Ill.); anti-OX-40 antibodies such as ACT35 (Affymetrix eBioscience, San Diego, CA); anti-GITR antibodies such as 621 (BioLegend, San Diego, CA); anti-HVEM antibodies such as 122 (BioLegend, San Diego, CA); anti-TIM3 antibodies such as F38-2E2 (BioLegend, San Diego, CA); anti-LAG3 antibodies such as 3DS223H (Affymetrix eBioscience, San Diego, CA); anti-BTLA antibodies such as MIH26 (BioLegend, San Diego, CA); anti-VISTA antibodies such as MAB71261 (R&D Systems, Minneapolis, MN); anti-TIGIT antibodies such as MBSA43 (Affymetrix eBioscience, San Diego, CA); anti-CEACAM antibodies such as D14HD11 (abcam, Cambridge, MA); anti-Gp100 antibodies such as ab52058 (abcam, Cambridge, MA); anti-NY-ESO-1 antibodies such as E978 (Thermo Scientific, Rockford, IL); anti-Sialyl Lewis X antigen antibodies such as MAB2096 (EMD Millipore, Billerica, MA); anti-Tn antigen antibodies such as MA1-90544 (Thermo Scientific, Rockford, IL); anti-HIV antibodies such as P4/D10 (U.S. Pat. No. 8,333,971), Ab 75, Ab 76, Ab 77 (Paulik et al., 1999, Biochem Pharmacol 58:1781-90), as well as the anti-HIV antibodies described in U.S. Pat. Nos. 5,831,034, 5,911,989, and Vcelar et al., AIDS 2007; 21(16):2161-2170 and Joos et al., Antimicrob. Agents Chemother. 2006; 50(5):1773-9; anti-albumin antibodies such as ab106582 (abcam, Cambridge, MA); anti-FcRn antibodies such as sc-271745 (Santa Cruz Biotechnology, Santa Cruz, CA); anti-transferrin receptor antibodies such as ab61021 (abcam, Cambridge, MA); anti-insulin receptor antibodies such as ab5500 (abcam, Cambridge, MA); anti-IGF-1 receptor antibodies such as ab5681 (abcam, Cambridge, MA); anti-leptin receptor antibodies such as ab5593 (abcam, Cambridge, MA); anti-TNF alpha antibodies such as ab31908 (abcam, Cambridge, MA); anti-amyloid beta antibodies such as ab2539 (abcam, Cambridge, MA); anti-hyaluronic acid antibodies such as ab53842 (abcam, Cambridge, MA); anti-BACE antibodies such as ab2077 (abcam, Cambridge, MA); anti-TSG-6 antibodies such as ab204049 (abcam, Cambridge, MA).

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to PD-1 and antagonizes a PD-1-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to PD-L1 and antagonizes a PD-L1-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to TIM3 and antagonizes a TIM3-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to LAG3 and antagonizes a LAG3-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to CD137 and agonizes a CD137-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to OX40 and agonizes an OX40-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to CD40 and agonizes a CD40-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to GITR and agonizes a GITR-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to CD27 and agonizes a CD27-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises human serum albumin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a human serum albumin-binding peptide. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a human serum albumin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a human serum albumin-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an FcRn-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an FcRn-binding peptide. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an Fc domain.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises transferrin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises insulin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises leptin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises IGF-1. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1-binding scFv antibody fragment. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1 receptor-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises basigin. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a basigin-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a basigin-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises Glut1. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a Glut1-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a Glut1-binding scFv antibody fragment.

In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises CD98hc. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a CD98hc-binding antibody moiety. In one specific embodiment, a binding molecule whose IgM, IgA, IgG/IgM, or IgG/IgA antibody binds to HVEM and agonizes an HVEM-mediated T-cell inhibitory signaling pathway has an ADME-modulating moiety on the J-chain that comprises a CD98hc-binding scFv antibody fragment.

In one specific embodiment, a binding molecule whose IgM, IgA, IgG/IgM, or IgG/IgA antibody binds to EGFR has an ADME-modulating moiety on the J-chain that comprises human serum albumin. In one specific embodiment, a binding molecule whose IgM, IgA, IgG/IgM, or IgG/IgA antibody binds to EGFR has an ADME-modulating moiety on the J-chain that comprises a human serum albumin-binding peptide. In one specific embodiment, a binding molecule whose IgM, IgA, IgG/IgM, or IgG/IgA antibody binds to EGFR has an ADME-modulating moiety on the J-chain that comprises a human serum albumin-binding antibody moiety. In one specific embodiment, a binding molecule whose IgM, IgA, IgG/IgM, or IgG/IgA antibody binds to EGFR has an ADME-modulating moiety on the J-chain that comprises a human serum albumin-binding scFv antibody fragment. In one specific embodiment, a binding molecule whose IgM, IgA, IgG/IgM, or IgG/IgA antibody binds to EGFR has an ADME-modulating moiety on the J-chain that comprises an FcRn-binding antibody moiety. In one specific embodiment, a binding molecule whose IgM, IgA, IgG/IgM, or IgG/IgA antibody binds to EGFR has an ADME-modulating moiety on the J-chain that comprises an FcRn-binding scFv antibody fragment. In one specific embodiment, a binding molecule whose IgM, IgA, IgG/IgM, or IgG/IgA antibody binds to EGFR has an ADME-modulating moiety on the J-chain that comprises an Fc domain.

In one specific embodiment, a binding molecule whose IgM, IgA, IgG/IgM, or IgG/IgA antibody binds to HER2 has an ADME-modulating moiety on the J-chain that comprises human serum albumin. In one specific embodiment, a binding molecule whose IgM, IgA, IgG/IgM, or IgG/IgA antibody binds to HER2 has an ADME-modulating moiety on the J-chain that comprises a human serum albumin-binding peptide. In one specific embodiment, a binding molecule whose IgM, IgA, IgG/IgM, or IgG/IgA antibody binds to HER2 has an ADME-modulating moiety on the J-chain that comprises a human serum albumin-binding antibody moiety. In one specific embodiment, a binding molecule whose IgM, IgA, IgG/IgM, or IgG/IgA antibody binds to HER2 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to HER2 has an ADME-modulating moiety on the J-chain that comprises an FcRn-binding antibody moiety. In one specific embodiment, a binding molecule whose IgM, IgA, IgG/IgM, or IgG/IgA antibody binds to HER2 has an ADME-modulating moiety on the J-chain that comprises an FcRn-binding scFv antibody fragment. In one specific embodiment, a binding molecule whose IgM, IgA, IgG/IgM, or IgG/IgA antibody binds to HER2 has an ADME-modulating moiety on the J-chain that comprises an Fc domain.

In one specific embodiment, a binding molecule whose IgM, IgA, IgG/IgM, or IgG/IgA antibody binds to HER3 has an ADME-modulating moiety on the J-chain that comprises human serum albumin. In one specific embodiment, a binding molecule whose IgM, IgA, IgG/IgM, or IgG/IgA antibody binds to HER3 has an ADME-modulating moiety on the J-chain that comprises a human serum albumin-binding peptide. In one specific embodiment, a binding molecule whose IgM, IgA, IgG/IgM, or IgG/IgA antibody binds to HER3 has an ADME-modulating moiety on the J-chain that comprises a human serum albumin-binding antibody moiety. In one specific embodiment, a binding molecule whose IgM, IgA, IgG/IgM, or IgG/IgA antibody binds to HER3 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to HER3 has an ADME-modulating moiety on the J-chain that comprises an FcRn-binding antibody moiety. In one specific embodiment, a binding molecule whose IgM, IgA, IgG/IgM, or IgG/IgA antibody binds to HER3 has an ADME-modulating moiety on the J-chain that comprises an FcRn-binding scFv antibody fragment. In one specific embodiment, a binding molecule whose IgM, IgA, IgG/IgM, or IgG/IgA antibody binds to HER3 has an ADME-modulating moiety on the J-chain that comprises an Fc domain.

In one specific embodiment, a binding molecule whose IgM, IgA, IgG/IgM, or IgG/IgA antibody binds to EPCAM has an ADME-modulating moiety on the J-chain that comprises human serum albumin. In one specific embodiment, a binding molecule whose IgM, IgA, IgG/IgM, or IgG/IgA antibody binds to EPCAM has an ADME-modulating moiety on the J-chain that comprises a human serum albumin-binding peptide. In one specific embodiment, a binding molecule whose IgM, IgA, IgG/IgM, or IgG/IgA antibody binds to EPCAM has an ADME-modulating moiety on the J-chain that comprises a human serum albumin-binding antibody moiety. In one specific embodiment, a binding molecule whose IgM, IgA, IgG/IgM, or IgG/IgA antibody binds to EPCAM has an ADME-modulating moiety on the J-chain that comprises a human serum albumin-binding scFv antibody fragment. In one specific embodiment, a binding molecule whose IgM, IgA, IgG/IgM, or IgG/IgA antibody binds to EPCAM has an ADME-modulating moiety on the J-chain that comprises an FcRn-binding antibody moiety. In one specific embodiment, a binding molecule whose IgM, IgA, IgG/IgM, or IgG/IgA antibody binds to EPCAM has an ADME-modulating moiety on the J-chain that comprises an FcRn-binding scFv antibody fragment. In one specific embodiment, a binding molecule whose IgM, IgA, IgG/IgM, or IgG/IgA antibody binds to EPCAM has an ADME-modulating moiety on the J-chain that comprises an Fe domain.

In one specific embodiment, a binding molecule whose IgM, IgA, IgG/IgM, or IgG/IgA antibody binds to CEACAM has an ADME-modulating moiety on the J-chain that comprises human serum albumin. In one specific embodiment, a binding molecule whose IgM, IgA, IgG/IgM, or IgG/IgA antibody binds to CEACAM has an ADME-modulating moiety on the J-chain that comprises a human serum albumin-binding peptide. In one specific embodiment, a binding molecule whose IgM, IgA, IgG/IgM, or IgG/IgA antibody binds to CEACAM has an ADME-modulating moiety on the J-chain that comprises a human serum albumin-binding antibody moiety. In one specific embodiment, a binding molecule whose IgM, IgA, IgG/IgM, or IgG/IgA antibody binds to CEACAM has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CEACAM has an ADME-modulating moiety on the J-chain that comprises an FcRn-binding antibody moiety. In one specific embodiment, a binding molecule whose IgM, IgA, IgG/IgM, or IgG/IgA antibody binds to CEACAM has an ADME-modulating moiety on the J-chain that comprises an FcRn-binding scFv antibody fragment. In one specific embodiment, a binding molecule whose IgM, IgA, IgG/IgM, or IgG/IgA antibody binds to CEACAM has an ADME-modulating moiety on the J-chain that comprises an Fc domain.

In one specific embodiment, a binding molecule whose IgM, IgA, IgG/IgM, or IgG/IgA antibody binds to GP100 has an ADME-modulating moiety on the J-chain that comprises human serum albumin. In one specific embodiment, a binding molecule whose IgM, IgA, IgG/IgM, or IgG/IgA antibody binds to GP100 has an ADME-modulating moiety on the J-chain that comprises a human serum albumin-binding peptide. In one specific embodiment, a binding molecule whose IgM, IgA, IgG/IgM, or IgG/IgA antibody binds to GP100 has an ADME-modulating moiety on the J-chain that comprises a human serum albumin-binding antibody moiety. In one specific embodiment, a binding molecule whose IgM, IgA, IgG/IgM, or IgG/IgA antibody binds to GP100 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to GP100 has an ADME-modulating moiety on the J-chain that comprises an FcRn-binding antibody moiety. In one specific embodiment, a binding molecule whose IgM, IgA, IgG/IgM, or IgG/IgA antibody binds to GP100 has an ADME-modulating moiety on the J-chain that comprises an FcRn-binding scFv antibody fragment. In one specific embodiment, a binding molecule whose IgM, IgA, IgG/IgM, or IgG/IgA antibody binds to GP100 has an ADME-modulating moiety on the J-chain that comprises an Fc domain.

In one specific embodiment, a binding molecule whose IgM, IgA, IgG/IgM, or IgG/IgA antibody binds to MAGE1 has an ADME-modulating moiety on the J-chain that comprises human serum albumin. In one specific embodiment, a binding molecule whose IgM, IgA, IgG/IgM, or IgG/IgA antibody binds to MAGE1 has an ADME-modulating moiety on the J-chain that comprises a human serum albumin-binding peptide. In one specific embodiment, a binding molecule whose IgM, IgA, IgG/IgM, or IgG/IgA antibody binds to MAGE1 has an ADME-modulating moiety on the J-chain that comprises a human serum albumin-binding antibody moiety. In one specific embodiment, a binding molecule whose IgM, IgA, IgG/IgM, or IgG/IgA antibody binds to MAGE1 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to MAGE1 has an ADME-modulating moiety on the J-chain that comprises an FcRn-binding antibody moiety. In one specific embodiment, a binding molecule whose IgM, IgA, IgG/IgM, or IgG/IgA antibody binds to MAGE1 has an ADME-modulating moiety on the J-chain that comprises an FcRn-binding scFv antibody fragment. In one specific embodiment, a binding molecule whose IgM, IgA, IgG/IgM, or IgG/IgA antibody binds to MAGE1 has an ADME-modulating moiety on the J-chain that comprises an Fc domain.

In one specific embodiment, a binding molecule whose IgM, IgA, IgG/IgM, or IgG/IgA antibody binds to NY-ESO-1 has an ADME-modulating moiety on the J-chain that comprises human serum albumin. In one specific embodiment, a binding molecule whose IgM, IgA, IgG/IgM, or IgG/IgA antibody binds to NY-ESO-1 has an ADME-modulating moiety on the J-chain that comprises a human serum albumin-binding peptide. In one specific embodiment, a binding molecule whose IgM, IgA, IgG/IgM, or IgG/IgA antibody binds to NY-ESO-1 has an ADME-modulating moiety on the J-chain that comprises a human serum albumin-binding antibody moiety. In one specific embodiment, a binding molecule whose IgM, IgA, IgG/IgM, or IgG/IgA antibody binds to NY-ESO-1 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to NY-ESO-1 has an ADME-modulating moiety on the J-chain that comprises an FcRn-binding antibody moiety. In one specific embodiment, a binding molecule whose IgM, IgA, IgG/IgM, or IgG/IgA antibody binds to NY-ESO-1 has an ADME-modulating moiety on the J-chain that comprises an FcRn-binding scFv antibody fragment. In one specific embodiment, a binding molecule whose IgM, IgA, IgG/IgM, or IgG/IgA antibody binds to NY-ESO-1 has an ADME-modulating moiety on the J-chain that comprises an Fc domain.

In one specific embodiment, a binding molecule whose IgM, IgA, IgG/IgM, or IgG/IgA antibody binds to Sialyl Lewis X antigen has an ADME-modulating moiety on the J-chain that comprises human serum albumin. In one specific embodiment, a binding molecule whose IgM, IgA, IgG/IgM, or IgG/IgA antibody binds to Sialyl Lewis X antigen has an ADME-modulating moiety on the J-chain that comprises a human serum albumin-binding peptide. In one specific embodiment, a binding molecule whose IgM, IgA, IgG/IgM, or IgG/IgA antibody binds to Sialyl Lewis X antigen has an ADME-modulating moiety on the J-chain that comprises a human serum albumin-binding antibody moiety. In one specific embodiment, a binding molecule whose IgM, IgA, IgG/IgM, or IgG/IgA antibody binds to Sialyl Lewis X antigen has an ADME-modulating moiety on the J-chain that comprises a human serum albumin-binding scFv antibody fragment. In one specific embodiment, a binding molecule whose IgM, IgA, IgG/IgM, or IgG/IgA antibody binds to Sialyl Lewis X antigen has an ADME-modulating moiety on the J-chain that comprises an FcRn-binding antibody moiety. In one specific embodiment, a binding molecule whose IgM, IgA, IgG/IgM, or IgG/IgA antibody binds to Sialyl Lewis X antigen has an ADME-modulating moiety on the J-chain that comprises an FcRn-binding scFv antibody fragment. In one specific embodiment, a binding molecule whose IgM, IgA, IgG/IgM, or IgG/IgA antibody binds to Sialyl Lewis X antigen has an ADME-modulating moiety on the J-chain that comprises an Fe domain.

In one specific embodiment, a binding molecule whose IgM, IgA, IgG/IgM, or IgG/IgA antibody binds to Tn antigen has an ADME-modulating moiety on the J-chain that comprises human serum albumin. In one specific embodiment, a binding molecule whose IgM, IgA, IgG/IgM, or IgG/IgA antibody binds to Tn antigen has an ADME-modulating moiety on the J-chain that comprises a human serum albumin-binding peptide. In one specific embodiment, a binding molecule whose IgM, IgA, IgG/IgM, or IgG/IgA antibody binds to Tn antigen has an ADME-modulating moiety on the J-chain that comprises a human serum albumin-binding antibody moiety. In one specific embodiment, a binding molecule whose IgM, IgA, IgG/IgM, or IgG/IgA antibody binds to Tn antigen has an ADME-modulating moiety on the J-chain that comprises a human serum albumin-binding scFv antibody fragment. In one specific embodiment, a binding molecule whose IgM, IgA, IgG/IgM, or IgG/IgA antibody binds to Tn antigen has an ADME-modulating moiety on the J-chain that comprises an FcRn-binding antibody moiety. In one specific embodiment, a binding molecule whose IgM, IgA, IgG/IgM, or IgG/IgA antibody binds to Tn antigen has an ADME-modulating moiety on the J-chain that comprises an FcRn-binding scFv antibody fragment. In one specific embodiment, a binding molecule whose IgM, IgA, IgG/IgM, or IgG/IgA antibody binds to Tn antigen has an ADME-modulating moiety on the J-chain that comprises an Fc domain.

In one specific embodiment, a binding molecule whose IgM, IgA, IgG/IgM, or IgG/IgA antibody binds to CD19 has an ADME-modulating moiety on the J-chain that comprises human serum albumin. In one specific embodiment, a binding molecule whose IgM, IgA, IgG/IgM, or IgG/IgA antibody binds to CD19 has an ADME-modulating moiety on the J-chain that comprises a human serum albumin-binding peptide. In one specific embodiment, a binding molecule whose IgM, IgA, IgG/IgM, or IgG/IgA antibody binds to CD19 has an ADME-modulating moiety on the J-chain that comprises a human serum albumin-binding antibody moiety. In one specific embodiment, a binding molecule whose IgM, IgA, IgG/IgM, or IgG/IgA antibody binds to CD19 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD19 has an ADME-modulating moiety on the J-chain that comprises an FcRn-binding antibody moiety. In one specific embodiment, a binding molecule whose IgM, IgA, IgG/IgM, or IgG/IgA antibody binds to CD19 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD19 has an ADME-modulating moiety on the J-chain that comprises an Fc domain.

In one specific embodiment, a binding molecule whose IgM, IgA, IgG/IgM, or IgG/IgA antibody binds to CD20 has an ADME-modulating moiety on the J-chain that comprises human serum albumin. In one specific embodiment, a binding molecule whose IgM, IgA, IgG/IgM, or IgG/IgA antibody binds to CD20 has an ADME-modulating moiety on the J-chain that comprises a human serum albumin-binding peptide. In one specific embodiment, a binding molecule whose IgM, IgA, IgG/IgM, or IgG/IgA antibody binds to CD20 has an ADME-modulating moiety on the J-chain that comprises a human serum albumin-binding antibody moiety. In one specific embodiment, a binding molecule whose IgM, IgA, IgG/IgM, or IgG/IgA antibody binds to CD20 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD20 has an ADME-modulating moiety on the J-chain that comprises an FcRn-binding antibody moiety. In one specific embodiment, a binding molecule whose IgM, IgA, IgG/IgM, or IgG/IgA antibody binds to CD20 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD20 has an ADME-modulating moiety on the J-chain that comprises an Fc domain.

In one specific embodiment, a binding molecule whose IgM, IgA, IgG/IgM, or IgG/IgA antibody binds to CD22 has an ADME-modulating moiety on the J-chain that comprises human serum albumin. In one specific embodiment, a binding molecule whose IgM, IgA, IgG/IgM, or IgG/IgA antibody binds to CD22 has an ADME-modulating moiety on the J-chain that comprises a human serum albumin-binding peptide. In one specific embodiment, a binding molecule whose IgM, IgA, IgG/IgM, or IgG/IgA antibody binds to CD22 has an ADME-modulating moiety on the J-chain that comprises a human serum albumin-binding antibody moiety. In one specific embodiment, a binding molecule whose IgM, IgA, IgG/IgM, or IgG/IgA antibody binds to CD22 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD22 has an ADME-modulating moiety on the J-chain that comprises an FcRn-binding antibody moiety. In one specific embodiment, a binding molecule whose IgM, IgA, IgG/IgM, or IgG/IgA antibody binds to CD22 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD22 has an ADME-modulating moiety on the J-chain that comprises an Fc domain.

In one specific embodiment, a binding molecule whose IgM, IgA, IgG/IgM, or IgG/IgA antibody binds to CD33 has an ADME-modulating moiety on the J-chain that comprises human serum albumin. In one specific embodiment, a binding molecule whose IgM, IgA, IgG/IgM, or IgG/IgA antibody binds to CD33 has an ADME-modulating moiety on the J-chain that comprises a human serum albumin-binding peptide. In one specific embodiment, a binding molecule whose IgM, IgA, IgG/IgM, or IgG/IgA antibody binds to CD33 has an ADME-modulating moiety on the J-chain that comprises a human serum albumin-binding antibody moiety. In one specific embodiment, a binding molecule whose IgM, IgA, IgG/IgM, or IgG/IgA antibody binds to CD33 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD33 has an ADME-modulating moiety on the J-chain that comprises an FcRn-binding antibody moiety. In one specific embodiment, a binding molecule whose IgM, IgA, IgG/IgM, or IgG/IgA antibody binds to CD33 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD33 has an ADME-modulating moiety on the J-chain that comprises an Fc domain.

In one specific embodiment, a binding molecule whose IgM, IgA, IgG/IgM, or IgG/IgA antibody binds to CD38 has an ADME-modulating moiety on the J-chain that comprises human serum albumin. In one specific embodiment, a binding molecule whose IgM, IgA, IgG/IgM, or IgG/IgA antibody binds to CD38 has an ADME-modulating moiety on the J-chain that comprises a human serum albumin-binding peptide. In one specific embodiment, a binding molecule whose IgM, IgA, IgG/IgM, or IgG/IgA antibody binds to CD38 has an ADME-modulating moiety on the J-chain that comprises a human serum albumin-binding antibody moiety. In one specific embodiment, a binding molecule whose IgM, IgA, IgG/IgM, or IgG/IgA antibody binds to CD38 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD38 has an ADME-modulating moiety on the J-chain that comprises an FcRn-binding antibody moiety. In one specific embodiment, a binding molecule whose IgM, IgA, IgG/IgM, or IgG/IgA antibody binds to CD38 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD38 has an ADME-modulating moiety on the J-chain that comprises an Fc domain.

In one specific embodiment, a binding molecule whose IgM, IgA, IgG/IgM, or IgG/IgA antibody binds to CD52 has an ADME-modulating moiety on the J-chain that comprises human serum albumin. In one specific embodiment, a binding molecule whose IgM, IgA, IgG/IgM, or IgG/IgA antibody binds to CD52 has an ADME-modulating moiety on the J-chain that comprises a human serum albumin-binding peptide. In one specific embodiment, a binding molecule whose IgM, IgA, IgG/IgM, or IgG/IgA antibody binds to CD52 has an ADME-modulating moiety on the J-chain that comprises a human serum albumin-binding antibody moiety. In one specific embodiment, a binding molecule whose IgM, IgA, IgG/IgM, or IgG/IgA antibody binds to CD52 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD52 has an ADME-modulating moiety on the J-chain that comprises an FcRn-binding antibody moiety. In one specific embodiment, a binding molecule whose IgM, IgA, IgG/IgM, or IgG/IgA antibody binds to CD52 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD52 has an ADME-modulating moiety on the J-chain that comprises an Fc domain.

In one specific embodiment, a binding molecule whose IgM, IgA, IgG/IgM, or IgG/IgA antibody binds to CD70 has an ADME-modulating moiety on the J-chain that comprises human serum albumin. In one specific embodiment, a binding molecule whose IgM, IgA, IgG/IgM, or IgG/IgA antibody binds to CD70 has an ADME-modulating moiety on the J-chain that comprises a human serum albumin-binding peptide. In one specific embodiment, a binding molecule whose IgM, IgA, IgG/IgM, or IgG/IgA antibody binds to CD70 has an ADME-modulating moiety on the J-chain that comprises a human serum albumin-binding antibody moiety. In one specific embodiment, a binding molecule whose IgM, IgA, IgG/IgM, or IgG/IgA antibody binds to CD70 has an ADME-modulating moiety on the J-chain that comprises a human serum albumin-binding scFv antibody fragment. In one specific embodiment, a binding molecule whose IgM, IgA, IgG/IgM, or IgG/IgA antibody binds to CD70 has an ADME-modulating moiety on the J-chain that comprises an FcRn-binding antibody moiety. In one specific embodiment, a binding molecule whose IgM, IgA, IgG/IgM, or IgG/IgA antibody binds to CD70 has an ADME-modulating moiety on the J-chain that comprises an FcRn-binding scFv antibody fragment. In one specific embodiment, a binding molecule whose IgM, IgA, IgG/IgM, or IgG/IgA antibody binds to CD70 has an ADME-modulating moiety on the J-chain that comprises an Fc domain.

In one specific embodiment, a binding molecule whose IgM, IgA, IgG/IgM, or IgG/IgA antibody binds to VEGF has an ADME-modulating moiety on the J-chain that comprises human serum albumin. In one specific embodiment, a binding molecule whose IgM, IgA, IgG/IgM, or IgG/IgA antibody binds to VEGF has an ADME-modulating moiety on the J-chain that comprises a human serum albumin-binding peptide. In one specific embodiment, a binding molecule whose IgM, IgA, IgG/IgM, or IgG/IgA antibody binds to VEGF has an ADME-modulating moiety on the J-chain that comprises a human serum albumin-binding antibody moiety. In one specific embodiment, a binding molecule whose IgM, IgA, IgG/IgM, or IgG/IgA antibody binds to VEGF has an ADME-modulating moiety on the J-chain that comprises a human serum albumin-binding scFv antibody fragment. In one specific embodiment, a binding molecule whose IgM, IgA, IgG/IgM, or IgG/IgA antibody binds to VEGF has an ADME-modulating moiety on the J-chain that comprises an FcRn-binding antibody moiety. In one specific embodiment, a binding molecule whose IgM, IgA, IgG/IgM, or IgG/IgA antibody binds to VEGF has an ADME-modulating moiety on the J-chain that comprises an FcRn-binding scFv antibody fragment. In one specific embodiment, a binding molecule whose IgM, IgA, IgG/IgM, or IgG/IgA antibody binds to VEGF has an ADME-modulating moiety on the J-chain that comprises an Fc domain. In one specific embodiment, a binding molecule whose IgM, IgA, IgG/IgM, or IgG/IgA antibody binds to VEGF has an ADME-modulating moiety on the J-chain that comprises a hyaluronic acid binding protein (HABP). In one specific embodiment, a binding molecule whose IgM, IgA, IgG/IgM, or IgG/IgA antibody binds to VEGF has an ADME-modulating moiety on the J-chain that comprises TSG-6. In one specific embodiment, a binding molecule whose IgM, IgA, IgG/IgM, or IgG/IgA antibody binds to VEGF has an ADME-modulating moiety on the J-chain that comprises a hyaluronic acid-binding antibody moiety. In one specific embodiment, a binding molecule whose IgM, IgA, IgG/IgM, or IgG/IgA antibody binds to VEGF has an ADME-modulating moiety on the J-chain that comprises a hyaluronic acid-binding scFv antibody fragment. In one specific embodiment, a binding molecule whose IgM, IgA, IgG/IgM, or IgG/IgA antibody binds to VEGF has an ADME-modulating moiety on the J-chain that comprises a TSG-6-binding antibody moiety. In one specific embodiment, a binding molecule whose IgM, IgA, IgG/IgM, or IgG/IgA antibody binds to VEGF has an ADME-modulating moiety on the J-chain that comprises a TSG-6-binding scFv antibody fragment.

In one specific embodiment, a binding molecule whose IgM, IgA, IgG/IgM, or IgG/IgA antibody binds to TNF alpha has an ADME-modulating moiety on the J-chain that comprises human serum albumin. In one specific embodiment, a binding molecule whose IgM, IgA, IgG/IgM, or IgG/IgA antibody binds to TNF alpha has an ADME-modulating moiety on the J-chain that comprises a human serum albumin-binding peptide. In one specific embodiment, a binding molecule whose IgM, IgA, IgG/IgM, or IgG/IgA antibody binds to TNF alpha has an ADME-modulating moiety on the J-chain that comprises a human serum albumin-binding antibody moiety. In one specific embodiment, a binding molecule whose IgM, IgA, IgG/IgM, or IgG/IgA antibody binds to TNF alpha has an ADME-modulating moiety on the J-chain that comprises a human serum albumin-binding scFv antibody fragment. In one specific embodiment, a binding molecule whose IgM, IgA, IgG/IgM, or IgG/IgA antibody binds to TNF alpha has an ADME-modulating moiety on the J-chain that comprises an FcRn-binding antibody moiety. In one specific embodiment, a binding molecule whose IgM, IgA, IgG/IgM, or IgG/IgA antibody binds to TNF alpha has an ADME-modulating moiety on the J-chain that comprises an FcRn-binding scFv antibody fragment. In one specific embodiment, a binding molecule whose IgM, IgA, IgG/IgM, or IgG/IgA antibody binds to TNF alpha has an ADME-modulating moiety on the J-chain that comprises an Fc domain. In one specific embodiment, a binding molecule whose IgM, IgA, IgG/IgM, or IgG/IgA antibody binds to TNF alpha has an ADME-modulating moiety on the J-chain that comprises a hyaluronic acid binding protein (HABP). In one specific embodiment, a binding molecule whose IgM, IgA, IgG/IgM, or IgG/IgA antibody binds to TNF alpha has an ADME-modulating moiety on the J-chain that comprises TSG-6. In one specific embodiment, a binding molecule whose IgM, IgA, IgG/IgM, or IgG/IgA antibody binds to TNF alpha has an ADME-modulating moiety on the J-chain that comprises a hyaluronic acid-binding antibody moiety. In one specific embodiment, a binding molecule whose IgM, IgA, IgG/IgM, or IgG/IgA antibody binds to TNF alpha has an ADME-modulating moiety on the J-chain that comprises a hyaluronic acid-binding scFv antibody fragment. In one specific embodiment, a binding molecule whose IgM, IgA, IgG/IgM, or IgG/IgA antibody binds to TNF alpha has an ADME-modulating moiety on the J-chain that comprises a TSG-6-binding antibody moiety. In one specific embodiment, a binding molecule whose IgM, IgA, IgG/IgM, or IgG/IgA antibody binds to TNF alpha has an ADME-modulating moiety on the J-chain that comprises a TSG-6-binding scFv antibody fragment.

In one specific embodiment, a binding molecule whose IgM, IgA, IgG/IgM, or IgG/IgA antibody binds to amyloid beta has an ADME-modulating moiety on the J-chain that comprises human serum albumin. In one specific embodiment, a binding molecule whose IgM, IgA, IgG/IgM, or IgG/IgA antibody binds to amyloid beta has an ADME-modulating moiety on the J-chain that comprises a human serum albumin-binding peptide. In one specific embodiment, a binding molecule whose IgM, IgA, IgG/IgM, or IgG/IgA antibody binds to amyloid beta has an ADME-modulating moiety on the J-chain that comprises a human serum albumin-binding antibody moiety. In one specific embodiment, a binding molecule whose IgM, IgA, IgG/IgM, or IgG/IgA antibody binds to amyloid beta has an ADME-modulating moiety on the J-chain that comprises a human serum albumin-binding scFv antibody fragment. In one specific embodiment, a binding molecule whose IgM, IgA, IgG/IgM, or IgG/IgA antibody binds to amyloid beta has an ADME-modulating moiety on the J-chain that comprises an FcRn-binding antibody moiety. In one specific embodiment, a binding molecule whose IgM, IgA, IgG/IgM, or IgG/IgA antibody binds to amyloid beta has an ADME-modulating moiety on the J-chain that comprises an FcRn-binding scFv antibody fragment. In one specific embodiment, a binding molecule whose IgM, IgA, IgG/IgM, or IgG/IgA antibody binds to amyloid beta has an ADME-modulating moiety on the J-chain that comprises an Fc domain.

In one specific embodiment, a binding molecule whose IgM, IgA, IgG/IgM, or IgG/IgA antibody binds to amyloid beta has an ADME-modulating moiety on the J-chain that comprises transferrin. In one specific embodiment, a binding molecule whose IgM, IgA, IgG/IgM, or IgG/IgA antibody binds to amyloid beta has an ADME-modulating moiety on the J-chain that comprises a transferrin-binding antibody moiety. In one specific embodiment, a binding molecule whose IgM, IgA, IgG/IgM, or IgG/IgA antibody binds to amyloid beta has an ADME-modulating moiety on the J-chain that comprises a transferrin-binding scFv antibody fragment. In one specific embodiment, a binding molecule whose IgM, IgA, IgG/IgM, or IgG/IgA antibody binds to amyloid beta has an ADME-modulating moiety on the J-chain that comprises a transferrin receptor-binding antibody moiety. In one specific embodiment, a binding molecule whose IgM, IgA, IgG/IgM, or IgG/IgA antibody binds to amyloid beta has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises leptin. In one specific embodiment, a binding molecule whose IgM, IgA, IgG/IgM, or IgG/IgA antibody binds to amyloid beta has an ADME-modulating moiety on the J-chain that comprises a leptin-binding antibody moiety. In one specific embodiment, a binding molecule whose IgM, IgA, IgG/IgM, or IgG/IgA antibody binds to amyloid beta has an ADME-modulating moiety on the J-chain that comprises a leptin-binding scFv antibody fragment. In one specific embodiment, a binding molecule whose IgM, IgA, IgG/IgM, or IgG/IgA antibody binds to amyloid beta has an ADME-modulating moiety on the J-chain that comprises a leptin receptor-binding antibody moiety. In one specific embodiment, a binding molecule whose IgM, IgA, IgG/IgM, or IgG/IgA antibody binds to amyloid beta has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises insulin. In one specific embodiment, a binding molecule whose IgM, IgA, IgG/IgM, or IgG/IgA antibody binds to amyloid beta has an ADME-modulating moiety on the J-chain that comprises an insulin-binding antibody moiety. In one specific embodiment, a binding molecule whose IgM, IgA, IgG/IgM, or IgG/IgA antibody binds to amyloid beta has an ADME-modulating moiety on the J-chain that comprises an insulin-binding scFv antibody fragment. In one specific embodiment, a binding molecule whose IgM, IgA, IgG/IgM, or IgG/IgA antibody binds to amyloid beta has an ADME-modulating moiety on the J-chain that comprises an insulin receptor-binding antibody moiety. In one specific embodiment, a binding molecule whose IgM, IgA, IgG/IgM, or IgG/IgA antibody binds to amyloid beta has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises IGF-1. In one specific embodiment, a binding molecule whose IgM, IgA, IgG/IgM, or IgG/IgA antibody binds to amyloid beta has an ADME-modulating moiety on the J-chain that comprises an IGF-1-binding antibody moiety. In one specific embodiment, a binding molecule whose IgM, IgA, IgG/IgM, or IgG/IgA antibody binds to amyloid beta has an ADME-modulating moiety on the J-chain that comprises an IGF-1-binding scFv antibody fragment. In one specific embodiment, a binding molecule whose IgM, IgA, IgG/IgM, or IgG/IgA antibody binds to amyloid beta has an ADME-modulating moiety on the J-chain that comprises an IGF-1 receptor-binding antibody moiety. In one specific embodiment, a binding molecule whose IgM, IgA, IgG/IgM, or IgG/IgA antibody binds to amyloid beta has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to amyloid beta has an ADME-modulating moiety on the J-chain that comprises basigin. In one specific embodiment, a binding molecule whose IgM, IgA, IgG/IgM, or IgG/IgA antibody binds to amyloid beta has an ADME-modulating moiety on the J-chain that comprises a basigin-binding antibody moiety. In one specific embodiment, a binding molecule whose IgM, IgA, IgG/IgM, or IgG/IgA antibody binds to amyloid beta has an ADME-modulating moiety on the J-chain that comprises a basigin-binding scFv antibody fragment.

In one specific embodiment, a binding molecule whose IgM, IgA, IgG/IgM, or IgG/IgA antibody binds to amyloid beta has an ADME-modulating moiety on the J-chain that comprises Glut1. In one specific embodiment, a binding molecule whose IgM, IgA, IgG/IgM, or IgG/IgA antibody binds to amyloid beta has an ADME-modulating moiety on the J-chain that comprises a Glut1-binding antibody moiety. In one specific embodiment, a binding molecule whose IgM, IgA, IgG/IgM, or IgG/IgA antibody binds to amyloid beta has an ADME-modulating moiety on the J-chain that comprises a Glut1-binding scFv antibody fragment.

In one specific embodiment, a binding molecule whose IgM, IgA, IgG/IgM, or IgG/IgA antibody binds to amyloid beta has an ADME-modulating moiety on the J-chain that comprises CD98hc. In one specific embodiment, a binding molecule whose IgM, IgA, IgG/IgM, or IgG/IgA antibody binds to amyloid beta has an ADME-modulating moiety on the J-chain that comprises a CD98hc-binding antibody moiety. In one specific embodiment, a binding molecule whose IgM, IgA, IgG/IgM, or IgG/IgA antibody binds to amyloid beta has an ADME-modulating moiety on the J-chain that comprises a CD98hc-binding scFv antibody fragment.

In one specific embodiment, a binding molecule whose IgM, IgA, IgG/IgM, or IgG/IgA antibody binds to BACE has an ADME-modulating moiety on the J-chain that comprises human serum albumin. In one specific embodiment, a binding molecule whose IgM, IgA, IgG/IgM, or IgG/IgA antibody binds to BACE has an ADME-modulating moiety on the J-chain that comprises a human serum albumin-binding peptide. In one specific embodiment, a binding molecule whose IgM, IgA, IgG/IgM, or IgG/IgA antibody binds to BACE has an ADME-modulating moiety on the J-chain that comprises a human serum albumin-binding antibody moiety. In one specific embodiment, a binding molecule whose IgM, IgA, IgG/IgM, or IgG/IgA antibody binds to BACE has an ADME-modulating moiety on the J-chain that comprises a human serum albumin-binding scFv antibody fragment. In one specific embodiment, a binding molecule whose IgM, IgA, IgG/IgM, or IgG/IgA antibody binds to BACE has an ADME-modulating moiety on the J-chain that comprises an FcRn-binding antibody moiety. In one specific embodiment, a binding molecule whose IgM, IgA, IgG/IgM, or IgG/IgA antibody binds to BACE has an ADME-modulating moiety on the J-chain that comprises an FcRn-binding scFv antibody fragment. In one specific embodiment, a binding molecule whose IgM, IgA, IgG/IgM, or IgG/IgA antibody binds to BACE has an ADME-modulating moiety on the J-chain that comprises an Fc domain.

In one specific embodiment, a binding molecule whose IgM, IgA, IgG/IgM, or IgG/IgA antibody binds to BACE has an ADME-modulating moiety on the J-chain that comprises transferrin. In one specific embodiment, a binding molecule whose IgM, IgA, IgG/IgM, or IgG/IgA antibody binds to BACE has an ADME-modulating moiety on the J-chain that comprises a transferrin-binding antibody moiety. In one specific embodiment, a binding molecule whose IgM, IgA, IgG/IgM, or IgG/IgA antibody binds to BACE has an ADME-modulating moiety on the J-chain that comprises a transferrin-binding scFv antibody fragment. In one specific embodiment, a binding molecule whose IgM, IgA, IgG/IgM, or IgG/IgA antibody binds to BACE has an ADME-modulating moiety on the J-chain that comprises a transferrin receptor-binding antibody moiety. In one specific embodiment, a binding molecule whose IgM, IgA, IgG/IgM, or IgG/IgA antibody binds to BACE has an ADME-modulating moiety on the J-chain that comprises a transferrin receptor-binding scFv antibody fragment.

In one specific embodiment, a binding molecule whose IgM, IgA, IgG/IgM, or IgG/IgA antibody binds to BACE has an ADME-modulating moiety on the J-chain that comprises leptin. In one specific embodiment, a binding molecule whose IgM, IgA, IgG/IgM, or IgG/IgA antibody binds to BACE has an ADME-modulating moiety on the J-chain that comprises a leptin-binding antibody moiety. In one specific embodiment, a binding molecule whose IgM, IgA, IgG/IgM, or IgG/IgA antibody binds to BACE has an ADME-modulating moiety on the J-chain that comprises a leptin-binding scFv antibody fragment. In one specific embodiment, a binding molecule whose IgM, IgA, IgG/IgM, or IgG/IgA antibody binds to BACE has an ADME-modulating moiety on the J-chain that comprises a leptin receptor-binding antibody moiety. In one specific embodiment, a binding molecule whose IgM, IgA, IgG/IgM, or IgG/IgA antibody binds to BACE has an ADME-modulating moiety on the J-chain that comprises a leptin receptor-binding scFv antibody fragment.

In one specific embodiment, a binding molecule whose IgM, IgA, IgG/IgM, or IgG/IgA antibody binds to BACE has an ADME-modulating moiety on the J-chain that comprises insulin. In one specific embodiment, a binding molecule whose IgM, IgA, IgG/IgM, or IgG/IgA antibody binds to BACE has an ADME-modulating moiety on the J-chain that comprises an insulin-binding antibody moiety. In one specific embodiment, a binding molecule whose IgM, IgA, IgG/IgM, or IgG/IgA antibody binds to BACE has an ADME-modulating moiety on the J-chain that comprises an insulin-binding scFv antibody fragment. In one specific embodiment, a binding molecule whose IgM, IgA, IgG/IgM, or IgG/IgA antibody binds to BACE has an ADME-modulating moiety on the J-chain that comprises an insulin receptor-binding antibody moiety. In one specific embodiment, a binding molecule whose IgM, IgA, IgG/IgM, or IgG/IgA antibody binds to BACE has an ADME-modulating moiety on the J-chain that comprises an insulin receptor-binding scFv antibody fragment.

In one specific embodiment, a binding molecule whose IgM, IgA, IgG/IgM, or IgG/IgA antibody binds to BACE has an ADME-modulating moiety on the J-chain that comprises IGF-1. In one specific embodiment, a binding molecule whose IgM, IgA, IgG/IgM, or IgG/IgA antibody binds to BACE has an ADME-modulating moiety on the J-chain that comprises an IGF-1-binding antibody moiety. In one specific embodiment, a binding molecule whose IgM, IgA, IgG/IgM, or IgG/IgA antibody binds to BACE has an ADME-modulating moiety on the J-chain that comprises an IGF-1-binding scFv antibody fragment. In one specific embodiment, a binding molecule whose IgM, IgA, IgG/IgM, or IgG/IgA antibody binds to BACE has an ADME-modulating moiety on the J-chain that comprises an IGF-1 receptor-binding antibody moiety. In one specific embodiment, a binding molecule whose IgM, IgA, IgG/IgM, or IgG/IgA antibody binds to BACE has an ADME-modulating moiety on the J-chain that comprises an IGF-1 receptor-binding scFv antibody fragment.

In one specific embodiment, a binding molecule whose IgM, IgA, IgG/IgM, or IgG/IgA antibody binds to BACE has an ADME-modulating moiety on the J-chain that comprises basigin. In one specific embodiment, a binding molecule whose IgM, IgA, IgG/IgM, or IgG/IgA antibody binds to BACE has an ADME-modulating moiety on the J-chain that comprises a basigin-binding antibody moiety. In one specific embodiment, a binding molecule whose IgM, IgA, IgG/IgM, or IgG/IgA antibody binds to BACE has an ADME-modulating moiety on the J-chain that comprises a basigin-binding scFv antibody fragment.

In one specific embodiment, a binding molecule whose IgM, IgA, IgG/IgM, or IgG/IgA antibody binds to BACE has an ADME-modulating moiety on the J-chain that comprises Glut1. In one specific embodiment, a binding molecule whose IgM, IgA, IgG/IgM, or IgG/IgA antibody binds to BACE has an ADME-modulating moiety on the J-chain that comprises a Glut1-binding antibody moiety. In one specific embodiment, a binding molecule whose IgM, IgA, IgG/IgM, or IgG/IgA antibody binds to BACE has an ADME-modulating moiety on the J-chain that comprises a Glut1-binding scFv antibody fragment.

In one specific embodiment, a binding molecule whose IgM, IgA, IgG/IgM, or IgG/IgA antibody binds to BACE has an ADME-modulating moiety on the J-chain that comprises CD98hc. In one specific embodiment, a binding molecule whose IgM, IgA, IgG/IgM, or IgG/IgA antibody binds to BACE has an ADME-modulating moiety on the J-chain that comprises a CD98hc-binding antibody moiety. In one specific embodiment, a binding molecule whose IgM, IgA, IgG/IgM, or IgG/IgA antibody binds to BACE has an ADME-modulating moiety on the J-chain that comprises a CD98hc-binding scFv antibody fragment.

It is to be understood that an IgM, IgA, IgG/IgM or IgG/IgA antibody that binds to any of the listed targets described herein can be combined with a modified J-chain with any of the ADME-modulating moieties listed herein to create a binding molecule. Thus, any antibody target listed herein can be combined with any ADME-modulating moiety listed herein. FIG. 13 provides a list of non-limiting examples of antibody targets and ADME-modulating moieties that can be included on a J-chain of a binding molecule in accordance with aspects of the invention. Any of the antibody targets listed in the left column of FIG. 13 can be combined with any of the ADME-modulating moieties listed in the right column of FIG. 13.

While certain preferred embodiments are specifically referred to herein, it is to be understood that IgM, IgA, IgG/IgM and IgG/IgA antibodies with binding specificity to any target, such as any tumor antigen, comprising a modified J-chain with any ADME-modulating moiety described herein are contemplated and are within the scope of the present invention.

In a preferred embodiment, the multi-specific IgM, IgA, IgG/IgM or IgG/IgA antibody binds to one or more of the tumor targets listed herein, while the J-chain comprises an ADME-modulating moiety.

In another preferred embodiment, the J-chain of the subject binding molecules includes an ADME-modulating moiety that is an scFv, and that reduces clearance of the binding molecule by binding to albumin. In one preferred embodiment, the ADME-modulating moiety on the J-chain is an scFv that binds to albumin.

In one preferred embodiment, a binding molecule includes an IgM antibody that binds to CD20, and the ADME-modulating moiety on the J-chain is human serum albumin (HSA). In another preferred embodiment, a binding molecule includes an IgM antibody that binds to CD20, and the ADME-modulating moiety on the J-chain is an anti-albumin scFv.

In one preferred embodiment, a binding molecule includes an IgM antibody that binds to DR5, and the ADME-modulating moiety on the J-chain is human serum albumin (HSA). In another preferred embodiment, a binding molecule includes an IgM antibody that binds to DR5, and the ADME-modulating moiety on the J-chain is an anti-albumin scFv.

In one preferred embodiment, a binding molecule includes an IgM antibody that binds to BACE, and the ADME-modulating moiety on the J-chain is transferrin. In another preferred embodiment, a binding molecule includes an IgM antibody that binds to BACE, and the ADME-modulating moiety on the J-chain is an anti-transferrin receptor scFv. In one preferred embodiment, a binding molecule includes an IgM antibody that binds to BACE, and the ADME-modulating moiety on the J-chain is an anti-transferrin scFv.

In one preferred embodiment, a binding molecule includes an IgM antibody that binds to VEGF, and the ADME-modulating moiety on the J-chain is hyaluronic acid binding protein (HABP). In another preferred embodiment, a binding molecule includes an IgM antibody that binds to VEGF, and the ADME-modulating moiety on the J-chain is an anti-hyaluronic acid scFv.

In one preferred embodiment, a binding molecule includes an IgM antibody that binds to TNF alpha, and the ADME-modulating moiety on the J-chain is hyaluronic acid binding protein (HABP). In another preferred embodiment, a binding molecule includes an IgM antibody that binds to TNF alpha, and the ADME-modulating moiety on the J-chain is an anti-hyaluronic acid scFv.

Figure 4A:
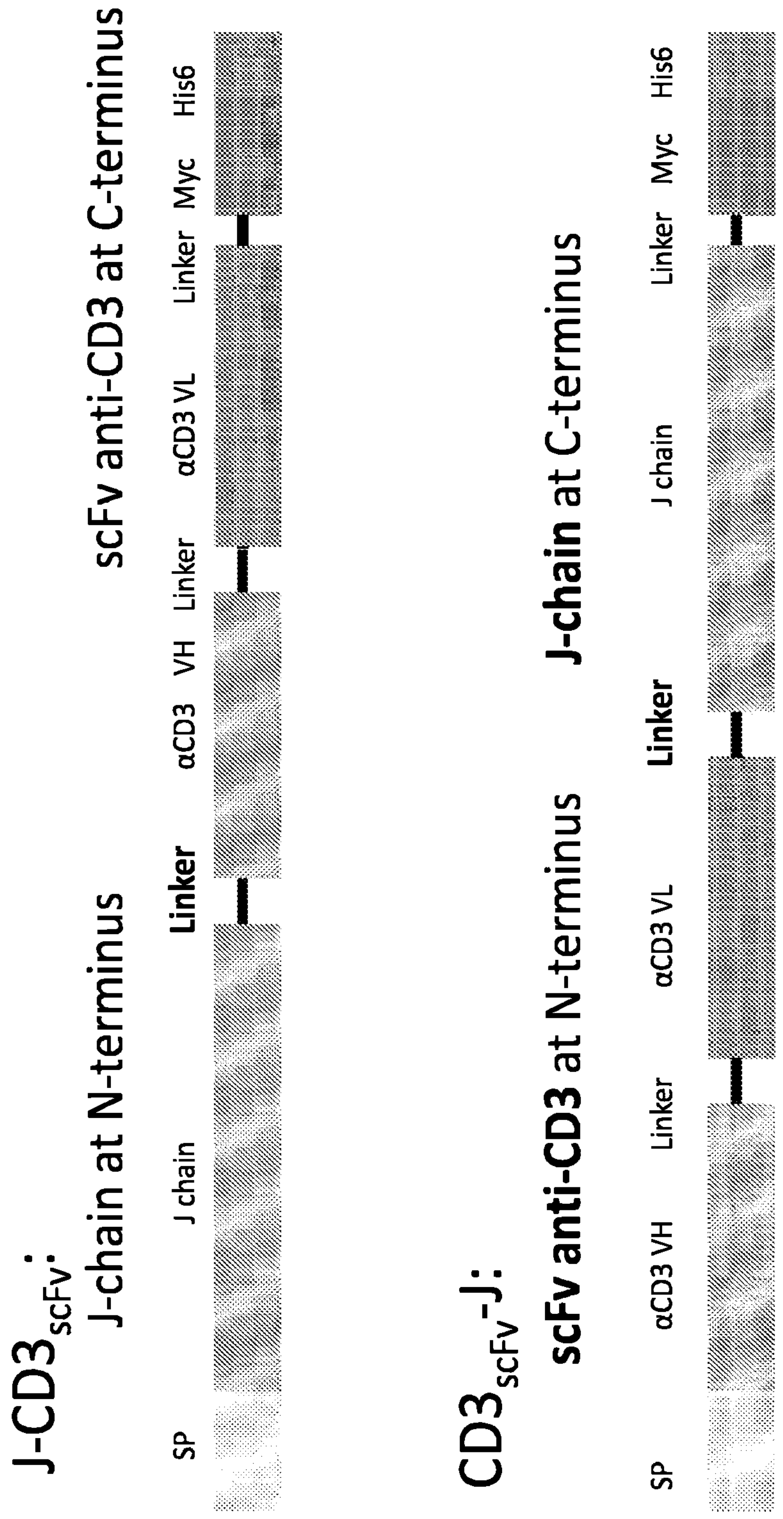
FIG. 4A illustrates two different orientations of J-chain constructs comprising a modified J-chain with a moiety that binds to CD3. The top illustration is an example of a modified J-chain that is in the J-linker-V orientation, with a binding moiety (e.g., an anti-CD3 scFv antibody fragment) positioned at the C-terminus of the modified J-chain. The bottom illustration is an example of a modified J-chain that is in the V-linker-J orientation, with a binding moiety (e.g., an anti-CD3 scFv antibody fragment) positioned at the N-terminus of the modified J-chain.
Figure 4B:
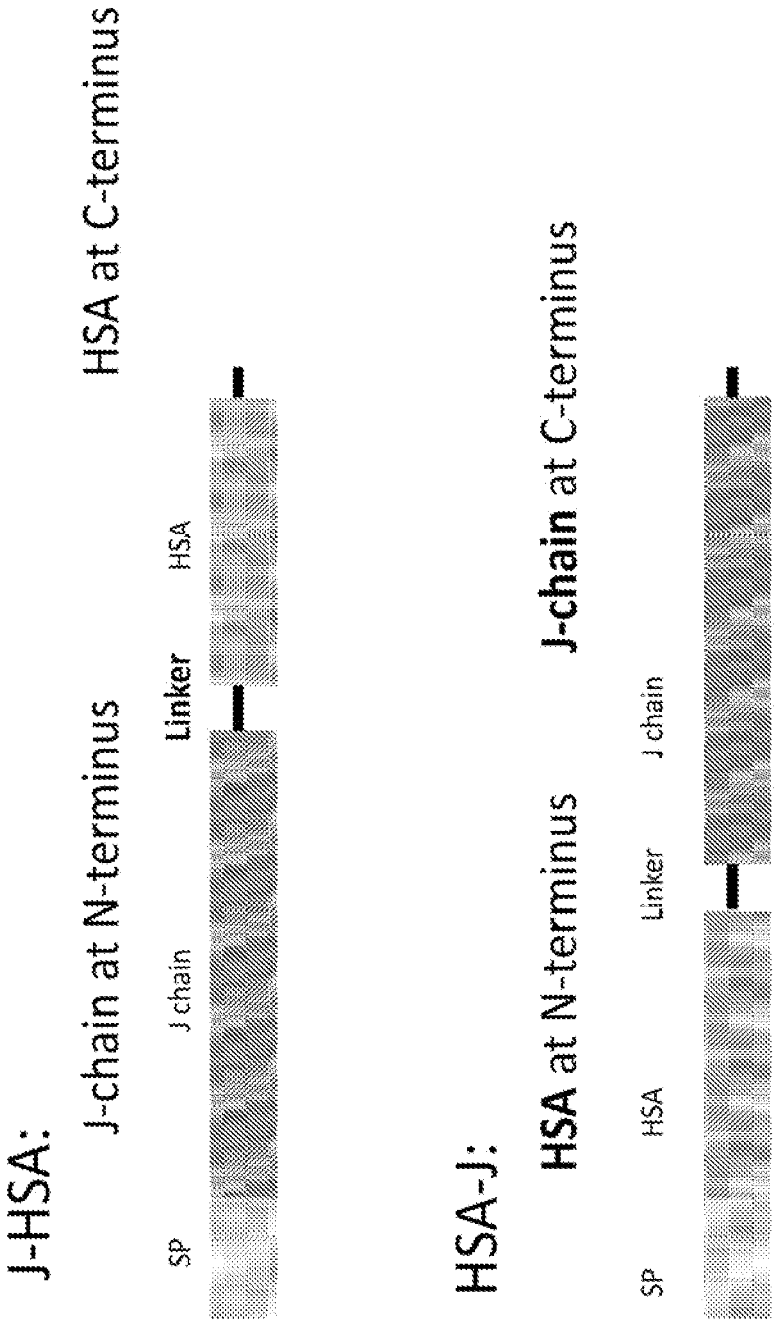
FIG. 4B illustrates two different orientations of J-chain constructs comprising a modified J-chain with an HSA-containing moiety. The top illustration is an example of a modified J-chain that is in the J-linker-ADME orientation, with an ADME modulating moiety (e.g., a human serum albumin (HSA) polypeptide) positioned at the C-terminus of the modified J-chain. The bottom illustration is an example of a modified J-chain that is in the ADME-linker-J orientation, with an ADME modulating moiety (e.g., a human serum albumin (HSA) polypeptide) positioned at the N-terminus of the modified J-chain.

In all embodiments, an ADME-modulating moiety of the modified J-chain may be introduced before or after the J-chain. Thus, a modified J-chain with an anti-albumin scFv ADME-modulating moiety that increases the retention of the binding molecule in the circulation by binding to albumin may have an anti-albumin scFv-J or a J-anti-albumin scFv configuration. A schematic illustration of two non-limiting examples of such configurations are provided in FIGS. 4A and 4B.

Due to their increased avidity, the subject binding molecules are superior relative to bispecific IgG antibodies. For example, as a result, they are suitable for targeting low level expression targets, such as Rituxan-resistant Burkitt lymphoma cells characterized by a low level of CD20 expression. In addition, the IgM, IgA, IgG/IgM and IgG/IgA antibodies herein comprising a modified J-chain have greatly enhanced potency relative to bispecific IgG antibodies.

Pharmaceutical Compositions of Antibodies with Modified J-Chain

For therapeutic uses, the subject binding molecules can be formulated into pharmaceutical compositions. A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it may be necessary to coat the compound with, or coadminister the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The compositions may also contain adjuvants such as preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

The following examples, sequence listing and figures are provided to aid the understanding of the present invention, the true scope of which is set forth in the appended claims. It is understood that modifications can be made in the procedures set forth without departing from the spirit of the invention.

Further details of the invention are illustrated by the following non-limiting Examples.

Example 1: IgMs can be Conjugated to Multiple scFvs on Either End of the J-Chain with No Effect on Functional Activity The J-chain of an IgM molecule can be linked in frame with an scFv designed to bind a target of interest at either its C- or N-terminus, and the resultant bispecific IgMs are not perturbed in structure or function as evidenced by no diminution in their CDC activity.

1. Generation of DNA Constructs with Designed Mutations

DNA construct synthesis. All the DNA constructs with designed mutations are synthesized by commercial vendors (Genescript), with compatible restriction sites at both ends for sub-cloning into respective expression vectors.

Constructing expression vectors. The synthesized DNA constructs are re-suspended in Tris-EDTA buffer at 1 μg/ml. DNA (1 μg) is subjected to enzyme digestion and the synthesized gene is separated from the carrier plasmid DNA by electrophoresis. The digested DNA is ligated to pre-digested plasmid DNA (pCAGGS for J-chain, Gene 108 (1991) 193-200) by standard molecular biology techniques. The ligated DNA is transformed into competent bacteria and plated on LB plates with multiple selective antibiotics. Several bacterial colonies are picked and DNA preparations are made by standard molecular biology techniques. The prepared DNA are verified by sequencing. Only the bacterial clones with 100% match of DNA sequence with the designed DNA sequence are used for plasmid DNA preparation and subsequently for cell transfection.

IgM heavy chain: This heavy chain construct has a full length μ chain for an anti-CD20 IgM which binds CD20 on the surface of B-cells:

```
IgM Heavy chain sequence of an anti-CD20 antibody:
                                        (SEQ ID: 16)
MGWSYIILFLVATATGVHSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSSGSASAPTLFP

LVSCENSPSDTSSVAVGCLAQDFLPDSITFSWKYKNNSDISSTRGFPSVL

RGGKYAATSQVLLPSKDVMQGTDEHVVCKVQHPNGNKEKNVPLPVIAELP

PKVSVFVPPRDGFFGNPRKSKLICQATGFSPRQIQVSWLREGKQVGSGVT

TDQVQAEAKESGPTTYKVTSTLTIKESDWLSQSMFTCRVDHRGLTFQQNA

SSMCVPDQDTAIRVFAIPPSFASIFLTKSTKLTCLVTDLTTYDSVTISWT

RQNGEAVKTHTNISESHPNATFSAVGEASICEDDWNSGERFTCTVTHTDL

PSPLKQTISRPKGVALHRPDVYLLPPAREQLNLRESATITCLVTGFSPAD

VFVQWMQRGQPLSPEKYVTSAPMPEPQAPGRYFAHSILTVSEEEWNTGET

YTCVVAHEALPNRVTERTVDKSTGKPTLYNVSLVMSDTAGTCY
```

This heavy chain construct has a molecular weight about 64 kD and when co-expressed with light chain, the resultant IgM is able to bind to CDIM positive B cells.

```
IgM Light chain sequence of an anti-CD20 antibody:
                                     (SEQ ID NO: 17)
MDMRVPAQLLGLLLLWLRGARCQIVLSQSPAILSASPGEKVTMTCRASSS

VSYIHWFQQKPGSSPKPWIYATSNLASGVPVRFSGSGSGTSYSLTISRVE

AEDAATYYCQQWTSNPPTFGGGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC
```

The light chain construct has a molecular weight of about 24 kD and when co-expressed with the appropriate heavy chain (SEQ ID NO: 16) is able to bind to CDIM positive B cells.

Different J-chains. In order to demonstrate that J-chain variants were able to couple with IgM, two different J-chain variants are constructed with distinct fusion sites incorporating anti-CD3 antibody (OKT3 scFv).

i. This construct is composed of an scFv of OKT3 (anti-CD3) fused with N-terminus of human J-chain (CD3scFv-15 aa Linker-J, O15J):

(SEQ ID NO: 18)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYSLDYWGQGTTLTVSSGGGGSGGGGSGGGGSQIVLTQSPAIMSA

SPGEKVTMTCSASSSVSYMNWYQQKSGTSPKRWIYDTSKLASGVPAHFR

GSGSGTSYSLTISGMEAEDAATYYCQQWSSNPFTFGSGTKLEIKGGGGS

GGGGSGGGGSQEDERIVLVDNKCKCARITSRIIRSSEDPNEDIVERNIR

IIVPLNNRENISDPTSPLRTRFVYHLSDLCKKCDPTEVELDNQIVTATQ

SNICDEDSATETCYTYDRNKCYTAVVPLVYGGETKMVETALTPDACYPD

GGGSEQKLISEEDLNSAVDHHHHHH

This construct has a molecular weight about 45 kD and is able to bind to soluble epsilon chain of CD3 (Sino Biological), or T cells; and is able to bind to anti-myc monoclonal antibody 4A6 or other anti-myc antibodies.

ii. This construct is composed of a scFv of OKT3 (anti-CD3) fused with C-terminus of human J-chain (J-15 aa Linker-CD3scFv, J15O):

(SEQ ID NO: 19)
QEDERIVLVDNKCKCARITSRIIRSSEDPNEDIVERNIRIIVPLNNREN

ISDPTSPLRTRFVYHLSDLCKKCDPTEVELDNQIVTATQSNICDEDSAT

ETCYTYDRNKCYTAVVPLVYGGETKMVETALTPDACYPDGGGGSGGGGS

GGGGSQVQLQQSGAELARPGASVKMSCKASGYTFTRYTMHWVKQRPGQG

LEWIGYINPSRGYTNYNQKFKDKATLTTDKSSSTAYMQLSSLTSEDSAV

YYCARYYDDHYSLDYWGQGTTLTVSSGGGGSGGGGSGGGGSQIVLTQSP

AIMSASPGEKVTMTCSASSSVSYMNWYQQKSGTSPKRWIYDTSKLASGV

PAHFRGSGSGTSYSLTISGMEAEDAATYYCQQWSSNPFTFGSGTKLEIK

EQKLISEEDLNSAVDHHHHHH-

This J-CD3scFv construct has a molecular weight about 45 kD and is able to bind to soluble epsilon chain of CD3 (Sino Biological), or T cells; and is able to bind to anti-myc monoclonal antibody 4A6 or other anti-myc antibodies.

To establish that assembly of bispecific IgM is feasible with a modified J-chain carrying an anti-CD3 scFv of a different sequence than that used in Examples 1 and 2, a J-chain carrying the variable regions from the antibody Visilizumab (Nuvion) was performed. Shown below are the sequences for two J-chains with the scFv corresponding to Visilizumab (V) fused to the J-chain through a linker containing 15 amino acid residues in two different orientations—V15J and J15V.

J chain sequence for V15J:
(SEQ ID NO: 20)
MGWSYIILFLVATATGVHSQVQLVQSGAEVKKPGASVKVSCKASGYTFI

SYTMHWVRQAPGQGLEWMGYINPRSGYTHYNQKLKDKATLTADKSASTA

YMELSSLRSEDTAVYYCARSAYYDYDGFAYWGQGTLVTVSSGGGGSGGG

-continued

GSGGGGSDIQMTQSPSSLSASVGDRVTITCSASSSVSYMNWYQQKPGKA

PKRLIYDTSKLASGVPSRFSGSGSGTDFTLTISSLQPEDFATYYCQQWS

SNPPTFGGGTKLEIKGGGGSGGGGSGGGGSQEDERIVLVDNKCKCARIT

SRIIRSSEDPNEDIVERNIRIIVPLNNRENISDPTSPLRTRFVYHLSDL

CKKCDPTEVELDNQIVTATQSNICDEDSATETCYTYDRNKCYTAVVPLV

YGGETKMVETALTPDACYPD

J-chain sequence for J15V:
(SEQ ID NO: 21)
MKNHLLFWGVLAVFIKAVHVKAQEDERIVLVDNKCKCARITSRIIRSSE

DPNEDIVERNIRIIVPLNNRENISDPTSPLRTRFVYHLSDLCKKCDPTE

VELDNQIVTATQSNICDEDSATETCYTYDRNKCYTAVVPLVYGGETKMV

ETALTPDACYPDGGGGSGGGGSGGGGSQVQLVQSGAEVKKPGASVKVSC

KASGYTFISYTMHWVRQAPGQGLEWMGYINPRSGYTHYNQKLKDKATLT

ADKSASTAYMELSSLRSEDTAVYYCARSAYYDYDGFAYWGQGTLVTVSS

GGGGSGGGGSGGGGSDIQMTQSPSSLSASVGDRVTITCSASSSVSYMNW

YQQKPGKAPKRLIYDTSKLASGVPSRFSGSGSGTDFTLTISSLQPEDFA

TYYCQQWSSNPPTFGGGTKLEIK

Figure 6:
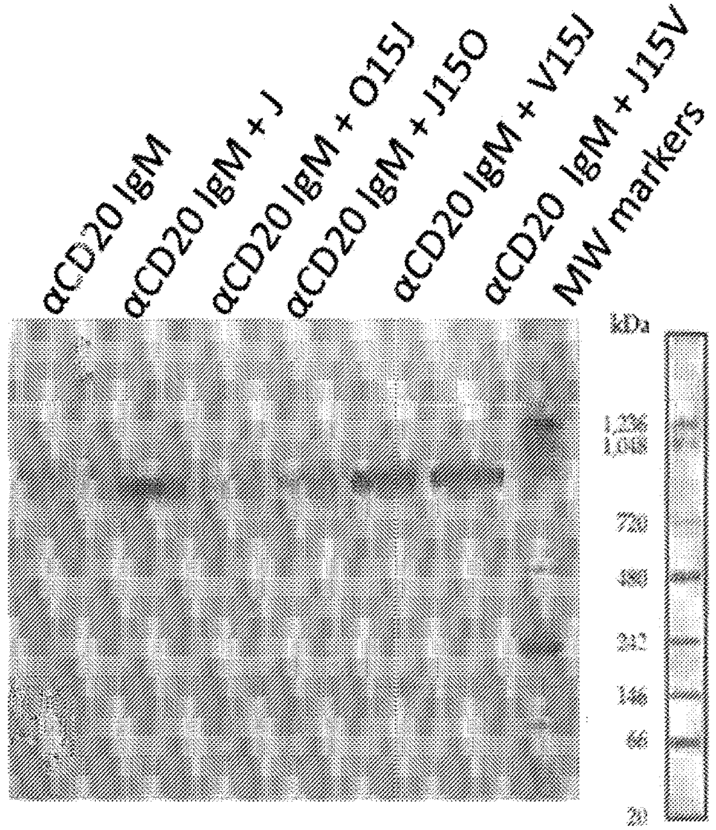
FIG. 6 shows SDS PAGE analysis of anti-CD20 IgM antibodies with or without various anti-CD3 binding moieties on the J-chain in either orientation. J-chain containing IgM pentamers are easily distinguished from the hexameric IgM without J-chain.

DNA corresponding to these sequences was synthesized and transfected into HEK293 cells along with the heavy and light chains for anti-CD20 IgM to produce protein which was then purified using the camelid antibody affinity matrix specific for IgM. As shown in FIG. 6, J-chains fused to the new anti-CD3 scFv with the 15 aa linker are able to incorporate into the IgM and the pentameric form of bispecific IgM with the corresponding J-chain is clearly distinguishable from the hexameric form without a J-chain.

2. Protein Expression, Purification and Characterization
   a. Transfection. Heavy, Light and Modified J-chain DNA is transfected into CHO cells. DNA for expression vectors are mixed typically in 1:1:1 ratio with PEI and then added to CHO-S cells. PEI transfection with CHO-S cells is conducted according to established techniques (see Biotechnology and Bioengineering, Vol 87, 553-545).
   b. Immunoprecipitation
      i. Capture Select IgM (BAC, Thermo Fisher). IgM proteins from transfected CHO cell supernatants are partially purified by immuno-precipitation with Capture Select IgM affinity matrix according to manufacturers' protocol (GE Life Sciences). After incubation at room temperature for 2 hours, the affinity matrix is separated from the supernatant by centrifugation. The matrix is further washed with PBS for 3 times before the PBS is carefully removed. The captured protein is eluted from the matrix by incubating with NuPage LDS protein buffer (Life Technology) for 5 minutes.
      ii. Anti-myc agarose affinity matrix (Sigma). IgM proteins from transfected CHO cell supernatants are partially purified by immunoprecipitation with anti-myc affinity matrix according to manufacturers' protocol. After incubation at room temperature for 2 hours, the affinity matrix is separated from the supernatant by centrifugation. The matrix is further washed with PBS for 3 times before the PBS is carefully removed after the final wash. The captured protein is eluted from the matrix by incubating with NuPage LDS protein buffer (Life Technology) for 5 minutes.

c. Gel electrophoresis i. Non-reducing SDS PAGE separates native IgM and its mutant forms according to size. Pentameric IgM, composed of homodimeric heavy and light chains, produces a protein band of approximately 1,000,000 molecular weight. NuPage LDS Sample Buffer (Life Technologies) is added to IgM protein samples at 25 C for 30 minutes before loading onto the gel. NativePage Novex 3-12% Bis-Tris Gel (Life Technologies) is used with Novex Tris-Acetate SDS Running Buffer (Life Technologies). Run gel until the dye front reaches the bottom of the gel.

ii. Reducing SDS-PAGE. NuPage LDS sample buffer (Life Technologies) and NuPage reducing agent dithiothreitol (Life Technologies) are added to IgM protein samples and heated to 80° C. for 10 minutes before loading on NuPage Novex 4-12% Bis-Tris Gel (Life Technologies). NuPage MES SDS Running Buffer (Life Technologies) is used for gel electrophoresis. Gels are run until the dye front reaches the bottom of the gel. After electrophoresis is complete, remove gel from apparatus and stain the gel using Colloidal Blue Staining (Life Technologies).

iii. The DNA corresponding to these heavy and light chains as well as that corresponding to either the wild-type (wt) J-chain, O15J or J15O J-chain sequences described above were co-transfected into HEK293 cells and proteins expressed and purified using the camelid resin as described before. As shown in FIG. 6, all four proteins express well. The anti-CD20 IgM hexamer without J-chain is clearly resolved from the J-chain containing pentamers for the IgM pentamer with the wild type J-chain as well as for the bispecific IgMs where the anti-CD3 scFv is linked to the J-chain in either orientation (O15J or J15O).

Figure 7:
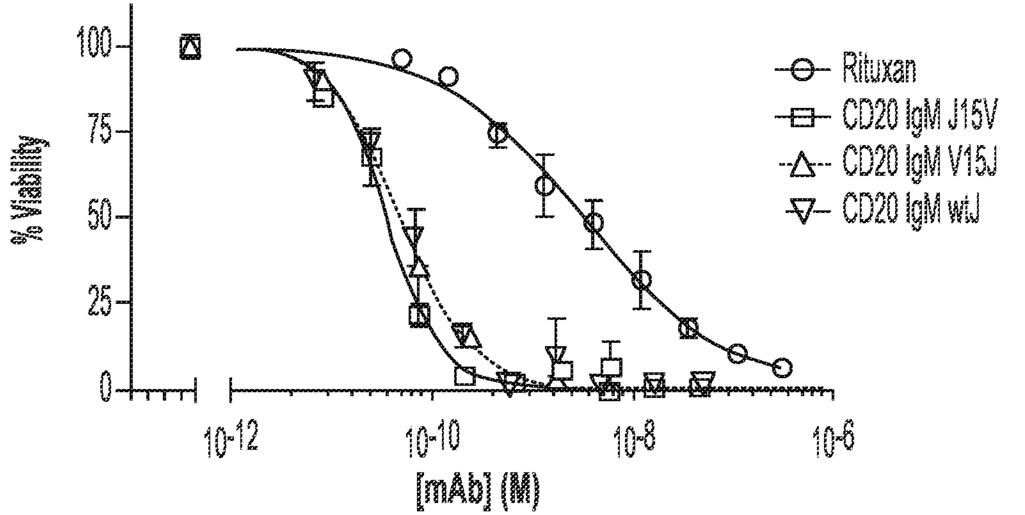
FIG. 7 is a graph showing cell viability as a function of antibody concentration for various antibody constructs in a complement dependent cytotoxicity assay in the presence of IgG, IgM or IgM's carrying various J-chains. A table is provided with the EC50 values for each construct.

Analysis of Complement Dependent Cytotoxicity for Family of IgMs with and without Incorporated J-Chains Complement dependent cytotoxicity is a key mechanism for cell killing by antibodies. IgM antibodies are known to have enhanced complement dependent cell killing (CDC) due to their multimeric form. A key aspect of this invention was to test if incorporation of modified J-chains, which carry scFv or camelid Vhh binders of effector cells at either their C- or N-termini, causes interference with binding of C1q—the key component of the complement pathway, and therefore may inhibit CDC. The CDC activity of each of the IgM and bispecific IgM constructs was measured. As shown in FIG. 7, incorporation of the modified J-chain has, unexpectedly, no deleterious effect on the CDC activity of the bispecific IgMs. Moreover, with the linker lengths tested, it was found that the bispecific IgMs have CDC activity between 60-100 fold enhanced over the corresponding IgG on a molar basis (FIG. 7).

Example 2: Bispecific IgMs can Bind Two Targets Simultaneously and Show Functional Effects The DNA corresponding to these heavy and light chains as well as that corresponding to either the wild-type (wt) J-chain (FIG. 3), V15J or J15V J-chain sequences shown above were co-transfected into HEK293 cells and proteins expressed and purified using the camelid resin as described before. As shown in FIG. 6, all four proteins express well. The anti-CD20 IgM hexamer without J-chain is clearly resolved from the J-chain containing pentamers for the IgM pentamer with the wild type J-chain as well as for the bispecific IgMs where the anti-CD3 scFv is linked to the J-chain in either orientation.

Figure 8:
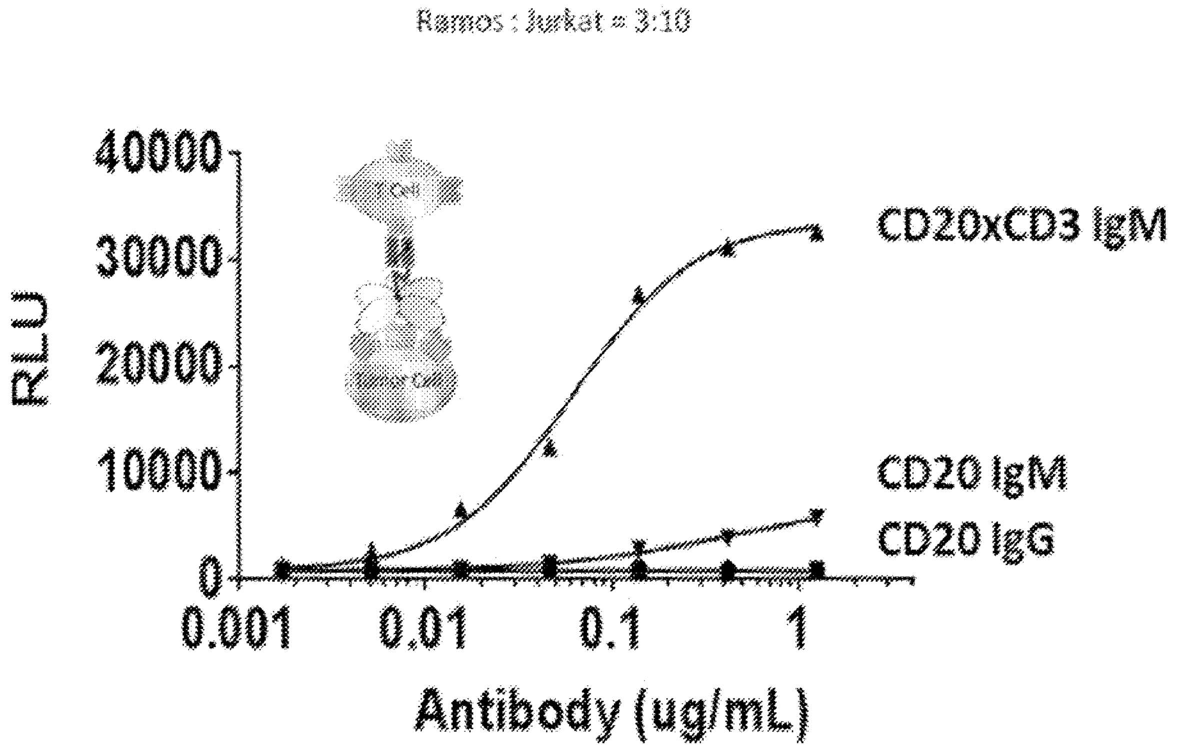
FIG. 8 is a graph showing results of a T-cell activation assay comparing the ability of an anti-CD20 IgM with a CD3 binding moiety on the J-chain to activate T-cells, as compared to anti-CD20 IgM antibodies without a CD3 binding moiety on the J-chain, as well as anti-CD20 IgG antibodies.

Purified proteins were analyzed for T-cell activation using a commercially available Luciferase reporter gene based kit (Promega). Briefly, purified protein was added to 7500 Ramos and 25000 engineered Jurkat cells (Promega CS176403) in 40 uL RPMI with 10% FBS. Mixture was incubated for 5h 37 C with 5% $CO_2$. Cells were mixed with lysis buffer containing luciferin to measure luciferase reporter activity. Light output was measured by EnVision plate reader and analyzed by Prism software. As shown in FIG. 8, only the antibodies that carried the CD3 specific scFv binding moiety on the J-chain are able to show dose dependent activation, whereas the IgM antibody lacking the modified J-chain or the IgG are unable to show any signal in this assay.

Figure 9:
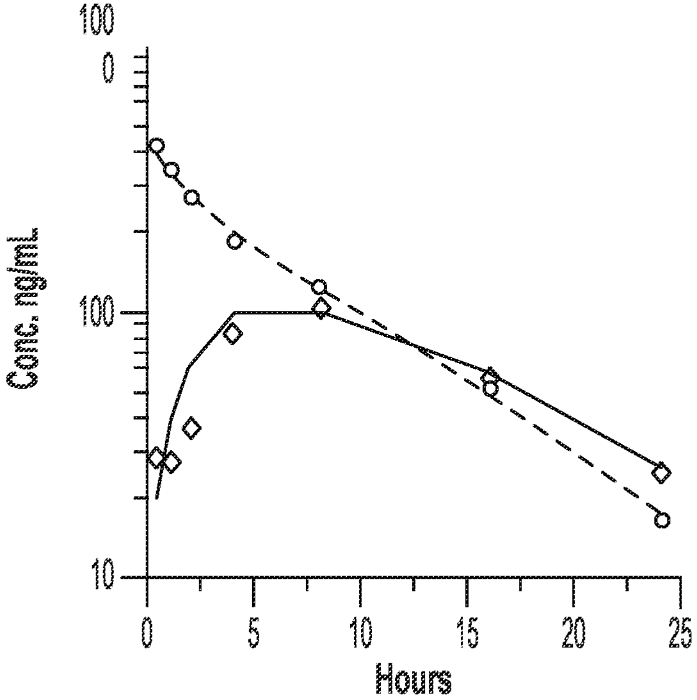
FIG. 9, Panel A is a graph showing IgM concentration in mice in the absence of half-life extension for CDIM binding IgM 55.5. Panel B is a table providing PK parameters.

Example 3: Construction and Testing of Anti-CD20 Antibody with Albumin Binding Domain Tethered to J-Chain The half-life of IgMs in human plasma is estimated to be around 2-3 days and shorter still in mice (FIG. 9). This is significantly shorter than for IgGs, which interact with the neonatal Fc receptor (FcRn) and are recycled after endocytosis enabling a much longer half-life of roughly 21 days. In order to increase the half-life of IgMs, tethering of scFvs to either terminus of the J-chain was performed, without significantly altering the effector functions of IgMs such as CDC (FIG. 7).

There are several approaches that have been described in the art to enable half-life extension of biologics. These include tethering of mutants of human serum albumin (Andersen et al, JBC VOL. 289, NO. 19, pp. 13492-13502, 2014), peptides (Dennis et al, *J Biol. Chem.* 2002, 277: 35035-35043) or scFvs that can bind human serum albumin (Muller et al mAbs 4:6, 673-685; 2012), Shown below is the sequence of an example J-chain that can be used to extend the half-life of IgMs by utilizing an albumin binding domain designed for binding to human serum albumin with high affinity (Hopp et al PEDS 23:pp 827-833 (2010)).

```
Albumin binding domain:
                                        (SEQ ID NO: 22)
QHDEAVDANSLAEAKVLANRELDKYGVSDYYKNLINNAKTVEGVKALID
EILAALP

Wt J-chain:
                                        (SEQ ID NO: 1)
QEDERIVLVDNKCKCARITSRIIRSSEDPNEDIVERNIRIIVPLNNREN
ISDPTSPLRTRFVYHLSDLCKKCDPTEVELDNQIVTATQSNICDEDSAT
ETCYTYDRNKCYTAVVPLVYGGETKMVETALTPDACYPD

A15J:
                                        (SEQ ID NO: 23)
QHDEAVDANSLAEAKVLANRELDKYGVSDYYKNLINNAKTVEGVKALID

EILAALPGGGGSGGGGSGGGGSQEDERIVLVDNKCKCARITSRIIRSSE

DPNEDIVERNIRIIVPLNNRENISDPTSPLRTRFVYHLSDLCKKCDPTE

VELDNQIVTATQSNICDEDSATETCYTYDRNKCYTAVVPLVYGGETKMV

ETALTPDACYPD
```

Expression and assembly of this ABD-J-chain fusion into IgMs was tested using the IgM sequence described in Example 1. In addition, fusion of this ABD to J-chain was verified not to perturb the CDC activity on anti-CD20 IgM on target cell lines carrying CD20 on their surface (eg. Ramos) as described in Example 1. Finally, the affinity of ABD in the context of the IgM, for binding to HSA was measured using immobilized HSA using surface plasmon resonance (Biacore).

Example 4: Construction and Testing of Anti-CD20 Antibody with Transferrin Binding scFv Delivery of biologic drugs to targets in the central nervous system, particularly the brain, is a challenging problem because of the Blood Brain Barrier (BBB). The transferrin receptor (TfR) is overexpressed in the endothelium of the BBB. It is thought to act as a shuttle to transport nutrients such as iron from the periphery to the brain. Receptor mediated transcytosis (RMT) has been used by several groups to deliver biologics to the brain. For example, Jones et al have described the use of transferrin binding antibodies as a method of shuttling biologics across the BBB (Jones, A. R., and E. V. Shusta. 2007. Blood-brain barrier transport of therapeutics via receptor-mediation. Pharm. Res. 24:1759-1771).

One such transferrin binding sequence was used (Vh sequence selected from phage display by Yang et al) to make an in-frame fusion with our J-chain as shown below.

Figure 10:
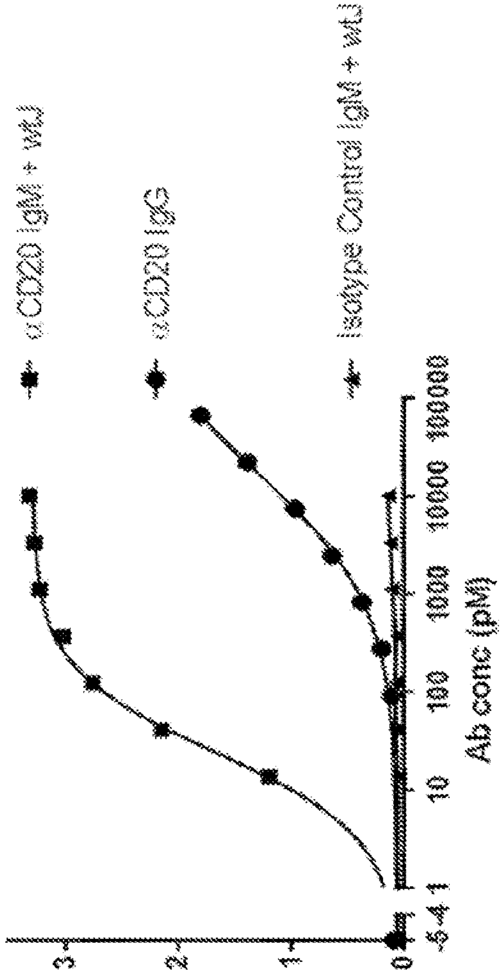
FIG. 10 is a graph showing results of a multimer specific ELISA for anti-CD20 IgM antibodies demonstrating the vastly tighter binding of IgM.

PBST washes, HRP-conjugated anti-human IgG Fc antibody (Abcam, diluted in StartingBlock at a ratio of 1:10,000) was added to each well, and the plate was further incubated at 37° C. for 1 hour. After three PBST washes, colorimetric TMB substrate (US Biological) was added to each well to perform a peroxidase reaction. After the addition of stop solution (1 M H2SO4), the absorbance was monitored at 450 nm and the equilibrium constant ($K_D$) for the antibody was calculated by fitting the resultant data with Graph Pad Prism. For testing CD20 binding, an ELISA using immobilized CD20-Fc (Acros Biosystems) was used as illustrated in FIG. 10. Detection antibody for this ELISA is a mouse anti-human kappa light chain antibody conjugated with HRP (Southern Biotech, 9230-05). Capture, detection and development are carried out as detailed above.

To verify that the resultant IgM binds to target cells by using FACS based assay such as those described in Example 1, on tumor cell lines known to overexpress the transferrin receptor for example the human erythroleukemia cell line K562. Mean fluorescence intensity readings were analyzed using GraphPad Prism to calculate a $K_d$.

Example 5: Use of Site Specific Chemoenzymatic Labeling to Generate Imaging Agents and Antibody Drug Conjugates with IgMs IgMs are very large biomolecules (>1 MDa with J-chain). Labeling of IgMs to enable visualization in animal studies is

```
Transferrin receptor binding Vh sequence:
                                                (SEQ ID NO: 24)
MAQVQLLESGGGLVQPGGSLRLSCAASGFIFNTEYMAWVRQ

APGKGLEWVSAIKEQSGSTYYADSVKGRFTISRDNSKNTLY

LQMNSLRAEDTAVYYCAAQMHHEAEVKFWGQGTLVTV

S

Transferrin receptor binding Vh sequence fused to J-chain at
N-terminus:
                                                (SEQ ID NO: 25)
MAQVQLLESGGGLVQPGGSLRLSCAASGFIFNTEYMAWVRQ

APGKGLEWVSAIKEQSGSTYYADSVKGRFTISRDNSKNTLY

LQMNSLRAEDTAVYYCAAQMHHEAEVKFWGQGTL

VTVSGGGGSGGGGSGGGGSQEDERIVLVDNKCKCARITSRIIRSSEDPNEDIVERNIRII

VPLNNRENISDPTSPLRTRFVYHLSDLCKKCDPTEVELDNQIVTATQSNICDEDSATET

CYTYDRNKCYTAVVPLVYGGETKMVETALTPDACYPD
```

The fusion J-chain was incorporated into a relevant IgM (for example the CD20 IgM described previously). In addition to the assays described earlier for expression and assembly, antigen binding, cell binding and cell internalization assays were carried out to verify that the resultant IgM+TfR J-chain is functional.

Antigen binding was tested using ELISAs with commercially available recombinant human transferrin receptor (R&D Systems) immobilized on plates. Briefly, ~100 ng of human transferrin receptor was added to a 96-Wellplate (Nunc Maxisorb plate) per well at 4 C, overnight. The plate was washed with PBS-0.05% Tween-20 three times and blocked with StartingBlock (Pierce) at 37 C for 1 hour. Then the plate was washed with PBST three times after the blocking solution was removed. The bispecific antibodies with different concentrations were added to each well and the plate was allowed to stand at 37 C for 1 hour. After three problematic because of the numerous free lysine residues. In order to enable labeling with stoichiometry and positions that retain the activity of IgMs, site specific labeling is carried out using chemo-enzymatic approaches as reviewed in Kline et al (Pharm Res 2014 Dec. 16).

One method for site specifically labeling IgM molecules is to use a glycan labeling strategy as described in Houghton et al (PNAS (52) 15850-15855). The method uses a combination of enzymes-beta galactosidase to remove a terminal galactose residue and then a promiscuous galactose transferase (GalTY289L) to install an azide labeled sugar (GlcNAz) that can be used to post-synthetically add a DIBO labeled dye or cytotoxin. Because the heavy chain of IgMs carries five glycans as opposed to the single glycan on each heavy chain of an IgG antibody, much more efficient labeling is expected using this approach with an antibody to dye/drug ratio of up to 1:102 if the glycan on the J-chain is also derivatized. As shown in FIG. 10, using an example IgM (1.5.3V15J15HSA) efficient labeling was demonstrated with this approach, and an Alexa 647 DIBO dye. Clearly, a similar approach can also be used to generate IgMs that are labeled with PET tracers and cytotoxic molecules.

Figure 12:
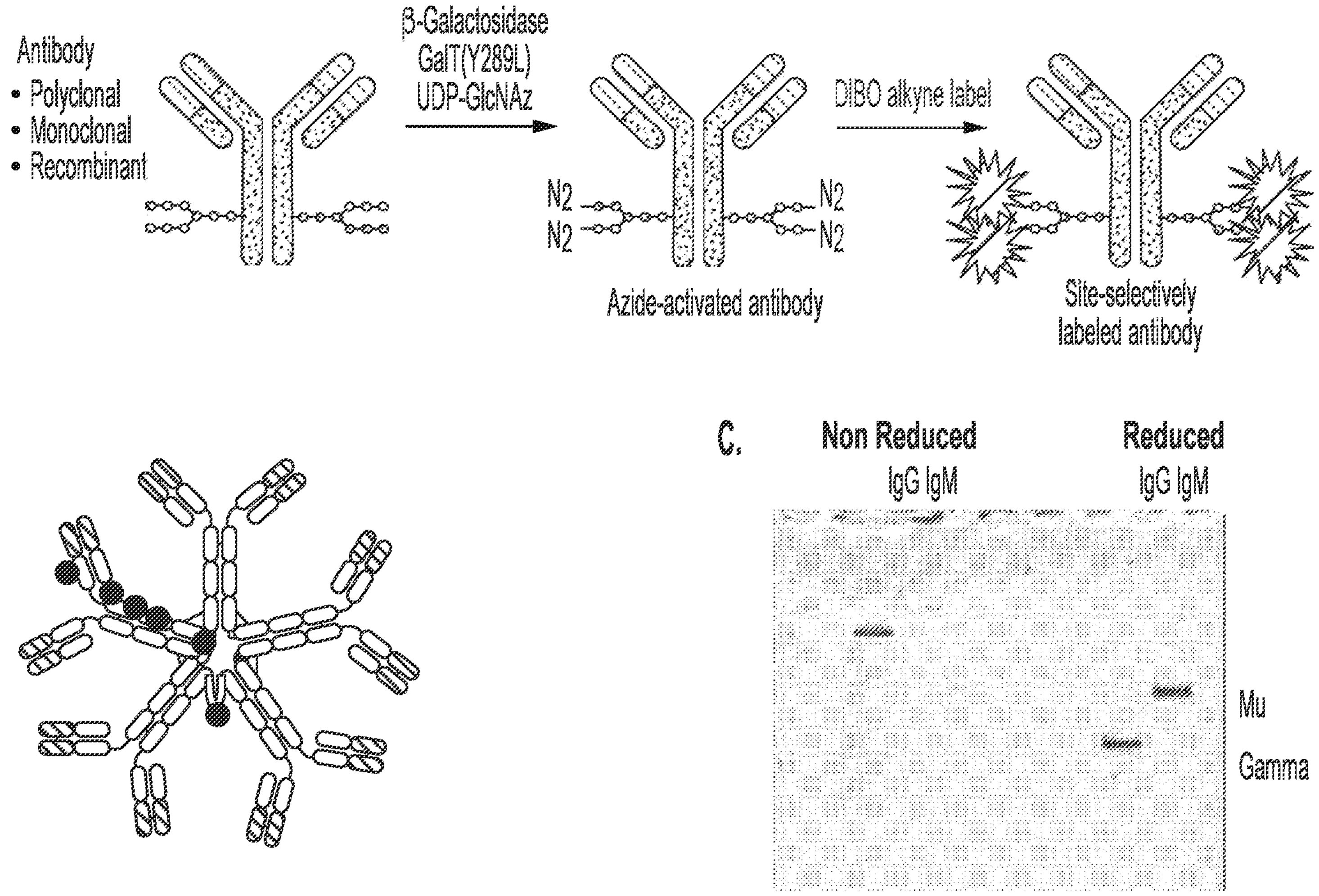
FIG. 12 Panel A is a schematic illustration depicting site specific labeling of glycans on IgG using chemoenzymatic approach. Panel B shows the position of glycans on IgM heavy chain and J-chain. Panel C shows the non-reduced and reduced gels for the labeled products after using chemoenzymatic labeling.

As a second example of using an acceptor sequence on the J-chain for post-translational site-specific labeling, the "LLQGA" recognition site of microbial transglutaminase (mTGase) is added to the C-terminus of J-chain as shown below (FIG. 12).

```
J chain with "Q Tag":
                                        (SEQ ID NO: 26)
QEDERIVLVDNKCKCARITSRIIRSSEDPNEDIVERNIRIIVPLNNRE

NISDPTSPLRTRFVYHLSDLCKKCDPTEVELDNQIVTATQSNICDEDS

ATETCYTYDRNKCYTAVVPLVYGGETKMVETALTPDACYPDGGGGSGG

GGSGGGGSLLQGA
```

Next, dye molecules with a primary amine at its terminus e.g Alexa 488 Cadaverine (Thermo Scientific) was reacted with IgMs incorporating this J-chain in the presence of mTGAse under standard conditions (Strop et al Bioconjugate Chemistry 2015 26(4) 650-9). After incubation overnight at room temperature with 5× molar excess of dye, free dye was separated from labeled IgM using size exclusion chromatography on a NAP-5 column (Biorad). Incorporation of dye was quantitated using absorbance at 488 nm.

It follows that such methods can also be used with other enzymes that can be used for chemo-enzymatic modification as well as other small molecules (e.g., cytotoxic drugs) that carry appropriate handles for functionalization.

Example 6: In Vivo Bio-Distribution Studies Using IgMs Labeled with Near Infra-Red Dye VivoTag680 (Perkin Elmer)

In order to follow the bio-distribution of IGM-55.5 in mice, the molecule was labeled with a near infra-red dye VivoTag680 (Perkin Elmer) using standard amine coupling with an NHS ester at neutral pH (Vasquez et al, PLoS One. 2011; 6: e20594). The injected group received an intravenous injection with 2 nmol/mouse of the labeled IgM molecule. The background control group remained un-injected as a way to distinguish the fluorescence signal of the labeled antibodies from low level background signal, which is primarily from food in the gut. The t0 imaging time point was performed immediately after injection with antibody. Mice were sacrificed after the final in vivo imaging timepoint, followed by resection of tissues and ex vivo imaging.

A generalized schematic of a temporal biodistribution model assessed by in vivo 3D FMT is presented in FIG. 11 Panel A. This type of study is well suited to non-invasively determine both the blood PK of labeled antibodies (determined from the decrease in fluorescence signal of blood in the heart), as well as kinetic biodistribution into various organ systems (brain, lungs, heart, liver, kidneys, stomach, intestines, bladder, and skin). For each animal at each time point, the blood fluorescence signal was subtracted from the total signal of each of the other organs to provide a more accurate determination of tissue accumulation. The in vivo tissues were also assessed ex vivo at the terminal time point by epifluorescence. Ex vivo epifluorescence measurements were also obtained for gall bladder, muscle, spleen, pancreas, white blood cells, lymph nodes, and intestines (which were flushed prior to imaging to remove fecal material).

Whole body and head bio-distribution imaging was performed on the FMT4000 at 0, 1, 2, 4, 8, 24, 48, and 96 h post-injection. Additional animals were bled at 0, 1, 2, 4, 8, 24, 48, 96 h, and these blood samples were shipped to IGM Biosciences for assay. For tomographic imaging, animals were positioned in the supine position within an imaging cassette that provided gentle restraint and mild compression. All images were successfully acquired at the planned timepoints. Whole body non-invasive biodistribution and blood pharmacokinetics showed rapid blood clearance ($t\frac{1}{2}$=20 minutes) and dominant liver accumulation with some stomach and kidney signal. Un-injected controls showed only low level signal within the stomach and intestines, and data from IgM-injected mice were corrected for these background levels. The accumulation in liver, kidney and stomach was very rapid and achieved the highest levels at 1 h post-injection, partially clearing by 96 h. The majority of the signal resided in the liver (approximately 5× that of the other tissues); but when normalizing for tissue weight, comparable signal intensity could be seen in the stomach, with somewhat lower signal intensity in the kidneys (FIG. 11, Panel B). Such in vivo studies can also be carried out with the IgMs carrying modified J-chains to assess the increase in half-life or tissue distribution.

Example 7: Pharmacokinetics of IgG v. IgM with J-Chain

Pharmacokinetic (PK) studies were conducted in Balb/c mice to assess clearance of IgG and IgM antibodies, with and without an attached modified J-chain. 100 ug of each antibody was administered to the mice via intravenous infusion. Approximately 500 uL of blood was collected by terminal cardiac puncture at each timepoint, with 3 mice per timepoint, and 8 or 15 timepoints total. ELISA was used to measure the concentration of each antibody in the blood. Quality metrics were verified on all ELISAs, and PK parameters were derived using standard curve fitting techniques.

Figure 16:
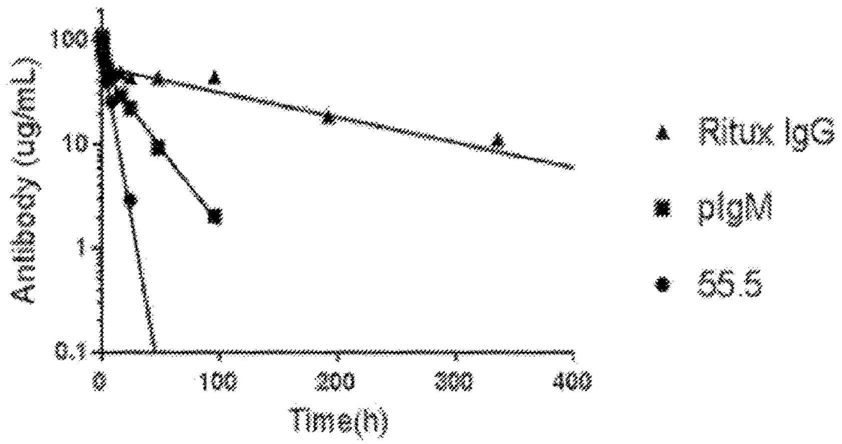
FIG. 16, Panel A, is a graph showing antibody concentration as a function of time in a BALB/c mouse PK experiment for a model IgG (Rituximab), serum derived polyclonal IgM from humans, and an engineered CHO cell derived IgM (55.5). Panel B is a table showing alpha and beta half-life, and AUC for these three different antibodies.

PK results from Rituximab, polyclonal IgM and IgM 55.5 are provided in FIG. 16. These results demonstrate that IgM half-life in mice is significantly shorter that IgG half-life, as evidenced by the fact Rituximab (IgG) had a longer half-life than either the polyclonal IgM of the IgM 55.5. In addition, the half-life of IgM 55.5, produced in CHO cells, was shorter than that of human polyclonal IgM.

Figure 17:
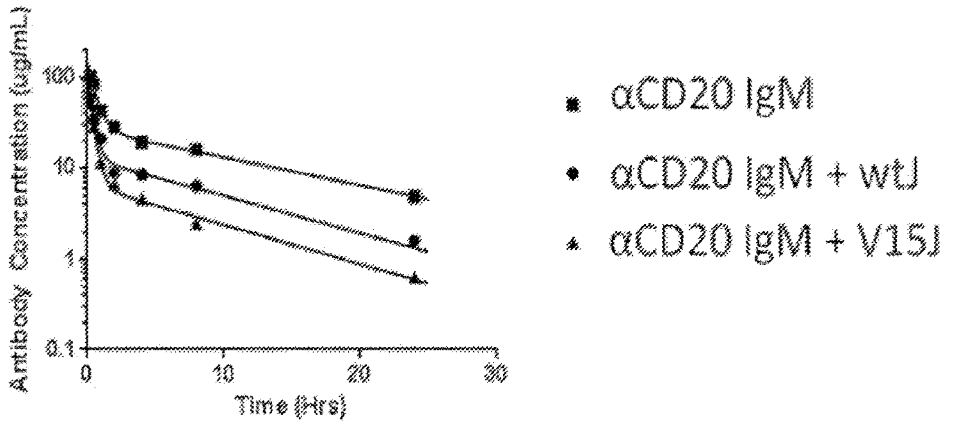
FIG. 17, Panel A, is a graph showing antibody concentration as a function of time in a PK experiment in BALB/c mice testing the effect of J-chain incorporation in IgM. Panel B is a table showing alpha and beta half-life, and AUC for three different IgM antibodies with wild type (wt) or J-chain fused with an scFv configured to bind T-cells.

Results from IgM 1.5.3 with and without J-chain are provided in FIG. 17. As shown, the half-life of IgM 1.5.3 with no J-chain (1.5.3 IgM) was comparable to the half-life of IgM 55.5. The addition of a wild-type J-chain reduced the half-life of IgM 1.5.3. Addition of a J-chain having the V-linker-J orientation (1.5.3. V15J) further reduced the half-life of the antibody. These results demonstrate that the addition of J-chain to an IgM antibody reduces the half-life of the antibody.

Example 8: Fusion of an Albumin Binding Domain to the J-Chain Significantly Reduces Clearance of IgMs As noted above, the pharmacokinetics of IgMs indicate rapid blood clearance. Experiments were performed to determine the serum half-life-extending effects of tethering an albumin binding domain (ABD) (SEQ ID NO: 22) to an IgM J-chain. DNA corresponding to the IgM heavy and light chains as shown in Example 1, as well as that corresponding to either the V15J sequence of Example 1 (Visilizumab (V) fused to the J-chain through a linker containing 15 amino acid residues) or the A15J sequence of Example 3 (an albumin-binding domain fused to the J-chain through a linker containing 15 amino acid residues) were co-transfected into HEK293 cells, and the proteins were expressed and purified using the camelid resin as described before. Three groups of mice received an intravenous injection with 100 ug/mouse of either V15J-1.5.3-IgM, A15J-1.5.3-IgM, or Rituximab (IgG). Blood samples were taken periodically following the initial injection, and the serum concentration of each injected antibody was measured in the samples using an ELISA that was adapted to measure the concentration of the tested antibodies in serum.

Figure 18:
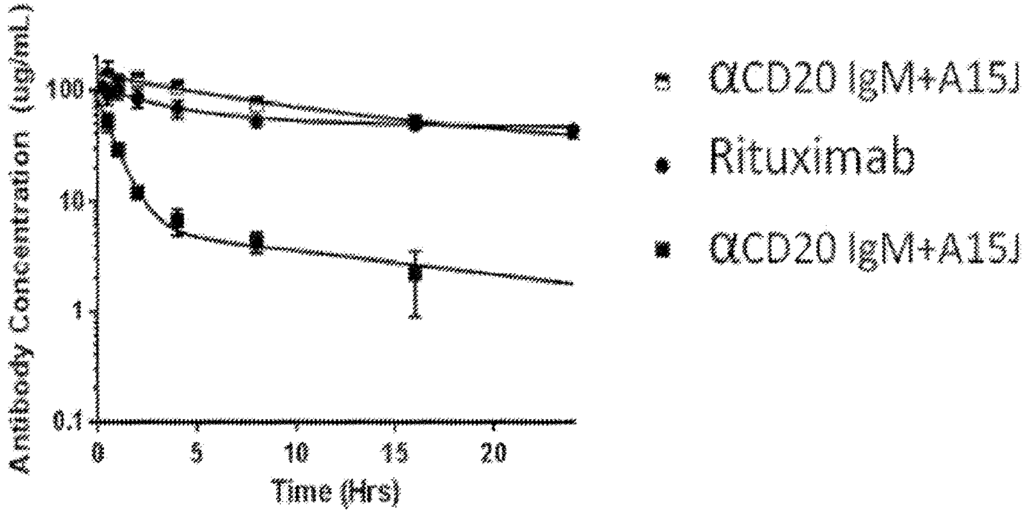
FIG. 18 is a graph showing serum concentration as a function of time for three different model antibodies: Rituximab (IgG); an anti-CD20 IgM with a domain configured to bind T-cells fused to the N-terminus of the J-chain; and an anti-CD20 IgM with an albumin binding domain (ABD) fused to the N-terminus of the J-chain with a 15-amino acid linker (A15J).

The data demonstrate that fusion of an albumin-binding domain to the J-chain resulted in a significant and relatively large increase in the half-life of IgMs. As shown in FIG. 18, the beta half-life of V15J-1.5.3-IgM, which did not include the albumin binding domain, was only 7 hours. By contrast, the beta half-life of A15J-1.5.3-IgM, which did include the albumin-binding domain on the J-chain, was 32 hours, which was comparable to Rituximab.

Example 9: IgM Albumin J-Chain Assembly and Expression

J-chain constructs that incorporate a human serum albumin (HSA) were prepared as provided in Example 1. Constructs were prepared with the HSA positioned at the N-terminus of the J-chain (HSA-15-J), and at the C-terminus of the J-chain (J-15-HSA). To verify that IgM antibodies incorporating J-chains containing HSA in either of these configurations could be assembled and expressed, SDS-PAGE gels under reducing conditions and Western blots were conducted.

Reducing SDS-PAGE: NuPage LDS sample buffer (Life Technologies) and NuPage reducing agent dithiothreitol (Life Technologies) were added to IgM protein samples and heated to 80° C. for 10 minutes before loading on NuPage Novex 4-12% Bis-Tris Gel (Life Technologies). NuPage MES SDS Running Buffer (Life Technologies) was used for gel electrophoresis. Gels were run until the dye front reached the bottom of the gel. After electrophoresis was complete, the gel was removed from the apparatus and stained using Colloidal Blue Staining (Life Technologies).

Western Blot: An acrylamide gel run under conditions described above was washed in a 20% ethanol solution for 10 minutes and then the protein was transferred to an iBlot PVDF membrane (Invitrogen) using the iBlot Dry Blotting System (Invitrogen) at 20V for 10 minutes. After transfer the PVDF membrane was blocked using 2% bovine serum albumin, 0.05% Tween 20 for at least 12 hours. A 1/500 dilution of Pierce J-chain antibody (ThermoFisher) was added to the membrane, incubated for 1 hour, and then a 1/5000 dilution of peroxidase-conjugated goat anti-rabbit IgG (Jackson ImmunoResearch) was added and allowed to incubate in darkness for 30 minutes. Finally, Super Signal West Pico Chemiluminescent Substrate (ThermoFisher) was added to the blot and the resulting signal was visualized using the ChemiDoc-It HR410 Imaging System (UVP) or by exposing the blot to X-ray film.

Figure 19:
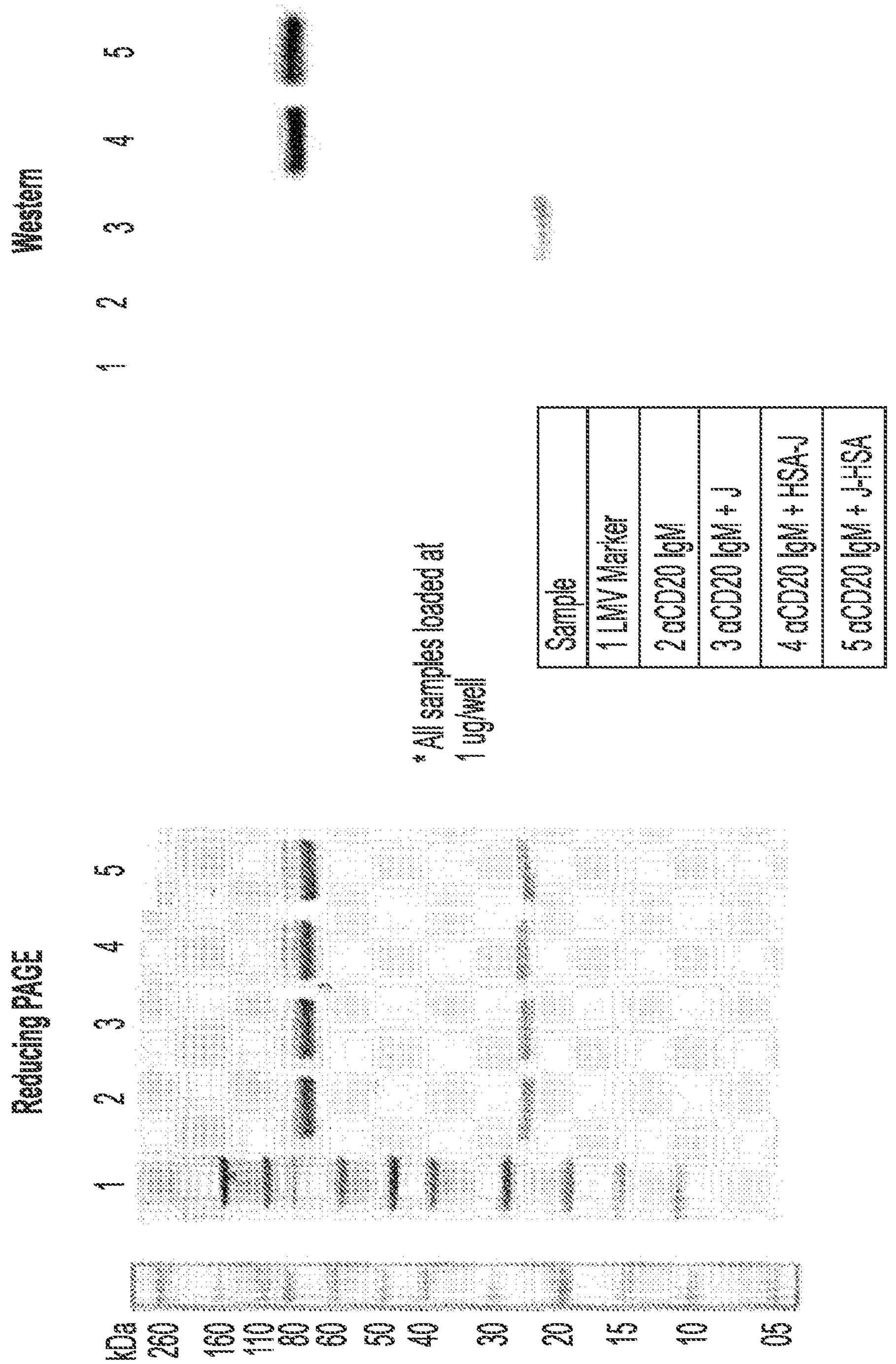
FIG. 19 is an image of a reducing PAGE gel and a Western blot analysis of the antibodies listed in the table. Incorporation of the J-chain with or without fused human serum albumin in either orientation with respect to J-chain is visualized using western blotting with an anti-J chain antibody.

The results are provided in FIG. 19, and demonstrate that J-chains having either of these configurations can be successfully incorporated into IgM antibodies, and that the resulting IgM antibodies can be assembled and expressed by CHO cells.

Example 10: CDC Activity of ABD/HSA-Containing J-Chains

Complement-dependent cytotoxicity (CDC) assays were conducted using IgM antibodies incorporating a J-chain having the HSA-15-J (HSA at the N-terminus of the J-chain, followed by a 15 amino acid linker sequence) or the J-15-HSA (HSA at the C-terminus of the J-chain, preceded by a 15 amino acid linker sequence) configuration.

Ramos, a CD20+ cell line, was seeded in 96 well half area white plates at 25,000 cells/well. The protein under evaluation and human complement (5% final, Quidel) were added to initiate the CDC analysis and the number of viable cells were measured using Cell Titer Glo and manufacturer's protocol. Luminescence was measured on an Envision multimode reader (Perkin Elmer) using 0.1 s integration time per well. The percentage of viable cells was calculated by normalizing the luminescence values (Relative luminescence units—RLU) versus wells with no added test compound. Data were analyzed using GraphPad Prism and a four parameter fit with top and bottom values fixed at 100 and 0% viability respectively.

Figure 20:
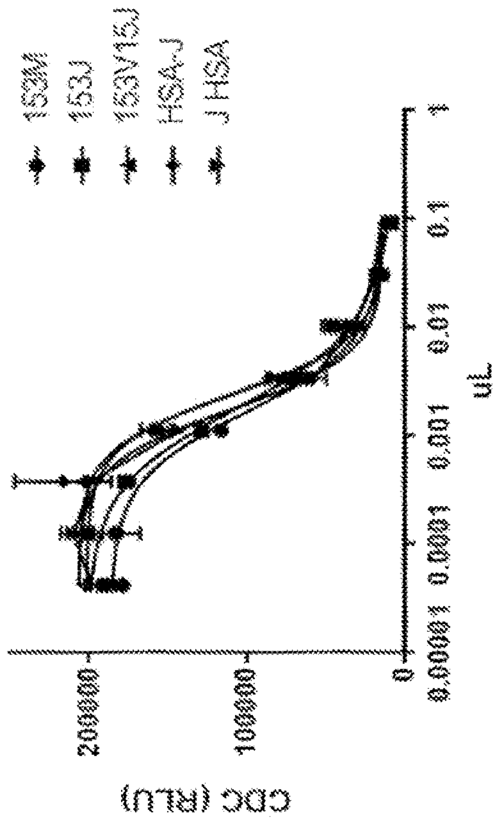
FIG. 20, is a graph showing CDC activity as a function of concentration for four IgM antibodies demonstrating that incorporating a moiety as large as 65 KDa HSA does not disrupt the CDC activity of IgM.

The results are provided in FIG. 20. The results demonstrate that the assembled IgM+HSA J-chain antibodies are functionally active in CDC assays in both orientations.

Example 11: Pharmacokinetics of J-HSA and HSA-J Constructs

Figure 21:
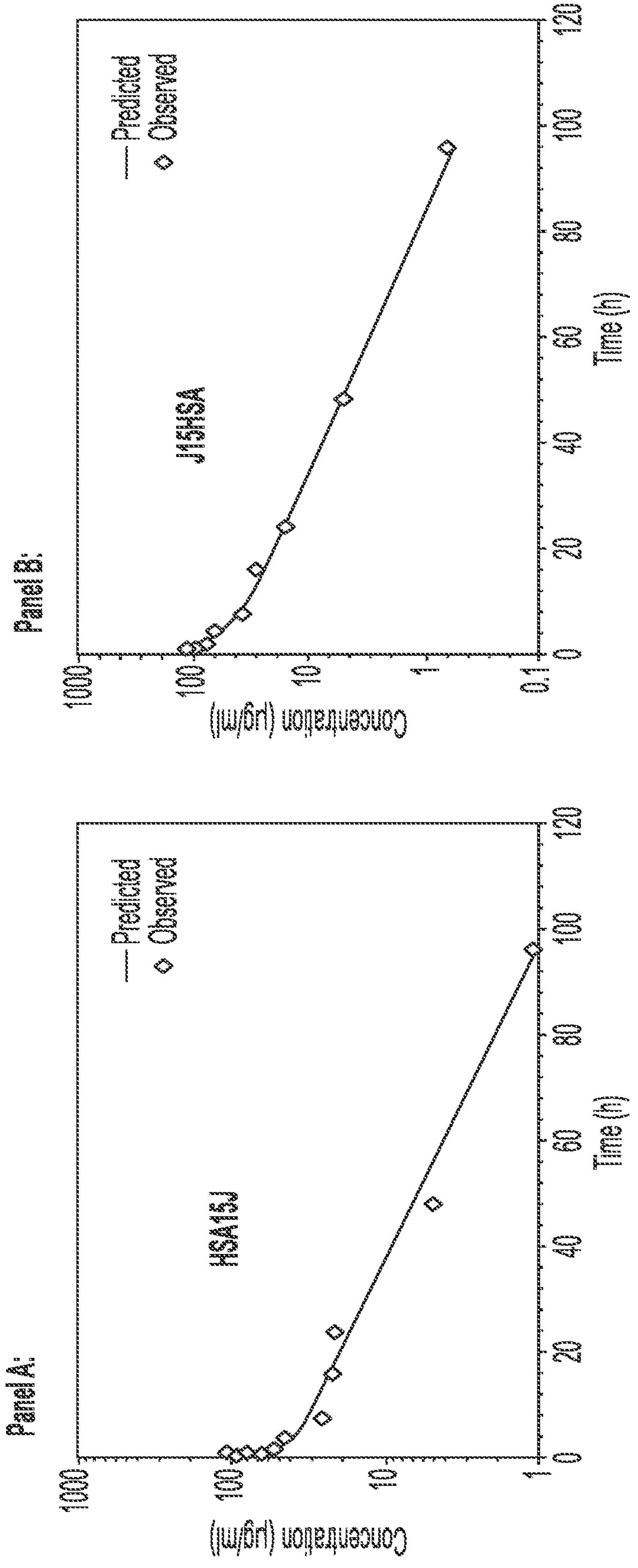
FIG. 21, Panel A, is a graph showing concentration as a function of time in a mouse pharmacokinetics experiment, for an IgM antibody that has an HSA-15-J configuration on the J-chain. Panel B is a graph showing concentration as a function of time for a mouse PK experiment with IgM antibody that has a J-15-HSA configuration on the J-chain.

PK studies, as described above, were conducted in mice to evaluate the PK characteristics of IgM antibodies incorporating a J-chain having the HSA-15-J or the J-15-HSA orientation. The results are provided in FIG. 21 and FIG. 22. The results demonstrate an orientation effect, wherein the HSA positioned at the N-terminus (HSA-15-J orientation) had diminished half-life in comparison to the J-15-HSA orientation (HSA located at the C-terminus).

Example 12: Assembly and Expression of "Bidentate" J-Chain Constructs

Assembly and expression studies were conducted as described above in Example 9 for constructs containing both a CD3-binding moiety (abbreviated as "V") and a half-life extending moiety (either an albumin-binding domain protein, abbreviated "ABD", or a human serum albumin protein, abbreviated as "HSA"). These constructs are referred to as "bidentate" constructs. A summary of all the constructs that were evaluated is provided below in Table 10.

Figure 23:
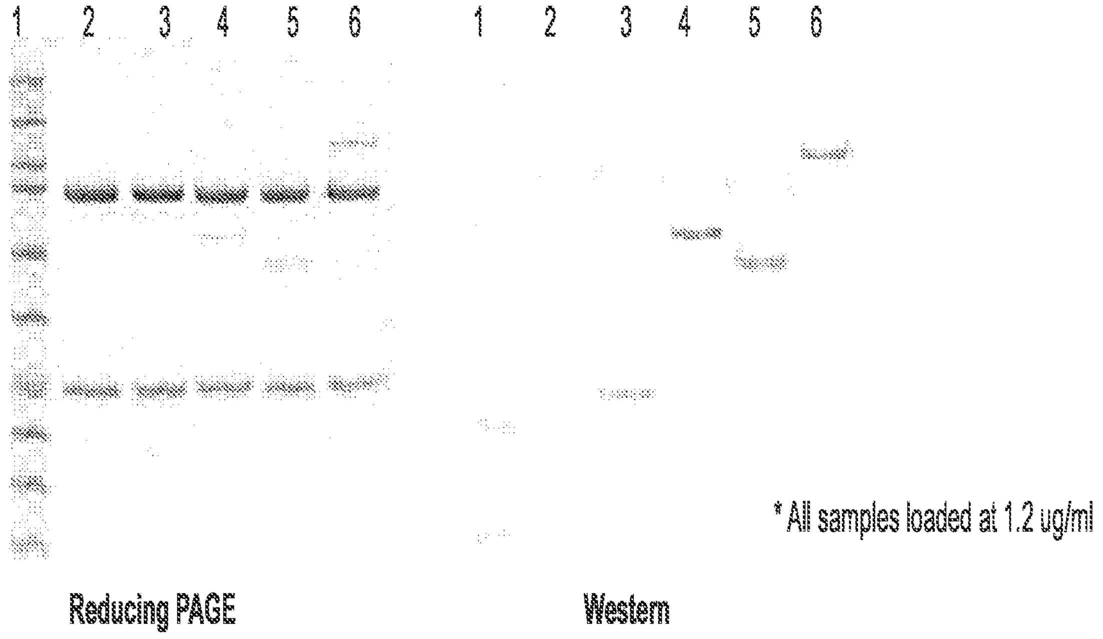
FIG. 23 is an image of a reducing PAGE gel and a Western blot analysis of the antibodies listed in the table, one of which (1.5.3V15J15ABD) has bidentate J-chain configuration.

Constructs were prepared with the half-life extending moiety (e.g., the "ABD" or the "HSA") positioned at the C-terminus of the J-chain, and the CD3-binding moiety (e.g., "V") positioned at the N-terminus. To verify that IgM antibodies incorporating J-chains having any of these configurations could be assembled and expressed, SDS-PAGE gels under reducing conditions and Western blots were conducted, as described above. The results are provided in FIG. 23, and demonstrate that J-chains having either of these configurations can be successfully incorporated into IgM molecules, and that the resulting IgM molecules can be assembled and expressed by CHO cells.

Example 13: CDC Activity of Bidentate J-Chain Constructs

Figure 24:
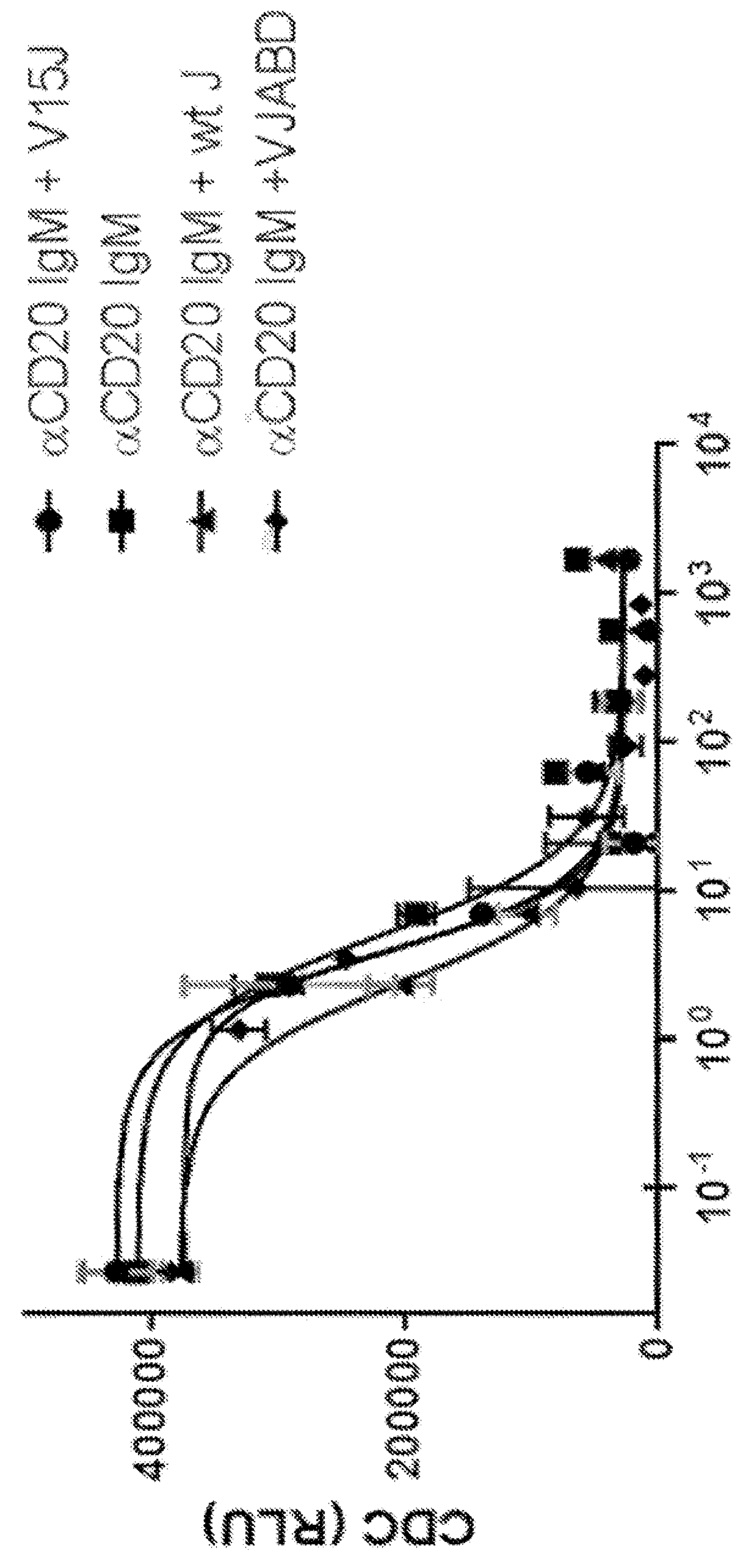
FIG. 24, is a graph showing CDC activity as a function of concentration for antibodies having the indicated J-chain configuration. The bidentate ABD-IgM has essentially the same activity as IgM with or without J-chain.
Figure 25:
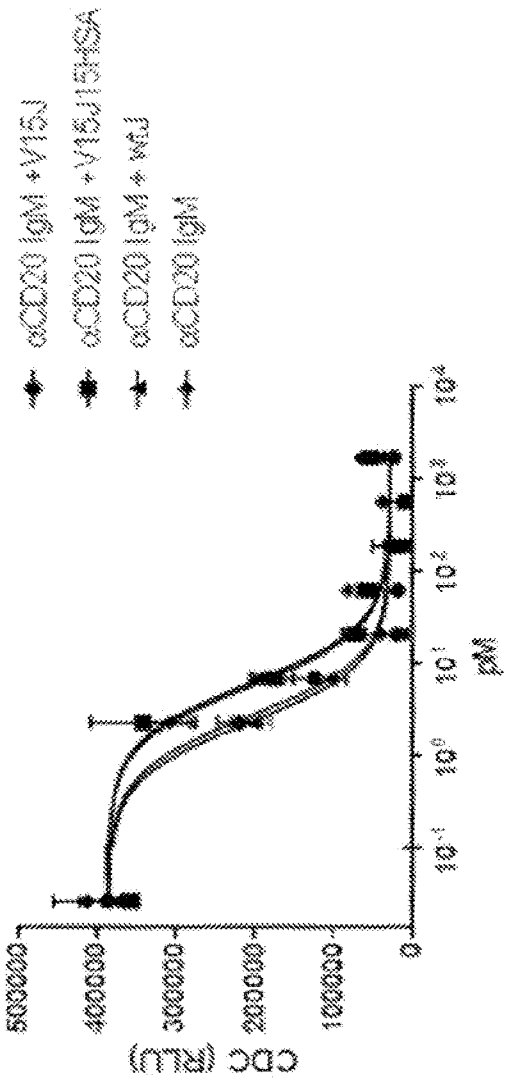
FIG. 25, is a graph showing CDC activity as a function of concentration for antibodies having the indicated J-chain configuration. The bidentate HSA-IgM has essentially the same activity as IgM with or without J-chain.

CDC assays, as described above in Example 10, were conducted using IgM antibodies incorporating the bidentate J-chains described above in Example 12. The results are provided in FIG. 24, and in FIG. 25. The results demonstrate that the bidentate J-chains that were evaluated did not diminish the CDC activity of the IgM antibodies that were tested.

Example 14: Pharmacokinetics of Bidentate J-Chain Constructs

Figure 26:
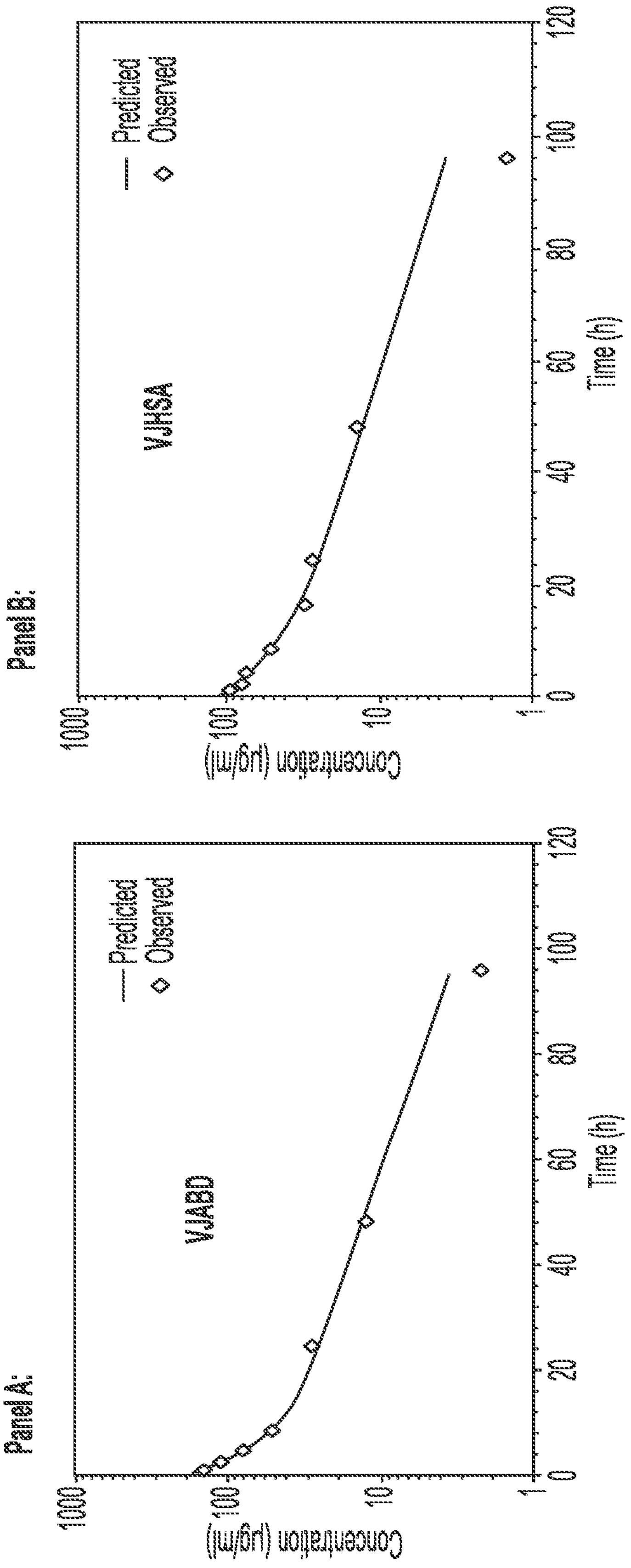
FIG. 26, Panel A, is a graph showing concentration as a function of time for an IgM antibody that has a V-J-ABD bidentate J-chain configuration. Panel B is a graph showing concentration as a function of time for an IgM antibody that has a V-J-HSA bidentate J-chain configuration.

PK studies, as described above, were conducted in mice to evaluate the PK characteristics of the IgM antibodies incorporating the bidentate J-chains described above in Example 12. The results are provided in FIG. 26 and FIG. 27. The results demonstrate that both the V-J-ABD and V-J-HSA bidentate J-chains exhibited good alpha and beta half-life, and that the overall $AUC_{0-inf}$ showed an approximately 60% increase as compared to 1.5.3 IgM J-15-HSA.

Example 15: In-Vivo Activity of Bidentate J-Chain Constructs

Figure 28:
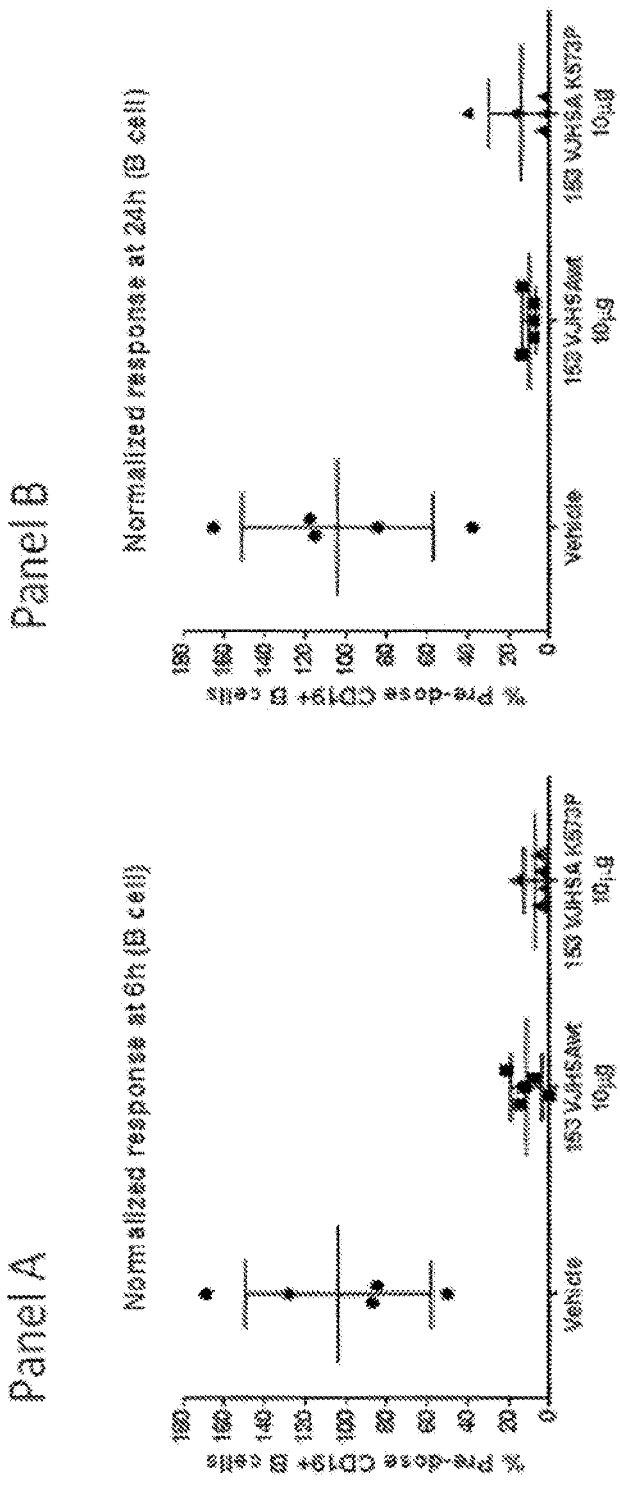
FIG. 28, Panel A and Panel B are graphs showing percentage of pre-dose CD19+B-cells as a function of dose (ng/mouse) for various constructs (e.g., 1.5.3V15J15HSAwt and 1.5.3V15J15HSA (K573P)).

CD34+ humanized NSG mouse studies were performed by In-Vivo Technologies, Inc. The mice were purchased from the Jackson Laboratory, and dosed with test articles through tail vein injection. Blood samples were collected at designated time points through facial vein. Blood samples from both the CD34+ mouse studies were sent back to IGM Biosciences Inc. for lymphocyte analysis. Blood samples were stained for human CD56, CD3, CD19 and CD45 markers to identify different populations of human lymphocytes. CountBright Absolute Counting Beads (LifeTechnologies, C36950) were used to quantify the absolute number of lymphocytes in the blood samples. The lymphocyte levels were plotted and analyzed using GraphPad Prism. As shown in FIG. 28, Panels A and B, the B-lymphocyte levels were essentially reduced to <10% of pre-dose levels, and this level was retained at the 24 hour timepoint for both 1.5.3V15J15HSA(K573P) and 1.5.3V15J15HSAwt with as little as 10 ug of article dosed one single time.

TABLE 10

Sequence Summary

| SEQ ID NO: | Short Name | Sequence |
|---|---|---|
| 27 | Rituximab VH | QVQLQQPGAELVKPGASVKMSCKASGYTFTSYNMHWVKQTPGRGLEWIGAIYPGNGDT SYNQKFKGKATLTADKSSSTAYMQLSSLTSEDSAVYYCARSTYYGGDWYFNVWGAGTT VTVSA |
| 28 | Rituximab HCDR1 | SYNMH |
| 29 | Rituximab HCDR2 | AIYPGNGDTSYNQKFKG |
| 30 | Rituximab HCDR3 | STYYGGDWYFNV |
| 31 | Rituximab VL | QIVLSQSPAILSASPGEKVTMTCRASSSVSYIHWFQQKPGSSPKPWIYATSNLASGVP VRFSGSGSGTSYSLTISRVEAEDAATYYCQQWTSNPPTFGGGTKLEIKR |
| 32 | Rituximab LCDR1 | RASSSVSYIH |
| 33 | Rituximab LCDR2 | ATSNLAS |
| 34 | Rituximab LCDR3 | QQWTSNPPT |
| 35 | 900 VH | EVQLVESGGG LVQPGGSLRL SCAASGYTFT SYNMHWVRQA PGKGLEWVGA IYPGNGDTSY NQKFKGRFTI SVDKSKNTLY LQMNSLRAED TAVYYCARVV YYSNSYWYFD VWGQGTLVTV SSASTKGPSV FPLAPSSKST SGGTAALGCL VKDYFPEPVT VSWNSGALTS GVHTFPAVLQ SSGLYSLSSV VTVPSSSLGT |
| 36 | 900 HCDR3 | VVYYSNSYWYFDV |
| 37 | 900 VL | DIQMTQSPSS LSASVGDRVT ITCRASSSVS YMHWYQQKPG KAPKPLIYAP SNLASGVPSR FSGSGSGTDF TLTISSLQPE DFATYYCQQW SFNPPTFGQG TKVEIKRTVA APSVFIFPPS DEQLKSGTAS VVCLLNNFYP REAKVQWKVD NALQSGNSQE SVTEQDSKDS TYSLSSTLTL SKADYEKHKV YACEVTHQGL |
| 38 | 900 LCDR1 | RASSSVSYMH |
| 39 | 900 LCDR2 | APSNLAS |
| 40 | 900 LCDR3 | QQWSFNPPT |
| 41 | 125 VH | EVQLVQSGAEVKKPGESLKISCKGSGRTFTSYNMHWVRQMPGKGLEWMGAIYPLTGDT SYNQKSKLQVTISADKSISTAYLQWSSLKASDTAMYYCARSTYVGGDWQFDVWGKGTT VTVSS |
| 42 | 125 HCDR2 | AIYPLTGDTSYNQKSKL |
| 43 | 125 HCDR3 | STYVGGDWQFDV |
| 44 | 125 VL | EIVLTQSPGTLSLSPGERATLSCRASSSVPYIHWYQQKPGQAPRLLIYATSALASGIP DRFSGSGSGTDFTLTISRLEPEDFAVYYCQQWLSNPPTFGQGTKLEIK |

TABLE 10-continued

| Sequence Summary | | |
|---|---|---|
| SEQ ID NO: | Short Name | Sequence |
| 45 | 125 LCDR1 | RASSSVPYIH |
| 46 | 125 LCDR2 | ATSALAS |
| 47 | 125 LCDR3 | QQWLSNPPT |
| 48 | 844 VH #2 | QVQLQQPGAELKKPGASVKVSCKASGYTFTSYNMHWVKQTPGRGLEWTGAIYPGNGDT SYNQKFKGKTTLTADKSSSTAYMELSSLRSEDTAVYYCARSTYYGGDWYFNVWGAGTT VTVSA |
| 49 | 844 VH #3 | QVQLQQPGAELKKPGASVKVSCKASGYTFTSYNMHWVKQTPGRGLEWIGAIYPGNGDT SYNQKFKGKTTLTADKSSSTAYMELSSLRSEDTAVYYCARSTYYGGDWYFNVWGAGTT VTVSA |
| 50 | 844 VL #5 | QIVLSQSPAIITASPGEKVTMTCRASTSASYIHWFQQKPTSSPKPWIYATSNLASGVP SRFSGSGSGTTYSMTISSLEAEDAATYYCQQWTSNPPTFGGGTKLEIK |
| 51 | 844 VL #5 LCDR1 | RASTSASYIH |
| 52 | 844 VL #6 | QIVLSQSPAIITASPGEKVTMTCRASTSVSYIHWFQQKPTSSPKPWIYATSNLASGVP SRFSGSGSGTTYSMTISSLEAEDAATYYCQQWTSNPPTFGGGTKLEIK |
| 53 | 844 VL #6, #7 LCDR1 | RASTSVSYIH |
| 54 | 844 VL #7 | QIVLSQSPAIITASPGEKVTMTCRASTSVSYIHWFQQKPGSSPKPWIYATSNLASGVP SRFSGSGSGTTYSMTISSLEAEDAATYYCQQWTSNPPTFGGGTKLEIK |
| 55 | 844 VL #8 | QIVLSQSPAIITASPGEKVTMTCRASSSVSYIHWFQQKPGSSPKPWIYATSNLASGVP SRFSGSGSGTTYSMTISSLEAEDAATYYCQQWTSNPPTFGGGTKLEIK |
| 56 | 844 VH #10 | EVQLQQSGAELKKPGASVKVSCKASGYTFTSYNMHWVKQTPGQGLEWIGAIYPGNGDT SYNQKFKGKTTLTADKSSSTAYMELSSLRSEDTAVYYCARSNYYGSSYWFFDVWGTGT TVTVSS |
| 57 | 844 VH #10 HCDR3 | SNYYGSSYWFFDV |
| 58 | 844 VL #12 | DIVLTQSPAIITASPGEKVTMTCRASSSVNYMDWYQKKPGSSPKPWIYATSNLASGVP SRFSGSGSGTTYSMTISSLEAEDAATYYCQQWSFNPPTFGGGTKLEIK |
| 59 | 844 VL #12 LCDR1 | RASSSVNYMD |
| 60 | 844 VL #12 LCDR3 | QQWSFNPPT |
| 61 | 164 VH | QVQLQQSGAEVKKPGSSVKVSCKASGYTFTSYNMHWVKQAPGQGLEWIGAIYPGNGDT SYNQKFKGKATLTADESTNTAYMELSSLRSEDTAFYYCARSTYYGGDWYFDVWGQGTT VTVSS |
| 62 | 164 VH HCDR3 | STYYGGDWYFDV |
| 63 | 164 VL | MGWSCIILFLVATATGVHSDIQLTQSPSSLSASVGDRVTMTCRASSSVSYIHWFQQKP GKAPKPWIYATSNLASGVPVRFSGSGSGTDYTFTISSLQPEDIATYYCQQWTSNPPTF GGGTKLEIK |
| 64 | 1.5.3 VH | EVQLVQSGAEVKKPGESLKISCKGSGYSFTSYWIGWVRQMPGKGLEWMGIIYPGDSDT RYSPSFQGQVTISADKSITTAYLQWSSLKASDTAMYYCARHPSYGSGSPNFDYWGQGT LVTVSS |
| 65 | 1.5.3 HCDR1 | GYSFTSYWIG |
| 66 | 1.5.3 HCDR2 | IIYPGDSDTRYSPSFQG |
| 67 | 1.5.3 HCDR3 | HPSYGSGSPNFDY |
| 68 | 1.5.3 VL | DIVMTQTPLSSPVTLGQPASISCRSSQSLVYSDGNTYLSWLQQRPGQPPRLLIYKISN RFSGVPDRFSGSGAGTDFTLKISRVEAEDVGVYYCVQATQFPLTFGGGTKVEIK |
| 69 | 1.5.3 LCDR1 | RSSQSLVYSDGNTYLS |

TABLE 10-continued

| Sequence Summary | | |
|---|---|---|
| SEQ ID NO: | Short Name | Sequence |
| 70 | 1.5.3 LCDR2 | KISNRFS |
| 71 | 1.5.3 LCDR3 | VQATQFPLT |
| 72 | human IgM constant region DNA | GCCCCAACCCTTTTCCCCCTCGTCTCCTGTGAGAATTCCCCGTCGGATACGAGCAGCG TGGCCGTTGGCTGCCTCGCACAGGACTTCCTTCCCGACTCCATCACTTTCTCCTGGAA ATACAAGAACAACTCTGACATCAGCAGCACCCGGGGCTTCCCATCAGTCCTGAGAGGG GGCAAGCACGCAGCCACCTCACAGGTGCTGCTGCCTTCCAAGGACGTCATGCAGGGCA CAGACGAACACGTGGTGTGCAAAGTCCAGCACCCCAACGGCAACAAAGAAAAGAACGT GCCTCTTCCAGTGATTGCTGAGCTGCCTCCCAAAGTGAGCGTCTTCGTCCCACCCCGC GACGGCTTCTTCGGCAACCCCCGCAAGTCCAAGCTCATCTGCCAGGCCACGGGTTTCA GTCCCCGGCAGATTCAGGTGTCCTGGCTGCGCGAGGGGAAGCAGGTGGGGTCTGGCGT CACCACGGACCAGGTGCAGGCTGAGGCAAAGGAGTCTGGGACCACGACCTACAAGGTG ACCAGCACACTGACCATCAAAGAGAGCGACTGGCTCAGCCAGAGCATGTTCACCTGCC GCGTGGATCACAGGGGCCTGACCTTCCAGCAGAATGCGTCCTCCATGTGTGGCCCCGA TCAAGACACAGCCATCCGGGTCTTCTCCATCCCCCCATCCTTTGCCAGCATCTTCCTC ACCAAGTCCACCAAGTTGACCTGCCTGGTCACAGACCTGACCACCTATGACAGCGTGA CCATCTCCTGGACCCGCCAGAATGGCGAAGCTGTGAAAACCCACACCAACATCTCCGA GAGCCACCCCAATGCCACTTTCAGCGCCGTGGGTGAGGCCAGCATCTGCGAGGATGAC TGGAATTCCGGGGAGAGGTTCACGTGCACCGTGACCCACACAGACCTGCCCTCGCCAC TGAAGCAGACCATCTCCCGGCCCAAGGGGGTGGCCCTGCACAGGCCCGATGTCTACTT GCTGCCACCAGCCCGGGAGCAGCTGAACCTGCGGGAGTCGGCCACCATCACGTGCCTG GTGACGGGCTTCTCTCCCGCGGACGTCTTCGTGCAGTGGATGCAGAGGGGGCAGCCCT TGTCCCCGGAGAAGTATGTGACCAGCGCCCCAATGCCTGAGCCCCAGGCCCCAGGCCG GTACTTCGCCCACAGCATCCTGACCGTGTCCGAAGAGGAATGGAACACGGGGGAGACC TACACCTGCGTGGTGGCCCATGAGGCCCTGCCCAACAGGGTCACCGAGAGGACCGTGG ACAAGTCCACCGGTAAACCCACCCTGTACAACGTGTCCCTGGTCATGTCCGACACAGC TGGCACCTGCTAC |
| 73 | human IgM constant region AA | GSASAPTLFPLVSCENSPSDTSSVAVGCLAQDFLPDSITFSWKYKNNSDISSTRGFPS VLRGGKYAATSQVLLPSKDVMQGTDEHVVCKVQHPNGNKEKNVPLPVIAELPPKVSVF VPPRDGFFGNPRKSKLICQATGFSPRQIQVSWLREGKQVGSGVTTDQVQAEAKESGPT TYKVTSTLTIKESDWLSQSMFTCRVDHRGLTFQQNASSMCVPDQDTAIRVFAIPPSFA SIFLTKSTKLTCLVTDLTTYDSVTISWTRQNGEAVKTHTNISESHPNATFSAVGEASI CEDDWNSGERFTCTVTHTDLPSPLKQTISRPKGVALHRPDVYLLPPAREQLNLRESAT ITCLVTGFSPADVFVQWMQRGQPLSPEKYVTSAPMPEPQAPGRYFAHSILTVSEEEWN TGETYTCVVAHEALPNRVTERTVDKSTGKPTLYNVSLVMSDTAGTCY |
| 74 | J Chain DNA | ATGAAGAACCATTTGCTTTTCTGGGGAGTCCTGGCGGTTTTTATTAAGGCTGTTCATG TGAAAGCCCAAGAAGATGAAAGGATTGTTCTTGTTGACAACAAATGTAAGTGTGCCCG GATTACTTCCAGGATCATCCGTTCTTCCGAAGATCCTAATGAGGACATTGTGGAGAGA AACATCCGAATTATTGTTCCTCTGAACAACAGGGAGAATATCTCTGATCCCACCTCAC CATTGAGAACCAGATTTGTGTACCATTTGTCTGACCTCTGTAAAAAATGTGATCCTAC AGAAGTGGAGCTGGATAATCAGATAGTTACTGCTACCCAGAGCAATATCTGTGATGAA GACAGTGCTACAGAGACCTGCTACACTTATGACAGAAACAAGTGCTACACAGCTGTGG TCCCACTCGTATATGGTGGTGAGACCAAAATGGTGGAAACAGCCTTAACCCCAGATGC CTGCTATCCTGACTAA |
| 75 | J Chain AA | MKNHLLFWGVLAVFIKAVHVKAQEDERIVLVDNKCKCARITSRIIRSSEDPNEDIVER NIIIVPLNNRENISDPTSPLRTRFVYHLSDLCKKCDPTEVELDNQIVTATQSNICDED SATETCYTYDRNKCYTAVVPLVYGGETKMVETALTPDACYPD |
| 76 | human CD20 amino acid | MTTPRNSVNGTFPAEPMKGPIAMQSGPKPLFRRMSSLVGPTQSFFMRESKTLGAVQIM NGLFHIALGGLLMIPAGIYAPICVTVWYPLWGGIMYIISGSLLAATEKNSRKCLVKGK MIMNSLSLFAAISGMILSIMDILNIKISHFLKMESLNFIRAHTPYINIYNCEPANPSE KNSPSTQYCYSIQSLFLGILSVMLIFAFFQELVIAGIVENEWKRTCSRPKSNIVLLSA EEKKEQTIEIKEEVVGLTETSSQPKNEEDIEIIPIQEEEEEETETNFPEPPQDQESSP IENDSSP |
| 77 | Ritux-IgM heavy chain DNA | CAGGTTCAGCTGCAGCAGCCCGGAGCCGAGCTGGTCAAACCTGGCGCTAGTGTGAAAA TGTCATGCAAGGCATCCGGATACACATTCACTAGCTATAACATGCACTGGGTGAAGCA GACCCCCGGCAGGGGTCTGGAGTGGATCGGAGCTATCTACCCCGGCAACGGAGACACA TCTTATAATCAGAAGTTTAAAGGCAAGGCCACCCTGACAGCTGATAAGTCCAGCTCTA CCGCATACATGCAGCTGAGTTCACTGACAAGCGAGGACTCCGCCGTGTACTATTGCGC CCGGTCCACTTACTATGGCGGAGATTGGTATTTCAATGTGTGGGGAGCAGGCACCACA GTCACCGTCTCGAGCGGCAGTGCTAGCGCCCCAACCCTTTTCCCCCTCGTCTCCTGTG AGAATTCCCCGTCGGATACGAGCAGCGTGGCCGTTGGCTGCCTCGCACAGGACTTCCT TCCCGACTCCATCACTTTCTCCTGGAAATACAAGAACAACTCTGACATCAGCAGCACC CGGGGCTTCCCATCAGTCCTGAGAGGGGGCAAGTACGCAGCCACCTCACAGGTGCTGC TGCCTTCCAAGGACGTCATGCAGGGCACAGACGAACACGTGGTGTGCAAAGTCCAGCA CCCCAACGGCAACAAAGAAAAGAACGTGCCTCTTCCAGTGATTGCTGAGCTGCCTCCC AAAGTGAGCGTCTTCGTCCCACCCCGCGACGGCTTCTTCGGCAACCCCCGCAAGTCCA AGCTCATCTGCCAGGCCACGGGTTTCAGTCCCCGGCAGATTCAGGTGTCCTGGCTGCG CGAGGGGAAGCAGGTGGGGTCTGGCGTCACCACGGACCAGGTGCAGGCTGAGGCCAAA GAGTCTGGGCCCACGACCTACAAGGTGACCAGCACACTGACCATCAAAGAGAGCGACT |

TABLE 10-continued

| Sequence Summary | | |
|---|---|---|
| SEQ ID NO: | Short Name | Sequence |
| | | GGCTCAGCCAGAGCATGTTCACCTGCCGCGTGGATCACAGGGGCCTGACCTTCCAGCA<br>GAATGCGTCCTCCATGTGTGTCCCCGATCAAGACACAGCCATCCGGGTCTTCGCCATC<br>CCCCCATCCTTTGCCAGCATCTTCCTCACCAAGTCCACCAAGTTGACCTGCCTGGTCA<br>CAGACCTGACCACCTATGACAGCGTGACCATCTCCTGGACCCGCCAGAATGGCGAAGC<br>TGTGAAAACCCACACCAACATCTCCGAGAGCCACCCCAATGCCACTTTCAGCGCCGTG<br>GGTGAGGCCAGCATCTGCGAGGATGACTGGAATTCCGGGGAGAGGTTCACGTGCACCG<br>TGACCCACACAGACCTGCCCTCGCCACTGAAGCAGACCATCTCCCGGCCCAAGGGGGT<br>GGCCCTGCACAGGCCCGATGTCTACTTGCTGCCACCAGCCCGGGAGCAGCTGAACCTG<br>CGGGAGTCGGCCACCATCACGTGCCTGGTGACGGGCTTCTCTCCCGCGGACGTCTTCG<br>TGCAGTGGATGCAGAGGGGGCAGCCCTTGTCCCCGGAGAAGTATGTGACCAGCGCCCC<br>AATGCCTGAGCCCCAGGCCCCAGGCCGGTACTTCGCCCACAGCATCCTGACCGTGTCC<br>GAAGAGGAATGGAACACGGGGGAGACCTACACCTGCGTGGTGGCCCATGAGGCCCTGC<br>CCAACAGGGTCACCGAGAGGACCGTGGACAAGTCCACCGGTAAACCCACCCTGTACAA<br>CGTGTCCCTGGTCATGTCCGACACAGCTGGCACCTGCTACTGA |
| 78 | Ritux-IgM heavy chain AA | QVQLQQPGAELVKPGASVKMSCKASGYTFTSYNMHWVKQTPGRGLEWIGAIYPGNGDT<br>SYNQKFKGKATLTADKSSSTAYMQLSSLTSEDSAVYYCARSTYYGGDWYFNVWGAGTT<br>VTVSSGSASAPTLFPLVSCENSPSDTSSVAVGCLAQDFLPDSITFSWKYKNNSDISST<br>RGFPSVLRGGKYAATSQVLLPSKDVMQGTDEHVVCKVQHPNGNKEKNVPLPVIAELPP<br>KVSVFVPPRDGFFGNPRKSKLICQATGFSPRQIQVSWLREGKQVGSGVTTDQVQAEAK<br>ESGPTTYKVTSTLTIKESDWLSQSMFTCRVDHRGLTFQQNASSMCVPDQDTAIRVFAI<br>PPSFASIFLTKSTKLTCLVTDLTTYDSVTISWTRQNGEAVKTHTNISESHPNATFSAV<br>GEASICEDDWNSGERFTCTVTHTDLPSPLKQTISRPKGVALHRPDVYLLPPAREQLNL<br>RESATITCLVTGFSPADVFVQWMQRGQPLSPEKYVTSAPMPEPQAPGRYFAHSILTVS<br>EEEWNTGETYTCVVAHEALPNRVTERTVDKSTGKPTLYNVSLVMSDTAGTCY- |
| 79 | Ritux-light chain DNA | CAAATTGTGCTGTCTCAGAGTCCAGCTATCCTGAGCGCATCTCCCGGAGAGAAGGTGA<br>CCATGACATGCAGAGCCTCCAGCTCTGTCTCCTACATCCACTGGTTCCAGCAGAAGCC<br>CGGCTCCTCCCCAAAACCCTGGATCTACGCCACCTCTAACCTGGCTAGTGGTGTGCCT<br>GTCAGGTTTAGTGGATCAGGGTCCGGCACCAGCTACTCTCTGACAATCAGCCGGGTGG<br>AGGCTGAAGACGCCGCTACATACTATTGCCAGCAGTGGACTTCTAATCCCCCTACCTT<br>CGGCGGAGGGACAAAGCTGGAGATCAAGCGTACGGTGGCTGCACCATCTGTCTTCATC<br>TTCCCGCCATCTGATGAGCAGTTGAAATCTGGAACTGCCTCTGTTGTGTGCCTGCTGA<br>ATAACTTCTATCCCAGAGAGGCCAAAGTACAGTGGAAGGTGGATAACGCCCTCCAATC<br>GGGTAACTCCCAGGAGAGTGTCACAGAGCAGGACAGCAAGGACAGCACCTACAGCCTC<br>AGCAGCACCCTGACGCTGAGCAAAGCAGACTACGAGAAACACAAAGTCTACGCCTGCG<br>AAGTCACCCATCAGGGCCTGAGCTCGCCCGTCACAAAGAGCTTCAACAGGGGAGAGTG<br>TTAG |
| 80 | Ritux-light chain AA | QIVLSQSPAILSASPGEKVTMTCRASSSVSYIHWFQQKPGSSPKPWIYATSNLASGVP<br>VRFSGSGSGTSYSLTISRVEAEDAATYYCQQWTSNPPTFGGGTKLEIKRTVAAPSVFI<br>FPPSDEQLKSGTASVVCLLNNFYPREAKVQWKVDNALQSGNSQESVTEQDSKDSTYSL<br>SSTLTLSKADYEKHKVYACEVTHQGLSSPVTKSFNRGEC- |
| 81 | 1.5.3 -IgM heavy chain DNA | GAGGTGCAGCTGGTGCAGTCCGGCGCCGAGGTGAAGAAGCCCGGCGAGTCCCTGAAGA<br>TCTCCTGCAAGGGCTCCGGCTACTCCTTCACCTCCTACTGGATCGGCTGGGTGAGGCA<br>GATGCCCGGCAAGGGCCTGGAGTGGATGGGCATCATCTACCCCGGCGACTCCGACACC<br>AGGTACTCCCCCTCCTTCCAGGGCCAGGTGACCATCTCCGCCGACAAGTCCATCACCA<br>CCGCCTACCTGCAGTGGTCCTCCCTGAAGGCCTCCGACACCGCCATGTACTACTGCGC<br>CAGGCACCCCTCCTACGGCTCCGGCTCCCCCAACTTCGACTACTGGGGCCAGGGCACC<br>CTGGTGACCGTGTCCTCCGGCAGTGCTAGCGCCCCAACCCTTTTCCCCCTCGTCTCCT<br>GTGAGAATTCCCCGTCGGATACGAGCAGCGTGGCCGTTGGCTGCCTCGCACAGGACTT<br>CCTTCCCGACTCCATCACTTTCTCCTGGAAATACAAGAACAACTCTGACATCAGCAGC<br>ACCCGGGGCTTCCCATCAGTCCTGAGAGGGGGCAAGTACGCAGCCACCTCACAGGTGC<br>TGCTGCCTTCCAAGGACGTCATGCAGGGCACAGACGAACACGTGGTGTGCAAAGTCCA<br>GCACCCCAACGGCAACAAAGAAAAGAACGTGCCTCTTCCAGTGATTGCTGAGCTGCCT<br>CCCAAAGTGAGCGTCTTCGTCCCACCCCGCGACGGCTTCTTCGGCAACCCCCGCAAGT<br>CCAAGCTCATCTGCCAGGCCACGGGTTTCAGTCCCCGGCAGATTCAGGTGTCCTGGCT<br>GCGCGAGGGGAAGCAGGTGGGGTCTGGCGTCACCACGGACCAGGTGCAGGCTGAGGCC<br>AAAGAGTCTGGGCCCACGACCTACAAGGTGACCAGCACACTGACCATCAAAGAGAGCG<br>ACTGGCTCAGCCAGAGCATGTTCACCTGCCGCGTGGATCACAGGGGCCTGACCTTCCA<br>GCAGAATGCGTCCTCCATGTGTGTCCCCGATCAAGACACAGCCATCCGGGTCTTCGCC<br>ATCCCCCCATCCTTTGCCAGCATCTTCCTCACCAAGTCCACCAAGTTGACCTGCCTGG<br>TCACAGACCTGACCACCTATGACAGCGTGACCATCTCCTGGACCCGCCAGAATGGCGA<br>AGCTGTGAAAACCCACACCAACATCTCCGAGAGCCACCCCAATGCCACTTTCAGCGCC<br>GTGGGTGAGGCCAGCATCTGCGAGGATGACTGGAATTCCGGGGAGAGGTTCACGTGCA<br>CCGTGACCCACACAGACCTGCCCTCGCCACTGAAGCAGACCATCTCCCGGCCCAAGGG<br>GGTGGCCCTGCACAGGCCCGATGTCTACTTGCTGCCACCAGCCCGGGAGCAGCTGAAC<br>CTGCGGGAGTCGGCCACCATCACGTGCCTGGTGACGGGCTTCTCTCCCGCGGACGTCT<br>TCGTGCAGTGGATGCAGAGGGGGCAGCCCTTGTCCCCGGAGAAGTATGTGACCAGCGC<br>CCCAATGCCTGAGCCCCAGGCCCCAGGCCGGTACTTCGCCCACAGCATCCTGACCGTG<br>TCCGAAGAGGAATGGAACACGGGGGAGACCTACACCTGCGTGGTGGCCCATGAGGCCC<br>TGCCCAACAGGGTCACCGAGAGGACCGTGGACAAGTCCACCGGTAAACCCACCCTGTA<br>CAACGTGTCCCTGGTCATGTCCGACACAGCTGGCACCTGCTACTGA |

TABLE 10-continued

| SEQ ID NO: | Short Name | Sequence |
|---|---|---|
| 82 | 1.5.3 -IgM heavy chain AA | EVQLVQSGAEVKKPGESLKISCKGSGYSFTSYWIGWVRQMPGKGLEWMGIIYPGDSDT RYSPSFQGQVTISADKSITTAYLQWSSLKASDTAMYYCARHPSYGSGSPNFDYWGQGT LVTVSSGSASAPTLFPLVSCENSPSDTSSVAVGCLAQDFLPDSITFSWKYKNNSDISS TRGFPSVLRGGKYAATSQVLLPSKDVMQGTDEHVVCKVQHPNGNKEKNVPLPVIAELP PKVSVFVPPRDGFFGNPRKSKLICQATGFSPRQIQVSWLREGKQVGSGVTTDQVQAEA KESGPTTYKVTSTLTIKESDWLSQSMFTCRVDHRGLTFQQNASSMCVPDQDTAIRVFA IPPSFASIFLTKSTKLTCLVTDLTTYDSVTISWTRQNGEAVKTHTNISESHPNATFSA VGEASICEDDWNSGERFTCTVTHTDLPSPLKQTISRPKGVALHRPDVYLLPPAREQLN LRESATITCLVTGFSPADVFVQWMQRGQPLSPEKYVTSAPMPEPQAPGRYFAHSILTV SEEEWNTGETYTCVVAHEALPNRVTERTVDKSTGKPTLYNVSLVMSDTAGTCY- |
| 83 | 1.5.3 light chain DNA | GACATCGTGATGACCCAGACCCCCCTGTCCTCCCCCGTGACCCTGGGCCAGCCCGCCT CCATCTCCTGCAGGTCCTCCCAGTCCCTGGTGTACTCCGACGGCAACACCTACCTGTC CTGGCTGCAGCAGAGGCCCGGCCAGCCCCCCAGGCTGCTGATCTACAAGATCTCCAAC AGGTTCTCCGGCGTGCCCGACAGGTTCTCCGGCTCCGGCGCCGGCACCGACTTCACCC TGAAGATCTCCAGGGTGGAGGCCGAGGACGTGGGCGTGTACTACTGCGTGCAGGCCAC CCAGTTCCCCCTGACCTTCGGCGGCGGCACCAAGGTGGAGATCAAGCGTACGGTGGCT GCACCATCTGTCTTCATCTTCCCGCCATCTGATGAGCAGTTGAAATCTGGAACTGCCT CTGTTGTGTGCCTGCTGAATAACTTCTATCCCAGAGAGGCCAAAGTACAGTGGAAGGT GGATAACGCCCTCCAATCGGGTAACTCCCAGGAGAGTGTCACAGAGCAGGACAGCAAG GACAGCACCTACAGCCTCAGCAGCACCCTGACGCTGAGCAAAGCAGACTACGAGAAAC ACAAAGTCTACGCCTGCGAAGTCACCCATCAGGGCCTGAGCTCGCCCGTCACAAAGAG CTTCAACAGGGGAGAGTGTTAG |
| 84 | 1.5.3 light chain AA | DIVMTQTPLSSPVTLGQPASISCRSSQSLVYSDGNTYLSWLQQRPGQPPRLLIYKISN RFSGVPDRFSGSGAGTDFTLKISRVEAEDVGVYYCVQATQFPLTFGGGTKVEIKRTVA APSVFIFPPSDEQLKSGTASVVCLLNNFYPREAKVQWKVDNALQSGNSQESVTEQDSK DSTYSLSSTLTLSKADYEKHKVYACEVTHQGLSSPVTKSFNRGEC- |
| 85 | human Ig A1 constant region aa P01876 | ASPTSPKVFPLSLCSTQPDGNVVIACLVQGFFPQEPLSVTWSESGQGVTARNFPPSQD ASGDLYTTSSQLTLPATQCLAGKSVTCHVKHYTNPSQDVTVPCPVPSTPPTPSPSTPP TPSPSCCHPRLSLHRPALEDLLLGSEANLTCTLTGLRDASGVTFTWTPSSGKSAVQGP PERDLCGCYSVSSVLPGCAEPWNHGKTFTCTAAYPESKTPLTATLSKSGNTFRPEVHL LPPPSEELALNELVTLTCLARGFSPKDVLVRWLQGSQELPREKYLTWASRQEPSQGTT TFAVTSILRVAAEDWKKGDTFSCMVGHEALPLAFTQKTIDRLAGKPTHVNVSVVMAEV DGTCY |
| 86 | human IgA2 constant region aa P01877 | ASPTSPKVFPLSLDSTPQDGNVVVACLVQGFFPQEPLSVTWSESGQNVTARNFPPSQD ASGDLYTTSSQLTLPATQCPDGKSVTCHVKHYTNPSQDVTVPCPVPPPPPCCHPRLSL HRPALEDLLLGSEANLTCTLTGLRDASGATFTWTPSSGKSAVQGPPERDLCGCYSVSS VLPGCAQPWNHGETFTCTAAHPELKTPLTANITKSGNTFRPEVHLLPPPSEELALNEL VTLTCLARGFSPKDVLVRWLQGSQELPREKYLTWASRQEPSQGTTTFAVTSILRVAAE DWKKGDTFSCMVGHEALPLAFTQKTIDRMAGKPTHVNVSVVMAEVDGTCY |
| 87 | Human Secretory Component Precursor | MLLFVLTCLLAVFPAISTKSPIFGPEEVNSVEGNSVSITCYYPPTSVNRHTRKYWCRQ GARGGCITLISSEGYVSSKYAGRANLTNFPENGTFVVNIAQLSQDDSGRYKCGLGINS RGLSFDVSLEVSQGPGLLNDTKVYTVDLGRTVTINCPFKTENAQKRKSLYKQIGLYPV LVIDSSGYVNPNYTGRIRLDIQGTGQLLFSVVINQLRLSDAGQYLCQAGDDSNSNKKN ADLQVLKPEPELVYEDLRGSVTFHCALGPEVANVAKFLCRQSSGENCDVVVNTLGKRA PAFEGRILLNPQDKDGSFSVVITGLRKEDAGRYLCGAHSDGQLQEGSPIQAWQLFVNE ESTIPRSPTVVKGVAGGSVAVLCPYNRKESKSIKYWCLWEGAQNGRCPLLVDSEGWVK AQYEGRLSLLEEPGNGTFTVILNQLTSRDAGFYWCLTNGDTLWRTTVEIKIIEGEPNL KVPGNVTAVLGETLKVPCHFPCKFSSYEKYWCKWNNTGCQALPSQDEGPSKAFVNCDE NSRLVSLTLNLVTRADEGWYWCGVKQGHFYGETAAVYVAVEERKAAGSRDVSLAKADA APDEKVLDSGFREIENKAIQDPRLFAEEKAVADTRDQADGSRASVDSGSSEEQGGSSR ALVSTLVPLGLVLAVGAVAVGVARARHRKNVDRVSIRSYRTDISMSDFENSREFGAND NMGASSITQETSLGGKEEFVATTESTTETKEPKKAKRSSKEEAEMAYKDFLLQSSTVA AEAQDGPQEA |
| 88 | human secretory component mature | KSPIFGPEEVNSVEGNSVSITCYYPPTSVNRHTRKYWCRQGARGGCITLISSEGYVSS KYAGRANLTNFPENGTFVVNIAQLSQDDSGRYKCGLGINSRGLSFDVSLEVSQGPGLL NDTKVYTVDLGRTVTINCPFKTENAQKRKSLYKQIGLYPVLVIDSSGYVNPNYTGRIR LDIQGTGQLLFSVVINQLRLSDAGQYLCQAGDDSNSNKKNADLQVLKPEPELVYEDLR GSVTFHCALGPEVANVAKFLCRQSSGENCDVVVNTLGKRAPAFEGRILLNPQDKDGSF SVVITGLRKEDAGRYLCGAHSDGQLQEGSPIQAWQLFVNEESTIPRSPTVVKGVAGGS VAVLCPYNRKESKSIKYWCLWEGAQNGRCPLLVDSEGWVKAQYEGRLSLLEEPGNGTF TVILNQLTSRDAGFYWCLTNGDTLWRTTVEIKIIEGEPNLKVPGNVTAVLGETLKVPC HFPCKFSSYEKYWCKWNNTGCQALPSQDEGPSKAFVNCDENSRLVSLTLNLVTRADEG WYWCGVKQGHFYGETAAVYVAVEERKAAGSRDVSLAKADAAPDEKVLDSGFREIENKA IQDPR |
| 89 | J15ABD DNA | ATGGAATGGAGCTGGGTCTTTCTCTTCTTCCTGTCAGTAACGACTGGTGTCCACTCCC AGGAAGATGAGCGGATCGTGCTGGTGGACAACAAGTGCAAGTGCGCCCGGATCACCTC CCGGATCATCCGGTCCTCCGAGGATCCCAACGAGGACATCGTGGAACGGAACATCAGA ATCATCGTGCCCCTGAACAACCGCGAGAACATCTCCGACCCCACCAGCCCTCTGCGGA |

TABLE 10-continued

Sequence Summary

| SEQ ID NO: | Short Name | Sequence |
|---|---|---|
| | | CCAGATTCGTGTACCACCTGTCCGACCTGTGCAAGAAGTGCGACCCTACCGAGGTGGA ACTGGACAACCAGATCGTGACCGCCACCCAGTCCAACATCTGCGACGAGGACTCCGCC ACCGAGACATGCTACACCTACGACCGGAACAAGTGCTACACCGCCGTGGTGCCTCTGG TGTACGGCGGCGAGACAAAGATGGTGGAAACCGCCCTGACCCCCGACGCCTGCTATCC TGATGGAGGCGGAGGATCTGGTGGCGGTGGTTCTGGCGGAGGGGGCTCTCAGCACGAT GAGGCCGTGGACGCCAATTCTCTGGCCGAGGCTAAGGTGCTGGCCAACAGAGAGCTGG ATAAGTACGGCGTGTCCGACTACTACAAGAACCTGATCAACAACGCCAAGACCGTGGA AGGCGTGAAGGCCCTGATCGACGAGATCCTGGCTGCCCTGCCTTGA |
| 90 | J15ABD AA | MEWSWVFLFFLSVTTGVHSQEDERIVLVDNKCKCARITSRIIRSSEDPNEDIVERNIR IIVPLNNRENISDPTSPLRTRFVYHLSDLCKKCDPTEVELDNQIVTATQSNICDEDSA TETCYTYDRNKCYTAVVPLVYGGETKMVETALTPDACYPDGGGGSGGGGSGGGGSQHD EAVDANSLAEAKVLANRELDKYGVSDYYKNLINNAKTVEGVKALIDEILAALP |
| 91 | ABD15J DNA | ATGGAATGGAGCTGGGTCTTTCTCTTCTTCCTGTCAGTAACGACTGGTGTCCACTCCC AGCACGATGAGGCCGTGGACGCCAATTCTCTGGCCGAGGCTAAGGTGCTGGCCAACAG AGAGCTGGATAAGTACGGCGTGTCCGACTACTACAAGAACCTGATCAACAACGCCAAG ACCGTGGAAGGCGTGAAGGCCCTGATCGACGAGATCCTGGCTGCCCTGCCTGGAGGCG GAGGATCTGGTGGCGGTGGTTCTGGCGGAGGGGGCTCTCAGGAAGATGAGCGGATCGT GCTGGTGGACAACAAGTGCAAGTGCGCCCGGATCACCTCCCGGATCATCCGGTCCTCC GAGGATCCCAACGAGGACATCGTGGAACGGAACATCAGAATCATCGTGCCCCTGAACA ACCGCGAGAACATCTCCGACCCCACCAGCCCTCTGCGGACCAGATTCGTGTACCACCT GTCCGACCTGTGCAAGAAGTGCGACCCTACCGAGGTGGAACTGGACAACCAGATCGTG ACCGCCACCCAGTCCAACATCTGCGACGAGGACTCCGCCACCGAGACATGCTACACCT ACGACCGGAACAAGTGCTACACCGCCGTGGTGCCTCTGGTGTACGGCGGCGAGACAAA GATGGTGGAAACCGCCCTGACCCCCGACGCCTGCTATCCTGATTGA |
| 92 | ABD15J AA | MEWSWVFLFFLSVTTGVHSQHDEAVDANSLAEAKVLANRELDKYGVSDYYKNLINNAK TVEGVKALIDEILAALPGGGGSGGGGSGGGGSQEDERIVLVDNKCKCARITSRIIRSS EDPNEDIVERNIRIIVPLNNRENISDPTSPLRTRFVYHLSDLCKKCDPTEVELDNQIV TATQSNICDEDSATETCYTYDRNKCYTAVVPLVYGGETKMVETALTPDACYPD |
| 93 | HSA15J DNA | ATGAAATGGGTCACCTTTATCTCCCTGCTGTTCCTGTTCTCCTCCGCCTACTCTCGGG GCGTGTTCAGAAGAGACGCCCACAAATCGGAGGTAGCGCACCGGTTCAAAGACTTGGG AGAAGAAAACTTTAAGGCCCTTGTACTCATTGCGTTTGCGCAGTATTTGCAGCAGTGC CCATTCGAGGACCATGTCAAACTTGTCAACGAAGTGACAGAGTTTGCGAAAACTTGCG TCGCCGACGAATCCGCGGAGAACTGTGACAAGTCGCTGCATACGTTGTTCGGGGATAA GCTCTGTACCGTAGCGACCTTGAGGGAAACTTACGGGGAAATGGCGGACTGTTGCGCT AAGCAGGAGCCGGAACGGAACGAGTGTTTCCTTCAGCATAAGGATGACAACCCCAACC TCCCTAGATTGGTCAGACCCGAAGTGGATGTGATGTGCACAGCATTCCATGACAATGA GGAAACCTTTCTCAAAAAGTATTTGTACGAGATTGCCCGACGACACCCCTATTTCTAC GCTCCCGAGTTGCTCTTCTTCGCGAAACGGTATAAAGCTGCCTTTACTGAATGCTGTC AAGCAGCGGACAAGGCCGCATGCCTCCTTCCCAAATTGGATGAACTCCGCGATGAAGG GAAGGCGTCATCGGCCAAACAGCGGCTTAAGTGCGCATCGCTTCAGAAATTCGGAGAG AGGGCGTTCAAAGCGTGGGCCGTCGCGAGACTGTCGCAGAGATTCCCTAAGGCGGAAT TTGCAGAGGTATCGAAGCTCGTGACAGACCTCACAAAGGTCCACACCGAATGTTGCCA TGGAGACCTGCTTGAGTGCGCCGATGATAGGGCAGACCTCGCAAAGTACATTTGTGAG AATCAGGACAGCATTAGCTCCAAGCTGAAAGAGTGCTGTGAGAAGCCTTTGCTGGAAA AATCCCACTGTATCGCCGAGGTAGAAAACGATGAAATGCCCGCTGATCTTCCCTCGCT GGCGGCAGACTTCGTCGAGTCGAAGGACGTCTGCAAGAATTACGCAGAGGCAAAAGAT GTGTTTCTTGGAATGTTCCTTTATGAGTATGCGAGAAGGCACCCGGATTATTCCGTGG TACTGCTCTTGCGATTGGCGAAAACGTACGAAACAACGCTTGAGAAGTGTTGTGCGGC TGCCGACCCGCATGAGTGCTACGCCAAGGTATTTGATGAGTTTAAACCTCTTGTCGAG GAACCCCAGAATCTTATCAAGCAGAACTGCGAGCTTTTCAAGCAGTTGGGTGAATACA AATTCCAGAACGCGCTTCTGGTGAGGTATACCAAGAAAGTACCTCAAGTCTCAACACC CACACTCGTCGAGGTGTCACGGAACCTCGGGAAAGTAGGGTCGAAGTGCTGTAAACAC CCAGAGGCCAAGCGCATGCCCTGTGCGGAGGACTACCTCTCGGTAGTGTTGAATCAAC TGTGTGTCCTCCACGAAAAGACGCCGGTGTCAGACCGCGTCACAAAGTGCTGCACGGA GAGCCTGGTCAATAGACGCCCCTGCTTCTCAGCGCTGGAGGTGGATGAGACATACGTC CCGAAAGAGTTTAACGCCGAAACGTTTACTTTTCATGCTGATATCTGTACGTTGTCAG AGAAGGAAAGGCAAATCAAGAAACAAACTGCGCTTGTGGAACTGGTGAAGCACAAACC GAAGGCGACTAAGGAACAGCTGAAGGCGGTGATGGATGACTTTGCCGCGTTCGTAGAG AAATGCTGTAAAGCAGACGATAAGGAGACTTGTTTTGCGGAAGAGGGACCTAAACTTG TTGCTGCAAGTCAAGCTGCCTTAGGCTTAGGAGGCGGAGGATCTGGTGGCGGTGGTTC TGGCGGAGGGGGCTCTCAGGAAGATGAGCGGATCGTGCTGGTGGACAACAAGTGCAAG TGCGCCCGGATCACCTCCCGGATCATCCGGTCCTCCGAGGATCCCAACGAGGACATCG TGGAACGGAACATCAGAATCATCGTGCCCCTGAACAACCGCGAGAACATCTCCGACCC CACCAGCCCTCTGCGGACCAGATTCGTGTACCACCTGTCCGACCTGTGCAAGAAGTGC GACCCTACCGAGGTGGAACTGGACAACCAGATCGTGACCGCCACCCAGTCCAACATCT GCGACGAGGACTCCGCCACCGAGACATGCTACACCTACGACCGGAACAAGTGCTACAC CGCCGTGGTGCCTCTGGTGTACGGCGGCGAGACAAAGATGGTGGAAACCGCCCTGACC CCCGACGCCTGCTATCCTGATTAG |
| 94 | HSA15J AA | MKWVTFISLLFLFSSAYSRGVFRRDAHKSEVAHRFKDLGEENFKALVLIAFAQYLQQC PFEDHVKLVNEVTEFAKTCVADESAENCDKSLHTLFGDKLCTVATLRETYGEMADCCA |

TABLE 10-continued

Sequence Summary

| SEQ ID NO: | Short Name | Sequence |
|---|---|---|
| | | KQEPERNECFLQHKDDNPNLPRLVRPEVDVMCTAFHDNEETFLKKYLYEIARRHPYFY<br>APELLFFAKRYKAAFTECCQAADKAACLLPKLDELRDEGKASSAKQRLKCASLQKFGE<br>RAFKAWAVARLSQRFPKAEFAEVSKLVTDLTKVHTECCHGDLLECADDRADLAKYICE<br>NQDSISSKLKECCEKPLLEKSHCIAEVENDEMPADLPSLAADFVESKDVCKNYAEAKD<br>VFLGMFLYEYARRHPDYSVVLLLRLAKTYETTLEKCCAAADPHECYAKVFDEFKPLVE<br>EPQNLIKQNCELFKQLGEYKFQNALLVRYTKKVPQVSTPTLVEVSRNLGKVGSKCCKH<br>PEAKRMPCAEDYLSVVLNQLCVLHEKTPVSDRVTKCCTESLVNRRPCFSALEVDETYV<br>PKEFNAETFTFHADICTLSEKERQIKKQTALVELVKHKPKATKEQLKAVMDDFAAFVE<br>KCCKADDKETCFAEEGPKLVAASQAALGLGGGGSGGGGSGGGGSQEDERIVLVDNKCK<br>CARITSRIIRSSEDPNEDIVERNIRIIVPLNNRENISDPTSPLRTRFVYHLSDLCKKC<br>DPTEVELDNQIVTATQSNICDEDSATETCYTYDRNKCYTAVVPLVYGGETKMVETALT<br>PDACYPD |
| 95 | J15HSA DNA | ATGAAGAACCATCTGCTGTTCTGGGGCGTGCTGGCCGTGTTCATCAAGGCCGTGCACG<br>TGAAGGCCCAGGAAGATGAGCGGATCGTGCTGGTGGACAACAAGTGCAAGTGCGCCCG<br>GATCACCTCCCGGATCATCCGGTCCTCCGAGGATCCCAACGAGGACATCGTGGAACGG<br>AACATCAGAATCATCGTGCCCCTGAACAACCGCGAGAACATCTCCGACCCCACCAGCC<br>CTCTGCGGACCAGATTCGTGTACCACCTGTCCGACCTGTGCAAGAAGTGCGACCCTAC<br>CGAGGTGGAACTGGACAACCAGATCGTGACCGCCACCCAGTCCAACATCTGCGACGAG<br>GACTCCGCCACCGAGACATGCTACACCTACGACCGGAACAAGTGCTACACCGCCGTGG<br>TGCCTCTGGTGTACGGCGGCGAGACAAAGATGGTGGAAACCGCCCTGACCCCCGACGC<br>CTGCTATCCTGATGGAGGCGGAGGATCTGGTGGCGGTGGTTCTGGCGGAGGGGGCTCT<br>GACGCCCACAAATCGGAGGTAGCGCACCGGTTCAAAGACTTGGGAGAAGAAAACTTTA<br>AGGCCCTTGTACTCATTGCGTTTGCGCAGTATTTGCAGCAGTGCCCATTCGAGGACCA<br>TGTCAAACTTGTCAACGAAGTGACAGAGTTTGCGAAAACTTGCGTCGCCGACGAATCC<br>GCGGAGAACTGTGACAAGTCGCTGCATACGTTGTTCGGGGATAAGCTCTGTACCGTAG<br>CGACCTTGAGGGAAACTTACGGGGAAATGGCGGACTGTTGCGCTAAGCAGGAGCCGGA<br>ACGGAACGAGTGTTTCCTTCAGCATAAGGATGACAACCCCAACCTCCCTAGATTGGTC<br>AGACCCGAAGTGGATGTGATGTGCACAGCATTCCATGACAATGAGGAAACCTTTCTCA<br>AAAAGTATTTGTACGAGATTGCCCGACGACACCCCTATTTCTACGCTCCCGAGTTGCT<br>CTTCTTCGCGAAACGGTATAAAGCTGCCTTTACTGAATGCTGTCAAGCAGCGGACAAG<br>GCCGCATGCCTCCTTCCCAAATTGGATGAACTCCGCGATGAAGGGAAGGCGTCATCGG<br>CCAAACAGCGGCTTAAGTGCGCATCGCTTCAGAAATTCGGAGAGAGGGCGTTCAAAGC<br>GTGGGCCGTCGCGAGACTGTCGCAGAGATTCCCTAAGGCGGAATTTGCAGAGGTATCG<br>AAGCTCGTGACAGACCTCACAAAGGTCCACACCGAATGTTGCCATGGAGACCTGCTTG<br>AGTGCGCCGATGATAGGGCAGACCTCGCAAAGTACATTTGTGAGAATCAGGACAGCAT<br>TAGCTCCAAGCTGAAAGAGTGCTGTGAGAAGCCTTTGCTGGAAAAATCCCACTGTATC<br>GCCGAGGTAGAAAACGATGAAATGCCCGCTGATCTTCCCTCGCTGGCGGCAGACTTCG<br>TCGAGTCGAAGGACGTCTGCAAGAATTACGCAGAGGCAAAAGATGTGTTTCTTGGAAT<br>GTTCCTTTATGAGTATGCGAGAAGGCACCCGGATTATTCCGTGGTACTGCTCTTGCGA<br>TTGGCGAAAACGTACGAAACAACGCTTGAGAAGTGTTGTGCGGCTGCCGACCCGCATG<br>AGTGCTACGCCAAGGTATTTGATGAGTTTAAACCTCTTGTCGAGGAACCCCAGAATCT<br>TATCAAGCAGAACTGCGAGCTTTTCAAGCAGTTGGGTGAATACAAATTCCAGAACGCG<br>CTTCTGGTGAGGTATACCAAGAAAGTACCTCAAGTCTCAACACCCACACTCGTCGAGG<br>TGTCACGGAACCTCGGGAAAGTAGGGTCGAAGTGCTGTAAACACCCAGAGGCCAAGCG<br>CATGCCCTGTGCGGAGGACTACCTCTCGGTAGTGTTGAATCAACTGTGTGTCCTCCAC<br>GAAAAGACGCCGGTGTCAGACCGCGTCACAAAGTGCTGCACGGAGAGCCTGGTCAATA<br>GACGCCCCTGCTTCTCAGCGCTGGAGGTGGATGAGACATACGTCCCGAAAGAGTTTAA<br>CGCCGAAACGTTTACTTTTCATGCTGATATCTGTACGTTGTCAGAGAAGGAAAGGCAA<br>ATCAAGAAACAAACTGCGCTTGTGGAACTGGTGAAGCACAAACCGAAGGCGACTAAGG<br>AACAGCTGAAGGCGGTGATGGATGACTTTGCCGCGTTCGTAGAGAAATGCTGTAAAGC<br>AGACGATAAGGAGACTTGTTTTGCGGAAGAGGGACCTAAACTTGTTGCTGCAAGTCAA<br>GCTGCCTTAGGCTTATAG |
| 96 | J15HSA AA | MKNHLLFWGVLAVFIKAVHVKAQEDERIVLVDNKCKCARITSRIIRSSEDPNEDIVER<br>NIRIIVPLNNRENISDPTSPLRTRFVYHLSDLCKKCDPTEVELDNQIVTATQSNICDE<br>DSATETCYTYDRNKCYTAVVPLVYGGETKMVETALTPDACYPDGGGGSGGGGSGGGGS<br>DAHKSEVAHRFKDLGEENFKALVLIAFAQYLQQCPFEDHVKLVNEVTEFAKTCVADES<br>AENCDKSLHTLFGDKLCTVATLRETYGEMADCCAKQEPERNECFLQHKDDNPNLPRLV<br>RPEVDVMCTAFHDNEETFLKKYLYEIARRHPYFYAPELLFFAKRYKAAFTECCQAADK<br>AACLLPKLDELRDEGKASSAKQRLKCASLQKFGERAFKAWAVARLSQRFPKAEFAEVS<br>KLVTDLTKVHTECCHGDLLECADDRADLAKYICENQDSISSKLKECCEKPLLEKSHCI<br>AEVENDEMPADLPSLAADFVESKDVCKNYAEAKDVFLGMFLYEYARRHPDYSVVLLLR<br>LAKTYETTLEKCCAAADPHECYAKVFDEFKPLVEEPQNLIKQNCELFKQLGEYKFQNA<br>LLVRYTKKVPQVSTPTLVEVSRNLGKVGSKCCKHPEAKRMPCAEDYLSVVLNQLCVLH<br>EKTPVSDRVTKCCTESLVNRRPCFSALEVDETYVPKEFNAETFTFHADICTLSEKERQ<br>IKKQTALVELVKHKPKATKEQLKAVMDDFAAFVEKCCKADDKETCFAEEGPKLVAASQ<br>AALGL |
| 97 | V15J15ABD DNA | ATGGGGTGGTCCTACATTATCCTGTTCCTCGTGGCCACCGCCACTGGCGTGCACTCAC<br>AGGTGCAGCTGGTGCAGTCTGGCGCCGAAGTGAAGAAACCTGGCGCCTCCGTGAAGGT<br>GTCCTGCAAGGCCTCCGGCTACACCTTCATCAGCTACACCATGCACTGGGTGCGACAG<br>GCCCCTGGACAGGGCCTGGAATGGATGGGCTACATCAACCCTAGATCTGGCTACACCC<br>ACTACAACCAGAAGCTGAAGGACAAGGCCACCCTGACCGCCGACAAGTCTGCCTCCAC<br>CGCCTACATGGAACTGTCCTCCCTGCGGAGCGAGGACACCGCCGTGTACTACTGTGCC |

TABLE 10-continued

| Sequence Summary | | |
|---|---|---|
| SEQ ID NO: | Short Name | Sequence |
| | | AGATCCGCCTACTACGACTACGACGGCTTCGCCTATTGGGGCCAGGGCACCCTCGTGA CAGTGTCTAGCGGTGGCGGAGGATCTGGCGGAGGCGGTAGTGGCGGTGGCGGATCTGA TATCCAGATGACCCAGTCCCCCTCCAGCCTGTCTGCCTCTGTGGGCGACAGAGTGACA ATTACCTGCTCCGCCAGCTCCTCCGTGTCTTACATGAACTGGTATCAGCAGAAGCCCG GCAAGGCCCCCAAGCGGCTGATCTACGACACCTCCAAGCTGGCCTCTGGCGTGCCCTC CAGATTCTCCGGCTCTGGCTCTGGCACCGACTTTACCCTGACCATCAGCTCCCTGCAG CCCGAGGACTTCGCCACCTACTACTGCCAGCAGTGGTCCTCCAACCCTCCCACCTTTG GCGGAGGCACCAAGGTGGAAATCAAAGGCGGCGGAGGAAGCGGGGGAGGCGGTTCTGG GGGTGGTGGATCTCAGGAAGATGAGCGGATCGTGCTGGTGGACAACAAGTGCAAGTGC GCCCGGATCACCTCCCGGATCATCCGGTCCTCCGAGGATCCCAACGAGGACATCGTGG AACGGAACATCAGAATCATCGTGCCCCTGAACAACCGCGAGAACATCTCCGACCCCAC CAGCCCTCTGCGGACCAGATTCGTGTACCACCTGTCCGACCTGTGCAAGAAGTGCGAC CCTACCGAGGTGGAACTGGACAACCAGATCGTGACCGCCACCCAGTCCAACATCTGCG ACGAGGACTCCGCCACCGAGACATGCTACACCTACGACCGGAACAAGTGCTACACCGC CGTGGTGCCTCTGGTGTACGGCGGCGAGACAAAGATGGTGGAAACCGCCCTGACCCCC GACGCCTGCTATCCTGATGGAGGCGGAGGATCTGGTGGCGGTGGTTCTGGCGGAGGGG GCTCTCAGCACGATGAGGCCGTGGACGCCAATTCTCTGGCCGAGGCTAAGGTGCTGGC CAACAGAGAGCTGGATAAGTACGGCGTGTCCGACTACTACAAGAACCTGATCAACAAC GCCAAGACCGTGGAAGGCGTGAAGGCCCTGATCGACGAGATCCTGGCTGCCCTGCCTT GA |
| 98 | V15J15ABD AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSQHDEAVDANSLAEAKVLANRELDKYGVSDYYKNLINN AKTVEGVKALIDEILAALP |
| 99 | V15J15HSA (K573P) DNA | ATGGGGTGGTCCTACATTATCCTGTTCCTCGTGGCCACCGCCACTGGCGTGCACTCAC AGGTGCAGCTGGTGCAGTCTGGCGCCGAAGTGAAGAAACCTGGCGCCTCCGTGAAGGT GTCCTGCAAGGCCTCCGGCTACACCTTCATCAGCTACACCATGCACTGGGTGCGACAG GCCCCTGGACAGGGCCTGGAATGGATGGGCTACATCAACCCTAGATCTGGCTACACCC ACTACAACCAGAAGCTGAAGGACAAGGCCACCCTGACCGCCGACAAGTCTGCCTCCAC CGCCTACATGGAACTGTCCTCCCTGCGGAGCGAGGACACCGCCGTGTACTACTGTGCC AGATCCGCCTACTACGACTACGACGGCTTCGCCTATTGGGGCCAGGGCACCCTCGTGA CAGTGTCTAGCGGTGGCGGAGGATCTGGCGGAGGCGGTAGTGGCGGTGGCGGATCTGA TATCCAGATGACCCAGTCCCCCTCCAGCCTGTCTGCCTCTGTGGGCGACAGAGTGACA ATTACCTGCTCCGCCAGCTCCTCCGTGTCTTACATGAACTGGTATCAGCAGAAGCCCG GCAAGGCCCCCAAGCGGCTGATCTACGACACCTCCAAGCTGGCCTCTGGCGTGCCCTC CAGATTCTCCGGCTCTGGCTCTGGCACCGACTTTACCCTGACCATCAGCTCCCTGCAG CCCGAGGACTTCGCCACCTACTACTGCCAGCAGTGGTCCTCCAACCCTCCCACCTTTG GCGGAGGCACCAAGGTGGAAATCAAAGGCGGCGGAGGAAGCGGGGGAGGCGGTTCTGG GGGTGGTGGATCTCAGGAAGATGAGCGGATCGTGCTGGTGGACAACAAGTGCAAGTGC GCCCGGATCACCTCCCGGATCATCCGGTCCTCCGAGGATCCCAACGAGGACATCGTGG AACGGAACATCAGAATCATCGTGCCCCTGAACAACCGCGAGAACATCTCCGACCCCAC CAGCCCTCTGCGGACCAGATTCGTGTACCACCTGTCCGACCTGTGCAAGAAGTGCGAC CCTACCGAGGTGGAACTGGACAACCAGATCGTGACCGCCACCCAGTCCAACATCTGCG ACGAGGACTCCGCCACCGAGACATGCTACACCTACGACCGGAACAAGTGCTACACCGC CGTGGTGCCTCTGGTGTACGGCGGCGAGACAAAGATGGTGGAAACCGCCCTGACCCCC GACGCCTGCTATCCTGATGGAGGCGGAGGATCTGGTGGCGGTGGTTCTGGCGGAGGGG GCTCTGACGCCCACAAATCGGAGGTAGCGCACCGGTTCAAAGACTTGGGAGAAGAAAA CTTTAAGGCCCTTGTACTCATTGCGTTTGCGCAGTATTTGCAGCAGTGCCCATTCGAG GACCATGTCAAACTTGTCAACGAAGTGACAGAGTTTGCGAAAACTTGCGTCGCCGACG AATCCGCGGAGAACTGTGACAAGTCGCTGCATACGTTGTTCGGGGATAAGCTCTGTAC CGTAGCGACCTTGAGGGAAACTTACGGGGAAATGGCGGACTGTTGCGCTAAGCAGGAG CCGGAACGGAACGAGTGTTTCCTTCAGCATAAGGATGACAACCCCAACCTCCCTAGAT TGGTCAGACCCGAAGTGGATGTGATGTGCACAGCATTCCATGACAATGAGGAAACCTT TCTCAAAAAGTATTTGTACGAGATTGCCCGACGACACCCCTATTTCTACGCTCCCGAG TTGCTCTTCTTCGCGAAACGGTATAAAGCTGCCTTTACTGAATGCTGTCAAGCAGCGG ACAAGGCCGCATGCCTCCTTCCCAAATTGGATGAACTCCGCGATGAAGGGAAGGCGTC ATCGGCCAAACAGCGGCTTAAGTGCGCATCGCTTCAGAAATTCGGAGAGAGGGCGTTC AAAGCGTGGGCCGTCGCGAGACTGTCGCAGAGATTCCCTAAGGCGGAATTTGCAGAGG TATCGAAGCTCGTGACAGACCTCACAAAGGTCCACACCGAATGTTGCCATGGAGACCT GCTTGAGTGCGCCGATGATAGGGCAGACCTCGCAAAGTACATTTGTGAGAATCAGGAC AGCATTAGCTCCAAGCTGAAAGAGTGCTGTGAGAAGCCTTTGCTGGAAAAATCCCACT GTATCGCCGAGGTAGAAAACGATGAAATGCCCGCTGATCTTCCCTCGCTGGCGGCAGA CTTCGTCGAGTCGAAGGACGTCTGCAAGAATTACGCAGAGGCAAAAGATGTGTTTCTT GGAATGTTCCTTTATGAGTATGCGAGAAGGCACCCGGATTATTCCGTGGTACTGCTCT TGCGATTGGCGAAAACGTACGAAACAACGCTTGAGAAGTGTTGTGCGGCTGCCGACCC GCATGAGTGCTACGCCAAGGTATTTGATGAGTTTAAACCTCTTGTCGAGGAACCCCAG AATCTTATCAAGCAGAACTGCGAGCTTTTCAAGCAGTTGGGTGAATACAAATTCCAGA ACGCGCTTCTGGTGAGGTATACCAAGAAAGTACCTCAAGTCTCAACACCCACACTCGT |

TABLE 10-continued

Sequence Summary

| SEQ ID NO: | Short Name | Sequence |
|---|---|---|
| | | CGAGGTGTCACGGAACCTCGGGAAAGTAGGGTCGAAGTGCTGTAAACACCCAGAGGCC |
| | | AAGCGCATGCCCTGTGCGGAGGACTACCTCTCGGTAGTGTTGAATCAACTGTGTGTCC |
| | | TCCACGAAAAGACGCCGGTGTCAGACCGCGTCACAAAGTGCTGCACGGAGAGCCTGGT |
| | | CAATAGACGCCCCTGCTTCTCAGCGCTGGAGGTGGATGAGACATACGTCCCGAAAGAG |
| | | TTTAACGCCGAAACGTTTACTTTTCATGCTGATATCTGTACGTTGTCAGAGAAGGAAA |
| | | GGCAAATCAAGAAACAAACTGCGCTTGTGGAACTGGTGAAGCACAAACCGAAGGCGAC |
| | | TAAGGAACAGCTGAAGGCGGTGATGGATGACTTTGCCGCGTTCGTAGAGAAATGCTGT |
| | | AAAGCAGACGATAAGGAGACTTGTTTTGCGGAAGAGGGACCTAAACTTGTTGCTGCAA |
| | | GTCAAGCTGCCTTAGGCTTATAG |
| 100 | V15J15HSA | MGWSYIILFLVATATGVHSQVQLVQSGAEVKKPGASVKVSCKASGYTFISYTMHWVRQ |
| | (K573P) | APGQGLEWMGYINPRSGYTHYNQKLKDKATLTADKSASTAYMELSSLRSEDTAVYYCA |
| | AA | RSAYYDYDGFAYWGQGTLVTVSSGGGGSGGGGSGGGGSDIQMTQSPSSLSASVGDRVT |
| | | ITCSASSSVSYMNWYQQKPGKAPKRLIYDTSKLASGVPSRFSGSGSGTDFTLTISSLQ |
| | | PEDFATYYCQQWSSNPPTFGGGTKVEIKGGGGSGGGGSGGGGSQEDERIVLVDNKCKC |
| | | ARITSRIIRSSEDPNEDIVERNIRIIVPLNNRENISDPTSPLRTRFVYHLSDLCKKCD |
| | | PTEVELDNQIVTATQSNICDEDSATETCYTYDRNKCYTAVVPLVYGGETKMVETALTP |
| | | DACYPDGGGGSGGGGSGGGGSDAHKSEVAHRFKDLGEENFKALVLIAFAQYLQQCPFE |
| | | DHVKLVNEVTEFAKTCVADESAENCDKSLHTLFGDKLCTVATLRETYGEMADCCAKQE |
| | | PERNECFLQHKDDNPNLPRLVRPEVDVMCTAFHDNEETFLKKYLYEIARRHPYFYAPE |
| | | LLFFAKRYKAAFTECCQAADKAACLLPKLDELRDEGKASSAKQRLKCASLQKFGERAF |
| | | KAWAVARLSQRFPKAEFAEVSKLVTDLTKVHTECCHGDLLECADDRADLAKYICENQD |
| | | SISSKLKECCEKPLLEKSHCIAEVENDEMPADLPSLAADFVESKDVCKNYAEAKDVFL |
| | | GMFLYEYARRHPDYSVVLLLRLAKTYETTLEKCCAAADPHECYAKVFDEFKPLVEEPQ |
| | | NLIKQNCELFKQLGEYKFQNALLVRYTKKVPQVSTPTLVEVSRNLGKVGSKCCKHPEA |
| | | KRMPCAEDYLSVVLNQLCVLHEKTPVSDRVTKCCTESLVNRRPCFSALEVDETYVPKE |
| | | FNAETFTFHADICTLSEKERQIKKQTALVELVKHKPKATKEQLKAVMDDFAAFVEKCC |
| | | KADDKETCFAEEGPKLVAASQAALGL |
| 101 | V15J15HSA | ATGGGGTGGTCCTACATTATCCTGTTCCTCGTGGCCACCGCCACTGGCGTGCACTCAC |
| | (wt) DNA | AGGTGCAGCTGGTGCAGTCTGGCGCCGAAGTGAAGAAACCTGGCGCCTCCGTGAAGGT |
| | | GTCCTGCAAGGCCTCCGGCTACACCTTCATCAGCTACACCATGCACTGGGTGCGACAG |
| | | GCCCCTGGACAGGGCCTGGAATGGATGGGCTACATCAACCCTAGATCTGGCTACACCC |
| | | ACTACAACCAGAAGCTGAAGGACAAGGCCACCCTGACCGCCGACAAGTCTGCCTCCAC |
| | | CGCCTACATGGAACTGTCCTCCCTGCGGAGCGAGGACACCGCCGTGTACTACTGTGCC |
| | | AGATCCGCCTACTACGACTACGACGGCTTCGCCTATTGGGGCCAGGGCACCCTCGTGA |
| | | CAGTGTCTAGCGGTGGCGGAGGATCTGGCGGAGGCGGTAGTGGCGGTGGCGGATCTGA |
| | | TATCCAGATGACCCAGTCCCCCTCCAGCCTGTCTGCCTCTGTGGGCGACAGAGTGACA |
| | | ATTACCTGCTCCGCCAGCTCCTCCGTGTCTTACATGAACTGGTATCAGCAGAAGCCCG |
| | | GCAAGGCCCCCAAGCGGCTGATCTACGACACCTCCAAGCTGGCCTCTGGCGTGCCCTC |
| | | CAGATTCTCCGGCTCTGGCTCTGGCACCGACTTTACCCTGACCATCAGCTCCCTGCAG |
| | | CCCGAGGACTTCGCCACCTACTACTGCCAGCAGTGGTCCTCCAACCCTCCCACCTTTG |
| | | GCGGAGGCACCAAGGTGGAAATCAAAGGCGGCGGAGGAAGCGGGGGAGGCGGTTCTGG |
| | | GGGTGGTGGATCTCAGGAAGATGAGCGGATCGTGCTGGTGGACAACAAGTGCAAGTGC |
| | | GCCCGGATCACCTCCCGGATCATCCGGTCCTCCGAGGATCCCAACGAGGACATCGTGG |
| | | AACGGAACATCAGAATCATCGTGCCCCTGAACAACCGCGAGAACATCTCCGACCCCAC |
| | | CAGCCCTCTGCGGACCAGATTCGTGTACCACCTGTCCGACCTGTGCAAGAAGTGCGAC |
| | | CCTACCGAGGTGGAACTGGACAACCAGATCGTGACCGCCACCCAGTCCAACATCTGCG |
| | | ACGAGGACTCCGCCACCGAGACATGCTACACCTACGACCGGAACAAGTGCTACACCGC |
| | | CGTGGTGCCTCTGGTGTACGGCGGCGAGACAAAGATGGTGGAAACCGCCCTGACCCCC |
| | | GACGCCTGCTATCCTGATGGAGGCGGAGGATCTGGTGGCGGTGGTTCTGGCGGAGGGG |
| | | GCTCTGACGCCCACAAATCGGAGGTAGCGCACCGGTTCAAAGACTTGGGAGAAGAAAA |
| | | CTTTAAGGCCCTTGTACTCATTGCGTTTGCGCAGTATTTGCAGCAGTGCCCATTCGAG |
| | | GACCATGTCAAACTTGTCAACGAAGTGACAGAGTTTGCGAAAACTTGCGTCGCCGACG |
| | | AATCCGCGGAGAACTGTGACAAGTCGCTGCATACGTTGTTCGGGGATAAGCTCTGTAC |
| | | CGTAGCGACCTTGAGGGAAACTTACGGGGAAATGGCGGACTGTTGCGCTAAGCAGGAG |
| | | CCGGAACGGAACGAGTGTTTCCTTCAGCATAAGGATGACAACCCCAACCTCCCTAGAT |
| | | TGGTCAGACCCGAAGTGGATGTGATGTGCACAGCATTCCATGACAATGAGGAAACCTT |
| | | TCTCAAAAAGTATTTGTACGAGATTGCCCGACGACACCCCTATTTCTACGCTCCCGAG |
| | | TTGCTCTTCTTCGCGAAACGGTATAAAGCTGCCTTTACTGAATGCTGTCAAGCAGCGG |
| | | ACAAGGCCGCATGCCTCCTTCCCAAATTGGATGAACTCCGCGATGAAGGGAAGGCGTC |
| | | ATCGGCCAAACAGCGGCTTAAGTGCGCATCGCTTCAGAAATTCGGAGAGAGGGCGTTC |
| | | AAAGCGTGGGCCGTCGCGAGACTGTCGCAGAGATTCCCTAAGGCGGAATTTGCAGAGG |
| | | TATCGAAGCTCGTGACAGACCTCACAAAGGTCCACACCGAATGTTGCCATGGAGACCT |
| | | GCTTGAGTGCGCCGATGATAGGGCAGACCTCGCAAAGTACATTTGTGAGAATCAGGAC |
| | | AGCATTAGCTCCAAGCTGAAAGAGTGCTGTGAGAAGCCTTTGCTGGAAAAATCCCACT |
| | | GTATCGCCGAGGTAGAAAACGATGAAATGCCCGCTGATCTTCCCTCGCTGGCGGCAGA |
| | | CTTCGTCGAGTCGAAGGACGTCTGCAAGAATTACGCAGAGGCAAAAGATGTGTTTCTT |
| | | GGAATGTTCCTTTATGAGTATGCGAGAAGGCACCCGGATTATTCCGTGGTACTGCTCT |
| | | TGCGATTGGCGAAAACGTACGAAACAACGCTTGAGAAGTGTTGTGCGGCTGCCGACCC |
| | | GCATGAGTGCTACGCCAAGGTATTTGATGAGTTTAAACCTCTTGTCGAGGAACCCCAG |
| | | AATCTTATCAAGCAGAACTGCGAGCTTTTCAAGCAGTTGGGTGAATACAAATTCCAGA |
| | | ACGCGCTTCTGGTGAGGTATACCAAGAAAGTACCTCAAGTCTCAACACCCACACTCGT |
| | | CGAGGTGTCACGGAACCTCGGGAAAGTAGGGTCGAAGTGCTGTAAACACCCAGAGGCC |
| | | AAGCGCATGCCCTGTGCGGAGGACTACCTCTCGGTAGTGTTGAATCAACTGTGTGTCC |

TABLE 10-continued

Sequence Summary

| SEQ ID NO: | Short Name | Sequence |
| --- | --- | --- |
| | | TCCACGAAAAGACGCCGGTGTCAGACCGCGTCACAAAGTGCTGCACGGAGAGCCTGGT CAATAGACGCCCCTGCTTCTCAGCGCTGGAGGTGGATGAGACATACGTCCCGAAAGAG TTTAACGCCGAAACGTTTACTTTTCATGCTGATATCTGTACGTTGTCAGAGAAGGAAA GGCAAATCAAGAAACAAACTGCGCTTGTGGAACTGGTGAAGCACAAACCGAAGGCGAC TAAGGAACAGCTGAAGGCGGTGATGGATGACTTTGCCGCGTTCGTAGAGAAATGCTGT AAAGCAGACGATAAGGAGACTTGTTTTGCGGAAGAGGGAAAGAAACTTGTTGCTGCAA GTCAAGCTGCCTTAGGCTTATAG |
| 102 | V15J15HSA (wt) AA | MGWSYIILFLVATATGVHSQVQLVQSGAEVKKPGASVKVSCKASGYTFISYTMHWVRQ APGQGLEWMGYINPRSGYTHYNQKLKDKATLTADKSASTAYMELSSLRSEDTAVYYCA RSAYYDYDGFAYWGQGTLVTVSSGGGGSGGGGSGGGGSDIQMTQSPSSLSASVGDRVT ITCSASSSVSYMNWYQQKPGKAPKRLIYDTSKLASGVPSRFSGSGSGTDFTLTISSLQ PEDFATYYCQQWSSNPPTFGGGTKVEIKGGGGSGGGGSGGGGSQEDERIVLVDNKCKC ARITSRIIRSSEDPNEDIVERNIRIIVPLNNRENISDPTSPLRTRFVYHLSDLCKKCD PTEVELDNQIVTATQSNICDEDSATETCYTYDRNKCYTAVVPLVYGGETKMVETALTP DACYPDGGGGSGGGGSGGGGSDAHKSEVAHRFKDLGEENFKALVLIAFAQYLQQCPFE DHVKLVNEVTEFAKTCVADESAENCDKSLHTLFGDKLCTVATLRETYGEMADCCAKQE PERNECFLQHKDDNPNLPRLVRPEVDVMCTAFHDNEETFLKKYLYEIARRHPYFYAPE LLFFAKRYKAAFTECCQAADKAACLLPKLDELRDEGKASSAKQRLKCASLQKFGERAF KAWAVARLSQRFPKAEFAEVSKLVTDLTKVHTECCHGDLLECADDRADLAKYICENQD SISSKLKECCEKPLLEKSHCIAEVENDEMPADLPSLAADFVESKDVCKNYAEAKDVFL GMFLYEYARRHPDYSVVLLLRLAKTYETTLEKCCAAADPHECYAKVFDEFKPLVEEPQ NLIKQNCELFKQLGEYKFQNALLVRYTKKVPQVSTPTLVEVSRNLGKVGSKCCKHPEA KRMPCAEDYLSVVLNQLCVLHEKTPVSDRVTKCCTESLVNRRPCFSALEVDETYVPKE FNAETFTFHADICTLSEKERQIKKQTALVELVKHKPKATKEQLKAVMDDFAAFVEKCC KADDKETCFAEEGKKLVAASQAALGL |

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. Various examples of changes, substitutions, and alterations are ascertainable by one skilled in the art and could be made without departing from the spirit and scope disclosed herein.

SEQUENCE LISTING

```
Sequence total quantity: 104
SEQ ID NO: 1            moltype = AA  length = 137
FEATURE                 Location/Qualifiers
source                  1..137
                        mol_type = protein
                        organism = Homo sapiens
SEQUENCE: 1
QEDERIVLVD NKCKCARITS RIIRSSEDPN EDIVERNIRI IVPLNNRENI SDPTSPLRTR  60
FVYHLSDLCK KCDPTEVELD NQIVTATQSN ICDEDSATET CYTYDRNKCY TAVVPLVYGG  120
ETKMVETALT PDACYPD                                                 137

SEQ ID NO: 2            moltype = AA  length = 11
FEATURE                 Location/Qualifiers
REGION                  1..11
                        note = source = /note="Description of Unknown: Albumin
                         binding peptide"
source                  1..11
                        mol_type = protein
                        organism = unidentified
SEQUENCE: 2
DLCLRDWGCL W                                                       11

SEQ ID NO: 3            moltype = AA  length = 11
FEATURE                 Location/Qualifiers
REGION                  1..11
                        note = source = /note="Description of Unknown: Albumin
                         binding peptide"
source                  1..11
                        mol_type = protein
```

```
                        organism = unidentified
SEQUENCE: 3
DICLPRWGCL W                                                11

SEQ ID NO: 4            moltype = AA  length = 15
FEATURE                 Location/Qualifiers
REGION                  1..15
                        note = source = /note="Description of Unknown: Albumin
                         binding peptide"
source                  1..15
                        mol_type = protein
                        organism = unidentified
SEQUENCE: 4
MEDICLPRWG CLWGD                                            15

SEQ ID NO: 5            moltype = AA  length = 20
FEATURE                 Location/Qualifiers
REGION                  1..20
                        note = source = /note="Description of Unknown: Albumin
                         binding peptide"
source                  1..20
                        mol_type = protein
                        organism = unidentified
SEQUENCE: 5
QRLMEDICLP RWGCLWEDDE                                       20

SEQ ID NO: 6            moltype = AA  length = 20
FEATURE                 Location/Qualifiers
REGION                  1..20
                        note = source = /note="Description of Unknown: Albumin
                         binding peptide"
source                  1..20
                        mol_type = protein
                        organism = unidentified
SEQUENCE: 6
QGLIGDICLP RWGCLWGRSV                                       20

SEQ ID NO: 7            moltype = AA  length = 21
FEATURE                 Location/Qualifiers
REGION                  1..21
                        note = source = /note="Description of Unknown: Albumin
                         binding peptide"
source                  1..21
                        mol_type = protein
                        organism = unidentified
SEQUENCE: 7
QGLIGDICLP RWGCLWGRSV K                                     21

SEQ ID NO: 8            moltype = AA  length = 15
FEATURE                 Location/Qualifiers
REGION                  1..15
                        note = source = /note="Description of Unknown: Albumin
                         binding peptide"
source                  1..15
                        mol_type = protein
                        organism = unidentified
SEQUENCE: 8
EDICLPRWGC LWEDD                                            15

SEQ ID NO: 9            moltype = AA  length = 18
FEATURE                 Location/Qualifiers
REGION                  1..18
                        note = source = /note="Description of Unknown: Albumin
                         binding peptide"
source                  1..18
                        mol_type = protein
                        organism = unidentified
SEQUENCE: 9
RLMEDICLPR WGCLWEDD                                         18

SEQ ID NO: 10           moltype = AA  length = 16
FEATURE                 Location/Qualifiers
REGION                  1..16
                        note = source = /note="Description of Unknown: Albumin
                         binding peptide"
source                  1..16
                        mol_type = protein
                        organism = unidentified
SEQUENCE: 10
```

```
MEDICLPRWG CLWEDD                                                 16

SEQ ID NO: 11           moltype = AA  length = 15
FEATURE                 Location/Qualifiers
REGION                  1..15
                        note = source = /note="Description of Unknown: Albumin
                         binding peptide"
source                  1..15
                        mol_type = protein
                        organism = unidentified
SEQUENCE: 11
MEDICLPRWG CLWED                                                  15

SEQ ID NO: 12           moltype = AA  length = 18
FEATURE                 Location/Qualifiers
REGION                  1..18
                        note = source = /note="Description of Unknown: Albumin
                         binding peptide"
source                  1..18
                        mol_type = protein
                        organism = unidentified
SEQUENCE: 12
RLMEDICLAR WGCLWEDD                                               18

SEQ ID NO: 13           moltype = AA  length = 20
FEATURE                 Location/Qualifiers
REGION                  1..20
                        note = source = /note="Description of Unknown: Albumin
                         binding peptide"
source                  1..20
                        mol_type = protein
                        organism = unidentified
SEQUENCE: 13
EVRSFCTRWP AEKSCKPLRG                                             20

SEQ ID NO: 14           moltype = AA  length = 20
FEATURE                 Location/Qualifiers
REGION                  1..20
                        note = source = /note="Description of Unknown: Albumin
                         binding peptide"
source                  1..20
                        mol_type = protein
                        organism = unidentified
SEQUENCE: 14
RAPESFVCYW ETICFERSEQ                                             20

SEQ ID NO: 15           moltype = AA  length = 11
FEATURE                 Location/Qualifiers
REGION                  1..11
                        note = source = /note="Description of Unknown: Albumin
                         binding peptide"
source                  1..11
                        mol_type = protein
                        organism = unidentified
SEQUENCE: 15
EMCYFPGICW M                                                      11

SEQ ID NO: 16           moltype = AA  length = 593
FEATURE                 Location/Qualifiers
REGION                  1..593
                        note = source = /note="Description of Artificial Sequence:
                         Synthetic polypeptide"
source                  1..593
                        mol_type = protein
                        organism = synthetic construct
SEQUENCE: 16
MGWSYIILFL VATATGVHSQ VQLQQPGAEL VKPGASVKMS CKASGYTFTS YNMHWVKQTP  60
GRGLEWIGAI YPGNGDTSYN QKFKGKATLT ADKSSSTAYM QLSSLTSEDS AVYYCARSTY  120
YGGDWYFNVW GAGTTVTVSS GSASAPTLFP LVSCENSPSD TSSVAVGCLA QDFLPDSITF  180
SWKYKNNSDI SSTRGFPSVL RGGKYAATSQ VLLPSKDVMQ GTDEHVVCKV QHPNGNKEKN  240
VPLPVIAELP PKVSVFVPPR DGFFGNPRKS KLICQATGFS PRQIQVSWLR EGKQVGSGVT  300
TDQVQAEAKE SGPTTYKVTS TLTIKESDWL SQSMFTCRVD HRGLTFQQNA SSMCVPDQDT  360
AIRVFAIPPS FASIFLTKST KLTCLVTDLT TYDSVTISWT RQNGEAVKTH TNISESHPNA  420
TFSAVGEASI CEDDWNSGER FTCTVTHTDL PSPLKQTISR PKGVALHRPD VYLLPPAREQ  480
LNLRESATIT CLVTGFSPAD VFVQWMQRGQ PLSPEKYVTS APMPEPQAPG RYFAHSILTV  540
SEEEWNTGET YTCVVAHEAL PNRVTERTVD KSTGKPTLYN VSLVMSDTAG TCY         593

SEQ ID NO: 17           moltype = AA  length = 235
FEATURE                 Location/Qualifiers
```

```
REGION                  1..235
                        note = source = /note="Description of Artificial Sequence:
                         Synthetic polypeptide"
source                  1..235
                        mol_type = protein
                        organism = synthetic construct
SEQUENCE: 17
MDMRVPAQLL GLLLLWLRGA RCQIVLSQSP AILSASPGEK VTMTCRASSS VSYIHWFQQK  60
PGSSPKPWIY ATSNLASGVP VRFSGSGSGT SYSLTISRVE AEDAATYYCQ QWTSNPPTFG  120
GGTKLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 18           moltype = AA  length = 417
FEATURE                 Location/Qualifiers
REGION                  1..417
                        note = source = /note="Description of Artificial Sequence:
                         Synthetic polypeptide"
source                  1..417
                        mol_type = protein
                        organism = synthetic construct
SEQUENCE: 18
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYSLDYWG QGTTLTVSSG  120
GGGSGGGGSG GGGSQIVLTQ SPAIMSASPG EKVTMTCSAS SSVSYMNWYQ QKSGTSPKRW  180
IYDTSKLASG VPAHFRGSGS GTSYSLTISG MEAEDAATYY CQQWSSNPFT FGSGTKLEIK  240
GGGGSGGGGS GGGGSQEDER IVLVDNKCKC ARITSRIIRS SEDPNEDIVE RNIRIIVPLN  300
NRENISDPTS PLRTRFVYHL SDLCKKCDPT EVELDNQIVT ATQSNICDED SATETCYTYD  360
RNKCYTAVVP LVYGGETKMV ETALTPDACY PDGGGSEQKL ISEEDLNSAV DHHHHHH     417

SEQ ID NO: 19           moltype = AA  length = 413
FEATURE                 Location/Qualifiers
REGION                  1..413
                        note = source = /note="Description of Artificial Sequence:
                         Synthetic polypeptide"
source                  1..413
                        mol_type = protein
                        organism = synthetic construct
SEQUENCE: 19
QEDERIVLVD NKCKCARITS RIIRSSEDPN EDIVERNIRI IVPLNNRENI SDPTSPLRTR  60
FVYHLSDLCK KCDPTEVELD NQIVTATQSN ICDEDSATET CYTYDRNKCY TAVVPLVYGG  120
ETKMVETALT PDACYPDGGG GSGGGGSGGG GSQVQLQQSG AELARPGASV KMSCKASGYT  180
FTRYTMHWVK QRPGQGLEWI GYINPSRGYT NYNQKFKDKA TLTTDKSSST AYMQLSSLTS  240
EDSAVYYCAR YYDDHYSLDY WGQGTTLTVS SGGGGSGGGG SGGGGSQIVL TQSPAIMSAS  300
PGEKVTMTCS ASSSVSYMNW YQQKSGTSPK RWIYDTSKLA SGVPAHFRGS GSGTSYSLTI  360
SGMEAEDAAT YYCQQWSSNP FTFGSGTKLE IKEQKLISEE DLNSAVDHHH HHH         413

SEQ ID NO: 20           moltype = AA  length = 412
FEATURE                 Location/Qualifiers
REGION                  1..412
                        note = source = /note="Description of Artificial Sequence:
                         Synthetic polypeptide"
source                  1..412
                        mol_type = protein
                        organism = synthetic construct
SEQUENCE: 20
MGWSYIILFL VATATGVHSQ VQLVQSGAEV KKPGASVKVS CKASGYTFIS YTMHWVRQAP  60
GQGLEWMGYI NPRSGYTHYN QKLKDKATLT ADKSASTAYM ELSSLRSEDT AVYYCARSAY  120
YDYDGFAYWG QGTLVTVSSG GGGSGGGGSG GGGSDIQMTQ SPSSLSASVG DRVTITCSAS  180
SSVSYMNWYQ QKPGKAPKRL IYDTSKLASG VPSRFSGSGS GTDFTLTISS LQPEDFATYY  240
CQQWSSNPPT FGGGTKLEIK GGGGSGGGGS GGGGSQEDER IVLVDNKCKC ARITSRIIRS  300
SEDPNEDIVE RNIRIIVPLN NRENISDPTS PLRTRFVYHL SDLCKKCDPT EVELDNQIVT  360
ATQSNICDED SATETCYTYD RNKCYTAVVP LVYGGETKMV ETALTPDACY PD          412

SEQ ID NO: 21           moltype = AA  length = 415
FEATURE                 Location/Qualifiers
REGION                  1..415
                        note = source = /note="Description of Artificial Sequence:
                         Synthetic polypeptide"
source                  1..415
                        mol_type = protein
                        organism = synthetic construct
SEQUENCE: 21
MKNHLLFWGV LAVFIKAVHV KAQEDERIVL VDNKCKCARI TSRIIRSSED PNEDIVERNI  60
RIIVPLNNRE NISDPTSPLR TRFVYHLSDL CKKCDPTEVE LDNQIVTATQ SNICDEDSAT  120
ETCYTYDRNK CYTAVVPLVY GGETKMVETA LTPDACYPDG GGGSGGGGSG GGGSQVQLVQ  180
SGAEVKKPGA SVKVSCKASG YTFISYTMHW VRQAPGQGLE WMGYINPRSG YTHYNQKLKD  240
KATLTADKSA STAYMELSSL RSEDTAVYYC ARSAYYDYDG FAYWGQGTLV TVSSGGGGSG  300
GGGSGGGGSD IQMTQSPSSL SASVGDRVTI TCSASSSVSY MNWYQQKPGK APKRLIYDTS  360
KLASGVPSRF SGSGSGTDFT LTISSLQPED FATYYCQQWS SNPPTFGGGT KLEIK       415
```

```
SEQ ID NO: 22          moltype = AA  length = 56
FEATURE                Location/Qualifiers
source                 1..56
                       mol_type = protein
                       organism = Homo sapiens
SEQUENCE: 22
QHDEAVDANS LAEAKVLANR ELDKYGVSDY YKNLINNAKT VEGVKALIDE ILAALP      56

SEQ ID NO: 23          moltype = AA  length = 208
FEATURE                Location/Qualifiers
REGION                 1..208
                       note = source = /note="Description of Artificial Sequence:
                        Synthetic polypeptide"
source                 1..208
                       mol_type = protein
                       organism = synthetic construct
SEQUENCE: 23
QHDEAVDANS LAEAKVLANR ELDKYGVSDY YKNLINNAKT VEGVKALIDE ILAALPGGGG  60
SGGGGSGGGG SQEDERIVLV DNKCKCARIT SRIIRSSEDP NEDIVERNIR IIVPLNNREN  120
ISDPTSPLRT RFVYHLSDLC KKCDPTEVEL DNQIVTATQS NICDEDSATE TCYTYDRNKC  180
YTAVVPLVYG GETKMVETAL TPDACYPD                                     208

SEQ ID NO: 24          moltype = AA  length = 120
FEATURE                Location/Qualifiers
REGION                 1..120
                       note = source = /note="Description of Artificial Sequence:
                        Synthetic polypeptide"
source                 1..120
                       mol_type = protein
                       organism = synthetic construct
SEQUENCE: 24
MAQVQLLESG GGLVQPGGSL RLSCAASGFI FNTEYMAWVR QAPGKGLEWV SAIKEQSGST  60
YYADSVKGRF TISRDNSKNT LYLQMNSLRA EDTAVYYCAA QMHHEAEVKF WGQGTLVTVS  120

SEQ ID NO: 25          moltype = AA  length = 272
FEATURE                Location/Qualifiers
REGION                 1..272
                       note = source = /note="Description of Artificial Sequence:
                        Synthetic polypeptide"
source                 1..272
                       mol_type = protein
                       organism = synthetic construct
SEQUENCE: 25
MAQVQLLESG GGLVQPGGSL RLSCAASGFI FNTEYMAWVR QAPGKGLEWV SAIKEQSGST  60
YYADSVKGRF TISRDNSKNT LYLQMNSLRA EDTAVYYCAA QMHHEAEVKF WGQGTLVTVS  120
GGGGSGGGGS GGGGSQEDER IVLVDNKCKC ARITSRIIRS SEDPNEDIVE RNIRIIVPLN  180
NRENISDPTS PLRTRFVYHL SDLCKKCDPT EVELDNQIVT ATQSNICDED SATETCYTYD  240
RNKCYTAVVP LVYGGETKMV ETALTPDACY PD                                272

SEQ ID NO: 26          moltype = AA  length = 157
FEATURE                Location/Qualifiers
REGION                 1..157
                       note = source = /note="Description of Artificial Sequence:
                        Synthetic polypeptide"
source                 1..157
                       mol_type = protein
                       organism = synthetic construct
SEQUENCE: 26
QEDERIVLVD NKCKCARITS RIIRSSEDPN EDIVERNIRI IVPLNNRENI SDPTSPLRTR  60
FVYHLSDLCK KCDPTEVELD NQIVTATQSN ICDEDSATET CYTYDRNKCY TAVVPLVYGG  120
ETKMVETALT PDACYPDGGG GSGGGGSGGG GSLLQGA                           157

SEQ ID NO: 27          moltype = AA  length = 121
FEATURE                Location/Qualifiers
REGION                 1..121
                       note = source = /note="Description of Artificial Sequence:
                        Synthetic polypeptide"
source                 1..121
                       mol_type = protein
                       organism = synthetic construct
SEQUENCE: 27
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
A                                                                  121

SEQ ID NO: 28          moltype = AA  length = 5
FEATURE                Location/Qualifiers
REGION                 1..5
```

```
                        note = source = /note="Description of Artificial Sequence:
                         Synthetic peptide"
source                  1..5
                        mol_type = protein
                        organism = synthetic construct
SEQUENCE: 28
SYNMH                                                                       5

SEQ ID NO: 29           moltype = AA  length = 17
FEATURE                 Location/Qualifiers
REGION                  1..17
                        note = source = /note="Description of Artificial Sequence:
                         Synthetic peptide"
source                  1..17
                        mol_type = protein
                        organism = synthetic construct
SEQUENCE: 29
AIYPGNGDTS YNQKFKG                                                          17

SEQ ID NO: 30           moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 30
STYYGGDWYF NV                                                               12

SEQ ID NO: 31           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 31
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIKR                 107

SEQ ID NO: 32           moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 32
RASSSVSYIH                                                                  10

SEQ ID NO: 33           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 33
ATSNLAS                                                                     7

SEQ ID NO: 34           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 34
QQWTSNPPT                                                                   9

SEQ ID NO: 35           moltype = AA  length = 200
FEATURE                 Location/Qualifiers
REGION                  1..200
                        note = source = /note="Description of Artificial Sequence:
```

```
                         Synthetic polypeptide"
source                  1..200
                        mol_type = protein
                        organism = synthetic construct
SEQUENCE: 35
EVQLVESGGG LVQPGGSLRL SCAASGYTFT SYNMHWVRQA PGKGLEWVGA IYPGNGDTSY  60
NQKFKGRFTI SVDKSKNTLY LQMNSLRAED TAVYYCARVV YYSNSYWYFD VWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT                                             200

SEQ ID NO: 36           moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 36
VVYYSNSYWY FDV                                                    13

SEQ ID NO: 37           moltype = AA  length = 200
FEATURE                 Location/Qualifiers
REGION                  1..200
                        note = source = /note="Description of Artificial Sequence:
                         Synthetic polypeptide"
source                  1..200
                        mol_type = protein
                        organism = synthetic construct
SEQUENCE: 37
DIQMTQSPSS LSASVGDRVT ITCRASSSVS YMHWYQQKPG KAPKPLIYAP SNLASGVPSR  60
FSGSGSGTDF TLTISSLQPE DFATYYCQQW SFNPPTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL                                             200

SEQ ID NO: 38           moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 38
RASSSVSYMH                                                        10

SEQ ID NO: 39           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 39
APSNLAS                                                           7

SEQ ID NO: 40           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 40
QQWSFNPPT                                                         9

SEQ ID NO: 41           moltype = AA  length = 121
FEATURE                 Location/Qualifiers
REGION                  1..121
                        note = source = /note="Description of Artificial Sequence:
                         Synthetic polypeptide"
source                  1..121
                        mol_type = protein
                        organism = synthetic construct
SEQUENCE: 41
EVQLVQSGAE VKKPGESLKI SCKGSGRTFT SYNMHWVRQM PGKGLEWMGA IYPLTGDTSY  60
NQKSKLQVTI SADKSISTAY LQWSSLKASD TAMYYCARST YVGGDWQFDV WGKGTTVTVS  120
```

```
S                                                                   121

SEQ ID NO: 42          moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 42
AIYPLTGDTS YNQKSKL                                                  17

SEQ ID NO: 43          moltype = AA  length = 12
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 43
STYVGGDWQF DV                                                       12

SEQ ID NO: 44          moltype = AA  length = 106
FEATURE                Location/Qualifiers
REGION                 1..106
                       note = source = /note="Description of Artificial Sequence:
                        Synthetic polypeptide"
source                 1..106
                       mol_type = protein
                       organism = synthetic construct
SEQUENCE: 44
EIVLTQSPGT LSLSPGERAT LSCRASSSVP YIHWYQQKPG QAPRLLIYAT SALASGIPDR  60
FSGSGSGTDF TLTISRLEPE DFAVYYCQQW LSNPPTFGQG TKLEIK                 106

SEQ ID NO: 45          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 45
RASSSVPYIH                                                          10

SEQ ID NO: 46          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 46
ATSALAS                                                             7

SEQ ID NO: 47          moltype = AA  length = 9
FEATURE                Location/Qualifiers
REGION                 1..9
                       note = source = /note="Description of Artificial Sequence:
                        Synthetic peptide"
source                 1..9
                       mol_type = protein
                       organism = synthetic construct
SEQUENCE: 47
QQWLSNPPT                                                           9

SEQ ID NO: 48          moltype = AA  length = 121
FEATURE                Location/Qualifiers
REGION                 1..121
                       note = source = /note="Description of Artificial Sequence:
                        Synthetic polypeptide"
source                 1..121
                       mol_type = protein
                       organism = synthetic construct
SEQUENCE: 48
QVQLQQPGAE LKKPGASVKV SCKASGYTFT SYNMHWVKQT PGRGLEWTGA IYPGNGDTSY  60
```

```
NQKFKGKTTL TADKSSSTAY MELSSLRSED TAVYYCARST YYGGDWYFNV WGAGTTVTVS  120
A                                                                 121

SEQ ID NO: 49          moltype = AA  length = 121
FEATURE                Location/Qualifiers
REGION                 1..121
                       note = source = /note="Description of Artificial Sequence:
                        Synthetic polypeptide"
source                 1..121
                       mol_type = protein
                       organism = synthetic construct
SEQUENCE: 49
QVQLQQPGAE LKKPGASVKV SCKASGYTFT SYNMHWVKQT PGRGLEWIGA IYPGNGDTSY  60
NQKFKGKTTL TADKSSSTAY MELSSLRSED TAVYYCARST YYGGDWYFNV WGAGTTVTVS  120
A                                                                 121

SEQ ID NO: 50          moltype = AA  length = 106
FEATURE                Location/Qualifiers
REGION                 1..106
                       note = source = /note="Description of Artificial Sequence:
                        Synthetic polypeptide"
source                 1..106
                       mol_type = protein
                       organism = synthetic construct
SEQUENCE: 50
QIVLSQSPAI ITASPGEKVT MTCRASTSAS YIHWFQQKPT SSPKPWIYAT SNLASGVPSR  60
FSGSGSGTTY SMTISSLEAE DAATYYCQQW TSNPPTFGGG TKLEIK                106

SEQ ID NO: 51          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 51
RASTSASYIH                                                        10

SEQ ID NO: 52          moltype = AA  length = 106
FEATURE                Location/Qualifiers
REGION                 1..106
                       note = source = /note="Description of Artificial Sequence:
                        Synthetic polypeptide"
source                 1..106
                       mol_type = protein
                       organism = synthetic construct
SEQUENCE: 52
QIVLSQSPAI ITASPGEKVT MTCRASTSVS YIHWFQQKPT SSPKPWIYAT SNLASGVPSR  60
FSGSGSGTTY SMTISSLEAE DAATYYCQQW TSNPPTFGGG TKLEIK                106

SEQ ID NO: 53          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 53
RASTSVSYIH                                                        10

SEQ ID NO: 54          moltype = AA  length = 106
FEATURE                Location/Qualifiers
REGION                 1..106
                       note = source = /note="Description of Artificial Sequence:
                        Synthetic polypeptide"
source                 1..106
                       mol_type = protein
                       organism = synthetic construct
SEQUENCE: 54
QIVLSQSPAI ITASPGEKVT MTCRASTSVS YIHWFQQKPG SSPKPWIYAT SNLASGVPSR  60
FSGSGSGTTY SMTISSLEAE DAATYYCQQW TSNPPTFGGG TKLEIK                106

SEQ ID NO: 55          moltype = AA  length = 106
FEATURE                Location/Qualifiers
REGION                 1..106
                       note = source = /note="Description of Artificial Sequence:
                        Synthetic polypeptide"
```

```
source                  1..106
                        mol_type = protein
                        organism = synthetic construct
SEQUENCE: 55
QIVLSQSPAI ITASPGEKVT MTCRASSSVS YIHWFQQKPG SSPKPWIYAT SNLASGVPSR  60
FSGSGSGTTY SMTISSLEAE DAATYYCQQW TSNPPTFGGG TKLEIK                106

SEQ ID NO: 56           moltype = AA  length = 122
FEATURE                 Location/Qualifiers
REGION                  1..122
                        note = source = /note="Description of Artificial Sequence:
                         Synthetic polypeptide"
source                  1..122
                        mol_type = protein
                        organism = synthetic construct
SEQUENCE: 56
EVQLQQSGAE LKKPGASVKV SCKASGYTFT SYNMHWVKQT PGQGLEWIGA IYPGNGDTSY  60
NQKFKGKTTL TADKSSSTAY MELSSLRSED TAVYYCARSN YYGSSYWFFD VWGTGTTVTV  120
SS                                                                122

SEQ ID NO: 57           moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 57
SNYYGSSYWF FDV                                                    13

SEQ ID NO: 58           moltype = AA  length = 106
FEATURE                 Location/Qualifiers
REGION                  1..106
                        note = source = /note="Description of Artificial Sequence:
                         Synthetic polypeptide"
source                  1..106
                        mol_type = protein
                        organism = synthetic construct
SEQUENCE: 58
DIVLTQSPAI ITASPGEKVT MTCRASSSVN YMDWYQKKPG SSPKPWIYAT SNLASGVPSR  60
FSGSGSGTTY SMTISSLEAE DAATYYCQQW SFNPPTFGGG TKLEIK                106

SEQ ID NO: 59           moltype = AA  length = 10
FEATURE                 Location/Qualifiers
REGION                  1..10
                        note = source = /note="Description of Artificial Sequence:
                         Synthetic peptide"
source                  1..10
                        mol_type = protein
                        organism = synthetic construct
SEQUENCE: 59
RASSSVNYMD                                                        10

SEQ ID NO: 60           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 60
QQWSFNPPT                                                         9

SEQ ID NO: 61           moltype = AA  length = 121
FEATURE                 Location/Qualifiers
REGION                  1..121
                        note = source = /note="Description of Artificial Sequence:
                         Synthetic polypeptide"
source                  1..121
                        mol_type = protein
                        organism = synthetic construct
SEQUENCE: 61
QVQLQQSGAE VKKPGSSVKV SCKASGYTFT SYNMHWVKQA PGQGLEWIGA IYPGNGDTSY  60
NQKFKGKATL TADESTNTAY MELSSLRSED TAFYYCARST YYGGDWYFDV WGQGTTVTVS  120
S                                                                 121

SEQ ID NO: 62           moltype = AA  length = 12
```

```
FEATURE                Location/Qualifiers
REGION                 1..12
                       note = source = /note="Description of Artificial Sequence:
                        Synthetic peptide"
source                 1..12
                       mol_type = protein
                       organism = synthetic construct
SEQUENCE: 62
STYYGGDWYF DV                                                          12

SEQ ID NO: 63          moltype = AA  length = 125
FEATURE                Location/Qualifiers
REGION                 1..125
                       note = source = /note="Description of Artificial Sequence:
                        Synthetic polypeptide"
source                 1..125
                       mol_type = protein
                       organism = synthetic construct
SEQUENCE: 63
MGWSCIILFL VATATGVHSD IQLTQSPSSL SASVGDRVTM TCRASSSVSY IHWFQQKPGK  60
APKPWIYATS NLASGVPVRF SGSGSGTDYT FTISSLQPED IATYYCQQWT SNPPTFGGGT  120
KLEIK                                                                  125

SEQ ID NO: 64          moltype = AA  length = 122
FEATURE                Location/Qualifiers
REGION                 1..122
                       note = source = /note="Description of Artificial Sequence:
                        Synthetic polypeptide"
source                 1..122
                       mol_type = protein
                       organism = synthetic construct
SEQUENCE: 64
EVQLVQSGAE VKKPGESLKI SCKGSGYSFT SYWIGWVRQM PGKGLEWMGI IYPGDSDTRY  60
SPSFQGQVTI SADKSITTAY LQWSSLKASD TAMYYCARHP SYGSGSPNFD YWGQGTLVTV  120
SS                                                                     122

SEQ ID NO: 65          moltype = AA  length = 10
FEATURE                Location/Qualifiers
REGION                 1..10
                       note = source = /note="Description of Artificial Sequence:
                        Synthetic peptide"
source                 1..10
                       mol_type = protein
                       organism = synthetic construct
SEQUENCE: 65
GYSFTSYWIG                                                             10

SEQ ID NO: 66          moltype = AA  length = 17
FEATURE                Location/Qualifiers
REGION                 1..17
                       note = source = /note="Description of Artificial Sequence:
                        Synthetic peptide"
source                 1..17
                       mol_type = protein
                       organism = synthetic construct
SEQUENCE: 66
IIYPGDSDTR YSPSFQG                                                     17

SEQ ID NO: 67          moltype = AA  length = 13
FEATURE                Location/Qualifiers
REGION                 1..13
                       note = source = /note="Description of Artificial Sequence:
                        Synthetic peptide"
source                 1..13
                       mol_type = protein
                       organism = synthetic construct
SEQUENCE: 67
HPSYGSGSPN FDY                                                         13

SEQ ID NO: 68          moltype = AA  length = 112
FEATURE                Location/Qualifiers
REGION                 1..112
                       note = source = /note="Description of Artificial Sequence:
                        Synthetic polypeptide"
source                 1..112
                       mol_type = protein
                       organism = synthetic construct
SEQUENCE: 68
DIVMTQTPLS SPVTLGQPAS ISCRSSQSLV YSDGNTYLSW LQQRPGQPPR LLIYKISNRF  60
```

```
SGVPDRFSGS GAGTDFTLKI SRVEAEDVGV YYCVQATQFP LTFGGGTKVE IK         112

SEQ ID NO: 69           moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 69
RSSQSLVYSD GNTYLS                                                 16

SEQ ID NO: 70           moltype = AA  length = 7
FEATURE                 Location/Qualifiers
REGION                  1..7
                        note = source = /note="Description of Artificial Sequence:
                         Synthetic peptide"
source                  1..7
                        mol_type = protein
                        organism = synthetic construct
SEQUENCE: 70
KISNRFS                                                           7

SEQ ID NO: 71           moltype = AA  length = 9
FEATURE                 Location/Qualifiers
REGION                  1..9
                        note = source = /note="Description of Artificial Sequence:
                         Synthetic peptide"
source                  1..9
                        mol_type = protein
                        organism = synthetic construct
SEQUENCE: 71
VQATQFPLT                                                         9

SEQ ID NO: 72           moltype = DNA  length = 1347
FEATURE                 Location/Qualifiers
source                  1..1347
                        mol_type = genomic DNA
                        organism = Homo sapiens
SEQUENCE: 72
gccccaaccc ttttcccccct cgtctcctgt gagaattccc cgtcggatac gagcagcgtg  60
gccgttggct gcctcgcaca ggacttcctt cccgactcca tcactttctc ctggaaatac  120
aagaacaact ctgacatcag cagcacccgg ggcttcccat cagtcctgag agggggcaag  180
cacgcagcca cctcacaggt gctgctgcct tccaaggacg tcatgcaggg cacagacgaa  240
cacgtggtgt gcaaagtcca gcaccccaac ggcaacaaag aaaagaacgt gcctcttcca  300
gtgattgctg agctgcctcc caaagtgagc gtcttcgtcc caccccgcga cggcttcttc  360
ggcaaccccc gcaagtccaa gctcatctgc caggccacgg gtttcagtcc ccggcagatt  420
caggtgtcct ggctgcgcga ggggaagcag gtggggtctg gcgtcaccac ggaccaggtg  480
caggctgagg caaaggagtc tgggaccacg acctacaagg tgaccagcac actgaccatc  540
aaagagagcg actggctcag ccagagcatg ttcacctgcc gcgtggatca caggggcctg  600
accttccagc agaatgcgtc ctccatgtgt ggccccgatc aagacacagc catccgggtc  660
ttctccatcc ccccatcctt tgccagcatc ttcctcacca agtccaccaa gttgacctgc  720
ctggtcacag acctgaccac ctatgacagc gtgaccatct cctggacccg ccagaatggc  780
gaagctgtga aaacccacac caacatctcc gagagccacc ccaatgccac tttcagcgcc  840
gtgggtgagg ccagcatctg cgaggatgac tggaattccg gggagaggtt cacgtgcacc  900
gtgacccaca cagacctgcc ctcgccactg aagcagacca tctcccggcc caagggggtg  960
gccctgcaca ggcccgatgt ctacttgctg ccaccagccc gggagcagct gaacctgcgg  1020
gagtcggcca ccatcacgtg cctggtgacg ggcttctctc ccgcggacgt cttcgtgcag  1080
tggatgcaga gggggcagcc cttgtccccg gagaagtatg tgaccagcgc cccaatgcct  1140
gagccccagg ccccaggccg gtacttcgcc cacagcatcc tgaccgtgtc cgaagaggaa  1200
tggaacacgg gggagaccta cacctgcgtg gtggcccatg aggccctgcc caacagggtc  1260
accgagagga ccgtggacaa gtccaccggt aaacccaccc tgtacaacgt gtccctggtc  1320
atgtccgaca cagctggcac ctgctac                                    1347

SEQ ID NO: 73           moltype = AA  length = 453
FEATURE                 Location/Qualifiers
source                  1..453
                        mol_type = protein
                        organism = Homo sapiens
SEQUENCE: 73
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL SQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL PSPLKQTISR PKGVALHRPD VYLLPPAREQ LNLRESATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                              453
```

```
SEQ ID NO: 74          moltype = DNA  length = 480
FEATURE                Location/Qualifiers
misc_feature           1..480
                       note = source = /note="Description of Artificial Sequence:
                        Synthetic polynucleotide"
source                 1..480
                       mol_type = other DNA
                       organism = synthetic construct
SEQUENCE: 74
atgaagaacc atttgctttt ctggggagtc ctggcggttt ttattaaggc tgttcatgtg  60
aaagcccaag aagatgaaag gattgttctt gttgacaaca aatgtaagtg tgcccggatt  120
acttccagga tcatccgttc ttccgaagat cctaatgagg acattgtgga gagaaacatc  180
cgaattattg ttcctctgaa caacagggag aatatctctg atcccacctc accattgaga  240
accagatttg tgtaccattt gtctgacctc tgtaaaaaat gtgatcctac agaagtggag  300
ctggataatc agatagttac tgctacccag agcaatatct gtgatgaaga cagtgctaca  360
gagacctgct acacttatga cagaaacaag tgctacacag ctgtggtccc actcgtatat  420
ggtggtgaga ccaaaatggt ggaaacagcc ttaaccccag atgcctgcta tcctgactaa  480

SEQ ID NO: 75          moltype = AA  length = 158
FEATURE                Location/Qualifiers
REGION                 1..158
                       note = source = /note="Description of Artificial Sequence:
                        Synthetic polypeptide"
source                 1..158
                       mol_type = protein
                       organism = synthetic construct
SEQUENCE: 75
MKNHLLFWGV LAVFIKAVHV KAQEDERIVL VDNKCKCARI TSRIIRSSED PNEDIVERNI  60
IIVPLNNREN ISDPTSPLRT RFVYHLSDLC KKCDPTEVEL DNQIVTATQS NICDEDSATE  120
TCYTYDRNKC YTAVVPLVYG GETKMVETAL TPDACYPD                        158

SEQ ID NO: 76          moltype = AA  length = 297
FEATURE                Location/Qualifiers
source                 1..297
                       mol_type = protein
                       organism = Homo sapiens
SEQUENCE: 76
MTTPRNSVNG TFPAEPMKGP IAMQSGPKPL FRRMSSLVGP TQSFFMRESK TLGAVQIMNG  60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEEETETNFP EPPQDQESSP IENDSSP     297

SEQ ID NO: 77          moltype = DNA  length = 1725
FEATURE                Location/Qualifiers
misc_feature           1..1725
                       note = source = /note="Description of Artificial Sequence:
                        Synthetic polynucleotide"
source                 1..1725
                       mol_type = other DNA
                       organism = synthetic construct
SEQUENCE: 77
caggttcagc tgcagcagcc cggagccgag ctggtcaaac ctggcgctag tgtgaaaatg  60
tcatgcaagg catccggata cacattcact agctataaca tgcactgggt gaagcagacc  120
cccggcaggg gtctggagtg gatcggagct atctaccccg gcaacggaga cacatcttat  180
aatcagaagt ttaaaggcaa ggccaccctg acagctgata agtccagctc taccgcatac  240
atgcagctga gttcactgac aagcgaggac tccgccgtgt actattgcgc ccggtccact  300
tactatggcg gagattggta tttcaatgtg tggggagcag gcaccacagt caccgtctcg  360
agcggcagtg ctagcgcccc aaccctttc ccctcgtct cctgtgagaa ttccccgtcg  420
gatacgagca gcgtggccgt tggctgcctc gcacaggact tccttcccga ctccatcact  480
ttctcctgga aatacaagaa caactctgac atcagcagca cccggggctt cccatcagtc  540
ctgagagggg gcaagtacgc agccacctca caggtgctgc tgccttccaa ggacgtcatg  600
cagggcacag acgaacacgt ggtgtgcaaa gtccagcacc ccaacggcaa caaagaaaag  660
aacgtgcctc ttccagtgat tgctgagctg cctcccaaag tgagcgtctt cgtcccaccc  720
cgcgacggct tcttcggcaa cccccgcaag tccaagctca tctgccaggc cacgggtttc  780
agtccccggc agattcaggt gtcctggctg cgcgaggggga agcaggtggg gtctggcgtc  840
accacggacc aggtgcaggc tgaggccaaa gagtctgggc ccacgaccta caaggtgacc  900
agcacactga ccatcaaaga gagcgactgg ctcagccaga gcatgttcac ctgccgcgtg  960
gatcacaggg gcctgacctt ccagcagaat gcgtcctcca tgtgtgtccc cgatcaagac  1020
acagccatcc gggtcttcgc catcccccca tcctttgcca gcatcttcct caccaagtcc  1080
accaagttga cctgcctggt cacagacctg accacctatg acagcgtgac catctcctgg  1140
acccgccaga atggcgaagc tgtgaaaacc cacaccaaca tctccgagag ccaccccaat  1200
gccactttca gcgccgtggg tgaggccagc atctgcgagg atgactggaa ttccggggag  1260
aggttcacgt gcaccgtgac ccacacagac ctgccctcgc cactgaagca gaccatctcc  1320
cggcccaagg gggtggccct gcacaggccc gatgtctact tgctgccacc agcccgggag  1380
cagctgaacc tgcgggagtc ggccaccatc acgtgcctgg tgacgggctt ctctcccgcg  1440
gacgtcttcg tgcagtggat gcagaggggg cagcccttgt ccccggagaa gtatgtgacc  1500
agcgccccaa tgcctgagcc ccaggcccca ggccggtact tcgcccacag catcctgacc  1560
```

```
gtgtccgaag aggaatggaa cacgggggag acctacacct gcgtggtggc ccatgaggcc  1620
ctgcccaaca gggtcaccga gaggaccgtg gacaagtcca ccggtaaacc caccctgtac  1680
aacgtgtccc tggtcatgtc cgacacagct ggcacctgct actga                  1725

SEQ ID NO: 78          moltype = AA  length = 574
FEATURE                Location/Qualifiers
REGION                 1..574
                       note = source = /note="Description of Artificial Sequence:
                        Synthetic polypeptide"
source                 1..574
                       mol_type = protein
                       organism = synthetic construct
SEQUENCE: 78
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
SGSASAPTLF PLVSCENSPS DTSSVAVGCL AQDFLPDSIT FSWKYKNNSD ISSTRGFPSV  180
LRGGKYAATS QVLLPSKDVM QGTDEHVVCK VQHPNGNKEK NVPLPVIAEL PPKVSVFVPP  240
RDGFFGNPRK SKLICQATGF SPRQIQVSWL REGKQVGSGV TTDQVQAEAK ESGPTTYKVT  300
STLTIKESDW LSQSMFTCRV DHRGLTFQQN ASSMCVPDQD TAIRVFAIPP SFASIFLTKS  360
TKLTCLVTDL TTYDSVTISW TRQNGEAVKT HTNISESHPN ATFSAVGEAS ICEDDWNSGE  420
RFTCTVTHTD LPSPLKQTIS RPKGVALHRP DVYLLPPARE QLNLRESATI TCLVTGFSPA  480
DVFVQWMQRG QPLSPEKYVT SAPMPEPQAP GRYFAHSILT VSEEEWNTGE TYTCVVAHEA  540
LPNRVTERTV DKSTGKPTLY NVSLVMSDTA GTCY                              574

SEQ ID NO: 79          moltype = DNA  length = 642
FEATURE                Location/Qualifiers
misc_feature           1..642
                       note = source = /note="Description of Artificial Sequence:
                        Synthetic polynucleotide"
source                 1..642
                       mol_type = other DNA
                       organism = synthetic construct
SEQUENCE: 79
caaattgtgc tgtctcagag tccagctatc ctgagcgcat ctcccggaga gaaggtgacc  60
atgacatgca gagcctccag ctctgtctcc tacatccact ggttccagca gaagcccggc  120
tcctccccaa aaccctggat ctacgccacc tctaacctgg ctagtggtgt gcctgtcagg  180
tttagtggat cagggtccgg caccagctac tctctgacaa tcagccgggt ggaggctgaa  240
gacgccgcta catactattg ccagcagtgg acttctaatc cccctacctt cggcggaggg  300
acaaagctgg agatcaagcg tacggtggct gcaccatctg tcttcatctt cccgccatct  360
gatgagcagt tgaaatctgg aactgcctct gttgtgtgcc tgctgaataa cttctatccc  420
agagaggcca aagtacagtg gaaggtggat aacgccctcc aatcgggtaa ctcccaggag  480
agtgtcacag agcaggacag caaggacagc acctacagcc tcagcagcac cctgacgctg  540
agcaaagcag actacgagaa acacaaagtc tacgcctgcg aagtcaccca tcagggcctg  600
agctcgcccg tcacaaagag cttcaacagg ggagagtgtt ag                     642

SEQ ID NO: 80          moltype = AA  length = 213
FEATURE                Location/Qualifiers
REGION                 1..213
                       note = source = /note="Description of Artificial Sequence:
                        Synthetic polypeptide"
source                 1..213
                       mol_type = protein
                       organism = synthetic construct
SEQUENCE: 80
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 81          moltype = DNA  length = 1728
FEATURE                Location/Qualifiers
misc_feature           1..1728
                       note = source = /note="Description of Artificial Sequence:
                        Synthetic polynucleotide"
source                 1..1728
                       mol_type = other DNA
                       organism = synthetic construct
SEQUENCE: 81
gaggtgcagc tggtgcagtc cggcgccgag gtgaagaagc ccggcgagtc cctgaagatc  60
tcctgcaagg gctccggcta ctccttcacc tcctactgga tcggctgggt gaggcagatg  120
cccggcaagg gcctggagtg gatgggcatc atctaccccg gcgactccga caccaggtac  180
tcccccctcct tccagggcca ggtgaccatc tccgccgaca agtccatcac caccgcctac  240
ctgcagtggt cctccctgaa ggcctccgac accgccatgt actactgcgc caggcacccc  300
tcctacggct ccggctcccc caacttcgac tactggggcc agggcaccct ggtgaccgtg  360
tcctccggca gtgctagcgc cccaaccctt ttccccctcg tctcctgtga gaattccccg  420
tcggatacga gcagcgtggc cgttggctgc ctcgcacagg acttccttcc cgactccatc  480
actttctcct ggaaatacaa gaacaactct gacatcagca gcacccgggg cttcccatca  540
gtcctgagag gggcaagta cgcagccacc tcacaggtgc tgctgccttc caaggacgtc  600
atgcagggca cagacgaaca cgtggtgtgc aaagtccagc accccaacgg caacaaagaa  660
```

```
aagaacgtgc ctcttccagt gattgctgag ctgcctccca aagtgagcgt cttcgtccca  720
ccccgcgacg gcttcttcgg caaccccgc aagtccaagc tcatctgcca ggccacgggt  780
ttcagtcccc ggcagattca ggtgtcctgg ctgcgcgagg ggaagcaggt ggggtctggc  840
gtcaccacgg accaggtgca ggctgaggcc aaagagtctg ggcccacgac ctacaaggtg  900
accagcacac tgaccatcaa agagagcgac tggctcagcc agagcatgtt cacctgccgc  960
gtggatcaca ggggcctgac cttccagcag aatgcgtcct ccatgtgtgt ccccgatcaa  1020
gacacagcca tccgggtctt cgccatcccc ccatcctttg ccagcatctt cctcaccaag  1080
tccaccaagt tgacctgcct ggtcacagac ctgaccacct atgacagcgt gaccatctcc  1140
tggacccgcc agaatggcga agctgtgaaa acccacacca acatctccga gagccacccc  1200
aatgccactt tcagcgccgt gggtgaggcc agcatctgcg aggatgactg gaattccggg  1260
gagaggttca cgtgcaccgt gacccacaca gacctgccct cgccactgaa gcagaccatc  1320
tcccggccca agggggtggc cctgcacagg cccgatgtct acttgctgcc accagcccgg  1380
gagcagctga acctgcggga gtcggccacc atcacgtgcc tggtgacggg cttctctccc  1440
gcggacgtct tcgtgcagtg gatgcagagg gggcagccct tgtccccgga gaagtatgtg  1500
accagcgccc caatgcctga gccccaggcc ccaggccggt acttcgccca cagcatcctg  1560
accgtgtccg aagaggaatg gaacacgggg gagacctaca cctgcgtggt ggcccatgag  1620
gccctgccca acagggtcac cgagaggacc gtggacaagt ccaccggtaa acccaccctg  1680
tacaacgtgt ccctggtcat gtccgacaca gctggcacct gctactga              1728
```

```
SEQ ID NO: 82          moltype = AA  length = 575
FEATURE                Location/Qualifiers
REGION                 1..575
                       note = source = /note="Description of Artificial Sequence:
                        Synthetic polypeptide"
source                 1..575
                       mol_type = protein
                       organism = synthetic construct
SEQUENCE: 82
EVQLVQSGAE VKKPGESLKI SCKGSGYSFT SYWIGWVRQM PGKGLEWMGI IYPGDSDTRY  60
SPSFQGQVTI SADKSITTAY LQWSSLKASD TAMYYCARHP SYGSGSPNFD YWGQGTLVTV  120
SSGSASAPTL FPLVSCENSP SDTSSVAVGC LAQDFLPDSI TFSWKYKNNS DISSTRGFPS  180
VLRGGKYAAT SQVLLPSKDV MQGTDEHVVC KVQHPNGNKE KNVPLPVIAE LPPKVSVFVP  240
PRDGFFGNPR KSKLICQATG FSPRQIQVSW LREGKQVGSG VTTDQVQAEA KESGPTTYKV  300
TSTLTIKESD WLSQSMFTCR VDHRGLTFQQ NASSMCVPDQ DTAIRVFAIP PSFASIFLTK  360
STKLTCLVTD LTTYDSVTIS WTRQNGEAVK THTNISESHP NATFSAVGEA SICEDDWNSG  420
ERFTCTVTHT DLPSPLKQTI SRPKGVALHR PDVYLLPPAR EQLNLRESAT ITCLVTGFSP  480
ADVFVQWMQR GQPLSPEKYV TSAPMPEPQA PGRYFAHSIL TVSEEEWNTG ETYTCVVAHE  540
ALPNRVTERT VDKSTGKPTL YNVSLVMSDT AGTCY                             575
```

```
SEQ ID NO: 83          moltype = DNA  length = 660
FEATURE                Location/Qualifiers
misc_feature           1..660
                       note = source = /note="Description of Artificial Sequence:
                        Synthetic polynucleotide"
source                 1..660
                       mol_type = other DNA
                       organism = synthetic construct
SEQUENCE: 83
gacatcgtga tgacccagac ccccctgtcc tcccccgtga ccctgggcca gcccgcctcc  60
atctcctgca ggtcctccca gtccctggtg tactccgacg gcaacaccta cctgtcctgg  120
ctgcagcaga ggcccggcca gccccccagg ctgctgatct acaagatctc caacaggttc  180
tccggcgtgc ccgacaggtt ctccggctcc ggcgccggca ccgacttcac cctgaagatc  240
tccagggtgg aggccgagga cgtgggcgtg tactactgcg tgcaggccac ccagttcccc  300
ctgaccttcg gcggcggcac caaggtggag atcaagcgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgttag  660
```

```
SEQ ID NO: 84          moltype = AA  length = 219
FEATURE                Location/Qualifiers
REGION                 1..219
                       note = source = /note="Description of Artificial Sequence:
                        Synthetic polypeptide"
source                 1..219
                       mol_type = protein
                       organism = synthetic construct
SEQUENCE: 84
DIVMTQTPLS SPVTLGQPAS ISCRSSQSLV YSDGNTYLSW LQQRPGQPPR LLIYKISNRF  60
SGVPDRFSGS GAGTDFTLKI SRVEAEDVGV YYCVQATQFP LTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```

```
SEQ ID NO: 85          moltype = AA  length = 353
FEATURE                Location/Qualifiers
source                 1..353
                       mol_type = protein
                       organism = Homo sapiens
```

```
SEQUENCE: 85
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY         353

SEQ ID NO: 86           moltype = AA  length = 340
FEATURE                 Location/Qualifiers
source                  1..340
                        mol_type = protein
                        organism = Homo sapiens
SEQUENCE: 86
ASPTSPKVFP LSLDSTPQDG NVVVACLVQG FFPQEPLSVT WSESGQNVTA RNFPPSQDAS  60
GDLYTTSSQL TLPATQCPDG KSVTCHVKHY TNPSSQDVTVP CPVPPPPPCC HPRLSLHRPA  120
LEDLLLGSEA NLTCTLTGLR DASGATFTWT PSSGKSAVQG PPERDLCGCY SVSSVLPGCA  180
QPWNHGETFT CTAAHPELKT PLTANITKSG NTFRPEVHLL PPPSEELALN ELVTLTCLAR  240
GFSPKDVLVR WLQGSQELPR EKYLTWASRQ EPSQGTTTFA VTSILRVAAE DWKKGDTFSC  300
MVGHEALPLA FTQKTIDRMA GKPTHVNVSV VMAEVDGTCY                        340

SEQ ID NO: 87           moltype = AA  length = 764
FEATURE                 Location/Qualifiers
source                  1..764
                        mol_type = protein
                        organism = Homo sapiens
SEQUENCE: 87
MLLFVLTCLL AVFPAISTKS PIFGPEEVNS VEGNSVSITC YYPPTSVNRH TRKYWCRQGA  60
RGGCITLISS EGYVSSKYAG RANLTNFPEN GTFVVNIAQL SQDDSGRYKC GLGINSRGLS  120
FDVSLEVSQG PGLLNDTKVY TVDLGRTVTI NCPFKTENAQ KRKSLYKQIG LYPVLVIDSS  180
GYVNPNYTGR IRLDIQGTGQ LLFSVVINQL RLSDAGQYLC QAGDDSNSNK KNADLQVLKP  240
EPELVYEDLR GSVTFHCALG PEVANVAKFL CRQSSGENCD VVVNTLGKRA PAFEGRILLN  300
PQDKDGSFSV VITGLRKEDA GRYLCGAHSD GQLQEGSPIQ AWQLFVNEES TIPRSPTVVK  360
GVAGGSVAVL CPYNRKESKS IKYWCLWEGA QNGRCPLLVD SEGWVKAQYE GRLSLLEEPG  420
NGTFTVILNQ LTSRDAGFYW CLTNGDTLWR TTVEIKIIEG EPNLKVPGNV TAVLGETLKV  480
PCHFPCKFSS YEKYWCKWNN TGCQALPSQD EGPSKAFVNC DENSRLVSLT LNLVTRADEG  540
WYWCGVKQGH FYGETAAVYV AVEERKAAGS RDVSLAKADA APDEKVLDSG FREIENKAIQ  600
DPRLFAEEKA VADTRDQADG SRASVDSGSS EEQGGSSRAL VSTLVPLGLV LAVGAVAVGV  660
ARARHRKNVD RVSIRSYRTD ISMSDFENSR EFGANDNMGA SSITQETSLG GKEEFVATTE  720
STTETKEPKK AKRSSKEEAE MAYKDFLLQS STVAAEAQDG PQEA                   764

SEQ ID NO: 88           moltype = AA  length = 585
FEATURE                 Location/Qualifiers
source                  1..585
                        mol_type = protein
                        organism = Homo sapiens
SEQUENCE: 88
KSPIFGPEEV NSVEGNSVSI TCYYPPTSVN RHTRKYWCRQ GARGGCITLI SSEGYVSSKY  60
AGRANLTNFP ENGTFVVNIA QLSQDDSGRY KCGLGINSRG LSFDVSLEVS QGPGLLNDTK  120
VYTVDLGRTV TINCPFKTEN AQKRKSLYKQ IGLYPVLVID SSGYVNPNYT GRIRLDIQGT  180
GQLLFSVVIN QLRLSDAGQY LCQAGDDSNS NKKNADLQVL KPEPELVYED LRGSVTFHCA  240
LGPEVANVAK FLCRQSSGEN CDVVVNTLGK RAPAFEGRIL LNPQDKDGSF SVVITGLRKE  300
DAGRYLCGAH SDGQLQEGSP IQAWQLFVNE ESTIPRSPTV VKGVAGGSVA VLCPYNRKES  360
KSIKYWCLWE GAQNGRCPLL VDSEGWVKAQ YEGRLSLLEE PGNGTFTVIL NQLTSRDAGF  420
YWCLTNGDTL WRTTVEIKII EGEPNLKVPG NVTAVLGETL KVPCHFPCKF SSYEKYWCKW  480
NNTGCQALPS QDEGPSKAFV NCDENSRLVS LTLNLVTRAD EGWYWCGVKQ GHFYGETAAV  540
YVAVEERKAA GSRDVSLAKA DAAPDEKVLD SGFREIENKA IQDPR                  585

SEQ ID NO: 89           moltype = DNA  length = 684
FEATURE                 Location/Qualifiers
misc_feature            1..684
                        note = source = /note="Description of Artificial Sequence:
                         Synthetic polynucleotide"
source                  1..684
                        mol_type = other DNA
                        organism = synthetic construct
SEQUENCE: 89
atggaatgga gctgggtctt tctcttcttc ctgtcagtaa cgactggtgt ccactcccag  60
gaagatgagc ggatcgtgct ggtggacaac aagtgcaagt gcgcccggat cacctcccgg  120
atcatccggt cctccgagga tcccaacgag gacatcgtgg aacggaacat cagaatcatc  180
gtgcccctga acaaccgcga gaacatctcc gaccccacca gccctctgcg gaccagattc  240
gtgtaccacc tgtccgacct gtgcaagaag tgcgacccta ccgaggtgga actggacaac  300
cagatcgtga ccgccaccca gtccaacatc tgcgacgagg actccgccac cgagacatgc  360
tacacctacg accggaacaa gtgctacacc gccgtggtgc ctctggtgta cggcggcgag  420
acaaagatgg tggaaaccgc cctgaccccc gacgcctgct atcctgatgg aggcggagga  480
tctggtggcg gtggttctgg cggagggggc tctcagcacg atgaggccgt ggacgccaat  540
tctctggccg aggctaaggt gctggccaac agagagctgg ataagtacgg cgtgtccgac  600
tactacaaga acctgatcaa caacgccaag accgtggaag gcgtgaaggc cctgatcgac  660
gagatcctgg ctgccctgcc ttga                                         684
```

```
SEQ ID NO: 90          moltype = AA  length = 227
FEATURE                Location/Qualifiers
REGION                 1..227
                       note = source = /note="Description of Artificial Sequence:
                        Synthetic polypeptide"
source                 1..227
                       mol_type = protein
                       organism = synthetic construct
SEQUENCE: 90
MEWSWVFLFF LSVTTGVHSQ EDERIVLVDN KCKCARITSR IIRSSEDPNE DIVERNIRII  60
VPLNNRENIS DPTSPLRTRF VYHLSDLCKK CDPTEVELDN QIVTATQSNI CDEDSATETC  120
YTYDRNKCYT AVVPLVYGGE TKMVETALTP DACYPDGGGG SGGGGSGGGG SQHDEAVDAN  180
SLAEAKVLAN RELDKYGVSD YYKNLINNAK TVEGVKALID EILAALP                227

SEQ ID NO: 91          moltype = DNA  length = 684
FEATURE                Location/Qualifiers
misc_feature           1..684
                       note = source = /note="Description of Artificial Sequence:
                        Synthetic polynucleotide"
source                 1..684
                       mol_type = other DNA
                       organism = synthetic construct
SEQUENCE: 91
atggaatgga gctgggtctt tctcttcttc ctgtcagtaa cgactggtgt ccactcccag  60
cacgatgagg ccgtggacgc caattctctg gccgaggcta aggtgctggc caacagagag  120
ctggataagt acggcgtgtc cgactactac aagaacctga tcaacaacgc caagaccgtg  180
gaaggcgtga aggccctgat cgacgagatc ctggctgccc tgcctggagg cggaggatct  240
ggtggcggtg gttctggcgg agggggctct caggaagatg agcggatcgt gctggtggac  300
aacaagtgca agtgcgcccg gatcacctcc cggatcatcc ggtcctccga ggatcccaac  360
gaggacatcg tggaacggaa catcagaatc atcgtgcccc tgaacaaccg cgagaacatc  420
tccgacccca ccagccctct gcggaccaga ttcgtgtacc acctgtccga cctgtgcaag  480
aagtgcgacc ctaccgaggt ggaactggac aaccagatcg tgaccgccac ccagtccaac  540
atctgcgacg aggactccgc caccgagaca tgctacacct acgaccggaa caagtgctac  600
accgccgtgg tgcctctggt gtacggcggc gagacaaaga tggtggaaac cgccctgacc  660
cccgacgcct gctatcctga ttga                                         684

SEQ ID NO: 92          moltype = AA  length = 227
FEATURE                Location/Qualifiers
REGION                 1..227
                       note = source = /note="Description of Artificial Sequence:
                        Synthetic polypeptide"
source                 1..227
                       mol_type = protein
                       organism = synthetic construct
SEQUENCE: 92
MEWSWVFLFF LSVTTGVHSQ HDEAVDANSL AEAKVLANRE LDKYGVSDYY KNLINNAKTV  60
EGVKALIDEI LAALPGGGGS GGGGSGGGGS QEDERIVLVD NKCKCARITS RIIRSSEDPN  120
EDIVERNIRI IVPLNNRENI SDPTSPLRTR FVYHLSDLCK KCDPTEVELD NQIVTATQSN  180
ICDEDSATET CYTYDRNKCY TAVVPLVYGG ETKMVETALT PDACYPD                227

SEQ ID NO: 93          moltype = DNA  length = 2286
FEATURE                Location/Qualifiers
misc_feature           1..2286
                       note = source = /note="Description of Artificial Sequence:
                        Synthetic polynucleotide"
source                 1..2286
                       mol_type = other DNA
                       organism = synthetic construct
SEQUENCE: 93
atgaaatggg tcacctttat ctccctgctg ttcctgttct cctccgccta ctctcggggc  60
gtgttcagaa gagacgccca caaatcggag gtagcgcacc ggttcaaaga cttgggagaa  120
gaaaacttta aggcccttgt actcattgcg tttgcgcagt atttgcagca gtgcccattc  180
gaggaccatg tcaaacttgt caacgaagtg acagagtttg cgaaaacttg cgtcgccgac  240
gaatccgcgg agaactgtga caagtcgctg catacgttgt tcggggataa gctctgtacc  300
gtagcgacct tgagggaaac ttacggggaa atggcggact gttgcgctaa gcaggagccg  360
gaacggaacg agtgtttcct tcagcataag gatgacaacc ccaacctccc tagattggtc  420
agacccgaag tggatgtgat gtgcacagca ttccatgaca atgaggaaac ctttctcaaa  480
aagtatttgt acgagattgc ccgacgacac ccctatttct acgctcccga gttgctcttc  540
ttcgcgaaac ggtataaagc tgcctttact gaatgctgtc aagcagcgga caaggccgca  600
tgcctccttc ccaaattgga tgaactccgc gatgaaggga aggcgtcatc ggccaaacag  660
cggcttaagt gcgcatcgct tcagaaattc ggagagaggg cgttcaaagc gtgggccgtc  720
gcgagactgt cgcagagatt ccctaaggcg gaatttgcag aggtatcgaa gctcgtgaca  780
gacctcacaa aggtccacac cgaatgttgc catggagacc tgcttgagtg cgccgatgat  840
agggcagacc tcgcaaagta catttgtgag aatcaggaca gcattagctc caagctgaaa  900
gagtgctgtg agaagccttt gctggaaaaa tcccactgta tcgccgaggt agaaaacgat  960
gaaatgcccg ctgatcttcc ctcgctggcg gcagacttcg tcgagtcgaa ggacgtctgc  1020
aagaattacg cagaggcaaa agatgtgttt cttggaatgt tcctttatga gtatgcgaga  1080
aggcacccgg attattccgt ggtactgctc ttgcgattgg cgaaaacgta cgaaacaacg  1140
```

```
cttgagaagt gttgtgcggc tgccgacccg catgagtgct acgccaaggt atttgatgag  1200
tttaaacctc ttgtcgagga accccagaat cttatcaagc agaactgcga gcttttcaag  1260
cagttgggtg aatacaaatt ccagaacgcg cttctggtga ggtataccaa gaaagtacct  1320
caagtctcaa cacccacact cgtcgaggtg tcacggaacc tcgggaaagt agggtcgaag  1380
tgctgtaaac acccagaggc caagcgcatg ccctgtgcgg aggactacct ctcggtagtg  1440
ttgaatcaac tgtgtgtcct ccacgaaaag acgccggtgt cagaccgcgt cacaaagtgc  1500
tgcacggaga gcctggtcaa tagacgcccc tgcttctcag cgctggaggt ggatgagaca  1560
tacgtcccga aagagtttaa cgccgaaacg tttacttttc atgctgatat ctgtacgttg  1620
tcagagaagg aaaggcaaat caagaaacaa actgcgcttg tggaactggt gaagcacaaa  1680
ccgaaggcga ctaaggaaca gctgaaggcg gtgatggatg actttgccgc gttcgtagag  1740
aaatgctgta aagcagacga taaggagact tgttttgcgg aagagggacc taaacttgtt  1800
gctgcaagtc aagctgcctt aggcttagga ggcggaggat ctggtggcgg tggttctggc  1860
ggaggggggct ctcaggaaga tgagcggatc gtgctggtgg acaacaagtg caagtgcgcc  1920
cggatcacct cccggatcat ccggtcctcc gaggatccca acgaggacat cgtggaacgg  1980
aacatcagaa tcatcgtgcc cctgaacaac cgcgagaaca tctccgaccc caccagccct  2040
ctgcggacca gattcgtgta ccacctgtcc gacctgtgca agaagtgcga ccctaccgag  2100
gtggaactgg acaaccagat cgtgaccgcc acccagtcca acatctgcga cgaggactcc  2160
gccaccgaga catgctacac ctacgaccgg aacaagtgct acaccgccgt ggtgcctctg  2220
gtgtacggcg gcgagacaaa gatggtggaa accgccctga cccccgacgc ctgctatcct  2280
gattag                                                            2286
```

```
SEQ ID NO: 94          moltype = AA  length = 761
FEATURE                Location/Qualifiers
REGION                 1..761
                       note = source = /note="Description of Artificial Sequence:
                        Synthetic polypeptide"
source                 1..761
                       mol_type = protein
                       organism = synthetic construct
SEQUENCE: 94
MKWVTFISLL FLFSSAYSRG VFRRDAHKSE VAHRFKDLGE ENFKALVLIA FAQYLQQCPF  60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ RLKCASLQKF GERAFKAWAV  240
ARLSQRFPKA EFAEVSKLVT DLTKVHTECC HGDLLECADD RADLAKYICE NQDSISSKLK  300
ECCEKPLLEK SHCIAEVEND EMPADLPSLA ADFVESKDVC KNYAEAKDVF LGMFLYEYAR  360
RHPDYSVVLL LRLAKTYETT LEKCCAAADP HECYAKVFDE FKPLVEEPQN LIKQNCELFK  420
QLGEYKFQNA LLVRYTKKVP QVSTPTLVEV SRNLGKVGSK CCKHPEAKRM PCAEDYLSVV  480
LNQLCVLHEK TPVSDRVTKC CTESLVNRRP CFSALEVDET YVPKEFNAET FTFHADICTL  540
SEKERQIKKQ TALVELVKHK PKATKEQLKA VMDDFAAFVE KCCKADDKET CFAEEGPKLV  600
AASQAALGLG GGGSGGGGSG GGGSQEDERI VLVDNKCKCA RITSRIIRSS EDPNEDIVER  660
NIRIIVPLNN RENISDPTSP LRTRFVYHLS DLCKKCDPTE VELDNQIVTA TQSNICDEDS  720
ATETCYTYDR NKCYTAVVPL VYGGETKMVE TALTPDACYP D                     761
```

```
SEQ ID NO: 95          moltype = DNA  length = 2280
FEATURE                Location/Qualifiers
misc_feature           1..2280
                       note = source = /note="Description of Artificial Sequence:
                        Synthetic polynucleotide"
source                 1..2280
                       mol_type = other DNA
                       organism = synthetic construct
SEQUENCE: 95
atgaagaacc atctgctgtt ctggggcgtg ctggccgtgt tcatcaaggc cgtgcacgtg  60
aaggcccagg aagatgagcg gatcgtgctg gtggacaaca agtgcaagtg cgcccggatc  120
acctcccgga tcatccggtc ctccgaggat cccaacgagg acatcgtgga acggaacatc  180
agaatcatcg tgcccctgaa caaccgcgag aacatctccg accccaccag ccctctgcgg  240
accagattcg tgtaccacct gtccgacctg tgcaagaagt gcgaccctac cgaggtggaa  300
ctggacaacc agatcgtgac cgccacccag tccaacatct gcgacgagga ctccgccacc  360
gagacatgct acacctacga ccggaacaag tgctacaccg ccgtggtgcc tctggtgtac  420
ggcggcgaga caaagatggt ggaaaccgcc ctgacccccg acgcctgcta tcctgatgga  480
ggcggaggat ctggtggcgg tggttctggc ggagggggct ctgacgccca caaatcggag  540
gtagcgcacc ggttcaaaga cttgggagaa gaaaacttta aggcccttgt actcattgcg  600
tttgcgcagt atttgcagca gtgcccattc gaggaccatg tcaaacttgt caacgaagtg  660
acagagtttg cgaaaacttg cgtcgccgac gaatccgcgg agaactgtga caagtcgctg  720
catacgttgt tcggggataa gctctgtacc gtagcgacct tgagggaaac ttacggggaa  780
atggcggact gttgcgctaa gcaggagccg gaacggaacg agtgtttcct tcagcataag  840
gatgacaacc ccaacctccc tagattggtc agacccgaag tggatgtgat gtgcacagca  900
ttccatgaca atgaggaaac ctttctcaaa aagtatttgt acgagattgc ccgacgacac  960
ccctatttct acgctcccga gttgctcttc ttcgcgaaac ggtataaagc tgcctttact  1020
gaatgctgtc aagcagcgga caaggccgca tgcctccttc ccaaattgga tgaactccgc  1080
gatgaaggga aggcgtcatc ggccaaacag cggcttaagt gcgcatcgct tcagaaattc  1140
ggagagaggg cgttcaaagc gtgggccgtc gcgagactgt cgcagagatt ccctaaggcg  1200
gaatttgcag aggtatcgaa gctcgtgaca gacctcacaa aggtccacac cgaatgttgc  1260
catggagacc tgcttgagtg cgccgatgat agggcagacc tcgcaaagta catttgtgag  1320
aatcaggaca gcattagctc caagctgaaa gagtgctgtg agaagccttt gctggaaaaa  1380
tcccactgta tcgccgaggt agaaaacgat gaaatgcccg ctgatcttcc ctcgctggcg  1440
gcagacttcg tcgagtcgaa ggacgtctgc aagaattacg cagaggcaaa agatgtgttt  1500
cttggaatgt tcctttatga gtatgcgaga aggcacccgg attattccgt ggtactgctc  1560
```

```
ttgcgattgg cgaaaacgta cgaaacaacg cttgagaagt gttgtgcggc tgccgacccg  1620
catgagtgct acgccaaggt atttgatgag tttaaacctc ttgtcgagga accccagaat  1680
cttatcaagc agaactgcga gcttttcaag cagttgggtg aatacaaatt ccagaacgcg  1740
cttctggtga ggtataccaa gaaagtacct caagtctcaa cacccacact cgtcgaggtg  1800
tcacggaacc tcgggaaagt agggtcgaag tgctgtaaac acccagaggc caagcgcatg  1860
ccctgtgcgg aggactacct ctcggtagtg ttgaatcaac tgtgtgtcct ccacgaaaag  1920
acgccggtgt cagaccgcgt cacaaagtgc tgcacggaga gcctggtcaa tagacgcccc  1980
tgcttctcag cgctggaggt ggatgagaca tacgtcccga aagagtttaa cgccgaaacg  2040
tttacttttc atgctgatat ctgtacgttg tcagagaagg aaaggcaaat caagaaacaa  2100
actgcgcttg tggaactggt gaagcacaaa ccgaaggcga ctaaggaaca gctgaaggcg  2160
gtgatggatg actttgccgc gttcgtagag aaatgctgta aagcagacga taaggagact  2220
tgttttgcgg aagagggacc taaacttgtt gctgcaagtc aagctgcctt aggcttatag  2280
```

```
SEQ ID NO: 96          moltype = AA  length = 759
FEATURE                Location/Qualifiers
REGION                 1..759
                       note = source = /note="Description of Artificial Sequence:
                        Synthetic polypeptide"
source                 1..759
                       mol_type = protein
                       organism = synthetic construct
SEQUENCE: 96
MKNHLLFWGV LAVFIKAVHV KAQEDERIVL VDNKCKCARI TSRIIRSSED PNEDIVERNI  60
RIIVPLNNRE NISDPTSPLR TRFVYHLSDL CKKCDPTEVE LDNQIVTATQ SNICDEDSAT  120
ETCYTYDRNK CYTAVVPLVY GGETKMVETA LTPDACYPDG GGGSGGGGSG GGGSDAHKSE  180
VAHRFKDLGE ENFKALVLIA FAQYLQQCPF EDHVKLVNEV TEFAKTCVAD ESAENCDKSL  240
HTLFGDKLCT VATLRETYGE MADCCAKQEP ERNECFLQHK DDNPNLPRLV RPEVDVMCTA  300
FHDNEETFLK KYLYEIARRH PYFYAPELLF FAKRYKAAFT ECCQAADKAA CLLPKLDELR  360
DEGKASSAKQ RLKCASLQKF GERAFKAWAV ARLSQRFPKA EFAEVSKLVT DLTKVHTECC  420
HGDLLECADD RADLAKYICE NQDSISSKLK ECCEKPLLEK SHCIAEVEND EMPADLPSLA  480
ADFVESKDVC KNYAEAKDVF LGMFLYEYAR RHPDYSVVLL LRLAKTYETT LEKCCAAADP  540
HECYAKVFDE FKPLVEEPQN LIKQNCELFK QLGEYKFQNA LLVRYTKKVP QVSTPTLVEV  600
SRNLGKVGSK CCKHPEAKRM PCAEDYLSVV LNQLCVLHEK TPVSDRVTKC CTESLVNRRP  660
CFSALEVDET YVPKEFNAET FTFHADICTL SEKERQIKKQ TALVELVKHK PKATKEQLKA  720
VMDDFAAFVE KCCKADDKET CFAEEGPKLV AASQAALGL                        759
```

```
SEQ ID NO: 97          moltype = DNA  length = 1452
FEATURE                Location/Qualifiers
misc_feature           1..1452
                       note = source = /note="Description of Artificial Sequence:
                        Synthetic polynucleotide"
source                 1..1452
                       mol_type = other DNA
                       organism = synthetic construct
SEQUENCE: 97
atggggtggt cctacattat cctgttcctc gtggccaccg ccactggcgt gcactcacag  60
gtgcagctgg tgcagtctgg cgccgaagtg aagaaacctg gcgcctccgt gaaggtgtcc  120
tgcaaggcct ccggctacac cttcatcagc tacaccatgc actgggtgcg acaggcccct  180
ggacagggcc tggaatggat gggctacatc aaccctagat ctggctacac ccactacaac  240
cagaagctga aggacaaggc caccctgacc gccgacaagt ctgcctccac cgcctacatg  300
gaactgtcct ccctgcggag cgaggacacc gccgtgtact actgtgccag atccgcctac  360
tacgactacg acggcttcgc ctattggggc cagggcaccc tcgtgacagt gtctagcggt  420
ggcggaggat ctggcggagg cggtagtggc ggtggcggat ctgatatcca gatgacccag  480
tccccctcca gcctgtctgc ctctgtgggc gacagagtga caattacctg ctccgccagc  540
tcctccgtgt cttacatgaa ctggtatcag cagaagcccg gcaaggcccc caagcggctg  600
atctacgaca cctccaagct ggcctctggc gtgccctcca gattctccgg ctctggctct  660
ggcaccgact ttaccctgac catcagctcc ctgcagcccg aggacttcgc cacctactac  720
tgccagcagt ggtcctccaa ccctcccacc tttggcggag gcaccaaggt ggaaatcaaa  780
ggcggcggag gaagcggggg aggcggttct gggggtggtg gatctcagga agatgagcgg  840
atcgtgctgg tggacaacaa gtgcaagtgc gcccggatca cctcccggat catccggtcc  900
tccgaggatc ccaacgagga catcgtggaa cggaacatca gaatcatcgt gcccctgaac  960
aaccgcgaga acatctccga ccccaccagc cctctgcgga ccagattcgt gtaccacctg  1020
tccgacctgt gcaagaagtg cgaccctacc gaggtggaac tggacaacca gatcgtgacc  1080
gccacccagt ccaacatctg cgacgaggac tccgccaccg agacatgcta cacctacgac  1140
cggaacaagt gctacaccgc cgtggtgcct ctggtgtacg gcggcgagac aaagatggtg  1200
gaaaccgccc tgacccccga cgcctgctat cctgatggag gcggaggatc tggtggcggt  1260
ggttctggcg gagggggctc tcagcacgat gaggccgtgg acgccaattc tctggccgag  1320
gctaaggtgc tggccaacag agagctggat aagtacggcg tgtccgacta ctacaagaac  1380
ctgatcaaca acgccaagac cgtggaaggc gtgaaggccc tgatcgacga gatcctggct  1440
gccctgcctt ga                                                     1452
```

```
SEQ ID NO: 98          moltype = AA  length = 483
FEATURE                Location/Qualifiers
REGION                 1..483
                       note = source = /note="Description of Artificial Sequence:
                        Synthetic polypeptide"
source                 1..483
                       mol_type = protein
                       organism = synthetic construct
```

```
SEQUENCE: 98
MGWSYIILFL VATATGVHSQ VQLVQSGAEV KKPGASVKVS CKASGYTFIS YTMHWVRQAP  60
GQGLEWMGYI NPRSGYTHYN QKLKDKATLT ADKSASTAYM ELSSLRSEDT AVYYCARSAY  120
YDYDGFAYWG QGTLVTVSSG GGGSGGGGSG GGGSDIQMTQ SPSSLSASVG DRVTITCSAS  180
SSVSYMNWYQ QKPGKAPKRL IYDTSKLASG VPSRFSGSGS GTDFTLTISS LQPEDFATYY  240
CQQWSSNPPT FGGGTKVEIK GGGGSGGGGS GGGGSQEDER IVLVDNKCKC ARITSRIIRS  300
SEDPNEDIVE RNIRIIVPLN NRENISDPTS PLRTRFVYHL SDLCKKCDPT EVELDNQIVT  360
ATQSNICDED SATETCYTYD RNKCYTAVVP LVYGGETKMV ETALTPDACY PDGGGGSGGG  420
GSGGGGSQHD EAVDANSLAE AKVLANRELD KYGVSDYYKN LINNAKTVEG VKALIDEILA  480
ALP                                                               483

SEQ ID NO: 99          moltype = DNA  length = 3039
FEATURE                Location/Qualifiers
misc_feature           1..3039
                       note = source = /note="Description of Artificial Sequence:
                        Synthetic polynucleotide"
source                 1..3039
                       mol_type = other DNA
                       organism = synthetic construct
SEQUENCE: 99
atggggtggt cctacattat cctgttcctc gtggccaccg ccactggcgt gcactcacag  60
gtgcagctgg tgcagtctgg cgccgaagtg aagaaacctg gcgcctccgt gaaggtgtcc  120
tgcaaggcct ccggctacac cttcatcagc tacaccatgc actgggtgcg acaggcccct  180
ggacagggcc tggaatggat gggctacatc aaccctagat ctggctacac ccactacaac  240
cagaagctga aggacaaggc caccctgacc gccgacaagt ctgcctccac cgcctacatg  300
gaactgtcct ccctgcggag cgaggacacc gccgtgtact actgtgccag atccgcctac  360
tacgactacg acggcttcgc ctattggggc cagggcaccc tcgtgacagt gtctagcggt  420
ggcggaggat ctggcggagg cggtagtggc ggtggcggat ctgatatcca gatgacccag  480
tccccctcca gcctgtctgc ctctgtgggc gacagagtga caattacctg ctccgccagc  540
tcctccgtgt cttacatgaa ctggtatcag cagaagcccg gcaaggcccc caagcggctg  600
atctacgaca cctccaagct ggcctctggc gtgccctcca gattctccgg ctctggctct  660
ggcaccgact ttaccctgac catcagctcc ctgcagcccg aggacttcgc cacctactac  720
tgccagcagt ggtcctccaa ccctcccacc tttggcggag gcaccaaggt ggaaatcaaa  780
ggcggcggag gaagcggggg aggcggttct gggggtggtg gatctcagga agatgagcgg  840
atcgtgctgg tggacaacaa gtgcaagtgc gcccggatca cctcccggat catccggtcc  900
tccgaggatc ccaacgagga catcgtggaa cggaacatca gaatcatcgt gcccctgaac  960
aaccgcgaga acatctccga ccccaccagc cctctgcgga ccagattcgt gtaccacctg  1020
tccgacctgt gcaagaagtg cgaccctacc gaggtggaac tggacaacca gatcgtgacc  1080
gccacccagt ccaacatctg cgacgaggac tccgccaccg agacatgcta cacctacgac  1140
cggaacaagt gctacaccgc cgtggtgcct ctggtgtacg gcggcgagac aaagatggtg  1200
gaaaccgccc tgacccccga cgcctgctat cctgatggag gcggaggatc tggtggcggt  1260
ggttctggcg gagggggctc tgacgcccac aaatcggagg tagcgcaccg gttcaaagac  1320
ttgggagaag aaaactttaa ggcccttgta ctcattgcgt ttgcgcagta tttgcagcag  1380
tgcccattcg aggaccatgt caaacttgtc aacgaagtga cagagtttgc gaaaacttgc  1440
gtcgccgacg aatccgcgga gaactgtgac aagtcgctgc atacgttgtt cggggataag  1500
ctctgtaccg tagcgacctt gagggaaact tacggggaaa tggcggactg ttgcgctaag  1560
caggagccgg aacggaacga gtgtttcctt cagcataagg atgacaaccc caacctccct  1620
agattggtca gacccgaagt ggatgtgatg tgcacagcat tccatgacaa tgaggaaacc  1680
tttctcaaaa agtatttgta cgagattgcc cgacgacacc cctatttcta cgctcccgag  1740
ttgctcttct tcgcgaaacg gtataaagct gcctttactg aatgctgtca agcagcggac  1800
aaggccgcat gcctccttcc caaattggat gaactccgcg atgaagggaa ggcgtcatcg  1860
gccaaacagc ggcttaagtg cgcatcgctt cagaaattcg gagagagggc gttcaaagcg  1920
tgggccgtcg cgagactgtc gcagagattc cctaaggcgg aatttgcaga ggtatcgaag  1980
ctcgtgacag acctcacaaa ggtccacacc gaatgttgcc atggagacct gcttgagtgc  2040
gccgatgata gggcagacct cgcaaagtac atttgtgaga atcaggacag cattagctcc  2100
aagctgaaag agtgctgtga gaagcctttg ctggaaaaat cccactgtat cgccgaggta  2160
gaaaacgatg aaatgcccgc tgatcttccc tcgctggcgg cagacttcgt cgagtcgaag  2220
gacgtctgca agaattacgc agaggcaaaa gatgtgtttc ttggaatgtt cctttatgag  2280
tatgcgagaa ggcacccgga ttattccgtg gtactgctct tgcgattggc gaaaacgtac  2340
gaaacaacgc ttgagaagtg ttgtgcggct gccgacccgc atgagtgcta cgccaaggta  2400
tttgatgagt ttaaacctct tgtcgaggaa ccccagaatc ttatcaagca gaactgcgag  2460
cttttcaagc agttgggtga atacaaattc cagaacgcgc ttctggtgag gtataccaag  2520
aaagtacctc aagtctcaac acccacactc gtcgaggtgt cacggaacct cgggaaagta  2580
gggtcgaagt gctgtaaaca cccagaggcc aagcgcatgc cctgtgcgga ggactacctc  2640
tcggtagtgt tgaatcaact gtgtgtcctc cacgaaaaga cgccggtgtc agaccgcgtc  2700
acaaagtgct gcacggagag cctggtcaat agacgcccct gcttctcagc gctggaggtg  2760
gatgagacat acgtcccgaa agagtttaac gccgaaacgt ttacttttca tgctgatatc  2820
tgtacgttgt cagagaagga aaggcaaatc aagaaacaaa ctgcgcttgt ggaactggtg  2880
aagcacaaac cgaaggcgac taaggaacag ctgaaggcgg tgatggatga ctttgccgcg  2940
ttcgtagaga aatgctgtaa agcagacgat aaggagactt gttttgcgga agagggacct  3000
aaacttgttg ctgcaagtca agctgcctta ggcttatag                         3039

SEQ ID NO: 100         moltype = AA  length = 1012
FEATURE                Location/Qualifiers
REGION                 1..1012
                       note = source = /note="Description of Artificial Sequence:
                        Synthetic polypeptide"
source                 1..1012
                       mol_type = protein
```

```
                        organism = synthetic construct
SEQUENCE: 100
MGWSYIILFL VATATGVHSQ VQLVQSGAEV KKPGASVKVS CKASGYTFIS YTMHWVRQAP  60
GQGLEWMGYI NPRSGYTHYN QKLKDKATLT ADKSASTAYM ELSSLRSEDT AVYYCARSAY  120
YDYDGFAYWG QGTLVTVSSG GGGSGGGGSG GGGSDIQMTQ SPSSLSASVG DRVTITCSAS  180
SSVSYMNWYQ QKPGKAPKRL IYDTSKLASG VPSRFSGSGS GTDFTLTISS LQPEDFATYY  240
CQQWSSNPPT FGGGTKVEIK GGGGSGGGGS GGGGSQEDER IVLVDNKCKC ARITSRIIRS  300
SEDPNEDIVE RNIRIIVPLN NRENISDPTS PLRTRFVYHL SDLCKKCDPT EVELDNQIVT  360
ATQSNICDED SATETCYTYD RNKCYTAVVP LVYGGETKMV ETALTPDACY PDGGGGSGGG  420
GSGGGGSDAH KSEVAHRFKD LGEENFKALV LIAFAQYLQQ CPFEDHVKLV NEVTEFAKTC  480
VADESAENCD KSLHTLFGDK LCTVATLRET YGEMADCCAK QEPERNECFL QHKDDNPNLP  540
RLVRPEVDVM CTAFHDNEET FLKKYLYEIA RRHPYFYAPE LLFFAKRYKA AFTECCQAAD  600
KAACLLPKLD ELRDEGKASS AKQRLKCASL QKFGERAFKA WAVARLSQRF PKAEFAEVSK  660
LVTDLTKVHT ECCHGDLLEC ADDRADLAKY ICENQDSISS KLKECCEKPL LEKSHCIAEV  720
ENDEMPADLP SLAADFVESK DVCKNYAEAK DVFLGMFLYE YARRHPDYSV VLLLRLAKTY  780
ETTLEKCCAA ADPHECYAKV FDEFKPLVEE PQNLIKQNCE LFKQLGEYKF QNALLVRYTK  840
KVPQVSTPTL VEVSRNLGKV GSKCCKHPEA KRMPCAEDYL SVVLNQLCVL HEKTPVSDRV  900
TKCCTESLVN RRPCFSALEV DETYVPKEFN AETFTFHADI CTLSEKERQI KKQTALVELV  960
KHKPKATKEQ LKAVMDDFAA FVEKCCKADD KETCFAEEGP KLVAASQAAL GL          1012

SEQ ID NO: 101          moltype = DNA  length = 3039
FEATURE                 Location/Qualifiers
misc_feature            1..3039
                        note = source = /note="Description of Artificial Sequence:
                         Synthetic polynucleotide"
source                  1..3039
                        mol_type = other DNA
                        organism = synthetic construct
SEQUENCE: 101
atggggtggt cctacattat cctgttcctc gtggccaccg ccactggcgt gcactcacag  60
gtgcagctgg tgcagtctgg cgccgaagtg aagaaacctg gcgcctccgt gaaggtgtcc  120
tgcaaggcct ccggctacac cttcatcagc tacaccatgc actgggtgcg acaggcccct  180
ggacagggcc tggaatggat gggctacatc aaccctagat ctggctacac ccactacaac  240
cagaagctga aggacaaggc caccctgacc gccgacaagt ctgcctccac cgcctacatg  300
gaactgtcct ccctgcggag cgaggacacc gccgtgtact actgtgccag atccgcctac  360
tacgactacg acggcttcgc ctattggggc cagggcaccc tcgtgacagt gtctagcggt  420
ggcggaggat ctggcggagg cggtagtggc ggtggcggat ctgatatcca gatgacccag  480
tcccccctcca gcctgtctgc ctctgtgggc gacagagtga caattacctg ctccgccagc  540
tcctccgtgt cttacatgaa ctggtatcag cagaagcccg gcaaggcccc caagcggctg  600
atctacgaca cctccaagct ggcctctggc gtgccctcca gattctccgg ctctggctct  660
ggcaccgact ttaccctgac catcagctcc ctgcagcccg aggacttcgc cacctactac  720
tgccagcagt ggtcctccaa ccctcccacc tttggcggag gcaccaaggt ggaaatcaaa  780
ggcggcggag gaagcggggg aggcggttct gggggtggtg gatctcagga agatgagcgg  840
atcgtgctgg tggacaacaa gtgcaagtgc gcccggatca cctcccggat catccggtcc  900
tccgaggatc ccaacgagga catcgtggaa cggaacatca gaatcatcgt gcccctgaac  960
aaccgcgaga acatctccga ccccaccagc cctctgcgga ccagattcgt gtaccacctg  1020
tccgacctgt gcaagaagtg cgaccctacc gaggtggaac tggacaacca gatcgtgacc  1080
gccacccagt ccaacatctg cgacgaggac tccgccaccg agacatgcta cacctacgac  1140
cggaacaagt gctacaccgc cgtggtgcct ctggtgtacg gcggcgagac aaagatggtg  1200
gaaaccgccc tgacccccga cgcctgctat cctgatggag gcggaggatc tggtggcggt  1260
ggttctggcg gagggggctc tgacgcccac aaatcggagg tagcgcaccg gttcaaagac  1320
ttgggagaag aaaactttaa ggcccttgta ctcattgcgt ttgcgcagta tttgcagcag  1380
tgcccattcg aggaccatgt caaacttgtc aacgaagtga cagagtttgc gaaaacttgc  1440
gtcgccgacg aatccgcgga gaactgtgac aagtcgctgc atacgttgtt cggggataag  1500
ctctgtaccg tagcgacctt gagggaaact tacggggaaa tggcggactg ttgcgctaag  1560
caggagccgg aacggaacga gtgtttcctt cagcataagg atgacaaccc caacctccct  1620
agattggtca gacccgaagt ggatgtgatg tgcacagcat tccatgacaa tgaggaaacc  1680
tttctcaaaa agtatttgta cgagattgcc cgacgacacc cctatttcta cgctcccgag  1740
ttgctcttct tcgcgaaacg gtataaagct gcctttactg aatgctgtca agcagcggac  1800
aaggccgcat gcctccttcc caaattggat gaactccgcg atgaagggaa ggcgtcatcg  1860
gccaaacagc ggcttaagtg cgcatcgctt cagaaattcg gagagagggc gttcaaagcg  1920
tgggccgtcg cgagactgtc gcagagattc cctaaggcgg aatttgcaga ggtatcgaag  1980
ctcgtgacag acctcacaaa ggtccacacc gaatgttgcc atggagacct gcttgagtgc  2040
gccgatgata gggcagacct cgcaaagtac atttgtgaga atcaggacag cattagctcc  2100
aagctgaaag agtgctgtga gaagcctttg ctggaaaaat cccactgtat cgccgaggta  2160
gaaaacgatg aaatgcccgc tgatcttccc tcgctggcgg cagacttcgt cgagtcgaag  2220
gacgtctgca agaattacgc agaggcaaaa gatgtgtttc ttggaatgtt cctttatgag  2280
tatgcgagaa ggcacccgga ttattccgtg gtactgctct tgcgattggc gaaaacgtac  2340
gaaacaacgc ttgagaagtg ttgtgcggct gccgacccgc atgagtgcta cgccaaggta  2400
tttgatgagt ttaaacctct tgtcgaggaa ccccagaatc ttatcaagca gaactgcgag  2460
cttttcaagc agttgggtga atacaaattc cagaacgcgc ttctggtgag gtataccaag  2520
aaagtacctc aagtctcaac acccacactc gtcgaggtgt cacggaacct cgggaaagta  2580
gggtcgaagt gctgtaaaca cccagaggcc aagcgcatgc cctgtgcgga ggactacctc  2640
tcggtagtgt tgaatcaact gtgtgtcctc cacgaaaaga cgccggtgtc agaccgcgtc  2700
acaaagtgct gcacggagag cctggtcaat agacgcccct gcttctcagc gctggaggtg  2760
gatgagacat acgtcccgaa agagtttaac gccgaaacgt ttacttttca tgctgatatc  2820
tgtacgttgt cagagaagga aaggcaaatc aagaaacaaa ctgcgcttgt ggaactggtg  2880
aagcacaaac cgaaggcgac taaggaacag ctgaaggcgg tgatggatga ctttgccgcg  2940
ttcgtagaga aatgctgtaa agcagacgat aaggagactt gttttgcgga agagggaaag  3000
```

-continued

```
aaacttgttg ctgcaagtca agctgcctta ggcttatag                      3039

SEQ ID NO: 102          moltype = AA  length = 1012
FEATURE                 Location/Qualifiers
REGION                  1..1012
                        note = source = /note="Description of Artificial Sequence:
                         Synthetic polypeptide"
source                  1..1012
                        mol_type = protein
                        organism = synthetic construct
SEQUENCE: 102
MGWSYIILFL VATATGVHSQ VQLVQSGAEV KKPGASVKVS CKASGYTFIS YTMHWVRQAP  60
GQGLEWMGYI NPRSGYTHYN QKLKDKATLT ADKSASTAYM ELSSLRSEDT AVYYCARSAY  120
YDYDGFAYWG QGTLVTVSSG GGGSGGGGSG GGGSDIQMTQ SPSSLSASVG DRVTITCSAS  180
SSVSYMNWYQ QKPGKAPKRL IYDTSKLASG VPSRFSGSGS GTDFTLTISS LQPEDFATYY  240
CQQWSSNPPT FGGGTKVEIK GGGGSGGGGS GGGGSQEDER IVLVDNKCKC ARITSRIIRS  300
SEDPNEDIVE RNIRIIVPLN NRENISDPTS PLRTRFVYHL SDLCKKCDPT EVELDNQIVT  360
ATQSNICDED SATETCYTYD RNKCYTAVVP LVYGGETKMV ETALTPDACY PDGGGGSGGG  420
GSGGGGSDAH KSEVAHRFKD LGEENFKALV LIAFAQYLQQ CPFEDHVKLV NEVTEFAKTC  480
VADESAENCD KSLHTLFGDK LCTVATLRET YGEMADCCAK QEPERNECFL QHKDDNPNLP  540
RLVRPEVDVM CTAFHDNEET FLKKYLYEIA RRHPYFYAPE LLFFAKRYKA AFTECCQAAD  600
KAACLLPKLD ELRDEGKASS AKQRLKCASL QKFGERAFKA WAVARLSQRF PKAEFAEVSK  660
LVTDLTKVHT ECCHGDLLEC ADDRADLAKY ICENQDSISS KLKECCEKPL LEKSHCIAEV  720
ENDEMPADLP SLAADFVESK DVCKNYAEAK DVFLGMFLYE YARRHPDYSV VLLLRLAKTY  780
ETTLEKCCAA ADPHECYAKV FDEFKPLVEE PQNLIKQNCE LFKQLGEYKF QNALLVRYTK  840
KVPQVSTPTL VEVSRNLGKV GSKCCKHPEA KRMPCAEDYL SVVLNQLCVL HEKTPVSDRV  900
TKCCTESLVN RRPCFSALEV DETYVPKEFN AETFTFHADI CTLSEKERQI KKQTALVELV  960
KHKPKATKEQ LKAVMDDFAA FVEKCCKADD KETCFAEEGK KLVAASQAAL GL          1012

SEQ ID NO: 103          moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 103
LLQGA                                                              5

SEQ ID NO: 104          moltype = AA  length = 6
FEATURE                 Location/Qualifiers
REGION                  1..6
                        note = source = /note="Description of Artificial Sequence:
                         Synthetic 6xHis tag"
source                  1..6
                        mol_type = protein
                        organism = synthetic construct
SEQUENCE: 104
HHHHHH                                                             6
```

What is claimed is:

1. An IgM, IgA, IgG/IgM or IgG/IgA antibody or an antigen binding fragment thereof, wherein the antibody or antigen-binding fragment thereof comprises a modified J chain that comprises an absorption, distribution, metabolism and/or excretion (ADME)-modulating moiety, wherein the ADME-modulating moiety comprises a human IgG Fc domain that binds to FcRn, wherein the modified J chain sequence comprises a direct or indirect fusion of the ADME-modulating moiety to the C-terminus or the N-terminus of a human J chain sequence, wherein the modified J chain sequence comprises the native human J chain sequence of SEQ ID NO: 1.

2. The IgM, IgA, IgG/IgM or IgG/IgA antibody or antigen-binding fragment thereof according to claim 1, wherein the ADME-modulating moiety is introduced by indirect fusion through a peptide linker.

3. The IgM, IgA, IgG/IgM or IgG/IgA antibody or antigen-binding fragment thereof according to claim 1, wherein the ADME-modulating moiety is introduced into the native human J chain sequence of SEQ ID NO: 1 at the C-terminus.

4. The IgM, IgA, IgG/IgM or IgG/IgA antibody or antigen-binding fragment thereof according to claim 1, wherein the ADME-modulating moiety is introduced into the native human J chain sequence of SEQ ID NO: 1 at the N-terminus.

5. The IgM, IgA, IgG/IgM or IgG/IgA antibody or antigen-binding fragment thereof according to claim 2, wherein the peptide linker is about 10 to 20 amino acids long.

6. The IgM, IgA, IgG/IgM or IgG/IgA antibody or antigen-binding fragment thereof according to claim 5, wherein the peptide linker is 15 to 20 amino acids long.

7. The IgM, IgA, IgG/IgM or IgG/IgA antibody or antigen-binding fragment thereof according to claim 6, wherein the peptide linker is 15 amino acids long.

8. The IgM, IgA, IgG/IgM or IgG/IgA antibody or antigen-binding fragment thereof according to claim 2, wherein the modified J chain is in an ADME-linker-J orientation, with the ADME-modulating moiety at an N-terminus of the modified J chain.

9. The IgM, IgA, IgG/IgM or IgG/IgA antibody or antigen-binding fragment thereof according to claim 2, wherein the modified J chain is in a J-linker-ADME orientation, with the ADME-modulating moiety at a C-terminus of the modified J chain.

10. The IgM, IgA, IgG/IgM or IgG/IgA antibody or antigen-binding fragment thereof according to claim 1, wherein the modified J chain further comprises a second binding moiety.

11. The IgM, IgA, IgG/IgM or IgG/IgA antibody or antigen-binding fragment thereof according to claim 10, wherein the ADME-modulating moiety is located at an N-terminus of the modified J chain, and the second binding moiety is located at a C-terminus of the modified J chain.

12. The IgM, IgA, IgG/IgM or IgG/IgA antibody or antigen-binding fragment thereof according to claim 10, wherein the ADME-modulating moiety is located at a C-terminus of the modified J chain, and the second binding moiety is located at an N-terminus of the modified J chain.

13. The IgM, IgA, IgG/IgM or IgG/IgA antibody or antigen-binding fragment thereof according to claim 1, wherein the antibody or antigen-binding fragment thereof is an IgM antibody.

* * * * *